US006495319B1

(12) United States Patent
McClelland et al.

(10) Patent No.: US 6,495,319 B1
(45) Date of Patent: Dec. 17, 2002

(54) REDUCED COMPLEXITY NUCLEIC ACID TARGETS AND METHODS OF USING SAME

(75) Inventors: Michael McClelland, Encinitas, CA (US); John Welsh, Leucadia, CA (US); Thomas Trenkle, San Diego, CA (US)

(73) Assignee: Sidney Kimmel Cancer Center, San Diego, CA (US)

( * ) Notice: Subject to any disclaimer, the term of this patent is extended or adjusted under 35 U.S.C. 154(b) by 0 days.

(21) Appl. No.: 09/300,958

(22) Filed: Apr. 27, 1999

Related U.S. Application Data

(60) Provisional application No. 60/083,331, filed on Apr. 27, 1998, provisional application No. 60/098,070, filed on Aug. 27, 1998, and provisional application No. 60/118,624, filed on Feb. 4, 1999.

(51) Int. Cl.[7] .......................... C12Q 1/68; C07H 21/02; C07H 21/04; G01N 33/566
(52) U.S. Cl. ....................... 435/6; 536/24.32; 536/24.3; 536/23.1; 436/504
(58) Field of Search ..................... 435/6, 91.2, 91.1, 435/7.1; 536/23.1, 24.3, 24.31, 24.32, 22.1, 24.33; 436/504

(56) References Cited

FOREIGN PATENT DOCUMENTS

| WO | 96 41893 | 12/1996 |
|---|---|---|
| WO | 97 22720 | 6/1997 |
| WO | 97 27317 | 7/1997 |

OTHER PUBLICATIONS

Pesole et al. WORDUP: an efficient algorithm for discovering statistically significant pattern in DNA sequences. Nucleic acids Research, vol. 20, No. 11, pp. 2871–2875, Jun. 1992.*
Perucho et al. Fingerprinting of DNA and RNA by arbitrarily primed polymerase chain reaction: Applicantions in Cancer Research. methods in Enzymology, vol. 54, pp. 275–290, Mar. 1995.*
Pozdnyakov et al. Accelerated method for comparing amino acid sequences with allowance fro possible gaps. Plotting optimum correspondence paths. International Journal of Peptide and Protein research, vol. 17, No. 3, Abstract, Mar. 1981.*
Dalal et al. Rapid isolation of tissue–specific and developmentally regulated brain cDNAs using RNA arbitarily primed PCR (RAP–PCR). J Mol Neurosci. 1994 Summer;5(2):93–104.
Hofler et al. In situ amplification of measles virus RNA by the self–sustained sequence replication reaction. Lab Invest. Oct. 1995;73(4):577–85.
Mathieu–Daude et al. Differentially expressed genes in the *Trypanosoma brucei* life cycle identified by RNA fingerprinting. Mol Biochem Parasitol. Apr. 1, 1998 92(1):15–28.
McClelland et al. RNA fingerprinting and differential display using arbitrarily primed PCR. Trends Genet. Jun. 1995;11(6):242–6.
McClelland and Welsh, DNA fingerprinting by arbitrarily primed PCR. PCR Methods Appl. Aug. 1994;4(1):S59–65. Review.

McClelland et al. Fingerprinting by arbitrarily primed PCR. Methods Mol Biol. 1997;85:13–24.
McClelland and Welsh, RNA fingerprinting by arbitrarily primed PCR. PCR Methods Appl. Aug. 1994;4(1):S66–81. Review.
McClelland et al. Arbitrary primed PCR fingerprinting of RNA applied to mapping differentially expressed genes. EXS. 1993;67:103–15. Review.
Trippler et al. Ligase chain reaction (LCR) assay for semi-quantitative detection of HBV DNA in mononuclear leukocytes of patients with chronic hepatitis B. J Viral Hepat. Sep. 1995;3(5):267–72.
Vogt et al. RNA fingerprinting displays UVB–specific disruption of transcriptional control in human melanocytes. Cancer Res. Aug. 15, 1997;57(16):3554–61.
Welsh and McClelland, Genomic fingerprinting using arbitrarily primed PCR and a matrix of pairwise combinations of primers. Nucleic Acids Res. Oct. 11, 1991;19(19):5275–9.
Zhang and Frohman, Using rapid amplification of cDNA ends (RACE) to obtain full–length cDNAs. Methods Mol Biol. 1997;69:61–87.
Caetano–Anolles, "Scanning of nucleic acids by in vitro amplification: New developments and applications," *Nature Biotechnol.*, 14:1668–1674 (1996).
Lopez–Nieto and Nigam, "Selective amplification of protein–coding regions of large sets of genes using statistically designed primer sets," *Nature Biotechnol.*, 14:857–861 (1996).
Pietu et al., "Novel Gene Transcripts Preferentially expressed in human muscles revealed by quantitative hybridisation of a high density cDNA array," *Genome Res.*, 6:492–503 (1996).
Trenkle et al., "Non–stoichiometric reduced complexity probes for cDNA arrays," *Nucleic Acids Res.*, 26:3883–3891 (1998).
Welsh et al., "Arbitrarily primed PCR fingerprinting of RNA," *Nucleic Acids Research*, 20:4965–4970 (1992).
Wong et al., "Stress–inducible gene of *Salmonella typhimurium* identified by arbitrarily primed PCR of RNA," *Proc. Natl. Acad. Sci. USA*, 91:639–643 (1994).

* cited by examiner

*Primary Examiner*—Kenneth R. Horlick
*Assistant Examiner*—Cynthia B Wilder
(74) *Attorney, Agent, or Firm*—Pennie & Edmonds LLP

(57) ABSTRACT

The invention provides a method of measuring the level of two or more nucleic acid molecules in a target by contacting a probe with a target comprising two or more nucleic acid molecules, wherein the nucleic acid molecules are arbitrarily sampled and wherein the arbitrarily sampled nucleic acid molecules comprise a subset of the nucleic acid molecules in a population of nucleic acid molecules; and detecting the amount of specific binding of the target to the probe. The invention also provides a method of measuring the level of two or more nucleic acid molecules in a target by contacting a probe with a target comprising two or more nucleic acid molecules, wherein the nucleic acid molecules are statistically sampled and wherein the statistically sampled nucleic acid molecules comprise a subset of the nucleic acid molecules in a population of nucleic acid molecules; and detecting the amount of specific binding of the target to the probe.

53 Claims, 49 Drawing Sheets

```
1   tttttttttt acaacaatgc agtcatttat ttattgagta tgtgcacatt atggtattat
61  tactatactg attatattta anaagtgact tctaattaga aaatgtatcc aaaannaaaa
121 cagcagatat acaaaattaa agagacagaa gatagacatt aacagataag gcaacttata
181 cattgaggaa tccaaatcca atacatttaa acatttggga aatgagggg acaaatggga
241 agccagatca aatttgtgta aaactattca gtatgtttcc cttggcttca tgtctgagga
301 agggctctcc cttncaatgg gggatggaca aactccaaat gccacacaan tgtttaacng
361 gtatactagg tttcacactg ggnacggggg ttaaa
```

FIG. 8

```
1   acacagcccc ccgcccagcc agcatcgcag ggcttcaggg accaaccgca tagctgccta
61  tgccccgca gaactggctg ctgcgtgtga actgaacaga cggagaagat gtgctaggga
121 gaatctgcct ccacagtcac ccatttcatt gctcgctgcg aaagagacgt gagactgaca
181 tatgccatta tctcttttcc agtattaaac actcatatgc ttatggcttn gagaaatttc
241 ttagttgggt gaattaaagg ttaatccgag aattagcatg gatataccgg gtcctcatgc
301 agcttggcag atatctgaga aatggtttaa ttcatgctca ggagctgtgt gcctttcca
361 tcccttccgg gtcccttacc cctnacttt
```

FIG. 9

```
1   tttttttttt tatcaacatt tatatgcttt attgaaagtt gacaagtgca acagttaaat
61  acagtgacac cttacaattg tgtagagaac atgcacagaa acatatgcat ataactacta
121 tacaggtgat atgcagaaac ccctactggg aaatccattt cattagttag aactgagcat
181 ttttcaaagt attcaaccag actcaattga aagacttcag tgaacaagga tttacttcag
241 cgtattcagg caggctagga tttcaggatt acacaaagtg aggtaactgt gccaaattct
301 taaaatttct ttagggtgtg ggtttttgtc atgtagcagt ttttatgtgg atctattata
361 taaagtcca cacctcctca gacngccaat ggaaacaact taaatttcca ntctgttaca
421 acctaattgg taggttacag tcccnttttg ttacaaatgg ttaca
```

FIG. 10

```
1    ggcacgaggg gatccgcatc tgcctgggat catcaagccc tagaagctgg gtttctttaa
61   attagggctg ccgttttctg tttctccctg ggctgcggaa agccagaaga ttttatctag
121  cttatacaag gctgctggtg ttccctcttt ttttccacga gggtgttttt ggctgcaatt
181  gcatgaaatc ccaatggtgt agaccagtgg cgatggatct aggagtttac caactgagac
241  atttttcaat ttctttcttg tcatccttgc tggggactga aaacgcttct gtgagacttg
301  ataatagctc ctctggtgca agtgtggtag ctattgacaa caaaatcgag caagctatgg
361  atctagtgaa aagccatttg atgtatgcgg tcagagaaga agtggaggtc ctcaaagagc
421  aaatcaaaga actaatagag aaaaattccc agctggagca ggagaacaat ctgctgaaga
481  cactggccag tcctgagcag cttgcccagt ttcaggccca gctgcagact ggctcccccc
541  ctgccaccac ccagccacag ggcaccacac agccccccgc ccagccagca tcgcagggct
601  caggaccaac cgcatagctg cctatgcccc cgcagaactg gctgctgcgt gtgaactgaa
661  cagacggaga agatgtgcta gggagaatct gcctccacag tcacccattt cattgctcgc
721  tgcgaaagag acgtgagact gacatatgcc attatctctt ttccagtatt aaacactcat
781  atgcttatgg cttggagaaa tttcttagtt gggtgaatta aaggttaatc cgagaattag
841  catggatata ccgggacctc atgcagcttg gcagatatct gagaaatggt ttaattcatg
901  ctcaggagct gtgtgccttt ccatcccttc cggctcccta ccctcactt ccaagggttc
961  tctctcctgc ttgcgcttag tgtcctacat ggggttgtga agcgatggag ctcctcactg
1021 gactcgcctc tctcctctcc tcccccagg aggaacttga aggagggta aaaagactaa
1081 aatgaggggg aacagagttc actgtacaaa tttgacaact gtcaccaaaa ttcataaaaa
1141 acaatagtac tgtgcctctt tcttctcaaa caatggatga cacaaaacta tgagagtgac
1201 aaaatggtga caggtagctg ggacctaggc tatcttacca tgaaggttgt tttgcttatt
1261 gtatatttgt gtatgtagtg taactatttt gtacaataga ggactgtaac tactatttag
1321 gttgtacaga ttgaaattta gttgtttcat tggctgtctg aggaggtgtg gacttttata
1381 tatagatcta cataaaaact gctacatgac aaaaaccaca cctaaagaaa ttttaagaat
1441 ttggcacagt tactcacttt gtgtaatctg aaatctagct gctgaatacg ctgaagtaaa
1501 tccttgttca ctgaagtctt tcaattgagc tggttgaata ctttgaaaaa tgctcagttc
1561 taactaatga aatggatttc ccagtagggg tttctgcata tcacctgtat agtagttata
1621 tgcatatgtt tctgtgcatg ttctctacac aattgtaagg tgtcactgta tttaactgtt
1681 gcacttgtca actttcaata aagcatataa atgttgat
```

FIG. 11

```
1    gctcctacca cccagacacc caaacagccg tggccccaga ggtcctggcc aaatatgggg
61   gcctgcctag gttggtggaa cagtgctcct tatgtaaact gagccctttg tttagaaaac
121  aattccaaat gtgaaactag aatgagaggg aagagatagc atggcatgca gcacacacgg
181  ctgctccagt tcatggcctc ccaggggtgc tggggatgca tccaaagtgg ttgtctgaga
241  cagagttggg aaaccctcac caactgggcc tctttcacct tccacattat cccgctgcca
301  ccggttgccc tgttttcatt gcaggtttca gggaccagct tngggttgcg tgcgtttttg
361  cntttgccag ttcaggccga gggtgttagt tt
```

FIG. 12

```
1    ttttttttta aggacacgag agagccatat ttatttcaca tggacaagca tgattccatt
61   gcatgctgaa catgaaagct cgtatgagca aagtacccgt aacagcagaa ttatgtgctt
121  ttgtccacag ggagcaggga gaatcacaaa gttgttttca gagacagtgt ttttcaagca
181  cagttgagac cataggctct ggaagtcact ggtttatttc atcaccaaag ggtctgtctc
241  ccagggagtg gccggagtgc tttcagcttt gcaatctctc aatgaattga taaggtctga
301  ggagggctga ggatggtctc ccatcccacc acccagagca tctttgaagg aaatgaagct
361  cagaggggaa ggttacatgc cattgggaat ttaacaaggg ccattcctgg gttggacaat
421  gacagggga
```

FIG. 13

```
1    cgcggctcag taattgaagg cctgaaacgc ccatgtgcca ctgactagga ggcttccctg
61   ctgcggcact tcatgaccca gcggcgcgcg gcccagtgaa gccaccgtgg tgtccagcat
121  ggccgcgctg ctcctgggcg cggtgctgct ggtggcccag ccccagctag tgccttcccg
181  ccccgccgag ctaggccagc aggagcttct gcggaaagcg gggaccctcc aggatgacgt
241  ccgcgatggc gtggccccaa acggctctgc ccagcagttg ccgcagacca tcatcatcgg
301  cgtgcgcaag ggcggcacgc gcgcactgct ggagatgctc agcctgcacc ccgacgtggc
361  ggccgcggag aacgaggtcc acttcttcga ctgggaggag cattacagcc acggcttggg
421  ctggtacctc agccagatgc ccttctcctg ccacaccag ctcacagtgg agaagacccc
481  cgcgtatttc acgtcgccca agtgcctga gcgagtctac agcatgaacc cgtccatccg
541  gctgctgctc atcctgcgag accgtcgga gcgcgtgcta tctgactaca cccaagtgtt
601  ctacaaccac atgcagaagc acaagcccta cccgtccatc gaggagttcc tggtgcgcga
661  tggcaggctc aatgtggact acaaggccct caaccgcagc ctctaccacg tgcacatgca
721  gaactggctg cgcttttcc cgctgcgcca catccacatt gtggacggcg accgcctcat
781  cagggacccc ttccctgaga tccaaaaggt cgagaggttc ctaaagctgt cgccgcagat
841  caatgcttcg aacttctact ttaacaaaac caagggcttt tactgcctgc gggacagcgg
901  ccgggaccgc tgcttacatg agtccaaagg ccgggcgcac ccccaagtcg atcccaaact
961  actcaataaa ctgcacgaat attttcatga gccaaataag aagttcttcg agcttgttgg
1021 cagaacattt gactggcact gatttgcaat aagctaagct cagaaacttt cctactgtaa
1081 gttctggtgt acatctgagg ggaaaaagaa ttttaaaaaa gcatttaagg tataatttat
1141 ttgtaaaatc cataaagtac ttctgtacag tattagattc acaattgcca tatatactag
1201 ttatattttt ctacttgtta aatggagggc attttgtatt gttttcatg gttgttaaca
1261 ttgtgtaata tgtctctata tgaaggaact aaactatttc actga
```

FIG. 14

```
1    gctcaggaca gatgccacac aaggatagat gctggcccag ggccaagagc ccagctccaa
61   ggggaatcag aactcaaatn gggccagatc cagcctgggg tctngagttg atctngaacc
121  cagactcaga cattngcacc taatccaggc agatccagga ctatatttgg gcctgctcca
181  gacctngatc ctggaggccc agttcaccct gatttaggag aagccaggaa tttcccagga
241  ccctgaaggg gccatgatgg caacagatct ngaacctcag cctggccaga cacaggccct
301  ccctgttncc cagagaaagg ggagcccact g
```

FIG. 15

```
1    tttattgcac ttgcaacaga gtttaaataa gtcctgggtn tctggtgcca aggtgaggga
61   agggttgggc agagagatga ggggcagcat cagtgcagct ggcaggcaga acccaaattc
121  tgcaggccca ggacagtggg ctccccttc tctggggaac agggagggcc tgtgtctggc
181  caggctgagg ttccagatct gttgccatca tggccccttc agggtcctgg ggaaattcct
241  gggcttctcc taaatcaggg tgaactgggc ctccagggat caggtntggg agcaggccca
301  aatataagtc ctgggatctn cctgggatta gggtgccaat gtctga
```

FIG. 16

```
   1 cgctggggcc cccggcgccg accccgctg ctgccgctgc tgttgctgct gctgccgccg
  61 ccacccaggg tcggggctt caacttagac gcggaggccc cagcagtact ctcggggccc
 121 ccgggctcct tcttcggatt ctcagtggag ttttaccggc cgggaacaga cggggtcagt
 181 gtgctggtgg gagcacccaa ggctaatacc agccagccag gagtgctgca gggtggtgct
 241 gtctacctct gtccttgggg tgccagcccc acacagtgca ccccattga atttgacagc
 301 aaaggctctc ggctcctgga gtcctcactg tccagctcag agggagagga gcctgtggag
 361 tacaagtcct tgcagtggtt cggggcaaca gttcgagccc atggctcctc catcttggca
 421 tgcgctccac tgtacagctg gcgcacagag aaggagccac tgagcgaccc cgtgggcacc
 481 tgctacctct ccacagataa cttcacccga attctggagt atgcaccctg ccgctcagat
 541 ttcagctggg cagcaggaca gggttactgc caaggaggct cagtgccga gttcaccaag
 601 actggccgtg tggttttagg tggaccagga agctatttct ggcaaggcca gatcctgtct
 661 gccactcagg agcagattgc agaatcttat taccccgagt acctgatcaa cctggttcag
 721 gggcagctgc agactcgcca ggccagttcc atctatgatg acagctacct aggatactct
 781 gtggctgttg gtgaattcag tggtgatgac acagaagact tgttgctgg tgtgcccaaa
 841 gggaacctca cttacggcta tgtcaccatc cttaatggct cagacattcg atccctctac
 901 aacttctcag gggaacagat ggcctcctac tttggctatg cagtggccgc cacagacgtc
 961 aatggggacg ggctggatga cttgctggtg ggggcacccc tgctcatgga tcggacccct
1021 gacgggcggc ctcaggaggt gggcagggtc tacgtctacc tgcagcaccc agccggcata
1081 gagcccacgc ccaccttac cctcactggc catgatgagt ttggccgatt tggcagctcc
1141 ttgaccccc tggggggacct ggaccaggat ggctacaatg atgtggccat cggggctccc
1201 tttggtgggg agacccagca gggagtagtg tttgtatttc ctgggggccc aggagggctg
1261 ggctctaagc cttcccaggt tctgcagccc ctgtgggcag ccagccacac cccagacttc
1321 tttggctctg cccttcgagg aggccgagac ctggatggca atggatatcc tgatctgatt
1381 gtggggtcct ttggtgtgga caaggctgtg gtatacaggg ccgcccat cgtgtccgct
1441 agtgcctccc tcaccatctt ccccgccatg ttcaacccag aggagcggag ctgcagctta
1501 gaggggaacc ctgtggcctg catcaacctt agcttctgcc tcaatgcttc tggaaaacac
1561 gttgctgact ccattggttt cacagtggaa cttcagctgg actggcagaa gcagaaggga
1621 ggggtacggc gggcactgtt cctggcctcc acgcaggcaa ccctgaccca gaccctgctc
1681 atccagaatg gggctcgaga ggattgcaga gagatgaaga tctacctcag gaacgagtca
1741 gaatttcgag acaaactctc gccgattcac atcgctctca acttctcctt ggaccccaa
1801 gccccagtgg acagccacgg cctcaggcca gccctacatt atcagagcaa gagccggata
1861 gaggacaagg ctcagatctt gctggactgt ggagaagaca acatctgtgt gcctgacctg
```

FIG. 17A

```
1921 cagctggaag tgtttgggga gcagaaccat gtgtacctgg gtgacaagaa tgccctgaac
1981 ctcactttcc atgcccagaa tgtgggtgag ggtggcgcct atgaggctga gcttcgggtc
2041 accgccctc cagaggctga gtactcagga ctcgtcagac acccagggaa cttctccagc
2101 ctgagctgtg actactttgc cgtgaaccag agccgcctgc tggtgtgtga cctgggcaac
2161 cccatgaagg caggagccag tctgtggggt ggccttcggt ttacagtccc tcatctccgg
2221 gacactaaga aaaccatcca gtttgacttc cagatcctca gcaagaatct caacaactcg
2281 caaagcgacg tggtttcctt tcggctctcc gtggaggctc aggcccaggt caccctgaac
2341 ggtgtctcca agcctgaggc agtgctattc ccagtaagcg actggcatcc ccgagaccag
2401 cctcagaagg aggaggacct gggacctgct gtccaccatg tctatgagct catcaaccaa
2461 ggccccagct ccattagcca gggtgtgctg gaactcagct gtcccaggc tctggaaggt
2521 cagcagctcc tatatgtgac cagagttacg ggactcaact gcaccaccaa tcacccatt
2581 aacccaaagg gcctggagtt ggatcccgag ggttccctgc accaccagca aaaacgggaa
2641 gctccaagcc gcagctctgc ttcctcggga cctcagatcc tgaaatgccc ggaggctgag
2701 tgtttcaggc tgcgctgtga gctcgggccc ctgcaccaac aagagagcca aagtctgcag
2761 ttgcatttcc gagtctgggc caagactttc ttgcagcggg agcaccagcc atttagcctg
2821 cagtgtgagg ctgtgtacaa agccctgaag atgccctacc gaatcctgcc tcggcagctg
2881 ccccaaaaag agcgtcaggt ggccacagct gtgcaatgga ccaaggcaga aggcagctat
2941 ggcgtcccac tgtggatcat catcctagcc atcctgtttg gcctcctgct cctaggtcta
3001 ctcatctaca tcctctacaa gcttggattc ttcaaacgct ccctcccata tggcaccgcc
3061 atggaaaaag ctcagctcaa gcctccagcc acctctgatg cctgagtcct cccaatttca
3121 gactcccatt cctgaagaac cagtcccccc accctcattc tactgaaaag gagggtctg
3181 ggtacttctt gaaggtgctg acggccaggg agaagctcct ctcccagcc cagagacata
3241 cttgaagggc cagagccagg ggggtgagga gctgggatc cctccccccc atgcactgtg
3301 aaggacccctt gtttacacat accctcttca tggatggggg aactcagatc cagggacaga
3361 ggcccagcct ccctgaagcc tttgcatttt ggagagtttc ctgaaacaac ttggaaagat
3421 aactaggaaa tccattcaca gttctttggg ccagacatgc cacaaggact tcctgtccag
3481 ctccaacctg caaagatctg tcctcagcct tgccagagat ccaaaagaag cccccagcta
3541 agaacctgga acttgggag ttaagacctg gcagctctgg acagcccac cctggtgggc
3601 caacaaagaa cactaactat gcatggtgcc ccaggaccag ctcaggacag atgccacaca
3661 aggatagatg ctggcccagg gccagagccc agctccaagg ggaatcagaa ctcaaatggg
3721 gccagatcca gcctggggtc tggagttgat ctggaaccca gactcagaca ttggcaccta
3781 atccaggcag atccaggact atatttgggc ctgctccaga cctgatcctg gaggcccagt
```

FIG. 17B 3841 tcaccctgat ttaggagaag ccaggaattt cccaggacct gaaggggcca tgatggcaac
3901 agatctggaa cctcagcctg gccagacaca ggccctccct gttccccaga gaaaggggag
3961 cccactgtcc tgggcctgca gaatttccct tctgcctgcc agctgcactg atgctgcccc
4021 tcatctctct gcccaacccct tccctcacct tggcaccaga cacccaggac ttatttaaac
4081 tctgttgcaa gtgcaataaa tctgacccag tgccccact gaccagaact ag

FIG. 17C 1    agcctgatct ctgtccaccg gtcctttata ccctcatgac ccgctgctgg gactacgacc
61   ccagtgaccg gccccgcttc accgagctgg tgtgcagcct cagtgacgtt tatcagatgg
121  agaaggacat tgccatggag caagagagga atgctcgcta ccgaacccc aaaatcttgg
181  agcccacagc cttccaggaa cccccaccca agcccagccg acctaagtac agacccctc
241  cgcaaaccaa cctcctgggc tccaaagctg cagttccagg ttcctgaggg tctgtgtgcc
301  agctctcctg acggcttcac cagccctatg ggagtattcc attcttcccg ttaaattcac
361  tggcacaccc cacctnttcc accgggcaca atgtntttca aaacggccac aggatggggg
421  ggagggaggg attttcattc caacccaggc aggccgagga agagggncca gcagttgttg
481  gggagg

FIG. 18

1    ttttttttt ttttgcaaat gggacaattt taattcaacc acaagtcaaa tagaaagaag
61   ttaaaagaat gtttatgcaa acacatgaga aagaagggt gcagatgaga atgggggttg
121  gggagagaaa gaggaggagt aagaaaagag ggaaaagcaa gggaaagtaa aggaagaaag
181  agaaagaggg gcaggaagag agcggatttg gcccaaggtc ctatcttggc cgcatctctc
241  tgcttcttcc ccctgatgct tggtttgttg acaacacagc atcctgtgcc tgggactccc
301  aattagcttg ttcctgggac tgtgccccag ggtcctccct caggagggnc acatgctgtn
361  cagtccagac caaactncac attnaaataa ttt

FIG. 19

```
   1  gaattccgtc agcccttttn ctcagccaca gcctccggag ccgttgcaca cctacctgcc
  61  cggccgactt acctgtactt gccgccgtcc cggctcacct ggcggtgccc gaggagtagt
 121  cgctggagtc cgcgcctccc tgggactgca atgtgccgat cttagctgct gcctgagagg
 181  atgtctgggg tgtccgagcc cctgagtcga gtaaagttgg gcacgttacg ccggcctgaa
 241  ggccctgcag agcccatggt ggtggtacca gtagatgtgg aaaaggagga cgtgcgtatc
 301  ctcaaggtct gcttctatag caacagcttc aatcctggga aaaacttcaa actggtcaaa
 361  tgcactgtcc agacggagat ccgggagatc atcacctcca tcctgctgag cgggcggatc
 421  gggcccaaca tccggttggc tgagtgctat gggctgaggc tgaagcacat gaagtccgat
 481  gagatccact ggctgcaccc acagatgacg gtgggtgagg tgcaggacaa gtatgagtgt
 541  ctgcacgtgg aagccgagtg gaggtatgac cttcaaatcc gctacttgcc agaagacttc
 601  atggagagcc tgaaggagga caggaccacg ctgctctatt tttaccaaca gctccggaac
 661  gactacatgc agcgctacgc cagcaaggtc agcgagggca tggccctgca gctgggctgc
 721  ctggagctca ggcggttctt caaggatatg ccccacaatg cacttgacaa gaagtccaac
 781  ttcgagctcc tagaaaagga agtggggctg gacttgtttt cccaaagca gatgcaggag
 841  aacttaaagc ccaaacagtt ccggaagatg atccagcaga ccttccagca gtacgcctcg
 901  ctcagggagg aggagtgcgt catgaagttc ttcaacactc tcgccccgtt cgccaacatc
 961  gaccaggaga cctaccgctg tgaactcatt caaggatgga acattactgt ggacctggtc
1021  attggcccta aagggatccg ccagctgact agtcaggacg caaagcccac ctgcctggcc
1081  gagttcaagc agatcaggtc catcaggtgc ctcccgctgg aggagggcca ggcagtactt
1141  cagctgggca ttgaaggtgc cccccaggcc ttgtccatca aacctcatc cctagcagag
1201  gctgagaaca tggctgacct catagacggc tactgccggc tgcagggtga gcaccaaggc
1261  tctctcatca tccatcctag gaaagatggt gagaagcgga acagcctgcc ccagatcccc
1321  atgctaaacc tggaggcccg gcggtcccac ctctcagaga gctgcagcat agagtcagac
1381  atctacgcag agattcccga cgaaaccctg cgaaggcccg gaggtccaca gtatggcatt
1441  gcccgtgaag atgtggtcct gaatcgtatt cttggggaag gcttttttgg ggaggtctat
1501  gaaggtgtct acacaaatca taaaggggag aaaatcaatg tagctgtcaa gacctgcaag
1561  aaagactgca ctctggacaa caaggagaag ttcatgagcg aggcagtgat catgaagaac
1621  ctcgaccacc cgcacatcgt gaagctgatc ggcatcattg aagaggagcc cacctggatc
1681  atcatggaat gtatcccta tggggagctg ggccactacc tggagcggaa caagaactcc
1741  ctgaaggtgc tcaccctcgt gctgtactca ctgcagatat gcaaagccat ggcctacctg
1801  gagagcatca actgcgtgca cagggacatt gctgtccgga acatcctggt ggcctcccct
1861  gagtgtgtga agctggggga ctttggtctt tcccggtaca ttgaggacga ggactattac
```

FIG. 20A

```
1921 aaagcctctg tgactcgtct ccccatcaaa tggatgtccc cagagtccat taacttccga
1981 cgcttcacga cagccagtya cgtctggatg ttcgccgtgt gcatgtggga gatcctgagc
2041 tttgggaagc agcccttctt ctggctggag aacaaggatg tcatcggggt gctggagaaa
2101 ggagaccggc tgcccaagcc tgatctctgt ccaccggtcc tttataccct catgacccgc
2161 tgctgggact acgacccag tgaccggccc cgcttcaccg agctggtgtg cagcctcagt
2221 gacgtttatc agatggagaa ggacattgcc atggagcaag agaggaatgc tcgctaccga
2281 accccaaaa tcttggagcc cacagccttc caggaacccc cacccaagcc cagccgacct
2341 aagtacagac cccctccgca aaccaacctc ctggctccaa agctgcagtt ccaggttcct
2401 gagggtctgt gtgccagctc tcctacgctc accagcccta tggagtatcc atctcccgtt
2461 aactcactgc acacccacc tctccaccgg cacaatgtct tcaaacgcca cagcatgggg
2521 gaggaggact tcatccaacc cagcagccga gaagaggccc agcagctgtg ggaggctgaa
2581 aaggtcaaaa tgcggcaaat cctggacaaa cagcagaagc agatggtgga ggactaccag
2641 tggctcaggc aggaggagaa gtccctggac cccatggttt atatgaatga taagtcccca
2701 ttgacgccag agaaggaggt cggctacctg gagttcacag ggccccaca gaagcccccg
2761 aggctgggcg cacagtccat ccagcccaca gctaacctgg accggaccga tgacctggtg
2821 tacctcaatg tcatggagct ggtgcgggcc gtgctggagc tcaagaatga gctctgtcag
2881 ctgccccccg agggctacgt ggtggtggtg aagaatgtgg ggctgaccct gcggaagctc
2941 atcgggagcg tggatgatct cctgccttcc ttgccgtcat cttcacggac agagatcgag
3001 ggcacccaga aactgctcaa caaagacctg gcagagctca tcaacaagat gcggctggcg
3061 cagcagaacg ccgtgacctc cctgagtgag gagtgcaaga ggcagatgct gacggcttca
3121 cacacctgg ctgtggacgc caagaacctg ctcgacgctg tggaccaggc caaggttctg
3181 gccaatctgg cccacccacc tgcagagtga cggagggtgg gggccacctg cctgcgtctt
3241 ccgcccctgc ctgccatgta cctcccctgc cttgctgttg gtcatgtggg tcttccaggg
3301 agaaggccaa ggggagtcac cttcccttgc cactttgcac gacgccctct ccccacccct
3361 acccctggct gtactgctca ggctgcagct ggacagaggg gactctgggc tatggacaca
3421 gggtgacggt gacaaagatg gctcagaggg ggactgctgc tgcctggcca ctgctcccta
3481 agccagcctg gtccatgcag ggggctcctg ggggtgggga ggtgtcacat ggtgccccta
3541 gctttatata tggacatggc aggccgattt gggaaccaag ctattccttt cccttcctct
3601 tctcccctca gatgtccctt gatgcacaga gaagctgggg aggagctttg ttttcggggg
3661 tcaggcagcc agtgagatga gggatgggcc tggcattctt gtacagtgta tattgaaatt
3721 tatttaatgt gaggtttggt ctggactgac agcatgtgcc ctcctgaggg aggaccaggg
3781 cacagtccag gaacaagcta attgggagtc caggcacagg atgctgtgtt gtcaacaaac
```

FIG. 20B 3841 caagcatcag ggggaagaag cagagagatg cggccaagat aggaccttgg gccaaatccg
3901 ctctcttcct gcccctcttt ctctttcttc ctttactttc ccttgctttt ccctcttttc
3961 ttactcctcc tctttctctc ccccaccccc attctcatct gcacccttct tttctcatgt
4021 gtttgcataa acattctttt aacttctttc tatttgactt gtggttgaat taaaattgtc
4081 ccatttgca

FIG. 20C 1 gacctggaga tcaacgggga gaaggtgaag ctgcagatct gggacacagc ggggcaggag
61 cgcttccgca ccatcacctc cacgtattat cgggggaccc acggggtcat ttgtggttta
121 cgacgtcacc agtgccgagt cctttntcaa cgtcaagcgg tggcttcacg aaatcaacca
181 gaactgtgat gatgtgtgcc gaatattagt gggtaataag aatgacgacc ctgagcggaa
241 ggtggtggag acggaagatg cctacaaatt cgccgggcag atgggcatcc agttgttcga
301 gaccagcgcc aaggagaatg tcaacgtggg aagagatgtt tcaactgcat tcacggagct
361 ggtcctccga gcaaagaaag acaaccttgg gcaaaacagc agcagcaaca acagaacgat
421 gttggttgaa gtttacgaag gaacattnaa cgaaagaaac gttt

FIG. 21

1 tttttttttt tttttttttt taattgtgag gaatttaatt cacttgattt ggcttcattt
61 tcttgatctg ttaaaataat cctcccatag ccccctgcc agcccatct ctgcacgaac
121 ctaccccgac ctttctgttg gaactgaaac ctgttggtgt aaatgagaag ccatggctgc
181 cctgggtttg gagctcagag gcatctagaa ggcaggacaa gaaatctgtt ggccaaaggg
241 caagacctgc cacctctgtg gaactgcagg gcctgccttg accaggtt ccccagctcc
301 cagaatggct gtggggacag gacaacgggg agggaaggga gctggcacag gccccggaga
361 aggggcaaga ccc

FIG. 22

```
1    gctgccggag cagcccgaag agctgcggat cgcgaggcca gtaccgaccc cgcccgcccg
61   cgcgctccgc ccccgcccgc catggcccgg gactacgacc acctcttcaa gctgctcatc
121  atcggcgaca gcggtgtggg caagagcagt ttactgttgc gtttgcaga caacactttc
181  tcaggcagct acatcaccac gatcggagtg gatttcaaga tccggaccgt ggagatcaac
241  ggggagaagg tgaagctgca gatctgggac acagcggggc aggagcgctt ccgcaccatc
301  acctccacgt attatcgggg gacccacggg gtcattgtgg tttacgacgt caccagtgcc
361  gagtcctttg tcaacgtcaa gcggtggctt cacgaaatca accagaactg tgatgatgtg
421  tgccgaatat tagtgggtaa taagaatgac gaccctgagc ggaaggtggt ggagacggaa
481  gatgcctaca aattcgccgg gcagatgggc atccagttgt tcgagaccag cgccaaggag
541  aatgtcaacg tggaagagat gttcaactgc atcacggagc tggtcctccg agcaaagaaa
601  gacaacctgg caaaacagca gcagcaacaa cagaacgatg tggtgaagct cacgaagaac
661  agtaaacgaa agaaacgctg ctgctaatgg cacccagtcc actgcagaga ctgcactgcg
721  gtccctcccc
```

FIG. 23

```
1    acagagtagc agctcagatg ccagagatcg aaagaaggct cgaatgagtg agctggaaca
61   naagtggtag atttagaaga agagaaccaa aaactttgc tagaaaatca gcttttacga
121  gagaaaactc atggccttgt agttgagaac caggagttaa gacagcgctt ggggatggat
181  gccctggttg ctgaagagga ggcggagcaa ggggaatgaa gtnaggccan tgcgggtctg
241  ctgagtccgc agcactcaga ctacgtgcac ctctgcagca ggtgcaggcc cagttgtcac
301  cctncagaac atctccccat ggattctggc ggta
```

FIG. 24

```
1    ttttttttg ctgcattgta ccttttaatt gcatgggtag ttttaaataa atggagaaag
61   cacctttcag aagctacact agcaggaaaa aattccatca agcatttaca tagtaaattn
121  ctataatttc acaaaagatt cttgatctta ctngaagtat acatgaggga aagagccccc
181  tcagcaggtg ttcccgttgc ttacagaagn aaactaaagg acctaaaact ggaggcaagc
241  cagggtgcca aaaggggga agagaaatga taaagaacca tcataaatt ccatgtctac
301  ttcaaggaca tttgtctaat gacccttaca taataagtat tttaggggaa aactaccacc
361  cttttaagg tnaaagtaca nttcttaaaa ggctggtagg tttctcaatt nt
```

FIG. 25

```
1    tagtctggag ctatggtggt ggtggcagcc gcgccgaacc cggccgacgg gacccctaaa
61   gttctgcttc tgtcggggca gcccgcctcc gccgccggag ccccggcggc caggctgccg
121  ctcatggtgc cagcccagag aggggccagc ccggaggcag cgagcggggg gctgccccag
181  gcgcgcaagc gacagcgcct cacgcacctg agccccgagg agaaggcgct gaggaggaaa
241  ctgaaaaaca gagtagcagc tcagactgcc agagatcgaa agaaggctcg aatgagtgag
301  ctggaacagc aagtggtaga tttagaagaa gagaaccaaa aacttttgct agaaaatcag
361  cttttacgag agaaaactca tggccttgta gttgagaacc aggagttaag acagcgcttg
421  gggatggatg ccctggttgc tgaagaggag gcggaagcca aggggaatga agtgaggcca
481  gtggccgggt ctgctgagtc cgcagcactc agactacgtg cacctctgca gcaggtgcag
541  gcccagttgt caccccctcca gaacatctcc ccatggattc tggcggtatt gactcttcag
601  attcagagtc tgatatcctg ttgggcattc tggacaactt ggaccagtc atgttcttca
661  aatgcccttc cccagagcct gccagcctgg aggagctccc agaggtctac ccagaaggac
721  ccagttcctt accagcctcc ctttctctgt cagtggggac gtcatcagcc aagctggaag
781  ccattaatga actaattcgt tttgaccaca tatataccaa gccctagtc ttagagatac
841  cctctgagac agagagccaa gctaatgtgg tagtgaaaat cgaggaagca cctctcagcc
901  cctcagagaa tgatcaccct gaattcattg tctcagtgaa ggaagaacct gtagaagatg
961  acctcgttcc ggagctgggt atctcaaatc tgctttcatc cagccactgc ccaaagccat
1021 cttcctgcct actggatgct acagtgactg tggatacggg ggttcccttt ccccattcag
1081 tgacatgtcc tctctgcttg gtgtaaacat tcttgggagg acactttgc caatgaactc
1141 tttccccagc tgattagtgt ctaaggaatg atccaatact gttgcccttt tccttgacta
1201 ttacactgcc tggaggatag cagagaagcc tgtctgtact tcattcaaaa agccaaaata
1261 gagagtatac agtcctagag aatccctcta tttgttcaga tctcatagat gaccccagg
1321 tattgccttt tgacatccag cagtccaagg tattgagaca tattactgga agtaagaaat
1381 attactataa ttgagaacta cagcttttaa gattgtactt ttaagattgt actttatct
1441 taaagggtg gtagttttcc ctaaatact tattatgtaa gggtcattag acaaatgtct
1501 tgaagtagac atggaattta tgaatggtct ttatcatttc tcttccccct ttttggcatc
1561 ctggcttgcc tccagtttta ggtcctttag tttgcttctg caagcaacgg gaacacctgc
1621 tgagggggct ctttccctca tgtatacttc aagtaagatc aagaatcttt tgtgaaatta
1681 tagaaattta ctatgtaaat gcttgatgga attttttcct gctagtgtag cttctgaaag
1741 gtgctttctc catttattta aaactaccc atgcaattaa aaggtacaat gcaaaaaaaa
1801 aaaaaaaaaa attttttt
```

FIG. 26

```
1    aaacagtaat tctttagact ttattaaaaa atgacataaa gtgcatctta ttaaaaaatg
61   tataaaancc acataaattc cagggncccc tgtgcctggg cagtgttgat atcccttaga
121  gtggaggaag gtgagggatg gagggtgaac tggggactgg ggagaggacc agggtgcagt
181  tagttccncg tgtttgagtt caaagatgga gcgagggtgg atatggtggg aaggggcaca
241  cgggttctca cgncaacaac ggaggaaggc aggcgacagt ctcttccctg aattctgagg
301  gaaaggcgta cattgtcacg aaatctctcc tgagctcgcg ctgtcctctc
```

FIG. 27

```
1    gaaggaactg gtctgctcac acttgctggc ttgcgcatca ggactggctt tatctcctga
61   ctcacggtgc aaaggtgcac tctgcgaacg ttaagtccgt ccccagcgct tggaatccta
121  cggcccccac agccggatcc cctcagcctt ccaggtcctc aactcccgtg gacgctgaac
181  aatggcctcc atggggctac aggtaatngg catcgcgctg gccgtcctgg gctggctggc
241  cgtcatgctg tgctgcgcgc tgcccatgtg gcgcgtgacg gcctttcatc ggcagcaaca
301  ttgtcaactt gcagaccatc tgggaagggc ctattggatg aactncgtgg ttcaaaagcc
361  ngtccaagat tgnatttnaa aggttttaac gatt
```

FIG. 28

```
  1 gaaggaactg gttctgctca cacttgctgg cttgcgcatc aggactggct ttatctcctg
 61 actcacggtg caaaggtgca ctctgcgaac gttaagtccg tccccagcgc ttggaatcct
121 acggccccca cagccggatc ccctcagcct tccaggtcct caactcccgt ggacgctgaa
181 caatggcctc catggggcta caggtaatgg gcatcgcgct ggccgtcctg ggctggctgg
241 ccgtcatgct gtgctgcgcg ctgcccatgt ggcgcgtgac ggccttcatc ggcagcaaca
301 ttgtcacctc gcagaccatc tgggagggcc tatggatgaa ctgcgtggtg cagagcaccg
361 gccagatgca gtgcaaggtg tacgactcgc tgctggcact gccgcaggac ctgcaggcgg
421 cccgcgccct cgtcatcatc agcatcatcg tggctgctct gggcgtgctg ctgtccgtgg
481 tgggggcaa gtgtaccaac tgcctggagg atgaaagcgc caaggccaag accatgatcg
541 tggcgggcgt ggtgttcctg ttggccggcc ttatggtgat agtgccggtg tcctggacgg
601 cccacaacat catccaagac ttctacaatc cgctggtggc ctccgggcag aagcgggaga
661 tgggtgcctc gctctacgtc ggctgggccg cctccggcct gctgctcctt ggcggggggc
721 tgctttgctg caactgtcca ccccgcacag acaagcctta ctccgccaag tattctgctg
781 cccgctctgc tgctgccagc aactacgtgt aaggtgccac ggctccactc tgttcctctc
841 tgctttgttc ttccctggac tgagctcagc gcaggctgtg accccaggag ggccctgcca
901 cgggccactg gctgctgggg actggggact gggcagagac tgagccaggc aggaaggcag
961 cagccttcag cctctctggc ccactcggac aacttcccaa ggccgcctcc tgctagcaag
1021 aacagagtcc accctcctct ggatattggg gagggacgga agtgacaggg tgtggtggtg
1081 gagtggggag ctggcttctg ctggccagga tagcttaacc ctgactttgg gatctgcctg
1141 catcggcgtt ggccactgtc cccatttaca ttttccccac tctgtctgcc tgcatctcct
1201 ctgttccggg taggccttga tatcacctct gggactgtgc cttgctcacc gaaacccgcg
1261 cccaggagta tggctgaggc cttgcccacc cacctgcctg ggaagtgcag agtggatgga
1321 cgggtttaga ggggaggggc gaaggtgctg taaacaggtt tgggcagtgg tgggggaggg
1381 ggccagagag gcggctcagg ttgcccagct ctgtggcctc aggactctct gcctcacccg
1441 cttcagccca gggcccctgg agactgatcc cctctgagtc ctctgcccct tccaaggaca
1501 ctaatgagcc tgggagggtg gcagggagga ggggacagct tcaccttgg aagtcctggg
1561 gttttcctc ttccttcttt gtggtttctg ttttgtaatt taagaagagc tattcatcac
1621 tgtaattatt attattttct acaataaatg ggacctgtgc acagg
```
FIG. 29

```
  1 aggtcctact ggaaggagtt cctggtgatg tgcacgctct ttgtgctggc cgtgctgctc
 61 ccagttttat tcttgctcta ccggcaccgg aacagcatga aagtcttcct gaagcagggg
121 gaatgtgcca gcgtgcaccc caagacctgc cctgtggtgc tgccccctga cccgcccca
181 ctcaacggcc tagggcccct agcaccccgc tcgatcaccg agggtaccag tccctgtcag
241 acagccccc ggggttcccg agtcttcact gagtcagaga agaggccact nagcatccaa
301 gacagcttcg tgggaggtat ccccagtgtg ccccggccc cgggg
```
FIG. 30

```
   1 gaagaaaggc tgattagaaa atttgaagct gaaaacatct ccaactacac ggcccttctg
  61 ctgagccagg atggaaagac gctgtatgtg ggggcccgag aggccctctt tgcacttaac
 121 agcaacctca gcttcttgcc aggcgggag taccaagagc tactgtggag tgcagatgct
 181 gacaggaagc agcagtgcag cttcaagggc aaggacccaa agcgtgactg tcaaaactac
 241 atcaagatcc tcctgccact caacagcagc cacctgctca cctgtggcac ggccgccttc
 301 agcccctgt gtgcttacat tcacatagcg agctttactt tagcccaaga tgaggccggt
 361 aatgtcattc tggaggatgg caagggtcat tgtccctttg accccaactt caagtccacg
 421 gctctggtgg ttgatggtga gctgtacact ggaacagtca gtagcttcca gggaaacgac
 481 ccagccattt cccggagcca gagttcccgc cccaccaaga ctgagagctc cctcaactgg
 541 ctacaagacc ctgcctttgt ggcctcggct acgtccccg agagcctggg cagccccata
 601 ggtgatgatg ataagatcta cttcttcttc agcgagacgg gccaggagtt tgagttcttt
 661 gagaacacca tcgtgtcccg agttgcccga gtctgtaagg gcgatgaggg tggagagcgg
 721 gtgttgcagc aacgctggac ctcctttctc aaggctcagc tcctgtgctc ccggcctgat
 781 gatggctttc cctttaacgt gctacaagat gtcttcaccc tgaacccaa ccctcaggat
 841 tggcgcaaga ccctttctat cggggtcttt acctcccagt ggcacagagg gaccacagaa
 901 ggctctgcca tctgcgtctt caccatgaat gatgtgcaga aggcctttga cggcctgtac
 961 aagaaagtaa acagagagac acagcagtgg tataccgaga cccaccaggt gcccacaccg
1021 cggccgggag cgtgcattac caacagtgcc cgggaacgga agatcaactc gtccctgcag
1081 ctcccagacc gagtgctgaa cttcctcaag gatcacttct tgatggatgg gcaggtccgc
1141 agtcgcctgc tgctgctgca gccagagcc cgctaccagc gtgtggctgt gcaccgtgtg
1201 cctggcctgc acagcactta tgatgtccta tttctgggca ctggtgatgg ccgcctgcac
1261 aaagcagtga ccctgagctc cagagtccac atcattgagg agctgcagat cttccctcaa
1321 ggacagcctg tgcagaacct gctcttggac agccatgggg gactgttgta tgcctcctcc
1381 cattccgggg tggtgcaagt gcccgtagcc aactgcagcc tgtacccaac ctgtggagac
1441 tgcctcctgg ctcgagaccc ctactgcgcc tggactggct ctgcctgcag gctcgctagc
1501 ctctaccagc ctgatctggc ctccaggcca tgacccagg acattgaggg tgccagtgtc
1561 aaggaactct gcaagaattc ctcatacaag gcccggtttc ttgtgccagg taagccatgt
1621 aaacaagtcc agatccaacc aaacacagtg aacaccctgg cctgcccact cctctcaaac
1681 ctggccactc ggctctgggt gcacaatgga gccccagtca atgcctctgc ctcctgccgc
1741 gtgttaccca ccggggacct gctgctggtg ggcagccagc agggtttggg ggtgttccag
1801 tgttggtcga tagaagaagg attccagcag cttgtggcca gctactgccc agaggtgatg
1861 gaggagggg taatggacca aaagaaccag cgtgatggta ccccagtcat tatcaacaca
```

FIG. 31A 1921 tcacgagtga gtgcaccggc tggtggcagg acagctggg gtgcggacaa gtcctactgg
1981 aatgaattcc tggtgatgtg tactctgttt gtgtttgcta tggtgctttt gtttctgttc
2041 tttctctacc gacatcggga tggcatgaaa ctcttcctaa agcagggcga gtgtgccagt
2101 gtgcacccca agactcgccc tatagtgcta ccacctgaga cccgaccgct gaatggtgtc
2161 ggccctccta gcaccccact tgaccaccga ggctaccagg ctctgtcgga tagctcccca
2221 gggcccagag tcttcactga atcagagaag aggccactga gcatccagga cagctttgta
2281 gaggtgtctc ccgtgtgtcc ccggcccga gttcgactgg gctctgagat ccgagactct
2341 gtggtatgag agctgacttt agatgtggtc accctgacct cagggttgtg agtgtcagtg
2401 gaagtcagct acctctgctc tcacagaaca cag

FIG. 31B 1   gtttggcaaa aactcaagcg gctggaagga ggaagaggtt ctccagagtc ggaactgagg
61  gttggaacta tacccgggac caaactcacg gaccactcga ggcctgcaaa ccttcctggg
121 aggacaggca ggccagatgg ccgctccact ggggaatgct cccagctgtg ctgtggagag
181 aagctgatgt tttggtgtat tgtcagccat cgtccttgga ctcggagact atggcctcgc
241 tccccaccct cctcttggaa ttacaagccc tggggtttga agctgacttt atagctgcaa
301 gtgtatctcc ttttatctgg tgcctcctca aacccagtct cagacactta aatgcagaca
361 acaccttnct cctgcagaca cctgggactg agccaaggag gncttgggga aggcccttag
421 ggggagcacc ctgatgggag aggacagagc aggggttnca gca

FIG. 32

1   agaaaaagcc cantnttcac tttattggag gtctctgcct ccattcacag gagaaaggag
61  ctgggagccc catcctaagg gtcccagcat cagcccactg gagggcctgg aacagtccag
121 cactctgtgg gagaggagtg gggaggggaa tgttttagaa aaaatagatc tctatgtaca
181 tctgacatat ttatatagca cataaattag ggagtgctct gaccctgcc cgtggagccc
241 aagcactgag cagggaggtg aacgccagtc cagaaagaag gtgctgggag cccctgctct
301 gtcctctcca tccacggtgc tnccctagg g 1   agaaaaagcc cantnttcac tttattggag gtctctgcct ccattcacag gagaaaggag
61  ctgggagccc catcctaagg gtcccagcat cagcccactg gagggcctgg aacagtccag
121 cactctgtgg gagaggagtg gggaggggaa tgttttagaa aaaatagatc tctatgtaca
181 tctgacatat ttatatagca cataaattag ggagtgctct gaccctgcc cgtggagccc
241 aagcactgag cagggaggtg aacgccagtc cagaaagaag gtgctgggag cccctgctct
301 gtcctctcca tccacggtgc tnccctagg g

FIG. 33

```
1    cggccagata cctcagcgct acctggcgga actggatttc tctcccgcct gccggcctgc
61   ctgccacagc cggactccgc cactccggta gcctcatggc tgcaacctgt gagattagca
121  acatttttag caactacttc agtgcgatgt acagctcgga ggactccacc ctggcctctg
181  ttccccctgc tgccaccttt ggggccgatg acttggtact gaccctgagc aacccccaga
241  tgtcattgga gggtacagag aaggccagct ggttggggga acagcccag ttctggtcga
301  agacgcaggt tctggactgg atcagctacc aagtggagaa gaacaagtac gacgcaagcg
361  ccattgactt ctcacgatgt gacatggatg cgccaccct tgcaattgt gcccttgagg
421  agctgcgtct ggtctttggg cctctggggg accaactcca tgcccagctg cgagacctca
481  cttccagctc ttctgatgag ctcagttgga tcattgagct gctggagaag gatggcatgg
541  ccttccagga ggccctagac ccagggcct ttgaccaggg cagccccttt gcccaggagc
601  tgctggacga cggtcagcaa gccagcccct accacccgg cagctgtggc gcaggagccc
661  cctccctgg cagctctgac gtctccaccg cagggactgg tgcttctcgg agctcccact
721  cctcagactc cggtggaagt gacgtggacc tggatcccac tgatggcaag ctcttcccca
781  gcgatggttt tcgtgactgc aagaagggg atcccaagca cgggaagcgg aaacgaggcc
841  ggccccgaaa gctgagcaaa gagtactggg actgtctcga gggcaagaag agcaagcacg
901  cgcccagagg cacccacctg tgggagttca tccgggacat cctcatccac ccggagctca
961  acgagggcct catgaagtgg gagaatcggc atgaaggcgt cttcaagttc ctgcgctccg
1021 aggctgtggc ccaactatgg ggccaaaaga aaaagaacag caacatgacc tacgagaagc
1081 tgagccgggc catgaggtac tactacaaac gggagatcct ggaacgggtg gatggccggc
1141 gactcgtcta caagtttggc aaaaactcaa gcggctggaa ggaggaagag gttctccaga
1201 gtcggaactg agggttggaa ctatacccgg gaccaaactc acggaccact cgaggcctgc
1261 aaaccttcct gggaggacag gcaggccaga tggcccctcc actggggaat gctcccagct
1321 gtgctgtgga gagaagctga tgttttggtg tattgtcagc catcgtcctt ggactcggag
1381 actatggcct cgcctcccca ccctcctctt ggaattacaa gccctggggt ttgaagctga
1441 ctttatagct gcaagtgtat ctcctttat ctggtgcctc ctcaaaccca gtctcagaca
1501 cttaaatgca gacaacacct tcttcctgca gacacttgga ctgagccaag gaggcttggg
1561 aggccctagg gagcaccgtg atggagagga cagagcaggg gctccagcac ttctttctgg
1621 actggcgttc acctccctgc tcagtgcttg gctccacgg gcagggtca gagcactccc
1681 taatttatgt gctatataaa tatgtcagat gtacatagag atctattttt tctaaaacat
1741 tcccctcccc actcctctcc cacagagtgc tggactgttc caggccctcc agtgggctga
1801 tgctgggacc cttaggatgg ggctcccagc tcctttctcc tgtgaatgga ggcagagacc
1861 tccaataaag tgccttctgg gcttttcta aaaaaaaaa aaaaaaa
```

FIG. 34

```
1    agtactacaa gcatcattct ctcaaggaag ggttcagaac cttagataca actctgcagt
61   ttccatacaa ggagccagaa cattcagctg gacagagggg taatagagca ggcaacagct
121  tgttaagtcc aaaagtgctg ggcattgcat cgctcggtat gacttctgtg caagagatat
181  gagagagttg tccttgttga aaggagatgt ggtgaagatt tacacaaaga tgagtgcaaa
241  tggctggtgg agaggagaag taaatggcag ggtgggctgg tttccatcca catatgtggg
301  aaggaggatg aataaattca aatcccgtgt tgcaccctgc accaaaattt tcagaggaag
361  gggataatta ggaagcctgc acagcttcgt ggatttaact tgaagtgttt ttaaaaagct
421  ggcttttntg ggctgtttca acatcctccc tccttaggcc cntccta
```

FIG. 35

```
1    ttttttttcc caacatgtaa ctctctcagt cttgtcagaa cacaacttct gctatggagg
61   aaatatttcc atcaggaaag ggccaagtta gtgtcttaac ttgactgcct tgaatgggga
121  ctctggaccc caggaagaat gtatttaggc tcctcacaaa aaagagtgat ggctgggcaa
181  aacaaatgta ctgcaagacc catcttccct ccagttaata cactcccagg gatgggnctg
241  cagaggggga gactctgaga gaagctggag gcccacaaaa gtccactgan cctctttctg
301  tcccagaaat gaataaagga cccagttgtg ctttccttcc aaaatcctca acaaagttgt
361  ttgtgctcca aggaaaatgt gggggantta aaaaaatcat gttcccgggt catctttgtg
421  tgtgttgcgg gggaggtngg tggggaggga aaa
```

FIG. 36

```
1    cccgccccgg cccagccgcg tcccggagcc gtcgggcatg gagccgtgga agcagtgcgc
61   gcagtggctc atccattgca aggtgctgcc caccaaccac cgggtgacct gggactcggc
121  tcaggtgttc gaccttgcgc agaccctccg cgatggagtc ctgctctgcc agctgcttaa
181  caacctccgg gcgcactcca tcaacctgaa ggagatcaac ctgaggccgc agatgtccca
241  gtttctctgt ttgaagaaca taaggacatt tctcacggcc tgttgtgaga cgtttggaat
301  gaggaaaagt gaacttttcg aggcatttga cttgtttgat gttcgtgact ttggagaggt
361  tatagaaaca ttatcacgac tttctcgaac acctatagca ttggccacag gaatcaggcc
421  cttcccaaca gaagaaagca ttaatgatga agacatctac aaaggccttc ctgatttaat
481  agatgaaacc cttgtggaag atgaagaaga tctctatgac tgtgtttatg gggaagatga
541  aggtggagaa gtctatgagg acttaatgaa ggcagaggaa gcacatcagc ccaaatgtcc
601  agaaaatgat atacgaagtt gttgtctagc agaaattaag cagacagaag aaaaatatac
661  agaaactttg gagtcaatag aaaaatattt catggcacca ctaaaaagat tctgacagc
721  agcagaattt gattcagtat tcatcaacat tcctgaactt gtaaaacttc atcggaacct
781  aatgcaagag attcatgatt ccattgtaaa taaaaatgac cagaacttgt accaagtttt
841  tattaactac aaggaaagat tggttattta cgggcagtac tgcagtggag tggagtcagc
901  catctctagt ttagactaca tttctaagtc aaaagaagat gtcaaactga attagagga
961  atgttccaaa agagcaaata tgggaaatt tactcttcga gacttgcttg tggttcctat
1021 gcaacgtgtt ttaaagtacc accttctcct ccaggaactg gtcaaacata ccactgatcc
1081 gactgagaag gcaaatctga aactggctct tgatgccatg aaggacttgg cacaatatgt
1141 gaatgaagtg aaaagagata atgagaccct tcgtgaaatt aaacagtttc agctatctat
1201 agagaatttg aaccaaccag ttttgctttt tggacgacct cagggagatg gtgaaattcg
1261 aataaccact ctagacaagc ataccaaaca agaaaggcat atcttcttat tgatttggc
1321 agtgatcgta tgtaagagaa aaggtgataa ctatgaaatg aaggaaataa tagatcttca
1381 gcagtacaag atagccaata atcctacaac cgataaagaa aacaaaaagt ggtcttatgg
1441 cttctacctc atccataccc aaggacaaaa tgggttagaa ttttattgca aaacaaaaga
1501 tttaaagaag aaatggctag aacagtttga aatggctttg tctaacataa gaccagacta
1561 tgcagactcc aatttccacg acttcaagat gcataccttc actcgagtca catcctgcaa
1621 agtctgccag atgctcctga ggggaacatt ttatcaaggc tatttatgtt ttaagtgtgg
1681 agcgagagca cacaaagaat gtttgggaag agtagacaat tgtggcagag ttaattctgg
1741 tgaacaaggg acactcaaac taccagagaa acggaccaat ggactgcgaa gaactcctaa
1801 acaggtggat ccaggtttac caaagatgca ggtcattagg aactattctg gaacaccacc
1861 cccagctctg catgaaggac cccctttaca gctccaggcc ggggataccg ttgaacttct
```

FIG. 37A

```
1921 gaaaggagat gcacacagtc tgttttggca gggcagaaat ttagcatctg gagaggttgg
1981 atttttccca agtgatgcag tcaagccttg cccatgtgtg cccaaaccag tagattattc
2041 ttgccaaccc tggtatgctg gagcaatgga aagattgcaa gcagagaccg aacttattaa
2101 tagggtaaat agtacttacc ttgtgaggca caggaccaaa gagtcaggag aatatgcaat
2161 tagcattaag tacaataatg aagcaaagca catcaagatt ttaacaagag atggcttttt
2221 tcacattgca gaaaatagaa aatttaaaag tttaatggaa cttgtggagt actacaagca
2281 tcattctctc aaggaagggt tcagaacctt agatacaact ctgcagtttc catacaagga
2341 gccagaacat tcagctggac agaggggtaa tagagcaggc aacagcttgt taagtccaaa
2401 agtgctgggc attgccatcg ctcggtatga cttctgtgca agagatatga gagagttgtc
2461 cttgttgaaa ggagatgtgg tgaagattta cacaaagatg agtgcaaatg gctggtggag
2521 aggagaagta aatggcaggg tgggctggtt tccatccaca tatgtggaag aggatgaata
2581 aattcaaatc ccgtgttgca ccctgcacca aaaatttcag agaagggata aatagaagcc
2641 tgcacagcat cgtgaattaa ctgaagtgtt taaaaagctg catttctggc tgttcaacat
2701 cctccctcct tagcccctcc taagtcttaa tgctgagatt tctaaagatg ctggtactga
2761 cagattaatg gcttgcctag agctgtgcaa gaaacagcct gccagtctgt cattgtcagg
2821 gaccagggca aaaccaagag ctgttcttcc cagaagagcc ctgcaaacac attggttcgt
2881 gcttcccttt acttcttctg gtcagatacc atgaatgcca gtcatcagta atcttaata
2941 cactttgct ttattctcac atgccattca ccagattatt tgatggtaca agaagcaga
3001 agtgtaattt tccttttccc agcatgacga aaaattggag ttctgccatt tgagcagctt
3061 actggagaga tccagcctta cttgtcttaa attgtccaac aaggtgactc attgcccggc
3121 aaacactttt accctcagat gttactcatg atattataaa atatgaggcc agtgctcagg
3181 tttgcatcat aagtgagcta tccctgaagg gttttaatta cttatttggt gtcctgatta
3241 tatttgcaaa cttctttata aaaggtgaaa aaagcacaca aaagagaggg tgtcttcata
3301 ttaaaccttc acaaccttca tgatttcata ggattatttt ggaaatatag cacttgactt
3361 tatgaaagga tctgggctag gtatattagg ggtagttgcc ataaccctga agaagctggc
3421 attgtttaca gaaacagatc aagggctata atttatgtca ttttatagca gcagtatcta
3481 ttaatacatg cctttttcctc ccatccacct cccccgcaca cacacaaaga tgacctggga
3541 catgattttt ttattcccac atttttcttgg agcacaaaca actttgttga ggatttgga
3601 aggaaagcac aactgggtcc tttattcatt tctgggacag aaagagggtc agtggacttt
3661 tgtgggcctc cagcttctct cagagtctcc ccctctgcag cccatcctgg gagtgtatta
3721 actggaggga agatgggtct tgcagtacat ttgtttgcc cagccatcac tcttttttgt
3781 gaggagccta aatacattct tcctggggtc cagagtcccc attcaaggca gtcaagttaa
```

FIG. 37B

```
3841 gacactaact tggcccttc ctgatggaaa tatttcctcc atagcagaag ttgtgttctg
3901 acaagactga gagagttaca tgttgggaaa aaaaagaagc attaacttag tagaactgaa
3961 ccaggagcat taagttctga aattttgaat catctctgaa atgaagcagg tgtagcctgc
4021 cctctcatca atccgtccgt ctgggtgcca gaactcaagg ttcagtggac acatccccct
4081 gttagagacc ctcatgggct aggacttttc atctaggata gattcaagac ctttacctca
4141 gaattatgta aactgtgatt gtgttttaga aaaattatta tttgctaaaa ccatttaagt
4201 ctttgtatat gtgtaaatga tcacaaaaat gtatttata aaatgttctg tacaataaag
4261 ttacacctca aagtgtactc ttggaatgga ttctttcctg taaagtctta tctgcgactc
4321 tgtctcggga atgttttgtc tgttgccgtc agccgaactt tgttatggag ggagcagcct
4381 cacacaagca gaaacactcc tgtggatggt attgtagcat gtattgttta ttttagtcaa
4441 tagaccctct ccttataaat ggtgtttagt cttcctgttg catttcatgg gcctgggggt
4501 ttcctrgcag aggatattgg agccccttt tgtgacatta ccaattacat ctttgtccac
4561 gtttaatact ttgttttgga aaatttaaat gctgcagatt tgtgtagagt tctaatacca
4621 aagacagaag taaatgtttt ccatatactt tgtcttgcct gtatgcagcc cttgtgtaat
4681 atggtgaatt agagtggtat ttcactttgt attatttgt aaatatgtca atataataaa
4741 tagtgactaa aaaaaaaaa aa
```

FIG. 37C

```
  1 tttttactt tattttcgtt ttaattttt ggaaggatat acaccacata tcccatgggc
 61 aataaagcgc attcaatgtn tttataagcc aaacagtcac tttgtttaag caaacacaag
121 tacaaagtaa aatagaacca caaataatg aactgcatgt tcataacata caaaaatcgc
181 cgcctactca gtaggtaact acaacattcc aactccngaa tatatttata aatttacatt
241 ttcagttaaa aaantagact tttgagagtt cagattttgt tttagatttt gttttcttac
301 attctggaga ncccgaagct ncagctcagc ccctcttccc ttattttgct ccccaaagcc
361 ttccccccaa atcancactg ncctgncccc cctntaaggg cttagaggtg agcatntccc
421 ct
```

FIG. 38

```
1    ccgcagaact tggggagccg ccgccgccat ccgccgccgc agccagcttc cgccgccgca
61   ggaccggccc ctgccccagc ctccgcagcc gcggcgcgtc cacgcccgcc cgcgcccagg
121  gcgagtcggg gtcgccgcct gcacgcttct cagtgttccc cgcgccccgc atgtaacccg
181  gccaggcccc cgcaacggtg tccctgcag ctccagcccc gggctgcacc ccccgcccc
241  gacaccagct ctccagcctg ctcgtccagg atggccgcgg ccaaggccga gatgcagctg
301  atgtccccgc tgcagatctc tgacccgttc ggatcctttc ctcactcgcc caccatggac
361  aactaccta agctggagga gatgatgctg ctgagcaacg gggctcccca gttcctcggc
421  gccgccgggg ccccagaggg cagcggcagc aacagcagca gcagcagcag cggggcggt
481  ggaggcggcg ggggcggcag caacagcagc agcagcagca gcaccttcaa ccctcaggcg
541  gacacgggcg agcagcccta cgagcacctg accgcagagt cttttcctga catctctctg
601  aacaacgaga aggtgctggt ggagaccagt tacccccagcc aaaccactcg actgccccc
661  atcacctata ctggccgctt ttccctggag cctgcaccca acagtggcaa caccttgtgg
721  cccgagcccc tcttcagctt ggtcagtggc ctagtgagca tgaccaaccc accggcctcc
781  tcgtcctcag caccatctcc agcggcctcc tccgcctccg cctcccagag cccaccctg
841  agctgcgcag tgccatccaa cgacagcagt cccatttact cagcggcacc caccttcccc
901  acgccgaaca ctgacatttt ccctgagcca caaagccagg ccttccgggg ctcggcaggg
961  acagcgctcc agtacccgcc tcctgcctac cctgccgcca agggtggctt ccaggttccc
1021 atgatccccg actacctgtt tccacagcag caggggatc tgggcctggg cacccagac
1081 cagaagccct tccagggcct ggagagccgc acccagcagc cttcgctaac ccctctgtct
1141 actattaagg cctttgccac tcagtcgggc tcccaggacc tgaaggccct caataccagc
1201 taccagtccc agctcatcaa acccagccgc atgcgcaagt atccccaaccg gcccagcaag
1261 acgcccccc acgaacgccc ttacgcttgc ccagtggagt cctgtgatcg ccgcttctcc
1321 cgctccgacg agctcacccg ccacatccgc atccacacag gccagaagcc cttccagtgc
1381 cgcatctgca tgcgcaactt cagccgcagc gaccacctca ccacccacat ccgcacccac
1441 acaggcgaaa agcccttcgc ctgcgacatc tgtggaagaa agtttgccag gagcgatgaa
1501 cgcaagaggc ataccaagat ccacttgcgg cagaaggaca agaaagcaga caaaagtgtt
1561 gtggcctctt cggccacctc ctctctctct tcctacccgt ccccggttgc tacctcttac
1621 ccgtccccgg ttactacctc ttatccatcc ccggccacca cctcataccc atcccctgtg
1681 cccacctcct tctcctctcc cggctcctcg acctacccat ccctgtgca cagtggcttc
1741 ccctccccgt cggtggccac cacgtactcc tctgttcccc ctgctttccc ggcccaggtc
1801 agcagcttcc cttcctcagc tgtcaccaac tccttcagcg cctccacagg gctttcggac
1861 atgacagcaa ccttttctcc caggacaatt gaaatttgct aaagggaaag gggaaagaaa
```

FIG. 39A

```
1921 gggaaaaggg agaaaaagaa acacaagaga cttaaaggac aggaggagga gatggccata
1981 ggagaggagg gttcctctta ggtcagatgg aggttctcag agccaagtcc tccctctcta
2041 ctggagtgga aggtctattg gccaacaatc ctttctgccc acttcccctt ccccaattac
2101 tattcccttt gacttcagct gcctgaaaca gccatgtcca agttcttcac ctctatccaa
2161 agaacttgat ttgcatggat tttggataaa tcatttcagt atcatctcca tcatatgcct
2221 gaccccttgc tcccttcaat gctagaaaat cgagttggca aatggggtt tgggcccctc
2281 agagccctgc cctgcaccct tgtacagtgt ctgtgccatg gatttcgttt tcttggggt
2341 actcttgatg tgaagataat ttgcatattc tattgtatta tttggagtta ggtcctcact
2401 tggggaaaaa aaaaaaaaaa aagccaagca aaccaatggt gatcctctat tttgtgatga
2461 tgctgtgaca ataagtttga accttttttt ttgaaacagc agtcccagta ttctcagagc
2521 atgtgtcaga gtgttgttcc gttaaccttt ttgtaaatac tgcttgaccg tactctcaca
2581 tgtggcaaaa tatggtttgg ttttctttt ttttttttga aagtgttttt tcttcgtcct
2641 tttggtttaa aaagtttcac gtcttggtgc ctttgtgtg atgccccttg ctgatggctt
2701 gacatgtgca attgtgaggg acatgctcac ctctagcctt aagggggca gggagtgatg
2761 atttggggga ggctttggga gcaaaataag gaagagggct gagctgagct tcggttctcc
2821 agaatgtaag aaaacaaaat ctaaaacaaa atctgaactc tcaaagtct attttttaa
2881 ctgaaaatgt aaatttataa atatattcag gagttggaat gttgtagtta cctactgagt
2941 aggcggcgat ttttgtatgt tatgaacatg cagttcatta ttttgtggtt ctattttact
3001 ttgtacttgt gtttgcttaa acaaagtgac tgtttggctt ataaacacat tgaatgcgct
3061 ttattgccca tgggatatgt ggtgtatatc cttccaaaaa attaaaacga aaataaagta
3121 gctgcgattg gg
```

FIG. 39B

```
  1   ttaaggtata cactttatt caactggtct caagtcagtg tacaggtaag ccctggctgc
 61   ctccacccac tcccagggag accaaaagcc ttcatacatc tcaagttggg ggacaaaaaa
121   ggggaaggg ggggcacgaa ggctcatcat tcaaaataaa acaaaataaa aaagtattaa
181   ggcgaagatt aaaaaaattt tgcattacat aatttacacg aaagcaatgc tatcacctcc
241   cctgtgtgga cttgggagag gactgggcca ttctccttag gagagaagtg ggggtgggct
301   tttagggatg ggcaagggga ctttcctgtt aacaacggca tcttcatatt ttgggaattg
361   actnttttaaa aaaaccaac aatgtggcaa ttcaaagtcc ntcgggccac atttgtggaa
421   ctttngggg gttgctcgnt cccacccgac tgttgttcac cttt
```

FIG. 40

```
1    gcccagcacc ccaaggcggc caacgccaaa actctccctc ctcctcttcc tcaatctcgc
61   tctcgctctt ttttttttc gcaaaaggag gggagagggg gtaaaaaaat gctgcactgt
121  gcggcgaagc cggtgagtga gcggcgcggg gccaatcagc gtgcgccgtt ccgaaagttg
181  cctttatgg ctcgagcggc cgcggcggcg ccctataaaa cccagcggcg cgacgcgcca
241  ccaccgccga gaccgcgtcc gcccgcgagc acagagcctc gcctttgccg atccgccgcc
301  cgtccacacc cgccgccagg taagcccggc cagccgaccg gggcatgcgg ccgcggccct
361  tcgcccgtgc agagccgccg tctgggccgc agcgggggc gcatggggcg gaaccggacc
421  gccgtggggg gcgcgggaga agccctggg cctccggaga tgggggacac cccacgccag
481  ttcgcaggcg cgaggccgcg ctgggcggg cgcgctccgg gggtgccgct ctggggcgg
541  gggcaaccgg cggggtcttt gtctgagccg ggctcttgcc aatggggatc gcacggtggg
601  cgcggcgtag cccccgtcag gcccggtggg ggctggggcg ccatgcgcgt gcgcgctggt
661  cctttgggcg ctaactgcgt gcgcgctggg aattggcgct aattgcgcgt gcgcgctggg
721  actcaatggc gctaatcgcg cgtgcgttct ggggcccggg cgcttgcgcc acttcctgcc
781  cgagccgctg gcgcccgagg gtgtggccgc tgcgtgcgcg cgcgcgaccc ggtcgctgtt
841  tgaaccgggc ggaggcgggg ctggcgcccg gttgggaggg ggttggggcc tggcttcctg
901  ccgcgcgccg cggggacgcc tccgaccagt gtttgccttt tatggtaata acgcggccgg
961  cccggcttcc tttgtcccca atctgggcgc gcgccggcgc ccctggcgg cctaaggact
1021 cggcgcgccg gaagtggcca gggcgggggc gacttcggct cacagcgcgc ccggctattc
1081 tcgcagctca ccatggatga tgatatcgcc gcgctcgtcg tcgacaacgg ctccggcatg
1141 tgcaaggccg gcttcgcggg cgacgatgcc cccgggccg tcttcccctc catcgtgggg
1201 cgccccaggc accaggtagg ggagctggct gggtggggca gccccgggag cgggcgggag
1261 gcaagggcgc tttctctgca caggagcctc ccggtttccg gggtgggctg cgcccgtgct
1321 cagggcttct tgtcctttcc ttcccagggc gtgatggtgg gcatgggtca gaaggattcc
1381 tatgtgggcg acgaggccca gagcaagaga ggcatcctca ccctgaagta ccccatcgag
1441 cacggcatcg tcaccaactg ggacgacatg gagaaaatct ggcaccacac cttctacaat
1501 gagctgcgtg tggctcccga ggagcacccc gtgctgctga ccgaggcccc cctgaacccc
1561 aaggccaacc gcgagaagat gacccaggtg agtggcccgc tacctcttct ggtggccgcc
1621 tccctccttc ctggcctccc ggagctgcgc cctttctcac tggttctctc ttctgccgtt
1681 ttccgtagga ctctcttctc tgacctgagt ctcctttgga actctgcagg ttctatttgc
1741 ttttcccag atgagctctt tttctggtgt ttgtctctct gactaggtgt ctgagacagt
1801 gttgtgggtg taggtactaa cactggctcg tgtgacaagg ccatgaggct ggtgtaaagc
1861 ggccttggag tgtgtattaa gtaggcgcac agtaggtctg aacagactcc ccatcccaag
```

FIG. 41A

```
1921 accccagcac acttagccgt gttctttgca ctttctgcat gtccccgtc tggcctggct
1981 gtccccagtg gcttccccag tgtgacatgg tgcatctctg ccttacagat catgtttgag
2041 accttcaaca ccccagccat gtacgttgct atccaggctg tgctatccct gtacgcctct
2101 ggccgtacca ctggcatcgt gatggactcc ggtgacgggg tcacccacac tgtgcccatc
2161 tacgaggggt atgccctccc ccatgccatc ctgcgtctgg acctggctgg ccgggacctg
2221 actgactacc tcatgaagat cctcaccgag cgcggctaca gcttcaccac cacggccgag
2281 cgggaaatcg tgcgtgacat taaggagaag ctgtgctacg tcgccctgga cttcgagcaa
2341 gagatggcca cggctgcttc cagctcctcc ctggagaaga gctacgagct gcctgacggc
2401 caggtcatca ccattggcaa tgagcggttc cgctgccctg aggcactctt ccagccttcc
2461 ttcctgggtg agtggagact gtctcccggc tctgcctgac atgagggtta cccctcgggg
2521 ctgtgctgtg gaagctaagt cctgccctca tttccctctc aggcatggag tcctgtggca
2581 tccacgaaac taccttcaac tccatcatga agtgtgacgt ggacatccgc aaagacctgt
2641 acgccaacac agtgctgtct ggcggcacca ccatgtaccc tggcattgcc gacaggatgc
2701 agaaggagat cactgccctg gcacccagca caatgaagat caaggtgggt gtctttcctg
2761 cctgagctga cctgggcagg tcagctgtgg ggtcctgtgg tgtgtgggga gctgtcacat
2821 ccagggtcct cactgcctgt ccccttccct cctcagatca ttgctcctcc tgagcgcaag
2881 tactccgtgt ggatcggcgg ctccatcctg gcctcgctgt ccaccttcca gcagatgtgg
2941 atcagcaagc aggagtatga cgagtccggc ccctccatcg tccaccgcaa atgcttctag
3001 gcggactatg acttagttgc gttacaccct ttcttgacaa aacctaactt gcgcagaaaa
3061 caagatgaga ttggcatggc tttatttgtt ttttttgttt tgttttggtt ttttttttt
3121 ttttggcttg actcaggatt taaaaactgg aacggtgaag gtgacagcag tcggttggag
3181 cgagcatccc ccaaagttca caatgtggcc gaggactttg attgcattgt tgttttttta
3241 atagtcattc caaatatgag atgcattgtt acaggaagtc ccttgccatc ctaaaagcca
3301 ccccacttct ctctaaggag aatggcccag tcctctccca agtccacaca ggggaggtga
3361 tagcattgct ttcgtgtaaa ttatgtaatg caaaattttt ttaatcttcg ccttaatact
3421 ttttatttt gttttatttt gaatgatgag ccttcgtgcc ccccttccc ccttttgtc
3481 ccccaacttg agatgtatga aggcttttgg tctccctggg agtgggtgga ggcagccagg
3541 gcttacctgt acactgactt gagaccagtt gaataaaagt gcacacctta aaatgaggc
3601 caagtgtgac tttgtggtgt ggctgggttg ggggcagcag agggtg//
```

FIG. 41B

```
  1  ctcgatttng ggaagttgta gactgcacaa ttaaaacaga tccagtcact nggagatcaa
 61  gaggatttgg atttgtgctt ttcaaagatg ctgctagtgt tgataaggtt ttggaactna
121  aagaacacaa actggatggc aaattgatag atcccaaaag ggccaaagct taaaaggga
181  aagaacctcc caaaaaggtt tttgtgggtg gattgagccc ggatacttct gaagaacaaa
241  ttaaagnata ttttggagcc tttggagaga ttgaaaatat tgaacttccc atggatacaa
301  naacaaattg aanggaag
```

FIG. 42

```
   1  gatctcttcc gccgccattt taaatccagc tccatacaac gctccgccgc cgctgctgcc
  61  gcgacccgga ctgcgcgcca gcacccccct gccgacagct ccgtcactat ggaggatatg
 121  aacgagtaca gcaatataga ggaattcgca gagggatcca agatcaacgc gagcaagaat
 181  cagcaggatg acggtaaaat gtttattgga ggcttgagct gggatacaag caaaaaagat
 241  ctgacagagt acttgtctcg atttggggaa gttgtagact gcacaattaa aacagatcca
 301  gtcactggga gatcaagagg atttggatt gtgcttttca aagatgctgc tagtgttgat
 361  aaggttttgg aactgaaaga acacaaactg gatggcaaat tgatagatcc caaagggcc
 421  aaagctttaa aagggaaaga acctcccaaa aaggtttttg tgggtggatt gagcccggat
 481  acttctgaag aacaaattaa agaatatttt ggagcctttg gagagattga aaatattgaa
 541  cttcccatgg atacaaaaac aaatgaaaga agaggatttt gttttatcac atatactgat
 601  gaagagccag taaaaaaatt gttagaaagc agataccatc aaattggttc tgggaagtgt
 661  gaaatcaaag ttgcacaacc caaagaggta tataggcagc aacagcaaca acaaaaaggt
 721  ggaagaggtg ctgcagctgg tggacgaggt ggtacgaggg gtcgtggccg aggtcagggc
 781  caaaactgga accaaggatt taataactat tatgatcaag gatatggaaa ttacaatagt
 841  gcctatggtg gtgatcaaaa ctatagtggc tatggcggat atgattatac tgggtataac
 901  tatgggaact atggatatgg acagggatat gcagactaca gtggccaaca gagcacttat
 961  ggcaaggcat ctcgaggggg tggcaatcac caaaacaatt accagccata ctaaaggaga
1021  acattggaga aaacaggagg agatgttaaa gtaacccatc ttgcaggacg acattgaaga
1081  ttggtcttct gttgatctaa gatgattatt ttgtaaaaga ctttctagtg tacaagacac
1141  cattgtgtcc aactgtatat agctgccaat tagttttctt tgtttttact ttgtcctttg
1201  ctatctgtgt tatgactcaa tgtggatttg tttatacaca ttttatttgt atcatttcat
1261  gttaaacctc aaataaatgc ttccttatgt g
```

FIG. 43

```
1    gaattcgcag agggatccaa gatcaacgcg agcaagaatc agcaggatga cggtaaaatg
61   tttattggag gcttgagctg ggatacaagc aaaaagatc tgacagagta cttgtctcga
121  tttggggaag ttgtagactg cacaattaaa acagatccag tcactgggag atcaagagga
181  tttggatttg tgcttttcaa agatgctgct agtgttgata aggttttgga actgaaagaa
241  cacaaactgg atggcaaatt gatagatccc aaaagggcca agctttaaa agggaaagaa
301  cctcccaaaa aggttttgt gggtggattg agcccggata cttctgaaga acaaattaaa
361  gaatattttg gagcctttgg agagattgaa atattgaac ttcccatgga tacaaaaaca
421  aatgaaagaa gaggattttg ttttatcaca tatactgatg aagagccagt aaaaaaattg
481  ttagaaagca gataccatca aattggttct gggaagtgtg aaatcaaagt tgcacaaccc
541  aaagaggtat ataggcagca acagcaacaa caaaaaggtg aagaggtgc tgcagctggt
601  ggacgaggtg gtacgagggg tcgtggccga ggtcagggcc aaaactggaa ccaaggattt
661  aataactatt atgatcaagg atatggaaat tacaatagtg cctatggtgg tgatcaaaac
721  tatagtggct atggcggata tgattatact gggtataact atgggaacta tggatatgga
781  cagggatatg cagactacag tggccaacag agcacttatg gcaaggcatc tcgagggggt
841  ggcaatcacc aaaacaatta ccagccatac taaggagaa cattggagaa acaggagga
901  gatgttaaag taacccatct tgcaggacga cattgaagat tggtcttctg ttgatctaag
961  atgattattt tgtaaaagac tttctagtgt acaagacacc attgtgtcca actgtatata
1021 gctgccaatt agtttctttt gttttactt tgtcctttgc tatctgtgtt atgactcaat
1081 gtggatttgt ttatacacat tttatttgta tcatttcatg ttaaacctca aataaatgct
1141 tccttatgtg attgcttttc tgcgtcaggt actacatagc tctgtaaaaa atgtaattta
1201 aaataagcaa taattaaggc acagttgatt ttgtagagta ttggtccata cagagaaact
1261 gtggtccttt ataaatagcc agccagcgtc accctcttct ccaatttgta ggtgtatttt
1321 atgctcttaa ggcttcatct tctccctgta actgagattt ctaccacacc tttgaacaat
1381 gttctttccc ttctggttat ctgaagactg tcctgaaagg aagacataag tgttgtgatt
1441 agtagaagct ttgtaatcat aacacaatga gtaattcttg tataaaagtt cagatacaaa
1501 aggagcactg taaaactggt aggagctatg gtttaagagc attggaagta gttacaactc
1561 aaggattttg gtagaaaggt atgagtttgg tcgaaaaatt aaaatagtgg caaaataaga
1621 tttagttgtg ttttctcaga gccgccacaa gattgaacaa atgttttct gtttgggcat
1681 cctgaggaag ttgtattagc tgttaatgct ctgtgagttt agagaaaagt cttgatagta
1741 aatctagttt ttgacacagt gcatgaacta agtagttaaa tatttacata ttcagaaagg
1801 aatagtggaa aaggtatctt ggttatgaca aagtcattac aaatgtgact aagtcattac
1861 aaatgtgact gagtcattac agtggaccct ctgggtgcat tgaaaagaat ccgttttata
```

FIG. 44A

```
1921 tccaggtttc agaggacctg gaataataat aagctttgga ttttgcattc agtgtagttg
1981 gattttggga ccttggcctc agtgttattt actgggattg gcatacgtgt tcacaggcag
2041 agtagttgat ctcacacaac gggtgatctc acaaaactgg taagtttctt atgctcatga
2101 gccctccctt ttttttttta atttggtgcc tgcaactttc ttaacaatga ttctacttcc
2161 tgggctatca cattataatg ctcttggcct ctttttttgct gctgtttttgc tattcttaaa
2221 cttaggccaa gtaccaatgt tggctgttag aagggattct gttcattcaa catgcaactt
2281 tagggaatgg aagtaagttc atttttaagt tgtgtggtca gtaggtgcgg tgtctagggt
2341 agtgaatcct gtaagttcaa atttatgatt aggtgacgag ttgacattga gattgtcctt
2401 ttcccctgat caaaaaaatg aataaagcct ttttaaacg
```

FIG. 44B

```
1    ttttacagat cttttttgact atcttcctct cactgccttg gtggatgggc agatcttctg
61   tctacatggt ggtctctcgc catctataga tacactggat catatcagag cacttgatcg
121  cctacaagaa gttccccatg agggtccaat gtgtgacttg ctgtggtcag atccagatga
181  ccgtggtggt tggggtatat ctcctcgagg agctggttac acctttgggc aagatatttc
241  tgagacattt aatcatgcca atggcctcac gttggtgtct agagctcacc agctagtgat
301  ggagggatat aactggtgcc atgaccggaa tgtagtaacg attttcagtg ctccaaacta
361  ttgttatcgt tgtggtaacc aagctgcaat catgggaact tgacgatact ctaaaatact
421  ctttcntgca gttttgaccc agcanctcgt agggccgag
```

FIG. 45

```
   1 gagagctcgg ctctcggagg aggaggcgca cggccagcgg cagtactgcg gtgagagcca
  61 gcggccagcg ccacgctcaa cagccgccag aagtacacga ggaaccggcg gcggcgtgtg
 121 cgtgtaagcc ggcggcggcg cgggaggagc cggagcggca gccggctggg gcgggtggca
 181 tcatggacga gaaggtgttc accaaggagc tggaccagtg gatcgagcag ctgaacgagt
 241 gcaagcagct gtccgagtcc caggtcaaga gcctctgcga gaaggctaaa gaaatcctga
 301 caaaagaatc aacgtgcaa gaggttcgat gtccagttac tgtctgtgga gatgtgcatg
 361 ggcaatttca tgatctcatg gaactgttta gaattggtgg caaatcacca gatacaaatt
 421 acttgtttat gggagattat gttgacagag gatattattc agttgaaaca gttacactgc
 481 ttgtagctct taaggttcgt taccgtgaac gcatcaccat tcttcgaggg aatcatgaga
 541 gcagacagat cacacaagtt tatggtttct atgatgaatg tttaagaaaa tatggaaatg
 601 caaatgtttg gaaatatttt acagatcttt ttgactatct tcctctcact gccttggtgg
 661 atgggcagat cttctgtcta catggtggtc tctcgccatc tatagataca ctggatcata
 721 tcagagcact tgatcgccta caagaagttc cccatgaggg tccaatgtgt gacttgctgt
 781 ggtcagatcc agatgaccgt ggtggttggg gtatatctcc tcgaggagct ggttacacct
 841 ttgggcaaga tatttctgag acatttaatc atgccaatgg cctcacgttg gtgtctagag
 901 ctcaccagct agtgatggag ggatataact ggtgccatga ccggaatgta gtaacgattt
 961 tcagtgctcc aaactattgt tatcgttgtg gtaaccaagc tgcaatcatg gaacttgacg
1021 atactctaaa atactctttc ttgcagtttg acccagcacc tcgtagaggc gagccacatg
1081 ttactcgtcg tacccagac tacttcctgt aatgaaattt taaacttgta cagtattgcc
1141 atgaaccata tatcgaccta atggaaatgg gaagagcaac agtaactcca aagtgtcaga
1201 aaatagttaa cattcaaaaa acttgttttc acatggacca aaagatgtgc catataaaaa
1261 tacaaagcct cttgtcatca acagccgtga ccactttaga atgaaccagt tcattgcatg
1321 ctgaagcgac attgttggtc aagaaaccag tttctggcat agcgctattt gtagttactt
1381 ttgtttctct gagagactgc agataataag atgtaaacat taacacctcg tgaatacaat
1441 ttaacttcca tttagctata gcttactca gcatgactgt agataaggat agcagcaaac
1501 aatcattgga gcttaatgaa cattttaaa aataattacc aaggcctccc ttctacttgt
1561 gagttttgaa attgttcttt ttattttcag ggataccgtt taatttaatt atatgatttg
1621 tctgcactca gttattccc tactcaaatc tcagcccat gttgttcttt gttattgtca
1681 gaacctggtg agttgttttg aacagaactg ttttttcccc ttcctgtaag acgatgtgac
1741 tgcacaagag cactgcagtg ttttcataa taaacttgtg aactaac
```

FIG. 46

```
1    gtttacagat gccacttagt tacactggtt ttnnttttc agtctcatct gggttgganc
61   caaagacatt cagaggcatg gnaagaggca aagcatcaga catctcattg gnggcaggta
121  cttccngact actgtaccac ctgctgtatc cttccccacc tcancacccc caaagccatt
181  tagngccaaa tgctacagta aaacccaat gcatttacat aaaanaatgc ctaactgcat
241  attnacattt ttnagaaaaa aaatcccatt angctcttct agaaagttat ggcaggaaag
301  gtaaggncca aggctntgag caagccatnt gtggnaactt aaagtagatg agcactgagt
361  ttctccatag ttggaaaaaa ngccacactg agcccncttt tcccgtggag ggcaagntga
421  gnccctccnt ttatacccg ttgagatntc ag
```

FIG. 47

```
1    gagaaaaggg ttggggagaa gcctctgcag tcctggaaga tgtggggttc tgggtgagag
61   gcatcagccc cacaagtatg tttttgtgtc ttaagatagc agtttacttt gaaaaagtga
121  aaaaggcttc cgggctgtcc tctgcccagt gagatggagg acgctagaga aagtgctgag
181  tgtcccgaga gaggcccccg agccagtgca tggnaggtcc ttcggcctgg ntcagctngg
241  ctgcaggatg cccactttga gga
```

FIG. 48

```
   1 cccgcgggca ggggcggcga gtgcgcgggc cgccgccctt ctcggcgggc agcgcgcgag
  61 gaccaggccg aggaggaagt ggcggcggcg gcggcgggct ccccgcccga ggaggaagat
 121 gcagaccttt ctgaaaggga agagagttgg ctactggctg agcgagaaga aaatcaagaa
 181 gctgaatttc caggctttcg ccgagctgtg caggaagcga gggatggagg ttgtgcagct
 241 gaaccttagc cggccgatcg aggagcaggg ccccctggac gtcatcatcc acaagctgac
 301 tgacgtcatc cttgaagccg accagaatga tagccagtcc ctggagctgg tgcacaggtt
 361 ccaggagtac atcgatgccc accctgagac catcgtcctg acccgctcc ctgccatcag
 421 aaccctgctt gaccgctcca gtcctatga gctcatccgg aagattgagg cctacatgga
 481 agacgacagg atctgctcgc cacccttcat ggagctcacg agcctgtgcg gggatgacac
 541 catgcggctg ctggagaaga acggcttgac tttcccattc atttgcaaaa ccagagtggc
 601 tcatggcacc aactctcacg agatggctat cgtgttcaac caggagggcc tgaacgccat
 661 ccagccaccc tgcgtggtcc agaatttcat caaccacaac gccgtcctgt acaaggtgtt
 721 cgtggttggc gagtcctaca ccgtggtcca gaggccctca ctcaagaact tctccgcagg
 781 cacatcagac cgtgagtcca tcttcttcaa cagccacaac gtgtcaaagc cggagtcgtc
 841 atcggtcctg acggagctgg acaagatcga gggcgtgttc gagcggccga gcgacgaggt
 901 catccgggag ctctcccggg ccctgcggca ggcactgggc gtgtcactct tcggcatcga
 961 catcatcatc aacaaccaga cagggcagca cgccgtcatt gacatcaatg ccttcccagg
1021 ctacgagggc gtgagcgagt tcttcacaga cctcctgaac cacatcgcca ctgtcctgca
1081 gggccagagc acagccatgg cagccacagg ggacgtggcc ctgctgaggc acagcaagct
1141 tctggccgag ccggcgggcg gcctggtggg cgagcggaca tgcaacgcca gccccggctg
1201 ctgcggcagc atgatgggcc aggacgcgcc ctggaaagct gaggccgacg cgggcggcac
1261 cgccaagctg ccgcaccaga gactcggctg caacgccggc gtgtctccca gcttccagca
1321 gcattgtgtg gcctccctgg ccaccaaggc ctcctcccag tagccacgga gcgggaccc
1381 agagggcagc gcaggcgcag gagcacaccc gctgggccag cagctcccaa cggcgatgct
1441 actactaaga atccccagtg atctgattct tctgtttttt aatttttaac ctgatttct
1501 gatgtcatga tctaaatgag gggtagaaga gagtaccagg tggtccaccg ttggggagcg
1561 gggccgtccg cctgctctct actgtgcaga cctcctaact gagtttacac acgcttgtgt
1621 tgcaacacta ggtctggatg ggaggtgagg ggggtgcgta tactgccatg ccagtgtctg
1681 tgcacatccc tgtctgttgt ctccatggcc actgtggact gggaccttg aagcctgccc
1741 atgtgggtgt gggaggctga tcagtgcgtg tgagagtggc ttcccttctg cctgactccc
1801 cactccctga cctgccctt ccttgttttt cctcctactg gtctccacca aggctttgtt
1861 agcccccacc ctgcctggtg tgcagctaac ccctccctcc ccacagccag aggaggccac
```

FIG. 49A

```
1921 agaccoctca gggagttccg cgctggggtc tgggctgtgc tccctcacta aagggaagga
1981 aaggaagctg ggcgtcctcc gggccccca acacacgtcc catttagccc tgcacagcgg
2041 tctccttccc ctaagccagc actgctgctc cctggagccg ggaaggaggc tgcctggctg
2101 gaggccgagc cgatgggcct gtgctgagga tttgtgctgt gatttgggca aatcattcca
2161 ggtctttggg cctccacccc ctcgtctcta gtggacattt gagatcagag agcaccacag
2221 ggctggcttt gtgcctaac ccctgggatg cagcctgcct ttccataaag tcacctaggt
2281 gaggataggc gcgggagcct cggcatgaca ccatggagat cggggccctc ttcccagtgg
2341 gttcactcct tttcacacct gctgggtccc tcctcgccca gcaggcctgg tccacctctc
2401 attgcaagcc cgcaagcact gagccgagta aggtgcttag tgtgagccac ccgccccca
2461 tagcttctgc acacctcaga ctcaccccat caccttggca gcaaagcact gctctgccgt
2521 ctgaccoctg atccaggcag cagccccctc cgcagagaaa agggttgggg agaagcctct
2581 gcagtcctgg aagatgtggg gtgctgggtg agaggcatca gcccccacaa gtatgttttt
2641 gtgtcttaag atagcagttt actttgaaaa agtgaaaaag gcttccgggc tgtcctctgc
2701 ccagtgagat ggaggacgct agagaaagtg ctgagtgtcc cgagagaggc ccccgagcca
2761 gtgcatggag gtcttcggcc tggctcagct gggctgcagg atgcccactt tgaggaggga
2821 ggcacagggc ttgggcgagg ggcagaggcc atcagaactg cccggctttt ttggaaactg
2881 aggacccaac aactaaccac gtttacacga cttgagtttt gaacccgat taatgtctgt
2941 acgtcacctt tcctagttct gaccctgagc cctggggaac aggaaagcgt ggctggcctc
3001 ttgcactgct ttgtctccaa aataaactac tgaaatcaaa ccgcatttc
```

FIG. 49B

```
  1  ggttgagccc tacaactgca tcctcaccac ccacaccacc ctggagcact ctgattgtgc
 61  cttcatggta gacaatgagg ccatctatga catctgtcgt agaaacctcg atatcgagcg
121  cccaacctac accaaccta accgccttat tagccagatt gtgtcctcca tcactgcttc
181  cctgagattt gatggagncc tgaatgttga cctgacagaa ttccagacca acctgggtgc
241  cctaccccg catccacttn cctctggcca catatgcccc tgtcatctct gctgagaang
301  cctaccacga acagcttact gtagtagaga tcaccaatgc ttgntttgag ccagccaacc
361  agatggtgaa atntggancc ttgncattgg taaattacat ggggtttgcn gtctgtt
```

FIG. 50

```
1     tgtcggggac ggtaaccggg acccgtgctc tgctcctgtc gccttcgcct cctgaatccc
61    tagccatatg cgtgagtgca tctccatcca cgttggccag gctggtgtcc agattggcaa
121   tgcctgctgg gagctctact gcctggaaca cggcatccag cccgatggcc agatgccaag
181   tgacaagacc attgggggag gagatgactc cttcaacacc ttcttcagtg agacgggcgc
241   tggcaagcac gtgccccggg ctgtgtttgt agacttggaa cccacagtca ttgatgaagt
301   tcgcactggc acctaccgcc agctcttcca ccctgagcag ctcatcacag gcaaggaaga
361   tgctgccaat aactatgccc gagggcacta caccattggc aaggagatca ttgaccttgt
421   gttggaccga attcgcaagc tggctgacca gtgcacccgt cttcagggct tcttggtttt
481   ccacagcttt ggtgggggaa ctggttctgg gttcacctcc ctgctcatgg aacgcctgtc
541   agttgattat ggcaagaaat ccaagctgga gttctccatt tacccggcac ccaggtttc
601   cacagctgta gttgagccct acaactccat cctcaccacc cacaccaccc tggagcactc
661   tgattgtgcc ttcatggtag acaatgaggc catctatgac atctgtcgta gaaacctcga
721   tatcgagcgc ccaacctaca ctaaccttaa ccgtcttatt agccagattg tgtcctccat
781   cactgcttcc ctgagatttg atggagccct gaatgttgac ctgacagaat ccagaccaa
841   cctggtcccc taccccgca tccacttccc tctggccaca tatgcccctg tcatctctgc
901   tgagaaagcc taccatgaac agctttctgt agcagacatc accaatgctt gctttgagcc
961   agccaaccag atggtgaaat gtgaccctgg ccatggtaaa tacatggctt gctgcctgtt
1021  gtaccgtggt gacgtggttc caaagatgt caatgctgcc attgccacca tcaaaaccaa
1081  gcgcacgatc cagtttgtgg attggtgccc cactggcttc adggttggca tcaactacca
1141  gcctccact gtggtgcctg gtggagacct ggccaaggta cagagagctg tgtgcatgct
1201  gagcaacacc acagccattg ctgaggcctg ggctcgcctg gaccacaagt ttgacctgat
1261  gtatgccaag cgtgcctttg ttcactggta cgtgggtgag gggatggagg aaggcgagtt
1321  tcagaggcc cgtgaagata tggctgccct tgagaaggat tatgaggagg ttggtgtgga
1381  ttctgttgaa ggagagggtg aggaagaagg agaggaatac taattatcca ttcctttgg
1441  ccctgcagca tgtcatgctc ccagaatttc agcttcagct taactgacag atgttaaagc
1501  tttctggtta gattgttttc acttggtgat catgtctttt ccatgtgtac ctgtaatatt
1561  tttccatcat atctcaaagt aaagtcatta acatca
```

FIG. 51

```
1    ctgtgaccca gaagtcttcg aattcactgg tttttcagac tctgccacgg cacatgcgac
61   gaagagccat gagccacaac gtcaaacgcc ttcccagacg gttacaggag attgcccaga
121  aagaggcgga gaaagccgta catcagaaaa aagaacattc aaaaaataaa tgccataaag
181  ctcgaagatg tcacatgaac cggacgctag aatttaaccg tagacaaaag aagaacattt
241  ggttagaaac tcacatctgg cacgccaagc ggtttcatat ggtcaagaag tggggctact
301  gccttgggga gaggccaaca gtcaagagcc acagagcctg ctatcgagcc atgacgaacc
361  ggtgcctcct gcaggattta tcctattact gttgtttgga gttgaaaggc aagaggaag
421  aaatactaaa ggcgctttct ggaatgtgta acatagacac agggctgacg tttgcagcag
481  ttcactgctt gtctggaaag cgccaaggga gccttgtgct ttatcgggtg aataaatatc
541  ccagagaaat gcttgggcct gttacgttta tctggaagtc ccagaggacc ccgggtgacc
601  cttctgagag caggcagctg tggatctggc tgcatccaac ccttaaacag gatatcttag
661  aggaaataaa agcagcgtgc cagtgtgtgg aacccatcaa atcagctgtc tgcatcgctg
721  acccacttcc aacaccatcc caagaaaaaa gccaaactga attgcctgac gagaaaattg
781  gcaagaaaag aaaaggaaa gatgatggag aaaatgctaa accaattaaa aaaattatcg
841  gtgatggaac tagagatcca tgtctaccat actcttggat ctctccaacc acaggcatta
901  taatcagcga tttgacgatg gagatgaaca gattccggct gattgggcca ctttcccact
961  ccatcctaac tgaagcaata aaagctgctt ctgtccacac tgtgggagag gacacagagg
1021 agacacctca ccgctggtgg atagaaacct gtaagaaacc tgacagcgtt tcccttcatt
1081 gcagacaaga agccattttc gagttgttgg gaggaataac atcaccagca gaaattccgg
1141 caggtactat tctgggactg acagttgggg atcctcgaat aaatttgccc caaaagaagt
1201 ccaaagcttt gcccaatcca gaaaaatgcc aagataatga gaaagttaga cagctgcttc
1261 tggagggtgt gcctgtggaa tgtacgcata gctttatctg gaaccaagat atctgtaaga
1321 gtgtcacaga gaataaaatc tcggatcagg atttaaaccg gatgaggagt gaattgctgg
1381 tgcctgggtc acagcttatt ttaggtcccc atgaatccaa gataccata cttttgattc
1441 agcagccagg aaaagtgact ggtgaagatc gactaggctg gggaagtggc tgggatgtcc
1501 tactcccaaa gggctggggc atggctttct ggattccatt tatttatcga ggtgtgagag
1561 tcggagggtt gaaagagtct gcagtgcatt ctcagtataa gaggtcgcct aatgtcccag
1621 gcgatttcc agactgccct gccgggatgc tgtttgcgga agagcaagct aagaatcttc
1681 ttgaaaagta caaagacgc cctcctgcaa aacggcccaa ctacgttaag cttggcactc
1741 tggcaccttt ctgctgtccc tgggagcagt taactcaaga ctgggagtca agagtccagg
1801 cttacgaaga accttctgta gcttcatctc caaatggtaa ggagagtgac ctaagaagat
1861 ctgaggtgcc ttgtgctccc atgcctaaaa aaactcatca gccatctgat gaagtgggca
1921 catccataga gcacccccagg gaggcagagg aggtaatgga tgcagggtgt caagaatcgg
```

FIG. 52A

```
1981 cagggcctga gaggatcaca gaccaggagg ccagtgaaaa ccatgttgct gccacaggga
2041 gtcacctctg cgttctcagg agtagaaaat tactgaagca actgtcagcc tggtgtgggc
2101 ccagttctga ggatagtcgg ggaggccggc gagctcccgg cagaggccag caaggattga
2161 ccagagaggc ttgcctgtcc atcttgggcc acttccccag ggccctggtt tgggtcagcc
2221 tgtccctgct cagcaagggc agccccgagc ctcacaccat gatctgtgtc ccagccaagg
2281 aggacttcct ccagctccat gaggactggc attactgtgg gccccaggaa tccaaacaca
2341 gtgacccatt caggagcaag atcctgaaac agaaagagaa gaagaaaagg gagaagaggc
2401 agaagccagg acgtgcctct tctgatggcc cggcggggga agagcccgtg gctgggcagg
2461 aagctctgac tctaggcctg tggtcaggcc ctctgccgcg tgtgacgttg cactgctcca
2521 gaactctcct aggctttgtg actcagggag atttttccat ggctgttggc tgtggagaag
2581 ccctggggtt tgttagcttg acaggcttgc tggatatgct gtccagccag cctgcagcgc
2641 agaggggctt agtgctactg aggcctcccg cctctctgca gtatcgattt gcgaggattg
2701 ctattgaggt gtgaatgcgt gcttgtatcc cagcagggca tagataatac gttattattg
2761 tctgccaagt tctacatgtg gagaatctgc ttctgcttta aatatcatg tgaaactccc
2821 tggaaacaag aataaaaaat tatgtattat gcagatgatg aaatgtttac atcattccag
2881 taatgtcatt gattttcatc tttccctgtc cttgctgtaa tacttttaaa ttatttggcc
2941 aaaagctttg tattatgatc tcttggtctg tgtagttgtg gctgaaaata atgagaagct
3001 ctacgagtta tcatccccctt tttttgttag aaacaaaggg cttgtcaggt ctatttgaaa
3061 aacctcatag tcatgtgata agcaacaata gatgtttaat gatttcactg ttatagcaga
3121 agacaagaga agacgcttgg cctctgtaca tgaaatatgg gctcctgatg gacctcattc
3181 aattctgtac tgtgatttcc atgccgaaca actcaagcct taaagagaga aatcatggac
3241 aactgatttc tgcctgtttt caggcaggca cagtttatgg cgtcagtgct aggctggaat
3301 tagaaagtgg gggtctatga cgtggacttc ctgactcttt gatctctttg ttgttgacca
3361 acacttgatc ctactagtta cttaattttt ttaagtaaaa aattattatt attttgtttc
3421 tgcaaagatt ttctcaaagc catagaggag catttctcag aatatgttct atgatatgtg
3481 tcacctaaaa aagtaagaga ttccaaggtc aggttgatat ggaaactcta ggttaaataa
3541 agttaagcat ttctttatga aagaacttct ggaaacttcc atgtgataat gtgcattgcg
3601 gatctctagg aaggaaatga tagtgtatag tattttctaa atacttgtga ttcctaaagt
3661 tctcttacaa ggagcccttt gtaggaccag tgttcttagt agcgcgcttt gggcagtgtg
3721 gctgtgtagt gcatagctac ctctgcaagg tgataactaa gccggcaagc tgcctttcaa
3781 cactcatgca gtcacgttgt ccacctgaga ttctcaacag ggtataaaag gaaggtctca
3841 tcttgcctca caggaagagt gggctcagtg tggcttttt ccaactatgg agaaactcag
3901 tgctcatcta ctttaagttt ccacatatgg cttgctcata gccttggtcc ttacctttcc
```

FIG. 52B

```
3961  tgccataact ttctagaaga gcttaatggg atttttttct aaaaaatgta aatatgcagt
4021  taggcattat tttatgtaaa tgcattgggt ttttactgta gcatttggca ctaaatggct
4081  ttgggggtga tgaggtgggg aaggatacag caggtggtac agtagtcagg aagtacctgc
4141  caccaatgag atgtctgatg ctttgcctct taccatgcct ctgaatgtct ttggatccaa
4201  cccagatgag actgaaaaaa aaaaaacagt gtaactaagt ggcatctgta aacagaataa
4261  atgaaaatgt cacctg
```

FIG. 52C

REDUCED COMPLEXITY NUCLEIC ACID TARGETS AND METHODS OF USING SAME

This application claims the benefit of priority of provisional application serial Nos. 60/083,331, filed Apr. 27, 1998, No. 60/098,070, filed Aug. 27, 1998, and No. 60/118,624, filed Feb. 4, 1999, each of which is incorporated herein by reference.

This invention was made with government support under grant number CA68822, NS33377, AI34829 awarded by the National Institutes of Health and under grant number BC961294 awarded by the Department of Defense. The government has certain rights in the invention.

BACKGROUND OF THE INVENTION

The present invention relates generally to methods of measuring nucleic acid molecules in a target and more specifically to methods of detecting differential gene expression.

Every living organism requires genetic material, deoxyribonucleic acid (DNA), which contains genes that impart a unique collection of characteristics to the organism. DNA is composed of two strands of complementary sequences of nucleotide building blocks. The two strands bind, or hybridize, with the complementary sequence to form a double helix. Genes are discreet segments of the DNA and provide the information required to generate a new organism and to give that organism its unique characteristics. Even simple organisms, such as bacteria, contain thousands of genes, and the number is many fold greater in complex organisms such as humans. Understanding the complexities of the development and functioning of living organisms requires knowledge of these genes.

For many years, scientists have searched for and identified a number of genes important in the development and function of living organisms. The search for new genes has greatly accelerated in recent years due to directed projects aimed at identifying genetic information with the ultimate goal being the determination of the entire genome of an organism and its encoded genes, termed genomic studies. One of the most ambitious of these genomic projects has been the Human Genome Project, with the goal of sequencing the entire human genome. Recent advances in sequencing technology have led to a rapid accumulation of genetic information, which is available in both public and private databases. These newly discovered genes as well as those genes soon to be discovered provide a rich resource of potential targets for the development of new drugs.

Despite the rapid pace of gene discovery, there remains a formidable task of characterizing these genes and determining the biological function of these genes. The characterization of newly discovered genes is often a time consuming and laborious undertaking, sometimes taking years to determine the function of a gene or its gene product, particularly in complex higher organisms.

Another level of complexity arises when complex interactions between genes and their gene products are contemplated. To understand how an organism works, it is important not only to understand what role a gene, its transcript and its gene product plays in the workings of an organism, it is also important to understand potentially complex interactions between the gene, its transcript, or its gene product and other genes and their gene products.

A number of approaches have been used to assess gene expression in a particular cell or tissue of an organism. These approaches have been used to characterize gene expression under various conditions, including looking at differences in expression under differing conditions. However, most of these methods are useful for detecting transcripts that are abundant transcripts but have proven less useful for detecting transcripts that are of low abundance, particularly when looking at the expression of a number of genes rather than a selected few genes. Since genes expressed at low levels often regulate the physiological pathways in a cell, it is desirable to detect transcripts having at low abundance.

Thus, a need exists for a method to characterize the expression pattern of genes under a given set of conditions and to detect low abundance transcripts. The present invention satisfies this need and provides related advantages as well.

SUMMARY OF THE INVENTION

The invention provides a method of measuring the level of two or more nucleic acid molecules in a target by contacting a probe with a target comprising two or more nucleic acid molecules, wherein the nucleic acid molecules are arbitrarily sampled and wherein the arbitrarily sampled nucleic acid molecules comprise a subset of the nucleic acid molecules in a population of nucleic acid molecules; and detecting the amount of specific binding of the target to the probe. The invention also provides a method of measuring the level of two or more nucleic acid molecules in a target by contacting a probe with a target comprising two or more nucleic acid molecules, wherein the nucleic acid molecules are statistically sampled and wherein the statistically sampled nucleic acid molecules comprise a subset of the nucleic acid molecules in a population of nucleic acid molecules; and detecting the amount of specific binding of the target to the probe.

BRIEF DESCRIPTION OF THE DRAWINGS

FIG. 8 shows the nucleotide sequence for GenBank accession number H11520 (SEQ ID NO:1).

FIG. 9 shows the nucleotide sequence for GenBank accession number H11161 (SEQ ID NO:2).

FIG. 10 shows the nucleotide sequence for GenBank accession number H11073 (SEQ ID NO:3).

FIG. 11 shows the nucleotide sequence for GenBank accession number U35048 (SEQ ID NO:4).

FIG. 12 shows the nucleotide sequence for GenBank accession number R48633 (SEQ ID NO:5).

FIG. 13 shows the nucleotide sequence for GenBank accession number H28735 (SEQ ID NO:6).

FIG. 14 shows the nucleotide sequence for GenBank accession number AF019386 (SEQ ID NO:7).

FIG. 15 shows the nucleotide sequence for GenBank accession number H25513 (SEQ ID NO:8).

FIG. 16 shows the nucleotide sequence for GenBank accession number H25514 (SEQ ID NO:9).

FIG. 17 shows the nucleotide sequence for GenBank accession number M13918 (SEQ ID NO:10).

FIG. 18 shows the nucleotide sequence for GenBank accession number H12999 (SEQ ID NO:11).

FIG. 19 shows the nucleotide sequence for GenBank accession number H05639 (SEQ ID NO:12).

FIG. 20 shows the nucleotide sequence for GenBank accession number L49207 (SEQ ID NO:13).

FIG. 21 shows the nucleotide sequence for GenBank accession number H15184 (SEQ ID NO:14).

FIG. 22 shows the nucleotide sequence for GenBank accession number H15124 (SEQ ID NO:15).

FIG. 23 shows the nucleotide sequence for GenBank accession number X79781 (SEQ ID NO:16).

FIG. 24 shows the nucleotide sequence for GenBank accession number H25195 (SEQ ID NO:17).

FIG. 25 shows the nucleotide sequence for GenBank accession number H24377 (SEQ ID NO:18).

FIG. 26 shows the nucleotide sequence for GenBank accession number M31627 (SEQ ID NO:19).

FIG. 27 shows the nucleotide sequence for GenBank accession number H23972 (SEQ ID NO:20).

FIG. 28 shows the nucleotide sequence for GenBank accession number H27350 (SEQ ID NO:21).

FIG. 29 shows the nucleotide sequence for GenBank accession number AB000712 (SEQ ID NO:22).

FIG. 30 shows the nucleotide sequence for GenBank accession number R75916 (SEQ ID NO:23).

FIG. 31 shows the nucleotide sequence for GenBank accession number X85992 (SEQ ID NO:24).

FIG. 32 shows the nucleotide sequence for GenBank accession number R73021 (SEQ ID NO:25).

FIG. 33 shows the nucleotide sequence for GenBank accession number R73022 (SEQ ID NO:26).

FIG. 34 shows the nucleotide sequence for GenBank accession number U66894 (SEQ ID NO:27).

FIG. 35 shows the nucleotide sequence for GenBank accession number H10098 (SEQ ID NO:28).

FIG. 36 shows the nucleotide sequence for GenBank accession number H10045 (SEQ ID NO:29).

FIG. 37 shows the nucleotide sequence for GenBank accession number AF067817 (SEQ ID NO:30).

FIG. 38 shows the nucleotide sequence for GenBank accession number R72714 (SEQ ID NO:31).

FIG. 39 shows the nucleotide sequence for GenBank accession number X52541 (SEQ ID NO:32).

FIG. 40 shows the nucleotide sequence for GenBank accession number H14529 (SEQ ID NO:33).

FIG. 41 shows the nucleotide sequence for GenBank accession number M10277 (SEQ ID NO:34).

FIG. 42 shows the nucleotide sequence for GenBank accession number H27389 (SEQ ID NO:35).

FIG. 43 shows the nucleotide sequence for GenBank accession number D89092 (SEQ ID NO:36).

FIG. 44 shows the nucleotide sequence for GenBank accession number D89678 (SEQ ID NO:37).

FIG. 45 shows the nucleotide sequence for GenBank accession number H05545 (SEQ ID NO:38).

FIG. 46 shows the nucleotide sequence for GenBank accession number J03804 (SEQ ID NO:39).

FIG. 47 shows the nucleotide sequence for GenBank accession number H27969 (SEQ ID NO:40).

FIG. 48 shows the nucleotide sequence for GenBank accession number R73247 (SEQ ID NO:41).

FIG. 49 shows the nucleotide sequence for GenBank accession number U51336 (SEQ ID NO:42).

FIG. 50 shows the nucleotide sequence for GenBank accession number H21777 (SEQ ID NO:43).

FIG. 51 shows the nucleotide sequence for GenBank accession number K00558 (SEQ ID NO:44).

FIG. 52 shows the nucleotide sequence for GenBank accession number D31765 (SEQ ID NO:45).

DETAILED DESCRIPTION OF THE INVENTION

Figure 1A:
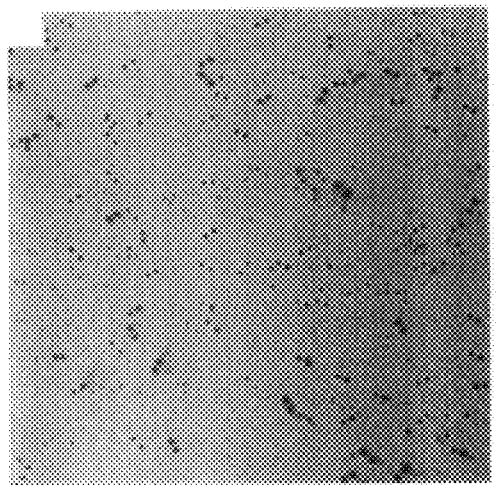
FIG. 1 shows differential hybridization to clone arrays. Each image is an authoradiogram that spans about 4000 double spotted E. coli colonies, each carrying a different EST clone. Panel A shows the binding of a total target made from 1 $\mu$g of polyA$^+$ RNA from confluent human keratinocytes that was radiolabeled during reverse transcription. Panels B and C show RAP-PCR fingerprint with a pair of arbitrary primers that was performed on cDNA from oligo (dT) primed cDNA of confluent human keratinocytes that were untreated (Panel B) and treated with epidermal growth factor (EGF) (Panel C). The two radiolabeled colonies from one differentially expressed cDNA are indicated with an arrow. Panel D shows a RAP-PCR fingerprint with a different pair of arbitrary primers that was performed on RNA from confluent human keratinocytes.
Figure 1B:
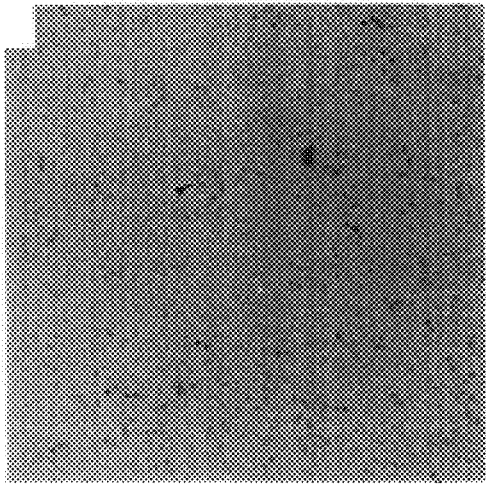
Figure 1C:
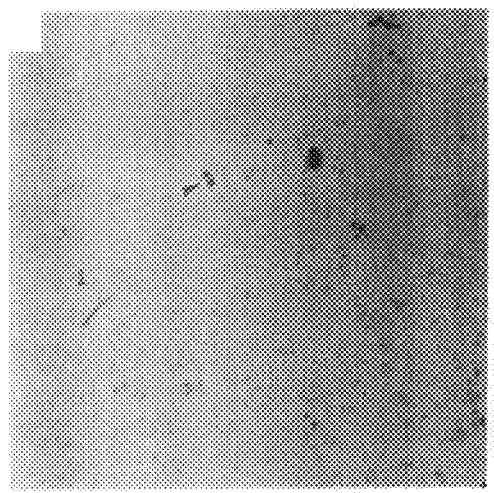

The invention provides methods for measuring the level of two or more nucleic acid molecules in a target by contacting a probe with an arbitrarily sampled target or a statistically sampled target and detecting the amount of specific binding to the probe. The invention also provides methods of identifying two or more differentially expressed nucleic acid molecules associated with a condition by measuring the level of two or more nucleic acid molecules in a target and comparing the expression levels to expression levels of the nucleic acid molecules in a second target. The methods of the invention are useful for obtaining a profile of nucleic acid molecules expressed in a target under a given set of conditions. The methods of the invention are particularly useful for comparing the relative abundance of low abundance nucleic acid molecules between two or more targets. The methods of the invention are advantageous in that a profile of nucleic acid molecule abundance can be determined and correlated with a given set of conditions or compared to another target to determine if the original target was exposed to a particular set of conditions, thereby providing information useful for assessing the diagnosis or treatment of a disease.

The invention provides a method of measuring the abundance of two or more nucleic acid molecules in a target. The method of the invention includes the steps of contacting a probe with a target comprising two or more nucleic acid molecules, wherein the nucleic acid molecules are arbitrarily sampled and wherein the arbitrarily sampled nucleic acid molecules comprise a subset of the nucleic acid molecules in a population of nucleic acid molecules; and detecting the amount of specific binding of the target to the probe.

As used herein, the term "nucleic acid molecule" refers to a nucleic acid of two or more nucleotides. A nucleic acid molecule can be RNA or DNA. For example, a nucleic acid molecule can include messenger RNA (mRNA), transfer RNA (tRNA) or ribosomal RNA (rRNA). A nucleic acid molecule can also include, for example, genomic DNA or cDNA. A nucleic acid molecule can be synthesized enzymatically, either in vivo or in vitro, or the nucleic acid molecule can be chemically synthesized by methods well known in the art. A nucleic acid molecule can also contain modified bases, for example, the modified bases found in tRNA such as inosine, methylinosine, dihyrouridine, ribothymidine, pseudouridine, methylguanosine and dimethylguanosine. Furthermore, a chemically synthesized nucleic acid molecule can incorporate derivatives of nucleotide bases.

As used herein, the term "population of nucleic acid molecules" refers to a group of two or more different nucleic acid molecules. A population of nucleic acid molecules can also be 3 or more, 5 or more, 10 or more, 20 or more, 50 or more, 100 or more, 1000 or more or even 10,000 or more different nucleic acid molecules. The nucleic acid molecules can differ, for example, by a single nucleotide or by modification of a single base. Generally, a population of nucleic acid molecules is obtained from a target sample, for example, a cell, tissue or organism. In such a case, the population of nucleic acid molecules contains the nucleic acid molecules of the target sample.

A population of nucleic acid molecules has characteristics that can differentiate one population of nucleic acid molecules from another. These characteristics are based on the number and nature of individual nucleic acid molecules comprising the population. Such characteristics include, for example, the abundance of nucleic acid molecules in the population. The abundance of an individual nucleic acid molecule can be an absolute amount in a given target sample or can be the amount relative to other nucleic acid molecules in the target sample. In a population of nucleic acid molecules obtained from a target, individual nucleic acid molecules can be more abundant or less abundant relative to other nucleic acid molecules in the sample target. A less abundant sequence can also be relative abundance between two samples.

As used herein, a less abundant nucleic acid molecule can be, for example, less than about 10% as abundant as the most abundant nucleic acid molecule in a population. A less abundant nucleic acid molecule can also be less than about 1% as abundant, less than about 0.1% as abundant or less than about 0.01% as abundant as the most abundant nucleic acid molecule in a population. For example, a low abundance nucleic acid molecule can be less than about 10 copies per cell, or even as low as 1 copy per cell.

Another characteristic of a population of nucleic acid molecules is the complexity of the population. As used herein, "complexity" refers to the number of nucleic acid molecules having different sequences in the population. For example, a population of nucleic acid molecules representative of the mRNA in a bacterial cell has lower complexity than a population of nucleic acid molecules representative of the mRNA in a eukaryotic cell, a tissue or an organism because a smaller number of genes are expressed in a bacterial cell relative to a eukaryotic cell, tissue or organism.

A population of nucleic acid molecules can also be characterized by the properties of individual nucleic acid molecules in the population. For example, the length of individual nucleic acid molecules contributes to the characteristics of a population of nucleic acid molecules. Similarly, the sequence of individual nucleic acid molecules in the population contributes to the characteristics of the population of nucleic acid molecules, for example, the G+C content of the nucleic acid sequences and any secondary structure that can form due to complementary stretches of nucleotide sequence that can undergo intrastrand hybridization.

As used herein, the term "subset of nucleic acids" means less than all of a set of nucleic acid molecules. For example, a subset of nucleic acid molecules of a target sample population would be less than all of the nucleic acid molecules in the target sample population. Specifically excluded from a subset of nucleic acid molecules is a group of nucleic acid molecules representative of all the nucleic acid molecules in a sample target, for example, a target generated using total cDNA or total mRNA.

As used herein, the term "target" refers to one or more nucleic acid molecules to which binding of a probe is desired. A target is detectable when bound to a probe. A target of the invention generally comprises two or more different nucleic acid molecules. A target can be derived from a population of nucleic acid molecules from a cell, tissue or organism. A target can also contain 3 or more, 5 or more, 10 or more, 20 or more, 30 or more, 50 or more, 100 or more, 200 or more, 500 or more, 1000 or more, 2000 or more, 5000 or more, or even 10,000 or more different nucleic acid molecules. A target can have a detectable moiety associated with it such as a radioactive label, a fluorescent label or any label that is detectable. When a target is labeled, for example, with a radioactive label, the target can be used "to probe" or hybridize with other nucleic acid molecules. Methods of making a target are disclosed herein.

A method of detection that directly measures binding of the target to a probe, without the need for a detectable moiety attached to the target, can also be used. In such a case, the nucleic acid molecules are directly detectable without modification of a nucleic acid molecule of the target, for example, by attaching a detectable moiety. An example of such a detection method using a target without a detectable moiety is detection of binding of a target using mass spectrometry. Another example of a method using a target containing nucleic acid molecules without an attached detectable moiety is binding the target to a probe that contains molecules having a detectable moiety. In such a case, the binding of a target to the probe containing molecules having a detectable moiety is detected and, as such, the target is detectable when bound to the probe. An example is the "molecular beacon," where probe binding causes separation of a fluorescent tag from a fluorescence quencher.

As used herein, the term "specific binding" means binding that is measurably different from a non-specific interaction. Specific binding can be measured, for example, by determining binding of a molecule compared to binding of a control molecule, which generally is a molecule of similar structure that does not have binding activity. For example, specific binding of a target to a probe can be determined by comparing binding of the target with binding control nucleic acids not included in the target. Specific binding can also be determined by competition with a control molecule that is similar to the target, for example, an excess of non-labeled target. In this case, specific binding is indicated if the binding of a labeled target to a probe is competitively inhibited by excess unlabeled target.

The term "specific binding," as used herein, includes both low and high affinity specific binding. Specific binding can be exhibited, for example, by a low affinity molecule having a Kd of at least about $10^{-4}$ M. Specific binding also can be exhibited by a high affinity molecule, for example, a molecule having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

In the case of a probe comprising an array of nucleic acid molecules, binding of a specific nucleic acid molecule of the probe to another nucleic acid molecule is also known as hybridizing or hybridization. As used herein, the term "hybridizing" or "hybridization" refers to the ability of two strands of nucleic acid molecules to hydrogen bond in a sequence dependent manner. Under appropriate conditions, complementary nucleotide sequences can hybridize to form double stranded DNA or RNA, or a double stranded hybrid of RNA and DNA. Nucleic acid molecules with similar but non-identical sequences can also hybridize under appropriate conditions.

As used herein, the term "probe" refers to a population of two or more molecules to which binding of a target is desired. The molecules of a probe include nucleic acid molecules, oligonucleotides and polypeptide-nucleic acid molecules. A probe can additionally be an array of molecules.

In general, a probe is comprised of molecules immobilized on a solid support and the target is in solution. However, it is understood that a target can be bound to a solid support and a probe can be in solution. Furthermore, both the probe and the target can be in solution. It is understood that the configuration of the probe and target can be in solution or bound to a solid support, so long as the probe and target can bind to each other. When bound to a solid support, the binding of the probe or target to the support can be covalent or non-covalent, so long as the bound probe or target remains bound under conditions of contacting the solid support with a probe or target in solution and washing of the solid support. If the probe and target hybridize or otherwise specifically interact, the probe or target bound to a solid support remains bound during the hybridization and washing steps.

As used herein, the term "sampled" or "samples," when used in reference to a nucleic acid molecule, refers to a nucleic acid molecule to which specific binding can be detected. A nucleic acid molecule that samples another molecule is capable of specifically binding to that molecule and being detected. For example, a probe can sample molecules in a target by detectably binding to molecules in the target. Those molecules in the target to which nucleic acid molecules in the probe specifically bind are therefore sampled.

As used herein, the term "arbitrarily sampled" or "arbitrarily sampled nucleic acid molecule" means that a nucleic acid molecule is sampled by binding based on its sequence without sampling based on a particular site where a molecule will bind. When generating a target comprising arbitrarily sampled nucleic acid molecules from a population of nucleic acid molecules, the target is generated without prior reference to the sequences of nucleic acid molecules in the population. Thus, it is not necessary to have previous knowledge of the nucleotide sequence of nucleic acid molecules in the population to arbitrarily sample the population. It is understood that knowledge of a nucleotide sequence of a nucleic acid molecule in the population does not preclude the ability to arbitrarily sample the population so long as the nucleotide sequence is not referenced before sampling the population. Methods for generating a probe containing arbitrarily sampled nucleic acid molecules are disclosed herein (see below and Examples I to III).

An arbitrarily sampled probe containing arbitrarily sampled nucleic acid molecules can be generated using one or more arbitrary oligonucleotides. As used herein, the term "arbitrary oligonucleotide" means that the oligonucleotide is a sequence that is selected randomly and is not selected based on its complementarity to any known sequence. As such, an arbitrary oligonucleotide can be used to arbitrarily sample a population of nucleic acid molecules.

An arbitrarily sampled nucleic acid molecule is sampled based on its sequence and is not based on binding to a predetermined sequence. For example, arbitrary oligonucleotides are oligonucleotides having an arbitrary sequence and, as such, will bind to a given nucleic acid molecule because the complementary sequence of the arbitrary oligonucleotide occurs by chance in the nucleic acid molecule. Because the oligonucleotides can bind to a nucleic acid molecule based on the presence of a complementary sequence, the sampling of the nucleic acid molecule is based on that sequence. However, the binding of the arbitrary oligonucleotide to any particular nucleic acid molecule in a population is not determined prior to the binding of the oligonucleotide, for example, by comparing the sequence of the arbitrary oligonucleotides to known nucleic acid sequences and selecting the oligonucleotides based on previously known nucleic acid sequences. The use of arbitrary oligonucleotides as primers for amplification is well known in the art (Liang and Pardee, *Science* 257:967–971 (1992)).

As used herein, the term "oligonucleotide" refers to a nucleic acid molecule of at least 2 and less than about 1000 nucleotides. An oligonucleotide can be, for example, at least about 5 nucleotides and less than about 100 nucleotides, for example less than about 50 nucleotides.

The invention also provides a method of measuring the level of two or more nucleic acid molecules in a target by contacting a probe with a target comprising two or more nucleic acid molecules, wherein the nucleic acid molecules are statistically sampled and wherein the statistically sampled nucleic acid molecules comprise a subset of the nucleic acid molecules in a population of nucleic acid molecules; and detecting the amount of specific binding of the target to the probe.

As used herein, the term "statistically sampled nucleic acid molecule" means that a nucleic acid sequence is sampled based on its sequence with prior reference to its nucleotide sequence by predetermining the statistical occurrence of a nucleotide sequence in two or more nucleic acid molecules. Thus, to obtain a statistically sampled nucleic acid molecule, it is necessary to have previous knowledge of the nucleotide sequence of at least two nucleic acid molecules in the population.

A statistically sampled nucleic acid molecule is sampled based on the sequence of a nucleic acid molecule with prior reference to its nucleotide sequence but without prior reference to a preselected portion of its nucleotide sequence. A group of oligonucleotides can be identified without prior reference to a preselected portion of a nucleotide sequence, for example, by determining a group of arbitrary oligonucleotides. The arbitrary oligonucleotides can then be referenced to known nucleotide sequences by determining which of the arbitrary primers match the known nucleotide sequences. Such arbitrary oligonucleotides referenced to known nucleotide sequences are selected based on the known sequences and thus become statistical primers. This method is in contrast to a method where a preselected site in a known nucleotide sequence is identified and an oligonucleotide is specifically designed to match that preselected site.

Statistical sampling is advantageous because a set of oligonucleotides can be determined based on the presence in a group of known sequences of a sequence complementary to the oligonucleotides. The oligonucleotides can further be ranked based on complexity binding. Complexity binding means that a given oligonucleotide binds to more than one nucleic acid molecule. The larger the number of molecules to which an oligonucleotide can bind, the higher the "complexity binding." Statistical selection can be used to enhance for complexity binding by ranking oligonucleotides based on the number of sequences to which the oligonucleotides will bind and selecting those that bind to the highest number (see, for example, WO 99/11823). Statistical sampling can be based, for example, on the binding of an oligonucleotide to 5 or more nucleic acid molecules, and can be based on the binding to 10 or more, 50 or more, 100 or more, 200 or more, 500 or more, 1000 or more, or even 10,000 or more nucleic acid molecules.

In addition, statistical sampling can enhance for the highest complexity binding for a given oligonucleotide, for example, by selecting the above average ranked oligonucleotides that are complementary to above the average number of nucleic acid molecules. The oligonucleotides can be selected for the any range of complexity binding, for example, the top 10% of highest ranked complexity binding, the top 20% of highest ranked complexity binding, or the top 50% of highest ranked complexity binding.

Furthermore, statistical selection can be used to exclude undesirable nucleotide sequences, including conserved sequences in a family of related nucleic acid molecules (WO 99/11823). A statistical oligonucleotide can be about 5 nucleotides in length to about 1000 nucleotides in length, for example, about 5, 6, 7, 8, 9, 10, 11, 12, 13, 14, 15, 16, 18, 20, 25, 30 or 50 nucleotides in length. A set of statistical primers can contain degenerate bases, for example, more than one nucleotide at any given position.

A sampled nucleic acid molecule obtained using a preselected portion of a nucleotide sequence is specifically excluded from the meaning of the term "statistically sampled nucleic acid molecule." For example, if a portion of a known nucleotide sequence is identified and an oligonucleotide that matches the identified portion is generated to sample a nucleic acid molecule, such a sampled nucleic acid molecule would not be a statistically sampled nucleic acid molecule. However, if a group of oligonucleotides is first identified and then compared to two or more known nucleotide sequences in a population of nucleic acid molecules to determine oligonucleotides statistically present in or similar to the known nucleotide sequences, such statistically identified oligonucleotides can be used to obtain a statistically sampled nucleic acid molecule. Methods for generating a target containing statistically sampled nucleic acid molecules are disclosed herein.

A statistically sampled target containing statistically sampled nucleic acid molecules can be generated using one or more statistical oligonucleotides. As used herein, the term "statistical oligonucleotide" means that an oligonucleotide is a sequence that is selected based on its statistical occurrence of complementarity in more than one known nucleic acid molecule. As such, a statistical oligonucleotide can be used to statistically sample a population of nucleic acid molecules.

The methods of the invention detect specific binding of a target to a probe. A target can be generated, for example, by amplifying nucleic acid molecules. As used herein, the term "amplified target" refers to a target generated by enzymatically copying a nucleic acid molecule to generate more than one copy of the nucleic acid molecules in a population of nucleic acid molecules. An amplified nucleic acid target can be generated, for example, using an amplification method such as polymerase chain reaction (PCR). A target having a single copy of each nucleic acid molecule in a target sample from which the target sample is derived, which would have identical abundance and complexity as the original population, would not be considered an amplified target. An amplified target can be useful, for example, if nucleic acid molecules sampled by the probe are in limited quantities in the target. A nucleic acid molecule that is to be sampled and which is present in very low quantities would be difficult to detect without amplification and increasing the mass of the nucleic acid molecules in the probe. However, a limited complexity target, in which the complexity or number of different molecules is limited, need not be amplified.

Other methods for generating an amplified target include, for example, the ligase chain reaction (LCR); self-sustained sequence replication (3SR); beta replicase reaction, for example, using Q-beta replicase; phage terminal binding protein reaction; strand displacement amplification (SDA); nucleic acid sequence based amplification (NASBA); cooperative amplification by cross hybridization (CATCH); rolling circle amplification (RCA) and AFLP (Trippler et al., *J. Viral. Hepat.* 3:267 (1996); Hofler et al., *Lab. Invest.* 73:577 (1995); Tyagi et al., *Proc. Natl. Acad. Sci. USA* 93:5395 (1996); Blanco et al., *Proc. Natl. Acad. Sci. USA* 91:12198 (1994); Spears et al., *Anal. Biochem.* 247:130 (1997); Spargo et al., *Mol. Cell. Probes* 10:247 (1996); Gobbers et al., *J. Virol. Methods* 66:293 (1997); Uyttendaele et al., *Int. J. Food Microbiol.* 37:13 (1997); and Leone et al., *J. Virol. Methods* 66:19 (1997); Ellinger et al., *Chem. Biol.* 5:729–741 (1998); Ehricht et al., *Nucleic Acids Res.* 25:4697–4699 (1997); Ehricht et al., *Eur. J. Biochem.* 243:358–364 (1997); Lizardi et al., *Nat. Genet.* 19:225–232 (1998)).

The methods of the invention are useful for measuring the level of two or more nucleic acid molecules in a target. The methods of the invention can also be used to compare expression levels between two targets. In particular, the methods of the invention are useful for measuring differential expression of nucleic acid molecules (see below).

A total target, using the full complexity of the mRNA population for target preparation, can easily examine the top few hundred or a few thousand of the mRNAs in the cell (Pietu et al., *Genome Res.* 6:492–503 (1996)). However, a total labeled cDNA target from a mammalian cell typically has a complexity of over 100 million bases which complicates attempts to detect differential expression among the rarer mRNAs using differential hybridization. Recent advances in the use of fluorescence and confocal microscopy have led to improvements in the sensitivity and dynamic range of differential hybridization methods, with a dynamic range of detection of 10,000-fold and the detection of transcripts at a sensitivity approaching 1/500,000 (Marshall and Hodgson, *Nat. Biotechnol.* 16:27–31 (1998); Ramsay, *Nat. Biotechnol.* 16:40–44 (1998)). Despite the improvements in sensitivity, methods using total target remain biased toward more abundant mRNAs in a sample.

The standard method for differential screening, which typically uses targets derived from reverse transcription of total message and autoradiography or phosphoimaging, can be used to detect differential expression (Pietu, supra, 1996). However, the method is limited to the most abundant messages. Only abundant transcripts are represented highly enough to yield effective targets with a sensitivity of perhaps 1/15,000 (Boll, *Gene* 50:41–53 (1986)). As disclosed herein, differential screening can be improved greatly by reducing the complexity of the target and by systematically increasing the amount of rarer nucleic acid molecules in the target. By enhancing the amount of less abundant nucleic acids in a target, differential screening is not confined to only the most abundant nucleic acid molecules, as observed using total target.

By reducing the complexity of the target, the ability to identify all mRNA species in a source simultaneously is sacrificed for improved kinetics and an improved signal to noise ratio. Complexity reduction methods generate a target having a subset of nucleic acid molecules in a population that allow a few rare mRNAs to contribute significantly to the final mass of the target, thereby enhancing the ability to observe differential gene expression among rare mRNAs in a source. Any method that generates a mixture of products that reliably enriches for only part of each mRNA or only a subset of the mRNA population is useful for generating a reduced complexity target.

There are two fundamentally different types of complexity reduction methods, methods that maintain the relative stoichiometry among the mRNAs they sample and methods that do not maintain stoichiometry. One class of methods yields nucleic acids representing a subset of the mRNA population and maintains the approximate stoichiometry of the input RNA. Such methods are exemplified by most amplified restriction fragment length polymorphism (AFLP) and restriction strategies that sample the 3' end or internal fragments of mRNAs (Habu et al., *Biochem. Biophys. Res. Commun.* 234:516–521 (1997); Money et al., *Nucleic Acids Res.* 24:2616–2617 (1996); Bachem et al., *Plant J.* 9:745–753 (1996)). Another example is the use of size fractionated mRNAs to generate cDNA targets. All the mRNAs, for example, the 2.0 to 2.1 kb range can be used as a reduced complexity target. Stoichiometry among these mRNAs would be mostly preserved in the target (Dittmar et al., *Cell Biol. Int.* 21:383–391 (1997)).

A second class of methods for generating reduced complexity targets does not preserve the stoichiometry of the starting mRNAs, though it does preserve differences among individual RNAs between target samples from which targets are made. One method to generate a reduced complexity target that does not maintain stoichiometry is to use subtracted targets, which have shown sensitivity for rare messages comparable to chips, in particular methods based on representational difference analysis or suppression subtractive hybridization (Rhyner et al., *J. Neurosci. Res.* 16:167–181 (1986); Lisitsyn et al., *Science* 259:946–951 (1993); Lisitsyn & Wigler, *Methods Enzymol.* 254:291–304 (1995); Jin et al., *Biotechniques* 23:1084–1086 (1997)).

Particularly useful methods for generating a reduced complexity target that does not maintain stoichiometry are exemplified by using arbitrarily sampled targets or statistically sampled targets. Methods using arbitrarily sampled targets and statistically sampled targets are disclosed herein. The methods using arbitrarily sampled or statistically sampled targets allow detection of low abundance nucleic acid molecules in a target. The methods of the invention are advantageous because they enhance the ability to detect low abundance nucleic acid molecules in a target and also allow detection of nucleic acid molecules in a target derived from limited quantities of nucleic acid molecules, such as a few cells or even a single cell.

An arbitrarily sampled target or statistically sampled target can be generated, for example, by amplification. If an amplified target is generated using arbitrary oligonucleotides or statistical oligonucleotides, the amplified products reflect a function of both the starting abundance of each target nucleic acid molecule and the quality of the match of the oligonucleotide to the target nucleic acid molecule to be sampled. Thus, the final mixture of amplified products can include quite abundant amplified products that derive from low abundance nucleic acid molecules that have a good match with the oligonucleotide primers used and have favorable "amplifiability" after the initial priming events. Amplifiability includes effects such as secondary structure and product size.

A consequence of generating an amplified target using arbitrary oligonucleotides or statistical oligonucleotides is that the same nucleic acid molecules in two different targets experience an identical combination of primability and amplifiability so that changes in abundance for particular mRNAs are maintained, even as the relative abundances between different nucleic acid molecules within one target are profoundly changed. This is in contrast to methods that maintain stoichiometry, where less abundant nucleic acid molecules would be present as less abundant nucleic acid molecules in the target.

When generating an amplified target, there are generally no particular constraints on the oligonucleotide primers. The oligonucleotide primers preferably contain at least a few C or G bases. The oligonucleotide primers also preferably do not contain 3' ends complementary with themselves or the other primer in the reaction, to avoid primer dimers. The oligonucleotide primers are also preferably chosen to have different sequences so that the same parts of mRNA are not amplified in different fingerprints.

As disclosed herein, methods of generating arbitrarily sampled targets or statistically sampled targets can be based on methods that have been traditionally used to "fingerprint" a target sample containing nucleic acid molecules. The fingerprints are characteristic of the expression of nucleic acid molecules in a target sample. To generate an arbitrarily sampled target, one method that can be used is based on RNA arbitrarily primed PCR (RAP-PCR) (see Examples I and II; Welsh et al., Nucleic Acids Res. 18:7213–7218 (1990); Welsh et al., Nucleic Acids Res. 20:4965–4970 (1992); Liang and Pardee, Science 257:967–971 (1992)).

In RAP-PCR, both the abundance and the extent of match with the primers contribute to the prevalence of any particular product. Thus, rare mRNAs that happen to have excellent matches with the primers and are efficiently amplified are found among the more abundant RAP-PCR products, which makes a target generated by RAP-PCR non-stoichiometric. This is a very useful feature of RAP-PCR because it allows the sampling of mRNAs that are difficult to sample using other methods.

In a typical RAP-PCR fingerprint, about 50–100 cDNA fragments per lane are visible on a polyacrylamide gel, including products from relatively rare mRNAs that happen to have among the best matches with the arbitrary primers. If only 100 cDNA clones could be detected in an array by each target, then hybridization to arrays would be inefficient. However, RAP-PCR fingerprints contain many products that are too rare to visualize by autoradiography of a polyacrylamide gel. Nonetheless, these rarer products are reproducible and of sufficient abundance to serve as target for arrays when labeled at high specific activity.

As disclosed herein, a single target derived from RAP-PCR can detect about a thousand cDNAs on an array containing about 18,000 EST clones, a 10–20 fold improvement over the performance of fingerprints displayed on denaturing polyacrylamide gels. In addition, when a differentially regulated gene is detected on a cDNA array, a clone representing the transcript is immediately available, and often sequence information for the clone is also available. Furthermore, the clones are usually much longer than the usual RAP-PCR product. In contrast, the standard approaches to RNA fingerprinting require that the product be gel purified and sequenced before verification of differential expression can be performed. As disclosed herein, differentially amplified RAP-PCR products that are below the detection capabilities of the standard denaturing polyacrylamide gel and autoradiography methods can be detected using hybridization to cDNA arrays.

An arbitrarily sampled target generated by RAP-PCR can sample the top few thousand highest expressed nucleic acid molecules in a target sample and can sample different subsets of the nucleic acid molecules in a population, depending on the oligonucleotide primers used for amplification. Some of the rare nucleic acid molecules in a target are sufficiently represented to be easily detected on arrays of colonies (see Examples I and II).

To generate an arbitrarily sampled target using RAP-PCR, the RAP-PCR fingerprint is made by arbitrarily primed reverse transcription and PCR of nucleic acid molecules in a target sample, for example, messenger RNA (McClelland et al., in Differential Display Methods and Protocols, Liang and Pardee, eds., Humana Press (1997)). Alternatively, first strand cDNA can be primed with oligo dT or with random short oligomers, followed by arbitrary priming. Analysis of such a RAP-PCR "fingerprint" by gel electrophoresis reveals a complex fingerprint showing relative abundances of an arbitrary sample of about 100 transcripts (see Example II).

As disclosed herein, RAP-PCR fingerprints were converted to targets to probe or hybridize human cDNA clones arrayed as E. coli colonies on nylon membranes (Example II). Each array contained 18,432 cDNA clones from the Integrated Molecular Analysis of Genomes and their Expression (I.M.A.G.E.) consortium. Hybridization to about 1000 cDNA clones was detected using each arbitrarily sampled target generated by RAP-PCR. Different RAP-PCR fingerprints gave hybridization patterns having very little overlap (<3%) with each other, or with hybridization patterns from total cDNA targets. Consequently, repeated application of RAP-PCR targets allows a greater fraction of the message population to be screened on this type of array than can be achieved with a radiolabeled total cDNA target.

The arbitrarily sampled targets were generated from HaCaT keratinocytes treated with EGF. Two RAP-PCR targets hybridized to 2000 clones, from which 22 candidate differentially expressed genes were observed (Example II). Differential expression was tested for 15 of these clones using RT-PCR and 13 were confirmed. The use of this cDNA array to analyze RAP-PCR fingerprints allowed for an increase in detection of 10- to 20-fold over the conventional denaturing polyacrylamide gel approach to RAP-PCR or differential display. Throughput is vastly improved by the reduction in cloning and sequencing afforded by the use of arrays. Also, repeated cloning and sequencing of the same gene, or of genes already known to be regulated in the system of interest, is minimized.

The use of RAP-PCR to generate an arbitrarily sampled target is particularly useful because it allows very high throughput discovery of differentially regulated genes (see Examples II and III). The throughput using this method is about 20 times faster. Essentially, once a RAP-PCR fingerprint has been generated, instead of analyzing the product by gel electrophoresis, the RAP-PCR fingerprint is used as a target to probe or hybridize to nucleic acid molecules. Such an arbitrarily sampled target generated by RAP-PCR is particularly useful as a target for an array.

Parameters of the RAP-PCR reaction can be varied, for example, to optimize complexity of the target and enhance complexity binding. For example, to increase the complexity, Taq polymerase Stoffel fragment, which is more promiscuous than AMPLITAQ, can be used for amplification. The oligonucleotide primers used herein (Example II) were 10 or 11 bases in length and were not degenerate, having a single base at each position. Longer oligonucleotide primers used at the same temperature can give a more complex product, as would primers with some degeneracy. However, the greater the complexity of the target, the more closely it will resemble a total mRNA target, which loses the advantage of non-stoichiometric sampling. To further vary RAP-PCR parameters, the oligonucleotide primer length, degeneracy, and 3' anchoring can be varied in the reverse transcription and PCR reactions. Various different polymerases can also be used.

The RAP-PCR fingerprint can be radiolabeled or labeled with fluorescent dyes, as described below, and used as a target to probe against dense arrays such as arrays of cDNA clones. Differences in the level of nucleic acid molecules between two targets can indicate, for example, differences in mRNA transcript levels, which usually reflects differences in gene expression levels. Differences in expression can also reflect degradation or post-translational processsing. Using an arbitrarily sampled target, each target is estimated to allow the detection of roughly 10% of the total complexity of the message population, and most importantly, this 10% very effectively includes the rare message class. The rare message class is included in the target because, while RAP-PCR reflects message abundance between target samples, the cDNAs selected for amplification in any particular RAP-PCR reaction is determined by sequence rather than abundance. When the sequence match between oligonucleotide primers and nucleic acid molecules is very good, even if the nucleic acid molecule is in low abundance, the low abundance nucleic acid molecules have a good chance of having a larger amount of the less abundant nucleic acid molecule relative to more abundant nucleic acid molecules in the final target.

To be suitable for either gel- or array-based analysis, RAP-PCR fingerprints should remain almost identical over an eight-fold dilution of the input RNA. Low quality RAP-PCR fingerprints are usually the consequence of poor control over RNA quality and concentration. Before proceeding with the array hybridization steps, the quality of the RAP-PCR products can be verified. Because the array method has such high throughput, this extra step is neither costly, nor time-consuming, and can greatly improve efficiency by reducing the number of false positives due to poor fingerprint reproducibility. The reproducibility of RAP-PCR fingerprints as targets is exemplified herein (see Example II).

The enhanced ability of the methods of the invention to detect low abundance nucleic acid molecules in a target sample provides a major improvement over previously used methods that have limited ability to detect rare messages. It is likely that the entire complexity of the message population of a cell could be examined in a short period of time, for example, in a few weeks.

For example, as disclosed in Example II, targets generated by RAP-PCR sample a population of mRNAs largely independent of message abundance. This is because the low abundance class of messages has much higher complexity than the abundant class, making it more likely that the arbitrary primers will find good matches. Unlike differential display, RAP-PCR demands two arbitrary priming events, possibly biasing RAP-PCR toward the complex class. It is likely that the majority of the mRNA population in a cell (<20,000 mRNAs) can be found in as few as ten RAP-PCR fingerprints.

In addition to using RAP-PCR, differential display can also be used to generate an arbitrarily sampled target (see Example III). For differential display, first, reverse transcription uses a 3' anchored primer such as an oligo(dT) primer. Next, second strand cDNA is primed with an arbitrary primer. Then PCR takes place between the arbitrary primer and the 3' anchor.

As disclosed in Example III, a combination of one arbitrary and one oligo(dT) anchor primer was used to generate an arbitrarily sampled target for cDNA arrays. Both the RAP-PCR and differential display approaches to target preparation can use less than ½₀₀th of the amount of RNA used in some other array hybridization methods. Each fingerprint detected about 5–10% of the transcribed mRNAs, sampled almost independent of abundance, using inexpensive E. coli colony arrays of EST clones. The differential display protocol was modified to generate a sufficient mass of PCR products for use as a target to probe nucleic acid molecules. The use of different oligo(dT) anchor primers with the same arbitrary primer resulted in considerable overlap among the genes sampled by each target. Overlap of sampled genes can be avoided by using different arbitrary primers with. each oligo(dT) anchor primer. Four genes not previously known to be regulated by EGF and three genes known to be regulated by EGF in other cell types were characterized using the arbitrarily sampled targets generated by differential display. The use of arbitrarily sampled targets generated by differential display is particularly useful for identification of differentially regulated genes.

A very large number of fingerprints that have been previously generated can be converted to effective targets to be probed by nucleic acid molecule arrays if the mass is increased by performing PCR on an aliquot of each fingerprint in the presence of sufficient dNTPs (100 $\mu$M) and primers (about 1 $\mu$M). Fingerprints can be reamplified, as previously shown (Ralph et al. Proc. Natl. Acad. Sci. USA 90:10710–10714 (1993)). Thus, previously determined differential display samples can be used to generate targets to probe arrays, allowing additional information to be obtained.

As disclosed herein, differential display was used to generate targets based on the method of Liang and Pardee (supra, 1992). The use of targets derived from oligo(dT) anchoring has some potential advantages for certain types of arrays. For example, some arrays are generated by oligo(dT) primed reverse transcription, and these clones are 3' biased. A target generated by an oligo(dT) anchored primer and an arbitrary primer should also be 3' biased so that each PCR product can hybridize to the corresponding 3' biased clone. In contrast, a target generated using arbitrary priming can sample regions internal to mRNAs. If the arbitrary product is located further 5' in the mRNA than the 3' truncated clone, the target cannot bind to the corresponding mRNA.

Arbitrarily sampled targets generated using differential display with 3' anchored oligonucleotide primers are particularly useful for probing 3' biased libraries and, in particular, 3' biased ESTs. 3' anchoring is not useful for sampling RNAs that do not have poly(A) tails, such as most bacterial RNAs. Targets generated using 3' anchor primers would also not be suitable for PCR arrays based on internal products. 3' biased targets are also less useful for random primed libraries.

Other methods for generating an arbitrarily sampled target can also be used. One such method is a variant of RAP-PCR, called complexity limited arbitrary sample sequencing (CLASS). CLASS was conceived as a solution to a well known and frustrating limitation of Serial Analysis of Gene Expression (SAGE) (Velculescu et al., *Science* 270:484–487 (1995)). SAGE is a method for generating small pieces of cDNA from two sources, linking them together, and sequencing them in large numbers. The average cell contains 200,000 mRNA transcripts, representing about 20,000 different sequences, and SAGE allows sequencing of about 40 at one time. Therefore, to compare two targets using a standard sequencing apparatus, a very large number of sequencing gels, about 100, would be required to obtain information on 400,000 mRNAs, representing 200,000 mRNAs from two populations being compared. Although the method is useful for obtaining information on expression of nucleic acid molecules, each additional RNA sample increases the number of gels needed by 50, which is very expensive and time consuming. The main problem is that all 100 gels have to be run to have confidence in the statistics on rare messages that have changed in expression from 1 to 10 copies per cell.

To solve this problem, CLASS was devised. CLASS is similar to RAP-PCR except that the oligonucleotide primers used have degenerate 3' ends. The degeneracy causes the primers to prime often, generating short sequence tags. By choosing a short PCR extension time, the predominant products come only from a fraction of the total complexity of the mRNA, and the size of this fraction can be adjusted at will by varying the number of 3+ degenerate bases. These short tags can then be concatenated and sequenced, rapidly yielding reliable statistics on a subsample of the message complexity, similar to the ligation and sequencing strategy used in SAGE (Valculescu et al., supra, 1995). The CLASS products can also be used as a target to probe, for example, against arrays.

The CLASS method is advantageous because additional sets of primers having degenerate 3' ends can be generated and used to obtain a different sampling of nucleic acid molecules. This iterative approach to determining nucleic acid molecule expression provides more information about a pattern of expression in a source of nucleic acid molecules than the holistic approach of SAGE (Velculescu et al., supra, 1995).

In contrast to SAGE, which requires nearly complete sequencing of the 100 gels to be certain of any of the rare messages, CLASS allows nucleic acid molecule populations to be partitioned into small groups so that, with 10% of the work, confidence is generated for the results of 10% of all of the genes in the cell. With one round of CLASS, no information is obtained on 90% of the rare messages in the first pass (10 gels), but there is high confidence in the results for 10% of the nucleic acid molecules in a target sample. The high confidence in 10% of the genes is preferable because, when hunting for differentially regulated genes, it is expected that a pattern or "type of behavior" occurs during differential gene regulation. It is seldom, if ever, that a single gene is activated without the coordinate regulation of others controlled by the same pathway. Thus, if one is seeking any one of 10 low abundance transcripts regulated, for example, by a topoisomerase inhibitor, SAGE would require running 100 sequencing gels that would yield all 10 low abundance genes. In contrast, CLASS allows running 10 gels, in one-tenth the time, to identify at least one gene, which can be sufficient to identify a pattern of gene expression. Furthermore, CLASS can be used iteratively using different primers to run additional gels, for example, 50 gels, to get information on five times as many genes, whereas running 50 gels with SAGE would reveal no statistically relevant information. Therefore, CLASS is a much more economic approach to identifying a gene expression pattern.

CLASS can be applied to any species, even those for which arrays are unavailable, and to mRNAs that have not yet been deposited on arrays. Thus, whereas use of targets generated by RAP-PCR on known arrays gives expression information on known genes, CLASS gives expression information on any gene, even if not previously encountered in libraries that have been arrayed. CLASS thus provides a low cost, relatively high throughput method for obtaining information on gene expression.

The invention also provides methods of measuring the level of nucleic acid molecules in a target using a statistically sampled target. Methods useful for generating a statistically sampled target have been previously described (WO 99/11823; McClelland et al., supra, 1997; Pesole et al., *Biotechniques* 25:112–123 (1998); Lopez-Nieto and Nigam, *Nature Biotechnoloay* 14:857–861 (1996)). An exemplary method for generating a statistically sampled target is statistically primed PCR (SP-PCR). The main difference between a statistical priming method and RAP-PCR is that the primers are selected by a computer program to determine the statistical occurrence of a nucleotide sequence in a group of nucleic acid molecules, rather than selecting primers arbitrarily.

A method for generating a statistically sampled target can be a directed statistical selection. For example, a program called GeneUP has been devised that uses an algorithm to select primer pairs to sample sequences in a list of interest, for example, a list of human mRNA associated with apoptosis, while excluding sequences in another list, for example, a list of abundantly expressed mRNA in human cells and structural RNAs such as rRNAs, Alu repeats and mtDNA (Pesole et al., supra, 1998). A directed statistical method provides a systematic determination of whether any given oligonucleotide matches any given nucleotide sequence and the number of different nucleic acid molecules to which a given oligonucleotide can bind. Such a directed statistical method can be used to generate a statistically sampled target useful in the invention.

Another method for generating a statistically sampled target is a Monte-Carlo statistical selection method (Lopez-Nieto and Nigam, supra, 1996). A Monte-Carlo statistical selection method randomly pairs a set of primers using a Monte-Carlo method. A Monte-Carlo method approximates the solution of determining primers that can be used for amplification by simulating a random process of primer matching. A Monte-Carlo statistical method differs from a directed statistical method in that a directed statistical method provides a systematic determination of whether any given oligonucleotide matches any given nucleotide sequence and the number of different nucleic acid molecules to which a given oligonucleotide can bind.

In general, two arbitrarily sampled targets, generated using different pairs of arbitrary oligonucleotides, will hybridize to largely non-overlapping sets of nucleic acid molecules in a target sample. Similarly, two statistically sampled targets, generated using different pairs of statistical oligonucleotides, will hybridize to largely non-overlapping sets of nucleic acid molecules in a target. Generally, fewer than 100 products overlap among the most intensely hybridizing 2000 colonies in two differently primed reduced complexity target (see Example I). The pattern of expression is also almost entirely different from the pattern generated by directly labeling the whole mRNA population. However, as more nucleic acid molecules are sampled by additional arbitrary sampling of the RNA population or additional statistic sampling of the RNA population, the number of non-overlapping nucleic acid molecules sampled will decrease. To some extent, the efficiency of coverage of nucleic acid molecules can be improved by the use of statistically selected primers (Pesole et al., supra, 1998). Multiple arbitrarily sampled targets generated by RAP-PCR could supply sufficient targets to cover all genes.

The methods described above for generating arbitrarily sampled targets and statistically sampled targets can be modified. For example, a subtraction strategy can be used to generate arbitrarily sampled targets or statistically sampled targets enriched for differentially regulated nucleic acids. A target from one source of nucleic acid molecules (A) is labeled, then mixed with a few-fold excess of unlabeled target from the other source (B). The whole mixture is denatured and added to the hybridization solution for binding to the probe. The amplified nucleic acid products present in both targets form double stranded nucleic acid molecules, and the remaining available labeled target is primarily from the differences between the two targets. The same experiment can be done with labeled target from source (B) and excess unlabeled target from source (A). The probe bound to both sets of subtracted targets are compared to detect differential gene expression. This procedure also partly quenches repeats present in the target cDNA mixtures. The use of such a subtraction method to generate an arbitrarily sampled target or statistically sampled target can thus be used to compare two conditions by using an unlabeled target from one condition to quench the labeled target from another condition.

A limitation of subtraction is that it can eliminate small differences in expression that can appear to be total absence of a mRNA. Furthermore, while subtraction is useful in a binary question, it is of limited utility in cases where a large number of conditions are to be compared, combinatorially.

Detection of specific binding is limited by background hybridization and incomplete blockage of repeats. Therefore, in addition to using the methods described above for generating reduced complexity targets, $Cot_1$ DNA can be used to quench nucleic acid repetitive elements. A $Cot_1$ DNA genomic fraction is enriched in repeats. A target that contains $Cot_1$ DNA is useful for looking at low abundance nucleic acid molecules that can be difficult to detect. Although low abundance sequences can be partly quenched by the use of total genomic DNA, $Cot_1$ DNA is useful for the more sophisticated arrays such as PCR-based arrays, where the signal to noise ratio is sufficiently high to be concerned about relatively poorly amplified products.

When generating an arbitrarily sampled target or a statistically sampled target, various promoters such as T7 polymerase, T3 polymerase, SP6 polymerase or others can be incorporated into a primer so that transcription with the corresponding polymerase is used to generate the target. Using transcription to generate the target has the advantage of generating a single stranded target. A primer comprising an RNA polymerase promoter can be used in combination with any other statistical or arbitrary primer.

An arbitrarily sampled target or a statistically sampled target can also be generated using digestion ligation. In this case, a population of nucleic acid molecules used to generate the target is digested with a restriction enzyme and an oligonucleotide primer is ligated to generate an amplified target. Ligation-mediated PCR is where a primer binding site or part of the primer binding site is placed on a template by ligation, for example, after site-specific cleavage.

Nested PCR can also be used to generate an arbitrarily sampled target or statistically sampled target. Nested PCR involves two PCR steps, with a first round of PCR performed using a first primer followed by PCR with a second primer that differs from the first primer in that it includes a sequence that extends one or more nucleotides beyond the first primer sequence.

Targets can be enriched for those that hybridize to a particular probe. Once a target generated by a particular arbitrary or statistically primed method has been used on a particular nucleic acid population and the resulting target used against a set of probes, then the set of targets that are detectably hybridized will be known. At that point it is possible to devise a new set of targets that includes only those that were detected or mostly those that were detected by that probe. For example, if a particular primer "A" is used for RAP-PCR using RNA from the human brain and the resulting target is hybridized to an array of cDNA clones, some of the clones will be detectably hybridized. It is then possible to make an array of only those probes that were hybridized by that particular target. Most of the cDNAs on the array can be expected to hybridize with a target developed from human brain RNA made with the same primer "A".

In some cases, the sequences of the nucleic acids that are the basis of targets are known. Some targets hybridize detectably with a particular probe and others do not. The sequence information associated with the targets can be used to deduce the rules of arbitrary or statistical priming events that resulted in the target that hybridized to those probes. Such information will help to predict what sequences are likely to be sampled by a particular primer if that sequence occurs in the target. Such information can improve the estimates of which sequences are sampled efficiently and which sequences are sampled efficiently by a particular primer.

The methods of the invention are particularly useful for measuring the level of a molecule in a target using an array. As used herein, the term "array" or "array of molecules" refers to a plurality of molecules stably bound to a solid support. An array can comprise, for example, nucleic acid, oligonucleotide or polypeptide-nucleic acid molecules. It is understood that, as used herein, an array of molecules specifically excludes molecules that have been resolved electrophoretically prior to binding to a solid support and, as such, excludes Southern blots, Northern blots and Western blots of DNA, RNA and proteins, respectively.

As used herein, the term "non-dot blot" array refers to an array in which the molecules of the array are attached to the solid support by a means other than vacuum filtration or spotting onto a nitrocellulose or nylon membrane in a configuration of at least about 2 spots per $cm^2$.

As used herein, the term "peptide-nucleic acid" or "PNA" refers to a peptide and nucleic acid molecule covalently bound (Nielson, Current Opin. Biotechnol. 10:71–75 (1999)).

As used herein, the term "polypeptide," when used in reference to PNA, means a peptide, polypeptide or protein of two or more amino acids. The term is similarly intended to refer to derivatives, analogues and functional mimetics thereof. For example, derivatives can include chemical modifications of the polypeptide such as alkylation, acylation, carbamylation, iodination, or any modification which derivatizes the polypeptide. Analogues can include modified amino acids, for example, hydroxyproline or carboxyglutamate, and can include amino acids that are not linked by peptide bonds. Mimetics encompass chemicals containing chemical moieties that mimic the function of the polypeptide regardless of the predicted three-dimensional structure of the compound. For example, if a polypeptide contains two charged chemical moieties in a functional domain, a mimetic places two charged chemical moieties in a spatial orientation and constrained structure so that the charged chemical function is maintained in three-dimensional space. Thus, all of these modifications are included within the term "polypeptide."

The solid support for the arrays can be nylon membranes, glass, derivatized glass, silicon or other substrates. The arrays can be flat surfaces such as membranes or can be spheres or beads, if desired. The molecules can be attached as "spots" on the solid support and generally can be spotted at a density of at least about $5/cm^2$ or $10/cm^2$, but generally does not exceed about $1000/cm^2$.

Various methods to manufacture arrays of DNA molecules have been described (reviewed in Ramsay, supra, 1998; Marshall and Hodgson, supra, 1998). Arrays are available containing nucleic acid molecules from various species, including yeast, mouse and human. The use of arrays is advantageous because differential expression of many genes can be determined in parallel.

One type of array contains thousands of PCR products per square centimeter. Arrays of PCR products from segments of mRNAs have been attached to glass, for example, and probed using cDNA populations from two sources. Each cDNA or cRNA population is labeled with a different fluorescent dye and hybridization is assessed using fluorescence (DeRisi et al., Nature Genet. 14:457–460 (1996); Schena et al., Science 270:467–470 (1995)). Arrays are also available containing over 5000 PCR products from selected I.M.A.G.E. clones. An array of PCR products also is available for every yeast ORF and for a subset of human ESTs.

Another type of array contains colonies of 18,432 E. coli clones, each carrying a different I.M.A.G.E. EST plasmid, and each spotted twice on a 22×22 cm membrane (Genome Systems). One advantage of using the arrays from the I.M.A.G.E. consortium is that more than 80% of the clones have single pass sequence reads from the 5' or 3' end, or both, deposited in the GenBank database. Thus, it is usually not necessary to clone or sequence any DNA to determine if there is a known gene or other ESTs that share the same sequence. UniGene clustering of human and mouse ESTs that appear to be from the same gene greatly aids in this process (http://www.ncbi.nlm.nih.gov/UniGene/index.html). Mapping onto chromosomes at a resolution of a few centiMorgans is also available for most of these clusters at the same web site. The clones on these arrays are all available to be used to probe nucleic acid molecules or to complete the sequencing (www-bio.llnl.gov). It is often possible to identify a close homolog in other species. In contrast to PCR product arrays and oligonucleotide arrays, which are free of other DNAs, each spotted EST is associated with E. coli genomic DNA from the host. Thus, the clone arrays can have higher background than PCR arrays or oligonucleotide arrays.

If EST arrays are used, 5' RACE can be used to extend beyond the ESTs currently available (Zhang and Frohman, Methods Mol. Biol. 69:61–87 (1997)). When cDNA libraries that contain near full length clones are available and end sequenced, it will be possible to go from a differentially hybridized spot to a full length cDNA, directly.

Another class of arrays uses oligonucleotides that are either attached to a glass or silicon surface or manufactured by sequential photochemistry on the DNA chip (Chee et al., Science 274:610–614 (1996)). Such chips can contain tens of thousands of different oligonucleotide sequences per square centimeter. Arrays of oligonucleotide nucleic acid analogs such as peptide-nucleic acids, for example, can be prepared (Weiler et al., Nucleic Acids Res. 25:2792–2799 (1997)).

Hybridization of fingerprints to arrays has the huge advantage that there is generally no need to isolate, clone, and sequence the genes detected. In principle, all known human mRNAs will fit on three membranes (about 50,000 genes), or in a smaller area on glass arrays or other solid supports. At present, each fingerprint has a sufficient complexity to hybridize to over 2000 of the 50,000 known genes.

The use of arrays, which can have thousands of genes that can bind to a target, particular genes for further characterization can be selected based on desired criteria. For example, identified genes can be chosen that are already known and for which a new role in the condition of interest can be deduced. Alternatively, some of the genes can be family members of known genes with known functions for which a plausible role can be determined.

In addition to arrays, a number of cDNA libraries are available, for example, from the I.M.A.G.E. consortium (www-bio.llnl.gov/bbrp/image/image.html), including libraries available on nylon membranes, for example, from Research Genetics (Huntsville Ala.; www.resgen.com), Genome Systems (St. Louis Mo.; www.genomesystems.com), and the German Human Genome Project (www.rzpd.de). These libraries include clones from various human tissues, stages of development, disease states and other sources.

The methods of the invention include the step of detecting the amount of specific binding of the probe to the target. As disclosed herein, a variety of detection methods can be used. For example, if a detectable moiety is a radioactive moiety, the method of detection can be autoradiography or phosphoimaging. Phosphoimaging is advantageous for quantitation and shortened data collection time. If a detectable moiety is a fluorescent moiety, the method of detection can be fluorescence spectroscopy or confocal microscopy.

The methods of the invention use nucleic acid probes to measure the level of expression of a nucleic acid molecule in a target. If a radioactive moiety is attached to a target, for example, incorporation of the radioactive moiety can be by any enzymatic or chemical method that allows attachment of the radioactive moiety. For example, end-labeling can be used to attach a radioactive moiety to the end of a nucleic acid molecule. Alternatively, a radioactive nucleotide, in particular a $^{32}$P-, $^{33}$P-, or $^{35}$S-labeled nucleotide, can be incorporated into the nucleic acid molecule during synthesis. The use of random primed synthesis is particularly useful for generating a high specific activity target. Generally, random primed synthesis generates approximately equal amounts of randomly primed nucleic acid molecules from both strands of double stranded PCR products, which will re-anneal to some degree during hybridization to the target (see Example I). If desired, the amount of re-annealing can be limited, for example, using exoIII digestion.

When generating a labeled target or probe, it is generally preferable to incorporate a labeled nucleotide that is not ATP or dATP. The use of labeled dATP can cause an increase in the background because any poly-A sequences in the target or probe will become heavily labeled and will hybridize to the strands containing poly-T stretches complementary to the poly-A tails present in all of the clones. Similarly, the use of dTTP would heavily label poly-T stretches complementary to the polyA tails in mRNA.

A fluorescent dye can also be attached to or incorporated in the probe or target. If desired, a different fluor detectable at different wavelengths can be incorporated into different targets and used simultaneously on the same probe. The use of different fluors is advantageous since multiple targets can be bound to the same probe and detected. A fluorescently labeled target can be detected using, for example, a fluorescent scanner or confocal microscope. Measuring the relative abundance of two targets simultaneously on the same array rather than on two different arrays eliminates problems that arise due to differences in the hybridization conditions or the quantity of target PCR product on replicates of the same array. Nylon membranes are typically unsuitable for most commercially available fluorescent tags due to background fluorescence from the membrane itself.

Infrared dyes are also useful as detectable moieties for attachment to a probe or target. Infrared dyes are particularly useful with targets or probes such as arrays attached to nylon membranes, provided the membrane is free of protein.

When determining the level of a nucleic acid molecule in a target, some variation can occur, in particular for certain amplification products that are very sensitive to the amplification conditions. To control for variation in amplification products between nucleic acid targets, the target can be generated at two concentrations of nucleic acid molecules, differing by a factor of two or more. The use of various nucleic acid concentrations to generate a target to confirm differential expression is described herein (see Examples II and III).

The methods of the invention are directed to detecting specific binding of a target to a probe. When hybridizing a target to a probe, the specificity of binding is determined by the stringency of the hybridization conditions. The length of oligonucleotide primers and the temperature of the amplification reaction contributes to the final product. The products are a function of both the starting abundance of each target nucleic acid molecule and the quality of the match between the oligonucleotide primer and the amplified nucleic acid target. For example, oligonucleotide primers of about 8 bases in length at reaction temperatures of about 60° C. can be used to generate a target. Hybridization conditions can range, for example, from about 32° C. in about 2×SSC to about 68° in about 0.1×SSC. The hybridization temperature can be, for example, about 40° C., about 45° C., about 50° C., about 55° C., about 60° C. or about 65° C. Furthermore, the SSC concentration (see below) can be, for example, about 0.2×, 0.3×, 0.5×, 1× or 1.5×.

The invention additionally provides a method for determining the relative amounts of nucleic acid molecules in two targets by comparing the amount of specific binding of a probe to the target, wherein the amount of specific binding corresponds to an expression level of the nucleic acid molecules in the target, to an expression level of the nucleic acid molecules in a second target. For example, if desired, the expression level in a first target, which can be a target for which the level of expression is unknown, can be compared to the expression level in a second target. The expression level in the second target can be determined, for example, by binding the same probe to the second target and determining the level of expression in the second target. The expression level in the first and second target can then be compared.

The relative expression level in a first target can also be compared to the expression level in a second target, where the abundance in the second target is already known. As used herein, the term "known" when used in reference to expression level of a nucleic acid molecule means that an abundance of a nucleic acid molecule has been previously determined. It is understood that such a known abundance would apply to a particular set of conditions. It is also understood that, for the purpose of comparing the abundance of a nucleic acid molecule in an unknown target to a known abundance, the same method of measuring the abundance between the targets is used.

The invention also provides a method of identifying two or more differentially expressed nucleic acid molecules associated with a condition. The method includes the step of measuring the level of two or more nucleic acid molecules in a target, for example using an arbitrarily sampled target or a statistically sampled target, wherein the amount of specific binding of the target to the probe corresponds to an abundance of the nucleic acid molecules in the target. The method further includes the step of comparing the relative expression level of the nucleic acid molecules in the target to an expression level of the nucleic acid molecules in a second target, whereby a difference in expression level between the targets indicates a condition.

As used herein, the term "differentially expressed" means that the abundance of a molecule is expressed at different levels between two targets. Two targets can be from different cells or tissues, or the target can be from the same cell or tissue under different conditions. The condition can be, for example, associated with a disease state such as cancer, autoimmune disease, infection with a pathogen, including bacteria, virus, fungal, yeast, or single-celled and multi-celled parasites; associated with a treatment such as efficacy, resistance or toxicity associated with a treatment; or associated with a stimulus such as a chemical, for example, a drug or a natural product, for example, a growth factor.

The methods of the invention are useful for determining differential gene expression between two targets. The methods of the invention can be applied to any system where differential gene expression is thought to be of significance, including drug and hormone responses, normal development, abnormal development, inheritance of a genotype, disease states such as cancer or autoimmunge disease, aging, infectious disease, pathology, drug treatment, hormone activity, aging, cell cycle, homeostatic mechanisms, and others, including combinations of the above conditions.

As disclosed herein, the abundance of nucleic acid molecules in two targets can be compared to identify two or more differentially expressed nucleic acid molecules (see Examples I to III). Using arbitrarily sampled targets, targets treated with and without EGF were hybridized with probes and a number of genes regulated by EGF were identified. EGF-regulated genes were found that increased in response to EGF and decreased in response to EGF (see Tables 1 and 2 in Examples II and III, respectively). The methods of the invention can therefore be used to determine nucleic acid molecules that increase in response to a stimulus or decrease in response to a stimulus (see Example II).

The arbitrarily sampled targets and statistically sampled targets used in the invention can readily detect less abundant nucleic acid molecules in a population. Therefore, the methods of the invention are particularly useful for identifying differentially expressed nucleic acid molecules since differentially expressed nucleic acid molecules are often less abundant.

The methods of the invention can be applied to any two targets to determine differential gene expression. The methods of the invention can be used, for example, to diagnose a disease state. In such a case, a "normal" target is compared to a potential disease target to determine differential gene expression associated with the disease. A normal target can be a target sample of the same tissue nearby the diseased tissue from the patient. A normal target can also be a sample of the same tissue from a different individual. Using methods of the invention, a profile of normal expression can be established by determining a gene expression pattern in one to many normal target samples, which can then be used to compare to a potentially diseased target sample. Differential gene expression between the normal and diseased tissue can be used to diagnose or confirm a particular disease state. Furthermore, a collection of target samples obtained from known diseased tissue can similarly be determined to identify an abundance profile of the target reflecting gene expression associated with that disease. In such a case, comparison of a potential disease target sample to a known disease target sample with no differential gene expression would indicate that the potential disease target sample was associated with the disease.

The methods of the invention can also be used to assess treatment of an individual with a drug. The analysis of gene expression patterns associated with a particular drug treatment is also known as pharmacogenomics. The methods of the invention can be used to determine efficacy of a treatment, resistance to a treatment or toxicity associated with a treatment. For example, a gene expression profile can be determined on an individual prior to treatment and after treatment for a particular disease or condition. A difference in gene expression can then be correlated with the effectiveness of the treatment. For example, if an individual is found to be responsive to treatment and if that treatment is associated with differential gene expression, the identification of differential gene expression can be used to correlate with efficacy of that treatment. As described above, a gene expression pattern associated with an untreated individual can be determined in the individual prior to treatment or can be determined in a number of individuals who have not been given the treatment. Similarly, a change in expression pattern associated with efficacy of the treatment can be determined in a number of individuals for which the treatment was efficacious. In such a case, comparison of a treated target sample to a known target sample associated with efficacious treatment with no differential gene expression would indicate that the treatment was likely to be efficacious. A similar approach can be used to determine the association of a treatment with toxicity of the treatment or resistance to a treatment. Resistance to a treatment could be associated with a change in expression pattern from an untreated target sample or could be associated with no change in the expression pattern compared to an untreated target sample.

The methods of the invention can also be used to determine co-regulated genes that can be potential targets for drug discovery. For example, a cell or organism can be treated with a stimulus and differential gene expression between the untreated target sample and the target sample treated with a stimulus can be determined. The stimulus can be, for example, a drug or growth factor. A difference in the abundance of nucleic acid molecules between an untreated target sample and a target sample treated with a stimulus can be used to identify differential gene expression associated with the stimulus. Such a differential expression pattern can be used to determine if a target sample has been exposed to a stimulus. Additionally, the gene expression profile can be used to identify other chemicals that mimic the stimulus by screening for compounds that elicit the same gene expression profile as the original stimulus. Thus, the methods of the invention can be used to identify new drugs that have a similar effect as a known drug.

The methods of the invention are useful for identifying a marker for a pathway that correlates with a drug response by determining an abundance profile for a given target sample that reflects the expression profile of the source population of nucleic acids such as the source RNA. For example, the methods of the invention can be used to define the "neighborhood" of potential therapeutic targets by identifying several genes regulated in response to a drug, thereby providing "neighbors" in a pathway that are potential drug targets. The invention can also be used to define bad neighborhoods, for example, pathways that "failed" therapeutics, which can indicate that a particular pathway should not be perturbed. Additional insights into the function of a pathway can be obtained by sequencing any differentially expressed genes for which complete sequence information is unavailable. The methods are particularly useful for drug comparison. Correlation of gene expression patterns with a drug response can be used to determine why two similar drugs have a somewhat different spectrum of effects.

With knowledge of the correlation between gene expression and response to a drug, drugs can be tested in cell types that are of more relevance to a particular disease or condition. By knowing the pathways that are present in a cell type associated with a pathology, predictions can be made regarding the drug responses of the cell type and thereby allow choice of drugs from a tested panels of drugs that are most likely to affect the pathology. The correlation of information on drug response and gene expression also can aid in choosing drugs that would be synergistic, for example, drugs that hit non-overlapping pathways, or, for example, drugs that affect overlapping pathways when genes in the overlap are targeted.

The methods of the invention can be applied to determining the response to a stimulus, in particular to determining a response to a stimulus for drug discovery. One potential application is to use the methods of the invention on the 60 cell lines in the National Cancer Institute (NCI) drug screening panel. These 60 cell lines are maintained by the NCI and used to assess drug activity.

For example, each of the 60 cell lines of the NCI panel can be used as a complex measuring device that reports the single variable of cell growth and, secondarily, apoptosis. Changes in each cell type's growth upon treatment with a chemical such as a drug is determined. Studies of tens of thousands of drugs, when compared over all 60 cell lines, have shown that similar effects on growth have proven to share mechanisms of action. Comparing the response of the 60 cell lines to various drugs allows grouping of drugs according to their detailed chemical functionality. Consequently, the panel of cell lines has become one of the most important analytical tools for drug discovery.

The methods of the invention can be applied to analyzing drug response in the 60 cell lines of the NCI panel. As disclosed herein, the methods are applicable to determining differential gene expression, which can be correlated with the response of the cells to a particular drug. The methods can be used to identify many differentially expressed genes associated with a drug response. Therefore, an analysis of gene expression in untreated cells in the 60 cell line NCI drug screening panel can be used to determine a profile of gene expression, based on the presence or absence of mRNAs, that correlate with some of the many 10,000's of drugs that have been used on the panel.

Differential gene expression patterns are expected to correlate with drug response. Following identification of such a correlation in 30 of the cell lines, prediction of drug responses in the remaining 30 cell lines can be tested. This strategy circumvents the need to determine extensive expression profiles for all 60 cell lines for every new drug to find genes that correlate with the ability to respond to the drug. This strategy differs from previous methods in that differential expression of the gene after treatment does not need to occur. All that is necessary is that the gene be differentially regulated between cell types prior to treatment.

Each of the 60 cell lines has its characteristic response to drugs, and these responses depend on the cell's phenotype. The response of any cell to any drug depends on which genetic systems are operative in that cell. Once treated, the cell's genetic mechanisms are perturbed, leading to differential gene expression, differential protein modification, and a wide variety of other changes that can be subtle. Nonetheless, it is the ground state genetic pattern or profile of gene expression, before any exposure to drug, that determines how the cell responds to drugs.

The ground state of genetic profile is an important state to characterize for cells, for example, cells of the NCI panel. The ground state of the cell has predictive power for how a given cell will respond to a given drug. Furthermore, the ground state is the only unifying point of reference for the behavior of almost 100,000 different drugs and can be used to determine response to additional drugs.

For example, if two steroids and two alkylating agents are applied to the panel of 60 cell lines, and their growth spectra are compared, the average responses of the cell lines to the steroids tends to be similar, the average responses to the alkylating agents tend to be similar, but a comparison of responses to steroids versus alkylating agents show fewer similarities. This reflects the fact that steroids elicit their effects through naturally existing receptors, whereas alkylating agents elicit their effects by causing widespread damage. The signal transduction pathways for handling steroidal signals versus handling damage are largely different.

When a panel of steroids are used to challenge the 60 cell lines, some of the cells are growth accelerated, some growth inhibited, and some are indifferent to steroids. Much of this data is available on the NCI web site (http://www.nci.nih.gov/). An obvious next step is to examine gene responses to the steroids to see which genes are activated, which are inactivated, and which are indifferent. Each cell type's genes will respond differently, depending on which of about 30 steroid receptor genes are expressed in the cell type before steroid treatment.

The various responses of genes to steroids are cell type-dependent, in large part due to which receptors are present. By comparing the ground state gene expression of the NCI panel of cells, the spectrum of steroid receptor genes expressed in each cell type can be described, thereby explaining what is needed, in genetic terms, for a cell to be responsive to any particular steroid.

The drug-receptor, or hormone-receptor, relationship described above is one example of a correlation that can be drawn between the NCI panel baseline gene expression database and the NCI panel drug response database. Other drug responses can be readily determined. For example, drugs that induce apoptosis also induce gene expression, and different apoptotic responses correlating with cell type can be used to determine gene products that control apoptosis.

It is understood that methods of the invention can be applied to any cell type, in addition to the NCI panel of cells, for characterization of a response to a drug or other stimulus.

The functional overlap between drugs is an important concern in drug discovery. A study of the responses of genes to drugs in different cell types is useful because gene expression determines the response of the cell to the drug. The methods of the invention can therefore be applied to determine the response of one or more cell lines to a particular drug.

The methods can also be applied to characterize the ground state of the NCI panel of cells. The methods described herein can be used to correlate the response of tens of thousands of drugs with genes in the pathways regulated by the drug. The methods of the invention can be applied to determine an expression profile for the >80,000 drugs previously tested with the NCI panel of cells. The methods are applicable to determining coordinate mechanisms of drug action, likely pathways controlling drug activity, pathways that correlate with toxicity, apoptosis and other effects of drugs.

The invention also provides methods for the use of the patterns of gene expression by a panel of different untreated cells or tissues to correlate basal gene expression with susceptibility to a treatment, such as differences in the growth of cells, for example, the NCI panel of cells, in the presence of a drug, pathogen or other stimulus. The methods can be applied to determine genes and pathways that are present prior to treatment and also to correlate treatment with the phenotype induced by the treatment.

To obtain additional information on gene expression, the expression pattern of two different RNA populations from different conditions can be determined (McClelland et al., *Nucleic Acids Res.* 22:4419–4431 (1994); McClelland et al., *Trends Genet.* 11:242–246 (1995)). For example, if interested in apoptosis, using a target from a cell that has been stressed but which has not undergone apoptosis can be used to determine genes responsive to apoptosis, genes responsive to stress, and genes that respond to both. The identification of differentially regulated genes can be used to further characterize transcriptional activity of genes under various conditions. The genes can be further characterized to correlate promoters of regulated genes with signal transduction pathways that respond to a given condition.

When determining differential expression of a nucleic acid molecule, the determination that an RNA sampled in a target is differentially regulated is initially made by comparing differential abundance at two different concentrations of nucleic acid in the target sample. Abundance is determined for the nucleic acid molecules of the target sample for which no difference in abundance is observed at two different concentrations of RNA source. Only those hybridization events that indicate differential expression at both RNA concentrations in both RNA sources are used (see Examples II and III).

For hybridization to an array to determine differential expression, four membranes were used for radioactively labeled target, one for each of two concentrations of RNA for each of the two RNA samples compared (see Examples I to III). If two color fluorescence is used for detecting the target, then two membranes are used, one for each of the two concentrations of starting target sample nucleic acids, because the two targets with different detectable fluorescent markers can be mixed and applied to the same probe. If a subsequent verification step is employed, for example, RT-PCR, one marker can be used for each target sample.

Confirmation of differential expression does not need a full length sequence and can be confirmed using RT-PCR of the known region. In particular, low stringency PCR can be used to generate products a few hundred bases in length (Mathieu-Daude et al., *Mol. Biochem. Parasitol.* 92:15–28 (1998)). This method generates internal "control" PCR products that can be used to confirm the quality of the PCR reaction and the quality and quantity of the RNA used.

The invention additionally provides a profile of five or more stimulus-regulated nucleic acid molecules. As used herein, the term "profile" refers to a group of two or more nucleic acid molecules that are characteristic of a target under a given set of conditions. The invention provides a profile comprising a portion of a nucleotide sequence selected from the group consisting of the nucleotide sequences referenced as SEQ ID NOS:1–45. The profile includes a portion of a nucleotide sequence of the GenBank accession numbers H11520, H11161, H11073, U35048, R48633, H28735, AF019386, H25513, H25514, M13918, H12999, H05639, L49207, H15184, H15124, X79781, H25195, H24377, M31627, H23972, H27350, AB000712, R75916, X85992, R73021, R73022, U66894, H10098, H10045, AF067817, R72714, X52541, H14529, M10277, H27389, D89092, D89678, H05545, J03804, H27969, R73247, U51336, H21777, K00558, and D31765. The profile of the invention includes a portion of the nucleotide sequences encoding TSC-22, fibronectin receptor α-subunit, ray gene, X-box binding protein-1, CPE receptor, epithelium-restricted ets protein ESX and Vav-3.

The invention also provides a target comprising a portion of each of the nucleotide sequences referenced as SEQ ID NOS:1–45. The target includes a portion of a nucleotide sequence of the GenBank accession numbers H11520, H11161 H11073, U35048, R48633, H28735, AF019386, H25513, H25514, M13918, H12999, H05639, L49207, H15184, H15124, X79781, H25195, H24377, M31627, H23972, H27350, AB000712, R75916, X85992, R73021, R73022, U66894, H10098, H10045, AF067817, R72714, X52541, H14529, M10277, H27389, D89092, D89678, H05545, J03804, H27969, R73247, U51336, H21777, K00558, and D31765. The invention also provides a probe comprising a portion of a nucleic acid sequence selected from the group consisting of SEQ ID NOS:1–45.

The invention further provides a substantially pure nucleic acid molecule comprising a nucleic acid sequence selected from the group consisting of SEQ ID NOS:1–45, or a functional fragment thereof, so long as the nucleic acid molecule does not include the exact SEQ ID NOS:1–45.

The invention additionally provides a method of measuring the amount of two or more nucleic acid molecules in a first target relative to a second target. The method includes the step of hybridizing a first amplified nucleic acid target comprising two or more nucleic acid molecules to a probe, wherein the target is amplified from a population of nucleic acid molecules using one or more oligonucleotides, wherein the oligonucleotide hybridizes by chance to a nucleic acid molecule in the population of nucleic acid molecules, wherein the amplification is not based on abundance of nucleic acids in the population of nucleic acid molecules, and wherein the amplified nucleic acids in the target are enhanced for less abundant nucleic acids in the population of nucleic acid molecules. Further included in the method are the steps of detecting the amount of hybridization of the first amplified nucleic acid target to the probe, wherein the amount of hybridization corresponds to an abundance of the nucleic acid molecules in the first target; and comparing the abundance of the nucleic acid molecules in the first target to the abundance of the nucleic acid molecules in a second target, wherein the amplified nucleic acid target comprises a subset of nucleic acids in the initial nucleic acid populations.

The invention further provides a method of measuring the amount of two or more nucleic acid molecules in a first target relative to a second target. The method includes the step of hybridizing a first amplified nucleic acid target comprising 50 or more nucleic acid molecules to a probe, wherein the target is amplified from a population of nucleic acid molecules, wherein the amplification is not based on abundance of nucleic acids in the population of nucleic acid molecules, and wherein the amplified nucleic acids in the target are enhanced for less abundant nucleic acids in the population of nucleic acid molecules. The method further includes the steps of detecting the amount of hybridization of the amplified nucleic acid target to the probe, wherein the amount of hybridization corresponds to an expression level of the nucleic acid molecules in the first target; and comparing the abundance of the nucleic acid molecules in the first target to an abundance of the nucleic acid molecules in a second target, wherein the amplified nucleic acid target comprises a subset of nucleic acids in each nucleic acid population such as an RNA population.

As used herein, the term "hybridizes by chance," when referring to an oligonucleotide, means that hybridization of the oligonucleotide to a complementary sequence is based on the statistical frequency of the complementary sequence occurring in a given nucleic acid molecule. An oligonucleotide that hybridizes by chance is generated by determining the sequence of the oligonucleotide and subsequently determining if the oligonucleotide will hybridize to one or more nucleic acid molecules. The hybridization of such an oligonucleotide is not predetermined by the sequence of a known nucleic acid molecule and therefore occurs by chance. As such, an arbitrary oligonucleotide is considered to hybridize by chance since the oligonucleotides are determined without reference to the exact sequence to be amplified. In contrast, an oligonucleotide that does not hybridize by chance is one that is generated by first analyzing a known sequence and then identifying an exact sequence in the nucleic acid molecule that can be used as an oligonucleotide that will amplify an exact sequence between the oligonucleotides. The hybridization of such an oligonucleotide has been predetermined by the sequence of a known nucleic acid molecule and, therefore, does not occur by chance.

As used herein, the phrase "amplification is not based on abundance" means a target comprises nucleic acid molecules which are representative of the nucleic acid molecules in a population of nucleic acid molecules without regard to the relative amount of individual nucleic acid molecules in the population.

As used herein, the phrase "enhanced for less abundant nucleic acids" means that individual nucleic acid molecules that are less abundant in the population of nucleic acid molecules are amplified so that the amount of these less abundant nucleic acid molecules would be increased relative to the amount of these nucleic acid molecules in the original population of nucleic acid molecules. Thus, the relative proportion of nucleic acid molecules in the population of nucleic acid molecules would not be maintained in the target.

As used herein, the term "single sample" when used in reference to a target means that the target is generated using nucleic acid molecules from a single cell, tissue or organism sample that has not been previously exposed to another sample. For example, if a target was generated from a population of nucleic acid molecules that was determined by the exposure of one sample to another, for example, the subtraction of the nucleic acid molecules of one sample from another, such a target would not be considered as coming from a single sample.

The following examples are intended to illustrate but not limit the present invention.

EXAMPLE I
Generation and Use of Arbitrarily Sampled Targets to Probe a DNA Array This example describes the generation of an arbitrarily sampled target having reduced complexity to probe a DNA array to determine mRNA expression.

A DNA fingerprint was generated using RAP-PCR and was converted to high specific activity probe using random hexamer oligonucleotides (Genosys Biotechnologies; The Woodlands Tex.). Up to 10 µg of PCR product from RAP-PCR was purified using a QIAQUICK PCR Purification Kit (Qiagen, Inc.; Chatsworth Calif.), which removes unincorporated bases, primers, and primer dimers smaller than 40 base pairs. The DNA was recovered in 100 µl of 10 mM Tris, pH 8.3. Random primed synthesis with incorporation of radioactive phosphorus from ($\alpha$-$^{32}$P)dCTP was used under standard conditions. 10% of the recovered fingerprint DNA (10 µl) was combined with 6 µg random hexamer oligonucleotide primer, and 1 µg of one of the fingerprint primers (Genosys) in a total volume of 28 µl, boiled for 3 min, then placed on ice. The hexamer/primer/DNA mix was mixed with 22 µl reaction mix to yield a 50 µl reaction containing a 0.05 mM concentration of three dNTP (dATP, dTTP and dGTP; minus dCTP), 100 µCi of 3000 Ci/mmol ($\alpha$-$^{32}$P) dCTP (10 µl), 1×Klenow fragment buffer (50 mM Tris-HCl, pH 8.0, 10 mM MgCl$_2$, 50 mM NaCl) and 8 U Klenow fragment (3.82 U/µl; Gibco-BRL Life Technologies; Gaithersburg Md.). The reaction was performed at room temperature for 4 hr. For maximum target length, the reaction was chased by adding 1 µl of 2.5 mM dCTP and incubated for 15 min at room temperature followed by an additional 15 min incubation at 37° C. The unincorporated nucleotides and hexamers were removed with the Qiagen Nucleotide Removal Kit (Qiagen) and the purified products were eluted twice in 140 µl 10 mM Tris, pH 8.3.

For hybridization to the array, four membranes were used for radioactively labeled target, one for each of two concentrations of RNA for each of the two RNA samples to be compared. To prepare the cDNA filters (Genome Systems), the filters were prewashed in three changes of 2×SSC and 0.1% sodium dodecyl sulfate (SDS) in a horizontally shaking flat bottom container to reduce the residual bacterial debris. 20×SSC contains 3 M NaCl, 0.3 M Na$_3$citrate-2H$_2$O, pH 7.0. The first wash was carried out in 500 ml for 10 min at room temperature. The second and third washes were carried out in 1 liter of prewarmed (50° C.) prewash solution for 10 min each.

For prehybridization, the filters were transferred to roller bottles and prehybridized in 60 ml prewarmed (42° C.) prehybridization solution containing 6×SSC, 5×Denhardt's reagent, 0.5% SDS, 100 µg/ml fragmented, denatured salmon sperm DNA (Pharmacia; Piscataway N.J.) and 50% formamide (Aldrich; Milwaukee Wis.) for 1–2 hr at 42° C. 50×Denhardt's solution contains 1% Ficoll, 1% polyvinylpyrrolidone and 1% bovine serum albumin, sterile filtered.

For hybridization, the prehybridization solution was removed and 7 ml prewarmed (42° C.) hybridization solution, containing 6×SSC, 0.5% SDS, 100 µg/ml fragmented, denatured salmon sperm DNA and 50% formamide, was added. To decrease the background hybridization due to repeated sequences such as Alu repeats, long interspersed repetitive elements (LINE) or centromeric DNA repeats, sheared human genomic DNA (1 µg/ml stock concentration) was denatured in a boiling water bath for 10 min and immediately added to the hybridization solution to a final concentration of 10 µg/ml. Simultaneously, the labeled target (280 µl) was denatured in a boiling water bath for 4 min and immediately added to the hybridization solution. Hybridization was carried out at 42° C. for 2 to 48 hrs, typically 18 hr, in a hybridization oven using roller bottles or sealed in a plastic bag and incubated in a water bath.

For the washes, the temperature was set to 55° C. in the incubator oven (Techne HB-1D; VWR Scientific; San Francisco Calif.). The hybridization solution was poured off and the membrane was washed twice with 50 ml 2×SSC and 0.1% SDS for 5 min at room temperature. The membrane was then washed with 100 ml 0.1×SSC and 0.1% SDS and incubated for 10 min at room temperature. For the further washes, the wash solution, containing 0.1×SSC and 0.1% SDS, was prewarmed to 50° C. and the filter was washed for 40 min in a roller bottle with 100 ml wash solution. The filter was then transferred to a horizontally shaking flat bottom container and washed in 1 liter of the wash solution for 20 min under gentle agitation. The filter was transferred back to a roller bottle containing 100 ml prewarmed 0.1×SSC and 0.1% SDS and incubated for 1 hr. The final wash solution was removed and the filter briefly rinsed in 2×SSC at room temperature.

After washing, the membranes were lightly dried with 3 MM paper and the slightly moist membranes were wrapped in SARAN wrap. The membranes were exposed to X-ray film.

FIG. 1 shows differential hybridization to clone arrays. All four images show a closeup of an autoradiogram for the same part of a larger membrane. Each image spans about 4000 double spotted *E. coli* colonies, each carrying a different EST clone. Panel A shows hybridization of 1 µg of polyA$^+$ RNA from confluent human keratinocytes that was radiolabeled during reverse transcription. About 500 clearly hybridizing clones can be seen. Panels B and C show RAP-PCR fingerprints with a pair of arbitrary primers that was performed on cDNA from oligo(dT) primed cDNA of confluent human keratinocytes that were untreated (Panel B) or treated with EGF (Panel C). The pattern of hybridizing genes was almost identical in Panels B and C, but entirely different from that seen with total polyA+RNA (compare to Panel A). The two radiolabeled colonies from one differentially expressed cDNA are indicated with an arrow. Differential expression of this gene was subsequently confirmed by specific RT-PCR (Trenkle et al., *Nucl. Acids Res.* 26:3883–3891 (1998)).

Figure 1D:
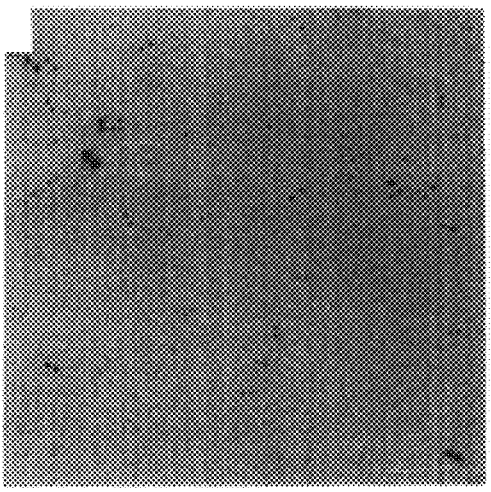

FIG. 1D shows a RAP-PCR fingerprint with a different pair of arbitrary primers that was performed on RNA from confluent human keratinocytes. This pattern of hybridization is almost entirely different from that found with the previous primer pair (Panel B) and with mRNA (Panel A), with very few overlapping spots between Panel D and Panels A and B.

These results demonstrate that arbitrarily sampled targets, which have reduced complexity, allow detection of mRNAs that are not detectable using total message as a target. Thus, unlike a total message target, which detects mRNAs based on their abundance, an arbitrarily sampled target can be used to detect less abundant mRNAs.

EXAMPLE II
An Arbitrarily Sampled Target Generated by RT-PCR Detects Genes Differentially Expressed in Response to EGF This example describes the use of RT-PCR with arbitrary primers to generate an arbitrarily sampled target for detecting differential gene expression upon treatment of cells with EGF.

An arbitrarily sampled target generated by RT-PCR was used to probe arrays for differential gene expression (Trenkle et al., *Nucleic Acids Res.* 26:3883–3891 (1998)). For RNA preparation, the immortal human keratinocyte cell line HaCaT (Boukamp et al., *Genes Chromosomes Cancer* 19:201–214 (1997)) was grown to confluence and maintained at confluence for two days. The media, DMEM containing 10% fetal bovine serum (FBS) and penicillin/streptomycin was changed one day prior to experiments. EGF (Gibco-BRL) was added at 20 ng/ml, or TGF-β (R&D Systems; Minneapolis Minn.) was added at 5 ng/ml. Treated and untreated cells were harvested after four hours by scraping the petri dishes in the presence of lysis buffer (RLT buffer; Qiagen) and homogenized through Qiashredder columns (Qiagen). On average, 7×10⁶ cells, grown to confluency in a 100 mm diameter petri dish, yielded 40 μg of total RNA from the RNEASY total RNA purification kit (Qiagen). RNA, in 20 mM Tris, 10 mM MgCl$_2$ buffer, pH 8 was incubated with 0.08 U/μl of RNase free DNase and 0.32 U/μl of RNase inhibitor (both from Boehringer Mannheim Biochemicals; Indianapolis Ind.) for 40 min at 37° C. and cleaned again using the RNEASY kit, which is important for removing small amounts of genomic DNA that can contribute to the fingerprints. RNA quantity was measured by spectrophotometry, and RNA samples were adjusted to 400 ng/μl in water. RNA samples were checked for quality and concentration by agarose gel electrophoresis and stored at −20° C.

For RNA fingerprinting, RAP-PCR was performed using standard protocols (McClelland et al., supra, 1994; Reverse transcription was performed on total RNA using four concentrations per sample (1000, 500, 250 and 125 ng per reaction) and a oligo d(T) primer (15-mer) (Genosys). RNA (5 μl) was mixed with 5 μl of buffer for a 10 μl final reaction volume containing 50 mM Tris, pH 8.3, 75 mM KCl, 3 mM MgCl$_2$, 20 mM dithiothreitol (DTT), 0.2 mM of each dNTP, 0.5 μM of primer, and 20 U of MuLV-reverse transcriptase (Promega; Madison Wis.). RNA samples are checked for DNA contaminants by including a reverse transcriptase-free control in initial RAP-PCR experiments. The reaction was performed at 37° C. for 1 hr, after a 5 min ramp from 25° C. to 37° C. The enzyme was inactivated by heating the samples at 94° C. for 5 min, and the newly synthesized cDNA was diluted 4-fold in water.

PCR was performed after the addition of a pair of two different 10- or 11-mer oligonucleotide primers of arbitrary sequence; pair A: GP14 (GTAGCCCAGC; SEQ ID NO:46) plus GP16 (GCCACCCAGA; SEQ ID NO:47), pair B: Nucl+(ACGAAGAAGAAGAG; SEQ ID NO:48) plus OPN24 (AGGGGCACCA; SEQ ID NO:49). In general, there are no particular constraints on the primers except that they contain at least a few C or G bases, that the 3' ends are not complementary with themselves or the other primer in the reaction, to avoid primer dimers, and that primer sets are chosen that are different in sequence so that the same parts of mRNA are not amplified in different fingerprints.

Diluted cDNAs (10 μl) were mixed with the same volume of 2×PCR mixture containing 20 mM Tris, pH 8.3, 20 mM KCl, 6.25 mM MgCl$_2$, 0.35 mM of each dNTP, 2 μM of each oligonucleotide primer, 2 μCi α-($^{32}$P)-dCTP (ICN; Irvine Calif.) and 5 U AMPLITAQ DNA polymerase Stoffel fragment, (Perkin-Elmer-Cetus; Norwalk Conn.) for a 20 μl final reaction volume. Thermocycling was performed using 35 cycles of 94° C. for 1 min, 35° C. for 1 min and 72° C. for 2 min.

A 3.5 μl aliquot of the amplification products was mixed with 9 μl of formamide dye solution, denatured at 85° C. for 4 min, and chilled on ice. 2.4 μl was loaded onto a 5% polyacrylamide, 43% urea gel prepared with 1×TBE buffer containing 0.09 M Tris-borate, 0.002 M ethylene diamine tetraacetic acid (EDTA). The PCR products resulting from the four different concentrations of the same RNA template were loaded side by side on the gel.

Electrophoresis was performed at 1,700 V or at a constant power of 50–70 Watts until the xylene cyanol tracking dye reached the bottom of the gel (approximately 4 h). The gel was dried under vacuum and placed on Kodak BioMax X-Ray film for 16 to 48 hours.

For labeling of RAP-PCR products for use as targets to probe arrays, up to 10 μg of PCR product from RAP-PCR was purified using a QIAQUICK PCR Purification Kit (QIAGEN) which removes unincorporated bases, primers, and primer dimers under 40 base pairs. The DNA was recovered in 50 μl of 10 mM Tris, pH 8.3.

Random primed synthesis with incorporation of α-($^{32}$P)-dCTP was performed essentially as described in Example I. Briefly, 10% of the recovered fingerprint DNA, typically about 100 ng in 5 μl, was combined with 3 μg random hexamer oligonucleotide primer and 0.3 μg of each of the fingerprint primers in a total volume of 14 μl, which was boiled for 3 min and then placed on ice.

The hexamer/primer/DNA mix was mixed with 11 μl reaction mix to yield a 25 μl reaction containing 0.05 mM of three dNTP (minus dCTP), 50 μCi of 3000 Ci/mmol α-($^{32}$P)-dCTP (5 μl), 1×Klenow fragment buffer, containing 50 mM Tris-HCl, 10 mM MgCl$_2$, 50 mM NaCl, pH 8.0, and 4 U Klenow fragment (Gibco-BRL). The reaction was performed at room temperature for 4 hrs. For maximum target length, the reaction was chased by adding 1 μl of 1.25 mM dCTP and incubated for 15 min at 25° C., followed by an additional 15 min incubation at 37° C. The unincorporated nucleotides, hexamers and primers were removed with the Qiagen Nucleotide Removal Kit (Qiagen) and the purified products were eluted using two aliquots of 140 μl of 10 mM Tris, pH 8.3.

For labeling of poly(A)⁺ mRNA and genomic DNA for use as a target, random hexamers were used to label poly (A)⁺-selected mRNA and genomic DNA. Genomic DNA (150 ng) was labeled using the same protocol used for labeling the RAP-PCR products described above. Poly(A)⁺ mRNA (1 μg) and 9 μg random hexamer in a volume of 27 μl were incubated at 70° C. for 2 min and chilled on ice. The RNA/hexamer mix was mixed with 23 μl master mix, which contained 10 μl 5×AMV reaction buffer, containing 250 mM Tris-HCl, pH 8.5, 40 mM MgCl$_2$, 150 mM KCl, 5 mM DTT, 1 μl three dNTP, each 33 mM (dATP, dTTP, dGTP; minus dCTP), 2 μl AMV reverse transcriptase (20 units; Boehringer Mannheim) and 10 μl 3000 Ci/mmol α-($^{32}$P)-dCTP in a final volume of 50 μl. The reaction was incubated at room temperature for 15 min, ramped for 1 hour to 47° C., held at 47° C. for 1 hr, and chased with 1 μl of 33 mM dCTP for another 30 min at 47° C. The labeled products were purified as described above.

For hybridization to the array, four membranes were used, one membrane for each of two concentrations of RNA for each of the two RNA samples to be compared. The cDNA filters (Genome Systems) were washed in three changes of 2×SSC and 0.1% SDS in a horizontally shaking flat bottom container to reduce the residual bacterial debris. The first wash was carried out in 500 ml for 10 min at room temperature. The second and third washes were carried out in 1 liter of prewash solution, prewarmed to 55° C., for 10 min each wash.

For prehybridization, the filters were transferred to roller bottles and prehybridized in 60 ml prehybridization solution, prewarmed to 42° C., containing 6×SSC, 5×Denhardt's reagent, 0.5% SDS, 100 μg/ml fragmented, denatured salmon sperm DNA, and 50% formamide for 1–2 hrs at 42° C. in a hybridization oven.

For hybridization, the prehybridization solution was removed and 7 ml hybridization solution, prewarmed to 42° C., containing 6×SSC, 0.5% SDS, 100 μg/ml fragmented, denatured salmon sperm DNA, and 50% formamide, was added. To decrease the background hybridization due to repeats such as Alu and Line elements, sheared human genomic DNA was denatured in a boiling water bath for 10 min and immediately added to the hybridization solution to a final concentration of 10 μg/ml. 10 ng/ml poly(dA) was added to block oligo d(T) stretches in the radiolabeled target. Simultaneously, the labeled target, in a total volume of 280 μl, was denatured in a boiling water bath for 4 min and immediately added to the hybridization solution. The hybridization was carried out at 42° C. for 2–48 hrs, typically 18 hrs, in large roller bottles.

For the washes, the incubator oven temperature was set to 68° C. The hybridization solution was poured off and the membrane was washed twice with 50 ml 2×SSC and 0.1% SDS at room temperature for 5 min. The wash solution was then replaced with 100 ml 0.1×SSC and 0.1% SDS and incubated for 10 min at room temperature. For the further washes, the wash solution, containing 0.1×SSC and 0.1% SDS, was prewarmed to 68° C. The membranes were incubated 40 min in 100 ml of wash solution in the roller bottles, then the filters were transferred to horizontally shaking flat bottom containers and washed in 1 liter for 20 min under gentle agitation. The filters were transferred back to the roller bottles containing 100 ml 0.1×SSC and 0.1% SDS, prewarmed to 68° C., and incubated for 1 hr. The final wash solution was removed and the filters are briefly rinsed in 2×SSC at room temperature.

After washing, the membranes were blotted with 3 MM paper, wrapped in SARAN wrap while moist, and exposed to X-ray film. The membranes were usually sufficiently radioactive that a one-day exposure with a screen revealed the top 1000 products on an array of 18,432 bacterial colonies carrying EST clones. Weaker targets or fainter hybridization events were visualized using an intensifying screen at −70° C. for a few days.

For confirmation of differential expression, low stringency RT-PCR was used. The initial confirmation of differential expression was the use of two RNA concentrations per sample. Only those hybridization events that indicated differential expression at both RNA concentrations in both RNA samples were relied upon.

More than 70% of the I.M.A.G.E. consortium clones have single pass sequence reads from the 5' or 3' end, or both, deposited in the GenBank database. In cases where there is no prior sequence information available, the clones can be ordered from Genome Systems and sequenced. Sequences were used to derive PCR primers of 18 to 25 bases in length using MacVector 6.0 (Oxford Molecular Group; Oxford UK). Generally, primers were chosen to generate PCR products of 50 to 250 base pairs and have melting temperatures of at least 60° C.

Reverse transcription was performed under the same conditions as in the RAP-PCR protocol described above, using an oligo-d(T) primer or a mixture of random 9-mer primers (Genosys). The PCR reaction was performed using the two pairs of specific primers described below (18 to 25-mers). The PCR conditions were the same as in the RAP-PCR fingerprint protocol except that 1.5 μM of each primer was used. A low stringency thermal profile was used: 94° C. for 40 sec, 47° C. for 40 sec, and 72° C. for 1 min, for 19, 22 and 25 cycles in three separate reaction tubes. The reactions were carried out in three sets of tubes at different cycle numbers because the abundance of the transcripts, the performance of the primer pairs, and the amplifiability of the PCR products can vary. PCR products were run under the same conditions as above on a 5% polyacrylamide and 43% urea gel. The gel was dried and exposed to X-ray film for 18 to 72 hours. Invariance among the other arbitrary products in the fingerprint was used as an internal control to indicate the reliability of the relative quantitation.

Primer pairs (Genosys) were used for confirmation of differential expression. For GenBank accession number H11520 (90 nucleotide product); primer A, AATGAGGGG-GACAAATGGGAAGC (SEQ ID NO:50); primer B, GGAGAGCCCTTCCTCAGACATGAAG (SEQ ID NO:51). For TSC-22 gene (GenBank accession numbers U35048, H11073, H11161; 179 nucleotide product); primer A, TGACAAAATGGTGACAGGTAGCTGG (SEQ ID NO:52); primer B, AAGTCCACACCTCCTCAGACAGCC (SEQ ID NO:53). For GenBank accession number R48633 (178 nucleotide product); primer A, CCCAGACAC-CCAAACAGCCGTG (SEQ ID NO:54); primer B, TGGAGCAGCCGTGTGTGCTG (SEQ ID NO:55).

The array analyzed contains 18,432 *E. coli* colonies, each carrying a different I.M.A.G.E. consortium EST plasmid (www-bio.llnl.gov/bbrp/image/image.html), spotted twice on a 22×22 cm membrane (Genome Systems). The Genome Systems arrays are advantageous in that they contain by far the largest number of ESTs per. unit cost. RNA fingerprinting for target preparation.

RAP-PCR amplifications were performed to look for differential gene expression in keratinocytes (HaCaT) when treated with EGF or TGF-β for four hours (Boukamp et al., supra, 1997). These experiments were designed to detect genes differentially regulated by EGF and TGF-β treatment in confluent keratinocytes. Using RAP-PCR, about 1% of the genes in normal or immortal keratinocytes responded to EGF, and fewer responded to TGF-β in this time frame.

Shown in FIG. 2 are RAP-PCR fingerprints of RNA from confluent keratinocytes treated with TGF-β or EGF using multiple RNA concentrations and two sets of arbitrarily chosen primers. Reverse transcription was performed with an oligo-dT primer on 250, 125, 62.5 and 31.25 ng RNA in lanes 1, 2, 3, and 4, respectively. RNA was from untreated, TGF-β treated or EGF treated HaCaT cells, as indicated. RAP-PCR was performed with two sets of primers, GP14 and GP16 (Panel A) or Nucl+and OPN24 (Panel B). The sizes of the two differentially amplified RAP-PCR products are indicated with arrows (317 and 291 nucleotides).

Figure 2A:
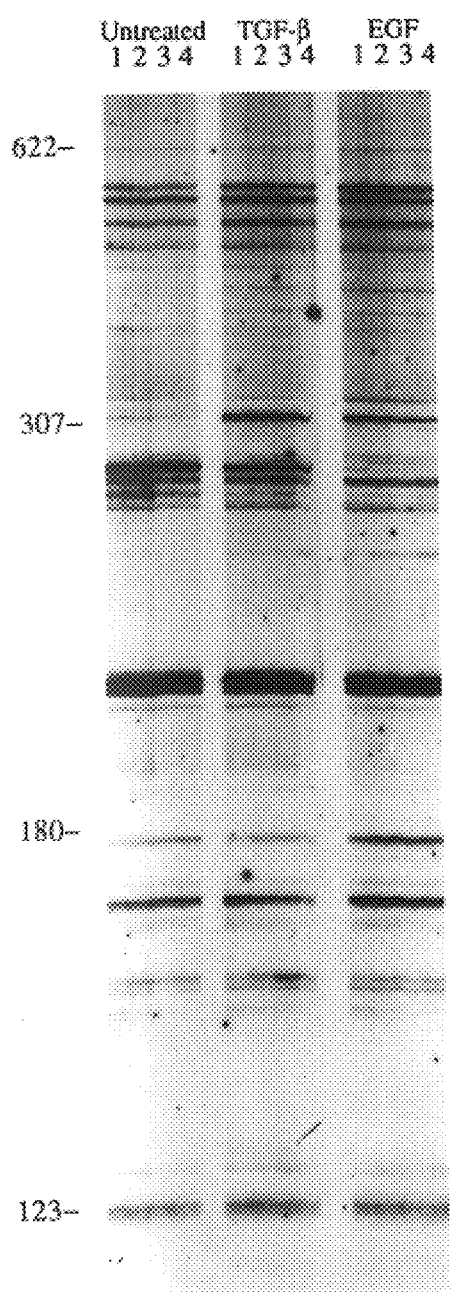
FIG. 2 shows RAP-PCR fingerprints resolved on a polyacrylamide-urea gel. Reverse transcription was performed with an oligo-dT primer on 250, 125, 62.5 and 31.25 ng RNA in lanes 1, 2, 3, and 4 respectively. RNA was from untreated, TGF-$\beta$ and EGF treated HaCaT cells, as indicated. RAP-PCR was performed with two sets of primers, primers GP14 and GP16 (Panel A) or Nucl+ and OPN24 (Panel B). Molecular weight markers are indicated on the left of each panel, and the sizes of the two differentially amplified RAP-PCR-products are indicated with arrows (317 and 291).
Figure 2B:
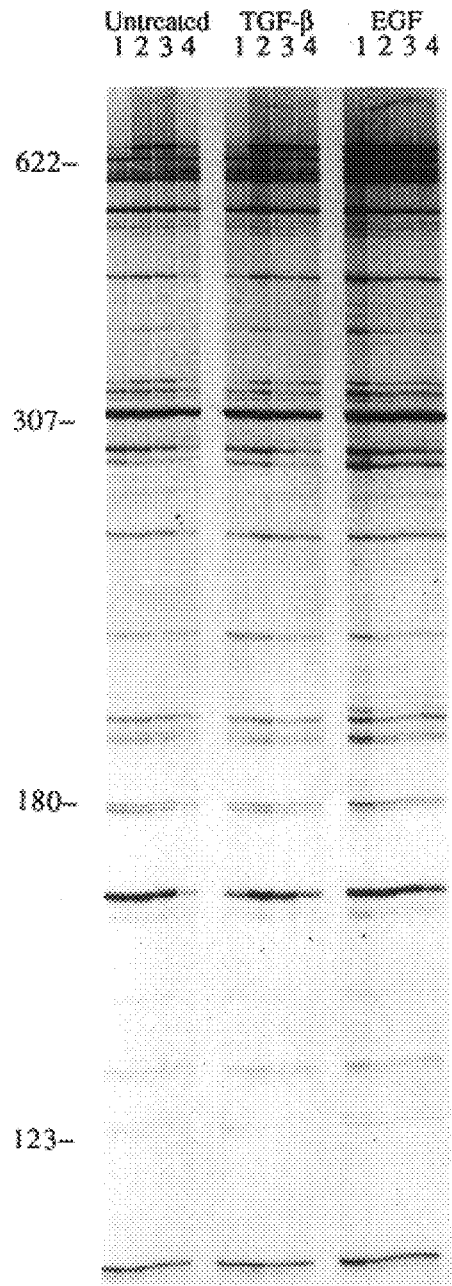

In the first fingerprint shown in FIG. 2A, two differentially regulated products were detected, which were cloned and sequenced. The sizes of these two products, 291 and 317 nucleotides, are indicated with arrows (see FIG. 2A). The Genome Systems arrays used were chosen based on the presence of these two clones. This fingerprint was used to demonstrate that differentially regulated genes in an array can be identified without isolating, cloning and sequencing the RAP-PCR products. The fingerprint shown in FIG. 2A and the second fingerprint shown in FIG. 2B, which displayed no differential regulation in response to the treatments, were also used to demonstrate that fainter differentially regulated products not visible on the fingerprint gel could, nevertheless, be observed by the array approach.

The results obtained were highly reproducible. Using gel electrophoresis, there were no differences among the ~100 bands visible in any of the fingerprints from a single treatment condition performed at different RNA concentrations (see FIG. 2). Similarly, more than 99% of the top 1000 clones hybridized by the targets derived from the fingerprint in FIG. 2A were visible at both input RNA concentrations. Furthermore, more than 98% of the products were the same between the two treatment conditions, plus and minus EGF, at a single RNA concentration. These results indicated high reproducibility among the top 1000 PCR products in the RAP-PCR amplification.

The untreated control and EGF-treated samples were further characterized. RAP-PCR fingerprints shown in FIG. 2 were converted into high specific activity radioactive targets by random primed synthesis using $\alpha$-($^{32}$P) -dCTP as described above. For each of the two conditions, EGF treated and untreated, fingerprints generated from RNA at two different concentrations were converted to target by random primed synthesis for each of the two different fingerprinting primer pairs. These radioactively labeled fingerprint targets were then used to probe by hybridizing to a set of identical arrays each containing 18,432 I.M.A.G.E. consortium cDNA clones. As controls, total genomic DNA and total poly(A)$^+$ mRNA were also labeled by random priming, as described above, and used as targets on identical arrays.

The RAP-PCR fingerprint targets, the total mRNA target and the genomic target were hybridized individually against replicates of a Genome Systems colony array. Genomic DNA was used as a blocking agent and as a competitor for highly repetitive sequences. Washing at 68° C. in 0.1×SSC and 0.1% SDS removed virtually all hybridization to known Alu elements on the membrane, presumably because Alu elements are sufficiently diverged from each other at this wash stringency.

Shown in FIG. 3 are autoradiograms from the same half of each membrane. All images presented are autoradiograms of the bottom half of duplicates of the same filter (Genome Systems) probed by hybridization with radiolabeled DNA. Panels A and B show hybridization of two RAP-PCR reactions generated using the same primers (GP14 and GP16) and derived from untreated (Panel A) or EGF treated (Panel B) HaCaT cells. Three double-spotted clones that show differential hybridization signals are marked on each array. The GenBank Accession numbers of the clone and the corresponding genes are H10045 and H10098, corresponding to vav-3 and AF067817 (square)(Katzav et al., *EMBO J.* 8:2283–2290 (1989); H28735, gene unknown, similar to heparan sulfate 3-O-sulfotransferase-1, AF019386 (circle) (Shworak et al., *J. Biol. Chem.* 272:28008–28019 (1997); and R48633, gene unknown (diamond).

FIG. 3 shows the results of hybridization of targets from these fingerprints to the arrays. As shown in FIGS. 3A and 3B, arrayed clones corresponding to the 291 nucleotide (vav-3, marked by square) and 317 nucleotide (similar to heparin sulfate N-sulfotransferase (N-HSST), marked by circle) RAP-PCR fragments are indicated. The sequences of these RAP-PCR fragments were determined. Also indicated on this array is a differentially regulated gene that could not be visualized on the original fingerprint gel (marked by diamond).

Figure 3A:
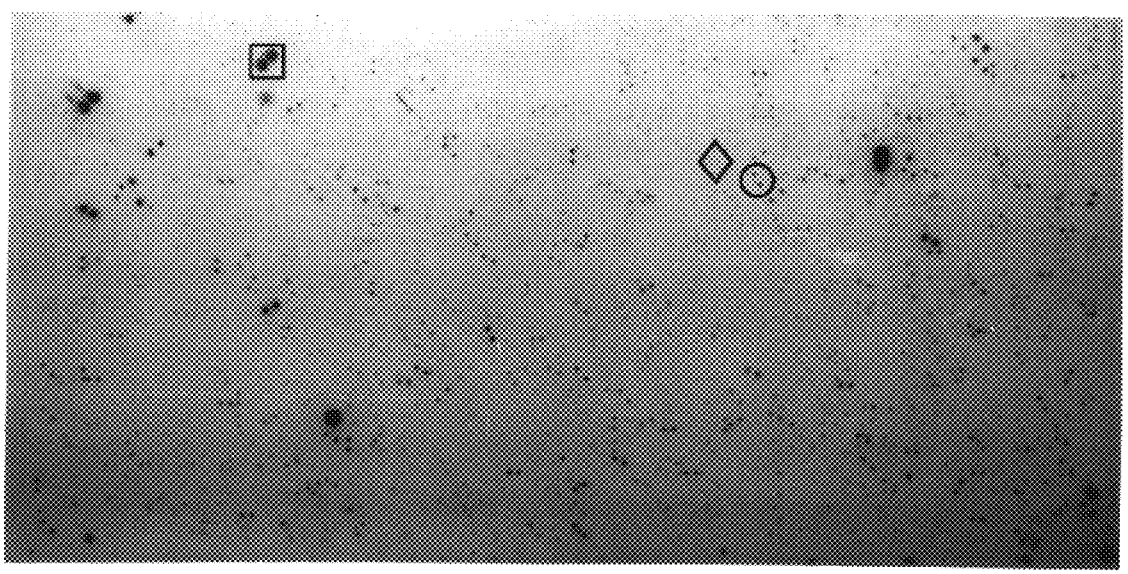
FIG. 3 shows hybridization of targets generated by RAP-PCR to arrays. Shown are autoradiograms of the bottom half of duplicates of the same filter (Genome Systems) hybridized with radiolabeled DNA. Panels A and B show hybridization of two RAP-PCR reactions generated using the same primers and derived from untreated (Panel A) and EGF treated (Panel B) HaCaT cells. Three double-spotted clones that show differential hybridization signals are marked on each array. The GenBank accession numbers of the clone and the corresponding genes are H10045 and H10098, corresponding to vav-3 and AF067817 (square); H28735, gene unknown, similar to $heparan sulfate 3-O-sulfotransferase-1, AF019386 (circle); R48633, gene unknown (diamond). Panel C shows an array hybridized with a RAP-PCR target generated using the same RNA as in panel A but with a different pair of primers. Panel D shows an array hybridized with cDNA target generated by reverse transcription of 1 μg poly(A)+-selected mRNA. Panel E shows an array hybridized with human genomic DNA labeled using random priming.
Figure 3B:
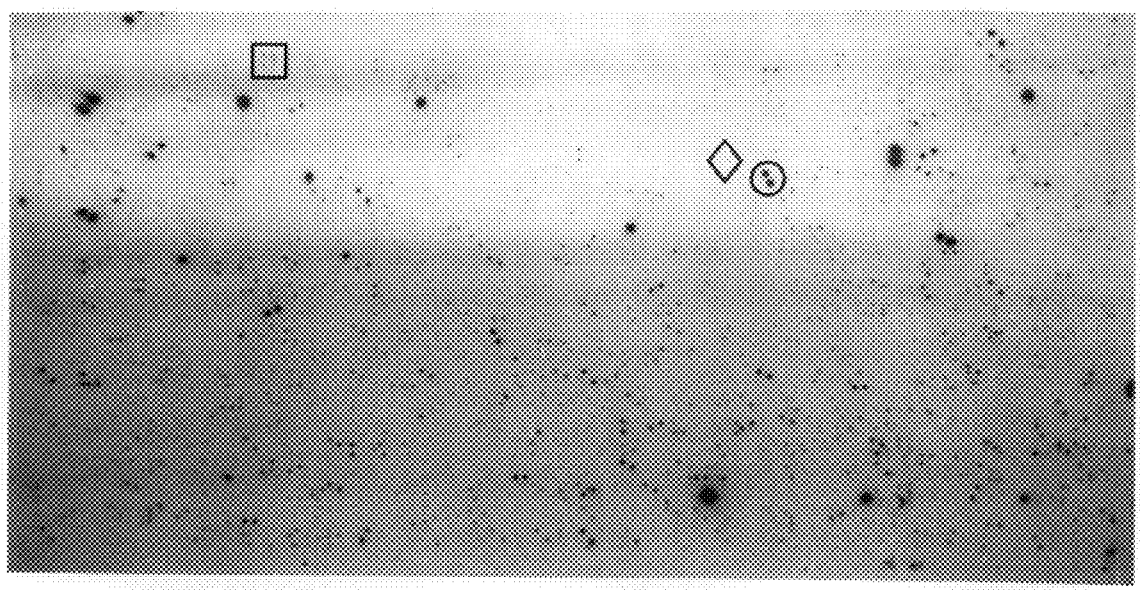

Comparing FIGS. 3A and 3B, a more than 10-fold down-regulation was observed for vav-3 upon treatment with EGF. The gene corresponding to H28735 was up-regulated more than 10-fold with EGF treatment. The gene corresponding to R48633 was up-regulated about 3-fold with EGF treatment. These changes in gene expression in response to EGF were independently confirmed by RT-PCR.

These results indicate that RAP-PCR samples a population of mRNAs largely independently of message abundance. This is because the low abundance class of messages has much higher complexity than the abundant class, making it more likely that the arbitrary primers will find good matches. Unlike differential display, RAP-PCR demands two such arbitrary priming events, possibly biasing RAP-PCR toward the complex class. Overall, these data suggest that the majority of the mRNA population in a cell (<20,000 mRNAs) can be found in as few as ten RAP-PCR fingerprints. This result indicates that differential gene regulation can be detected by the combined fingerprinting and array approach even when the event cannot be detected using the standard gel electrophoresis approach.

Figure 3C:
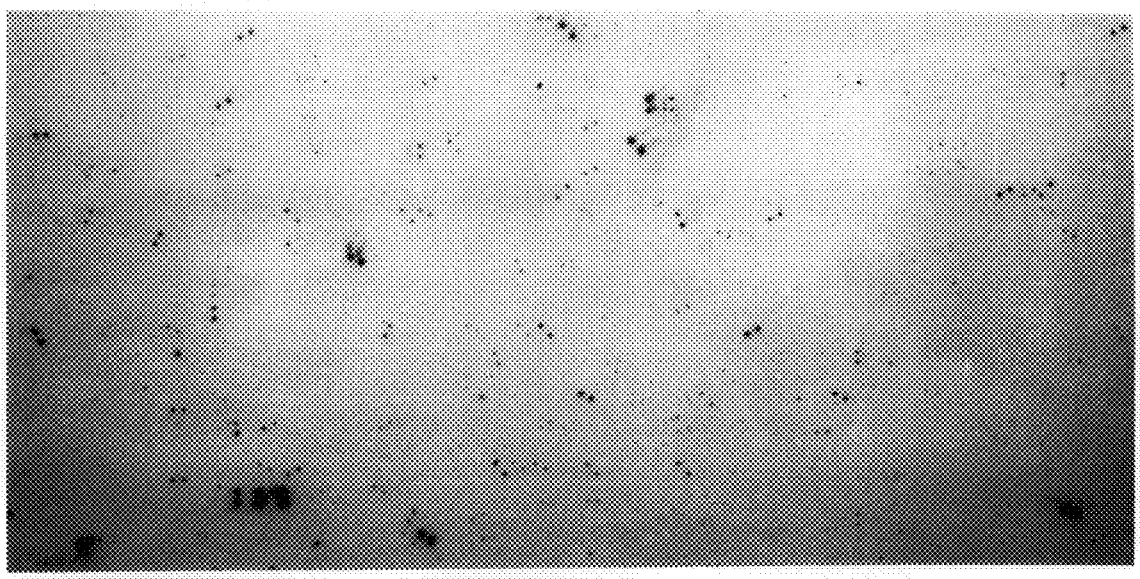
Figure 3D:
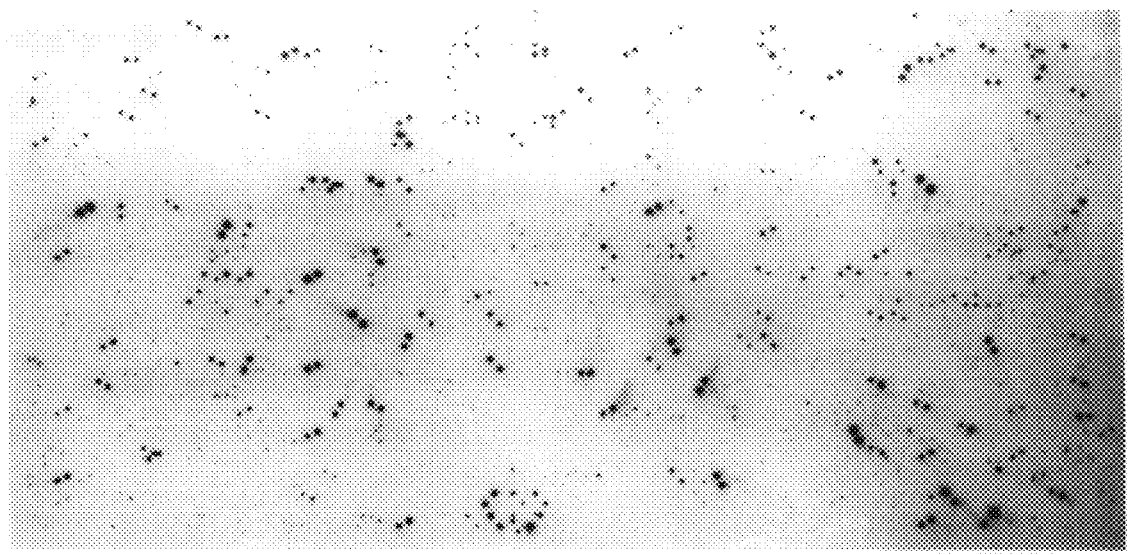
Figure 3E:
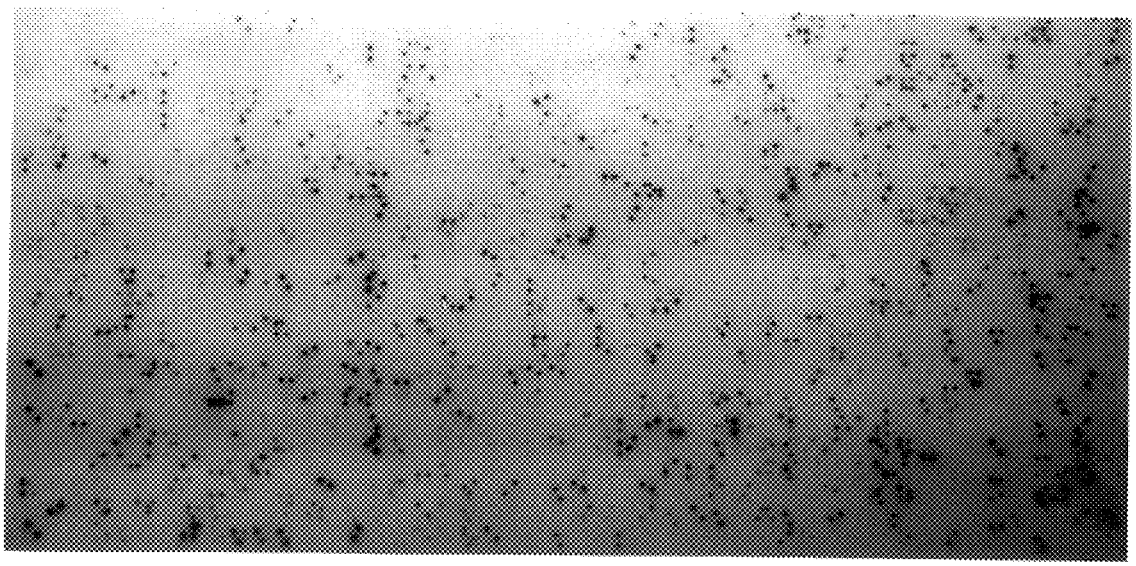

FIG. 3C shows an array hybridized with a RAP-PCR target using the same RNA as in panel A but with a different pair of primers, Nucl+ and OPN24. As shown in FIG. 3C, using a different set of primers yields an entirely different pattern of hybridizing genes. FIG. 3D shows an array hybridized with a cDNA generated by reverse transcription of 1 $\mu$g poly (A)$^+$-selected mRNA. FIG. 3E shows an array hybridized with human genomic DNA labeled using random priming.

The data were analyzed in a number of ways. First, estimates were made of the overlap between the clones hybridized by each target. In all pairwise comparisons between all of the different types of targets, there was less than 5% overlap among the 500 clones that hybridized most intensely (compare FIGS. 3A, 3B, 3D, and 3E). Of the top 500 clones hybridized by the genomic target, which included nearly all clones known to contain the Alu repeats, less than 5% overlapped with the top 500 clones hybridized by the fingerprint targets or the total poly(A)$^+$ mRNA target. This indicated that, except for the case of a genomic target, there was no significant hybridization to dispersed repeats. The overlap among the clones hybridized by the two RAP-PCR fingerprints generated with different primers was less than 3%, and the overlaps of either fingerprint with the poly(A)$^+$ mRNA target were both less than 3%. Thus, most of the cDNAs detected using a target from the fingerprints could not be detected using the total mRNA target. These results indicate that RAP-PCR samples a population of mRNAs largely independently of message abundance. This is because the low abundance class of messages has much higher complexity than the abundant class, making it more likely that the arbitrary primers will find good matches. Unlike differential display, RAP-PCR demands two such arbitrary priming events, possibly biasing RAP-PCR toward the complex class. Overall, these data suggest that the majority of the mRNA population in a cell (<20,000 mRNAs) can be found in as few as ten RAP-PCR fingerprints.

A total of 30 differentially hybridizing cDNA clones were detected among about 2000 hybridizing colonies using targets derived from both sets of arbitrary primers (FIG. 2) at a threshold of about three-fold differential hybridization. Twenty-two of these differentially hybridizing clones displayed differential hybridization at both RNA concentrations. These 22 were further characterized by RT-PCR. Differentially expressed genes exhibiting greater than a two-fold difference in expression in response to EGF treatment are shown in Table 1. For the results shown in Table 1, differential expression was confirmed by low stringency RT-PCR. The left column gives the accession numbers of the EST clones (5' or 3', or both when available). The right column gives the corresponding gene or the closest homolog. In cases of very low homologies, the gene is considered unknown. The cutoff for homology was p<e-20 in tblastx.

TABLE 1

Genes Regulated More than Two-fold After EGF Treatment of HaCaT Keratinocytes.

| Accession number | | | Gene name |
|---|---|---|---|
| Up-regulated | | | |
| H11520 | (3') | | unknown |
| H11161 | (5')/H11073 | (3') | TSC-22 (U35048) |
| R48633 | (5') | | unknown |
| H28735 | (3') | | similar to heparan sulfate 3-O-sulfotransferase-1 precursor (AF019386) |
| H25513 | (5')/H25514 | (3') | Fibronectin receptor α-subunit (M13918) |
| H12999 | (5')/H05639 | (3') | similar to Focal adhesion kinase (FAK2) (L49207) |
| H15184 | (5')/H15124 | (3') | ray gene (X79781) |
| H25195 | (5')/H24377 | (3') | X-box binding protein-1 (XBP-1) (M31627) |
| H23972 | ('') | | unknown |
| H27350 | (5') | | CPE-receptor (hCPE-R) (AB000712) |
| R75916 | (5') | | similar to semaphorin C (X85992) |
| Down-regulated | | | |
| R73021 | (5')/R73022 | (3') | epithelium-restricted Ets protein ESX (U66894) |
| H10098 | (5')/H10045 | (3') | vav-3 (AF067817) |

The eight false-positive clones that appeared to be regulated at only one concentration were further characterized. Of these eight, five false-positive clones showed differential hybridization at one concentration but were present and not regulated on the membranes for the other concentration. The most likely source of this type of false-positive is the membranes. Although each clone is spotted twice, it is possible that occasionally one membrane received substantially more, or less, DNA in both spots than the other three membranes for these clones. However, this potential difference was easily detected and is rare, occurring only five times in over 2000 clones. The other three false-positive clones hybridized under only one treatment condition and at only one RNA concentration used for RAP-PCR. These three false-positive clones could be differentially expressed genes or could be false-positives from variable PCR products. However, the number of false positives was very low and were easily identified by comparing the results of two targets derived from PCR of different starting concentrations of RNA.

Differential expression was confirmed using low stringency RT-PCR. Only those hybridization events that indicated differential expression at both input RNA concentrations were further characterized. For confirmation of differential expression, RT-PCR was used with specific targets rather than Northern blots, which are much less sensitive than RT-PCR, because it was expected that many of the mRNAs would be rare and in low abundance. One of the advantages of using the arrays from the I.M.A.G.E. consortium is that more than 70% of the clones have single pass sequence reads from the 5' or 3' end, or both, deposited in the GenBank database.

Clones for which some sequence is available in the database were chosen for further characterization. Five of the 22 ESTs representing differentially regulated genes on the array had not been sequenced and two of the remaining 17 ESTs were from the same gene. The remaining 15 unique sequenced genes were aligned with other sequences in the database in order to derive a higher quality sequence from multiple reads and longer sequence from overlapping clones. The UniGene database clusters human and mouse ESTs that appear to be from the same gene (Schuler, *J. Mol. Med.* 75:694–698 (1997)). This database greatly aids in the process of assembling a composite sequence from different clones of the same mRNA (http://www.ncbi.nlm.nih.gov/UniGene/index.html). These composite sequences were then used to choose primers for RT-PCR.

For each gene, two specific primers were used in RT-PCR under low stringency conditions similar to those used to generate RAP-PCR fingerprints. In addition to the product of interest, a pattern of arbitrary products was generated, which is largely invariant and behaves as an internal control for RNA quality and quantity, and for reverse transcription efficiency (Mathieu-Daude et al., supra, 1998). The number of PCR cycles was adjusted to between 14 to 25 cycles, according to the abundance of the product, in order to preserve the differences in starting template mRNA abundances. This is necessary because rehybridization of abundant products during the PCR inhibits their amplification, and the difference in product abundances diminishes as the number of PCR cycles increases (Mathieu-Daude et al., *Nucleic Acids Res.* 24:2080–2086 (1996)).

Low stringency RT-PCR experiments confirmed the differential expression of the two transcripts that were identified in the RAP-PCR fingerprints of FIG. 2A and showed differential hybridization to the cDNA array (compare FIGS. 3A versus 3B). One of these differentially expressed genes corresponds to a new family member of the vav protooncogene family (Katzav et al., supra, 1989; Katzav, *Crit. Rev. Oncoa.* 6:87–97 (1995); Bustelo, *Crit. Rev. Oncog.* 7:65–88 (1996); Romero and Fischer, *Cell Signal.* 8:545–553 (1996)). The other differentially expressed gene has homology to heparan sulfate 3-O-sulfotransferase-1 (Shworak et al., supra, 1997).

Figure 4:
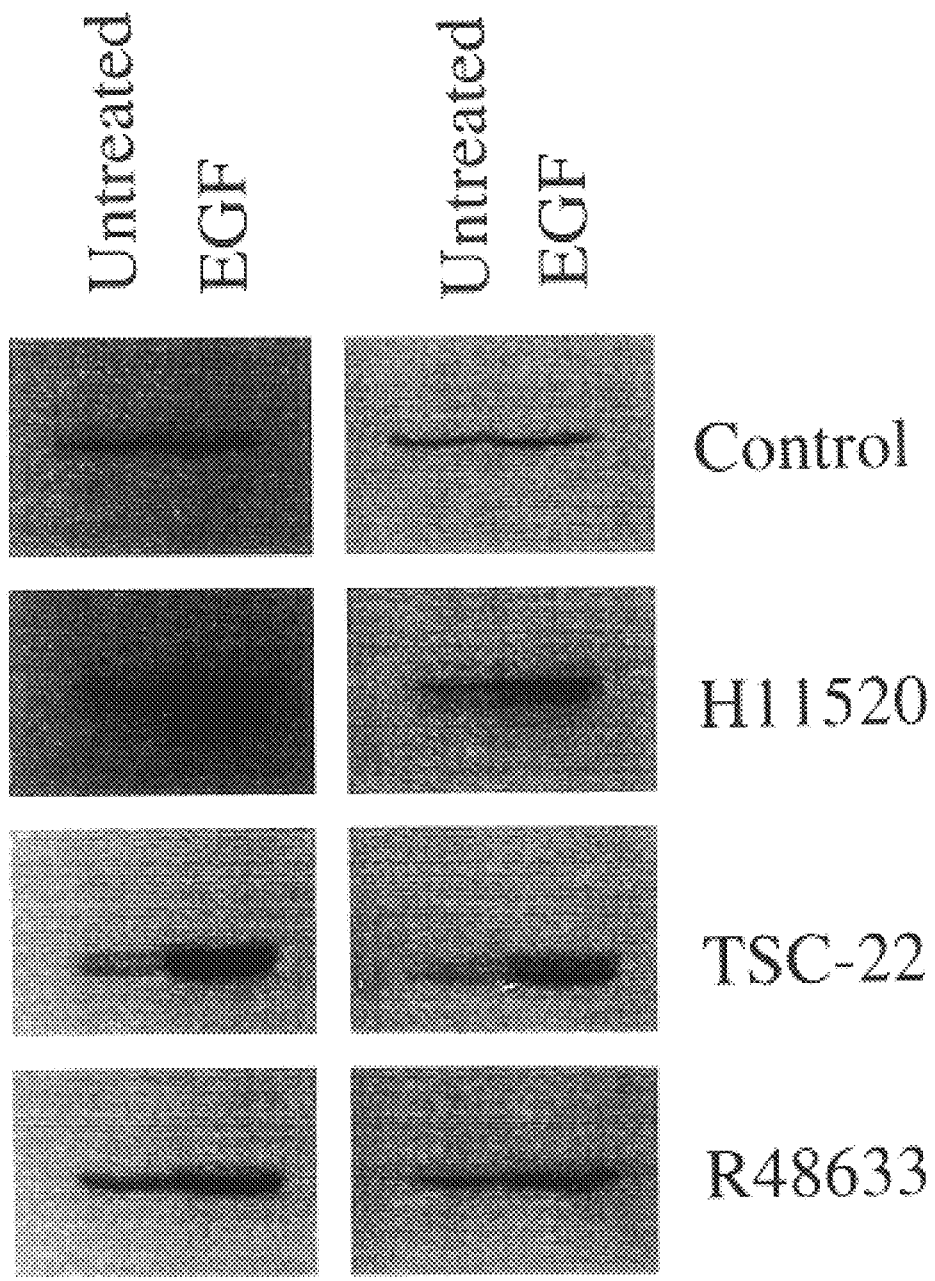
FIG. 4 shows resolution of RT-PCR products on polyacrylamide-urea gels and confirmation of differential regulation in response to EGF using low stringency RT-PCR. Reverse transcription was performed at two RNA concentrations (500 ng, left column; 250 ng, right column) at different cycle numbers. Shown are bands for the control (22 cycles); for GenBank accession number H11520 (22 cycles); for TSC-22, corresponding to GenBank accession numbers H11073 and H11161 (19 cycles); and for R48633 (19 cycles).

The other 13 differentially expressed were also tested and 11 were confirmed using low stringency RT-PCR. Some of the differentially expressed genes are shown in FIG. 4. Reverse transcription was performed at two RNA concentrations (500 ng, left column; 250 ng, right column). The reaction was diluted 4-fold in water and one fourth was used for low stringency RT-PCR at different cycle numbers. The RT-PCR products were resolved on polyacrylamide-urea gels. Shown are bands for the control (22 cycles); for GenBank accession number H11520 (22 cycles); for TSC-22, corresponding to GenBank accession numbers H11073 and H11161 (19 cycles) (Jay et al., *Biochem. Biophys. Res. Commun.* 222:821–826 (1996); Dmitrenko et al., *Tsitol. Genet.* 30:41–47 (1996); Ohta et al., *Eur. J. Biochem.* 242:460–466 (1996)); and for GenBank accession number R48633 (19 cycles). Genes corresponding to H11520 and TSC-22 are up-regulated about 8–10 fold with EGF treatment. The gene corresponding to R48633 is up-regulated about 3-fold with EGF treatment.

Of the two differentially expressed genes that were not confirmed, one proved unamplifiable. The other gene gave a product but appeared to not be differentially regulated when analyzed by RT-PCR.

RAP-PCR targets were very effective at detecting rare, low abundance mRNAs. Each fingerprint hybridized to a set of clones almost entirely different from the set hybridized by a target derived from poly(A)+-selected mRNA (see FIG. 3). In addition, numerous other primer pairs, membranes, and sources of RNA consistently showed less than a 5% overlap between clones hybridized by any two fingerprints, or between a fingerprint and a total poly(A)+-selected cDNA target. Detection of differentially expressed vav-3 mRNA, which is a new member of the vav oncogene family, was attempted using a Northern blot of poly(A)+-selected RNA.

Despite being able to detect serially diluted vector down to the equivalent of a few copies per cell, vav-3 mRNA was undetectable on the Northern blot, whereas RT-PCR confirmed expression. A G3PDH control was used to confirm that the conditions used in the Northern blot could detect a control gene. Therefore, vav-3 appears to be a low abundance message that is represented in a RAP-PCR fingerprint as a prominent band.

The frequency of homologs of cDNAs detected by the RAP-PCR targets in the EST database was determined (>98% identity). This was compared to the frequency of homologs for a random set of other cDNAs on the same membrane. If the RAP-PCR fingerprints were heavily biased towards common mRNAs, then many would occur often in the EST database because it is partly derived from cDNA libraries that are not normalized or incompletely normalized. However, the cDNAs detected by RAP-PCR had frequencies in the EST database comparable to the frequencies for randomly selected cDNAs, including cases where the clone was unique in the database. These results indicate that sampling by arbitrarily sampled targets generated by RAP-PCR is at least as good as random sampling of the partly normalized libraries used to construct the array, and very different from that obtained for a target such as total mRNA target.

These results demonstrate that an arbitrarily sampled target generated using RT-PCR and arbitrary primers can detect genes differentially expressed in response to EGF.

EXAMPLE III
An Arbitrarily Sampled Target Generated by Differential Display Detects Genes Differentially Expressed in Response to EGF This example shows the use of differential display to generate an arbitrarily sampled target and detection of differentially expressed genes responsive to EGF.

RNA was prepared from the human keratinocyte cell line HaCaT as described in Example II. Briefly, cells were grown to confluence and maintained at confluence for 2 days. The medium was changed 1 day prior to the experiment. EGF (Gibco-BRL) was added at 20 ng/ml. Treated and untreated cells were harvested after 4 hrs and total RNA was prepared with the RNEASY total RNA purification kit (Qiagen) according to the manufacturer's protocol. To remove remaining genomic DNA, the extracted total RNA was treated with RNase-free DNase (Boehringer Mannheim) and cleaned again using the RNEASY kit. The purified RNA was adjusted to 400 ng/$\mu$l in water and checked for quality by agarose gel electrophoresis.

For standard differential display, differential display was performed using the materials supplied in the RNAIMAGE kit (GenHunter Corporation; Nashville Tenn.), AMPLITAQ DNA polymerase (Perkin-Elmer-ABI; Foster City Calif.) and $\alpha$-($^{32}$P) -dCTP according to the manufacturer's protocol, except that each RNA template was used at four different concentrations, 800, 400, 200 and 100 ng per 20 $\mu$l reaction, with each anchored oligo(dT) primer (0.2 $\mu$M). The PCR reaction contained 2 $\mu$M dNTPs, for a total of 4 $\mu$M, including the carryover from the cDNA mix, 0.2 $\mu$M each primer, and one tenth of the newly synthesized cDNA, corresponding to 80, 40, 20 and 10 ng RNA. The anchored oligo(dT) primers were used in all possible combinations with four different arbitrary primers. The anchored oligo(dT) primers used were H-$T_{11}$G (AAGCTTTTTTTTTTTG; SEQ ID NO:56); H-$T_{11}$A (AAGCTTTTTTTTTTTA; SEQ ID NO:57); and H-$T_{11}$C (AAGCTTTTTTTTTTTC; SEQ ID NO:58), where H is AAGC, which is an arbitrary sequence used as a clamp to ensure the primers stay in register and have a high Tm at subsequent PCR steps. The arbitrary primers used were H-AP1 (AAGCTTGATTGCC; SEQ ID NO:59); H-AP2 (AAGCTTCGACTGT; SEQ ID NO:60); H-AP3 (AAGCTTTGGTCAG; SEQ ID NO:61); and H-AP4 (AAGCTTCTCAACG; SEQ ID NO:62).

For modified differential display, reverse transcription was performed using four different concentrations of each RNA template, 1000, 500, 250 and 125 ng per 10 $\mu$l reaction. The reaction mix contained 1.5 $\mu$M oligo(dT) anchored primers $AT_{15}A$, $GT_{15}G$, and $T_{13}V$, 50 mM Tris, pH 8.3, 75 mM KCl, 3 mM $MgCl_2$, 20 mM DTT, 0.2 mM each dNTP, 8 U RNase inhibitor (Boehringer Mannheim) and 20 U MuLV reverse transcriptase (Promega). The anchored primers were $AT_{15}A$ (ATTTTTTTTTTTTTTA; SEQ ID NO:63); $GT_{15}G$ (GTTTTTTTTTTTTTTG; SEQ ID NO:64); and $T_{13}V$ (TTTTTTTTTTTTTV; SEQ ID NO:65; where V is A, G or C)). The reaction mix was ramped for 5 min from 25° C. to 37° C., held at 37° C. for 1 hr, and finally the enzyme was inactivated at 94° C. for 5 min. The newly synthesized cDNA was diluted 4-fold in water.

The PCR was performed after adding 10 $\mu$l of reaction mix to 10 $\mu$l of the diluted cDNAs, corresponding to 250, 125, 62.5 and 31.25 ng of RNA, to yield a 20 $\mu$l final reaction volume containing 2 $\mu$M anchored oligo(dT) primer, 0.4 $\mu$M arbitrary primer, either KA2 (GGTGCCTTTGG; SEQ ID NO:66) or OPN28 (GCACCAGGGG; SEQ ID NO:67), 2.5 units AMPLITAQ DNA polymerase Stoffel fragment (Perkin Elmer-ABI), 2 $\mu$Ci $\alpha$-($^{32}$P)-dCTP, 175 $\mu$M each dNTP, 10 mM Tris, pH 8.3, 10 mM KCl, and 3.125 mM $MgCl_2$. These concentrations do not include the carryover from the reverse transcription reaction. The reactions were thermocycled for 35 cycles of 94° C. for 40 sec, 40° C. for 1 min and 40 sec, and 72° C. for 40 sec.

An aliquot of the PCR products resulting from the four different concentrations of the same RNA template were displayed side by side on a 5% polyacrylamide gel and visualized by autoradiography as described in Example II.

For labeling of differential display products for use as targets to probe arrays, random primed labeling of the differential display products was performed as described in Example II. The differential display PCR reactions (14 $\mu$l) were purified using a QIAQUICK PCR Purification Kit (Qiagen) and the DNA was recovered in 50 $\mu$l 10 mM Tris, pH 8.3. Random primed synthesis was performed using a standard protocol. Briefly, 5 $\mu$l of the recovered differential display products were combined with 3 $\mu$g random hexamers, boiled for 3 min and placed on ice. The hexamer/DNA mix was combined with the reaction mix to yield a 25 $\mu$l reaction containing 0.05 mM three dNTPs (minus dCTP), 50 $\mu$Ci of 3000 Ci/mmol $\alpha$-($^{32}$P)-dCTP, 1×Klenow fragment buffer, and 4 U Klenow fragment (Gibco-BRL). The reaction was performed at room temperature for 4 hrs, chased for 15 min at room temperature by adding 1 $\mu$l of 1.25 mM dCTP, and incubated for an additional 15 min at 37° C. The unincorporated nucleotides and hexamers were removed with the Qiagen Nucleotide Removal Kit and the purified products were eluted using two aliquots of 140 $\mu$l 10 mM Tris, pH 8.3.

Hybridization to the array was performed essentially as described in Examples I and II. Briefly, the cDNA membranes (Genome Systems) were prewashed in three changes of prewash solution, containing 2×SSC and 0.1% SDS, in a horizontally shaking flat bottom container to reduce the residual bacterial debris. The first wash used 500 ml of prewash buffer for 10 min at room temperature. The second and third washes were each carried out in 1 liter of prewash solution, prewarmed to 55° C., for 10 min.

The membranes were transferred to large roller bottles and prehybridized in 60 ml prehybridization solution, prewarmed to 42° C., containing 6×SSC, 5×Denhardt's reagent, 0.5% SDS, 100 μg/ml fragmented, denatured salmon sperm DNA, and 50% formamide for 1–2 hrs at 42° C.

The prehybridization solution was removed, and 10 ml hybridization solution, prewarmed to 42° C. and containing 6×SSC, 0.5% SDS, 100 μg/ml fragmented, denatured salmon sperm DNA and 50% formamide, was added to the bottles. To decrease the background hybridization due to repeats such as Alu and Line elements, sheared human genomic DNA was denatured in a boiling water bath for 10 min and immediately added to the hybridization solution to a final concentration of 10 μg/ml. An aliquot of 10 ng/ml poly(dA) was added to block oligo (dT) stretches in the radiolabeled target. Simultaneously, the labeled target was denatured in a boiling water bath for 4 min and immediately added to the hybridization solution. The hybridizations were carried out at 42° C. for 18–20 hrs.

Following hybridization, the hybridization solution was poured off and the membranes were thoroughly washed in six changes of wash solution, including a transfer of the membranes from the roller bottles to a horizontally shaking flat bottom container and back to the roller bottles, over 2–3 hrs. The stringency of the washes was increased stepwise from 2×SSC and 0.1% SDS at room temperature to 0.1×SSC and 0.1% SDS at 64° C. The separate washes were maintained at exactly the same indicated temperatures for all of the membranes. The last high stringency wash was at least 40 min to ensure exactly equilibrated temperatures in all bottles. The final wash solution was removed, and the membranes were briefly rinsed in 2×SSC at room temperature, blotted with 3 MM paper, wrapped in SARAN wrap while moist, and placed against Kodak Biomax film (Eastman-Kodak; Rochester, N.Y.).

Differential expression was confirmed using low stringency RT-PCR. The first level of confirmation was the use of two RNA concentrations per sample. Only those hybridization events that indicated differential expression at both RNA concentrations in both RNA samples were further characterized.

Nucleotide sequences, which were available from Genome Systems, the commercial source of the array, or were sequenced, were used to derive PCR primers of 18 to 25 bases in length using MacVector 6.0 (Oxford Molecular Group). Generally, primers were chosen that generate PCR products of 100 to 250 base pairs, have melting temperatures of at least 60° C., and were preferably located close to the polyadenylation site of the mRNA so as to reduce the chance of sampling family members.

Reverse transcription was performed on total RNA using two RNA concentrations per sample and an oligo-(dT$_{15}$) primer (TTTTTTTTTTTTTTT; SEQ ID NO:68; Genosys). The reactions contained 100 and 50 ng per liter total RNA, 0.5 μM oligo-(dT$_5$) primer (SEQ ID NO:68), 50 mM Tris, pH 8.3, 75 mM KCl, 3 mM MgCl$_2$, 20 mM DTT, 0.2 mM of each dNTP, 0.8 U/μl RNase inhibitor (Boehringer Mannheim) and 2 U/μl of MuLV-reverse transcriptase (Promega). The reactions were ramped for 5 min from 25° C to 37° C. and held at 37° C. for 1 hr. The enzyme was inactivated by heating the reactions at 94° C. for 5 min and the newly synthesized cDNA was diluted 4-fold in water.

Diluted cDNAs (10 μl) were mixed with 2×PCR mixture containing 20 mM Tris, pH 8.3, 20 mM KCl, 6.25 mM MgCl$_2$, 0.35 mM of each dNTP, 3 μM of each specific primer, 2 μCi α-($^{32}$P) -dCTP (ICN, Irvine, Calif.) and 2 U AMPLITAQ DNA polymerase Stoffel fragment (Perkin-Elmer-Cetus) for a 20 μl final reaction volume. A low stringency thermal profile was used: 94° C. for 40 sec, 40° C. for 40 sec, and 72° C. for 1 min, for 17 and 19 cycles in separate tubes. The reaction was carried out in two sets of tubes at different cycle numbers because the abundance of the transcripts, the performance of the primer pairs and the amplifiability of the PCR products can vary. PCR products were run under the same conditions as described above on a 5% polyacrylamide and 43% urea gel. The gel was dried and placed for 18 to 72 hours on a phosphoimager screen and read with a STORM phosphoimager (Molecular Dynamics; Sunnyvale Calif.). Invariance among the other arbitrary products in the fingerprint was used as an internal control to indicate the reliability of the relative quantitation. The gene-specific products from four sets of reactions per differentially regulated gene were quantitated using IMAGEQUANT Software (Molecular Dynamics).

Primer pairs were used to confirm differential expression. For GenBank accession number R72714 (Egr-1)(155 nt product); primer A, CACGTCTTGGTGCCTTTTGTGTG (SEQ ID NO:69); primer B, GAAGCTCAGCTCAGC-CCTCTTCC (SEQ ID NO:70). For GenBank accession number H14529 (ACTB, β-actin)(174 nt product); primer A, CCAGGGAGACCAAAAGCCTTCATAC (SEQ ID NO:71); primer B, CACAGGGGAGGTGATAGCATTGC (SEQ ID NO:72). For GenBank accession number H27389 (A+U-rich element RNA binding factor)(144 nt product); primer A, GTGCTTTTCAAAGATGCTGCTAGTG (SEQ ID NO:73); primer B, GCTCAATCCACCCACAAAAACC (SEQ ID NO:74). For GenBank accession number H05545 (protein phosphatase 2A catalytic subunit)(141 nt product); primer A, TCCTCTCACTGCCTTGGTGGATG (SEQ ID NO:75); primer B, CACAGCAAGTCACACATTGGACCC (SEQ ID NO:76). For GenBank accession number H27969 (103 nt product); primer A, CCAAAGACATTCAGAG-GCATGG (SEQ ID NO:77); primer B, GAGGTGGG-GAAGGATACAGCAG (SEQ ID NO:78). For GenBank accession number R73247 (inositol tris phosphate kinase) (168 nt product); primer A, GAAAAGGGTTGGG-GAGAAGCCTC (SEQ ID NO:79); primer B, TCTCTAGCGTCCTCCATCTCACTGG (SEQ ID NO:80). For GenBank accession number H21777 (α-tubulin isoform 1) (155 nt product); primer A, ACAACTGCATCCTCAC-CACCCAC (SEQ ID NO:81); primer B, GGACA-CAATCTGGCTAATAAGGCGG (SEQ ID NO:82).

Total RNA was obtained from immortalized HaCaT keratinocytes, treated and untreated with EGF, as described in Example II (Boukamp et al., supra, 1997). The first differential display protocol tried was the RNAimage kit 1 (cut G50'; GenHunter. The anchor primers, oligo (dT)-G (H-T$_{11}$G; SEQ ID NO:83), oligo (dT)-C (H-T$_{11}$C; SEQ ID NO:84) or oligo(dT)-A (H-T$_{11}$A; SEQ ID NO:85), were used for reverse transcription, and then each cDNA was used for PCR in combination with four different arbitrary primers, H-AP1 (SEQ ID NO:59), H-AP2 (SEQ ID NO:60), H-AP3 (SEQ ID NO:61) and H-AP4 (SEQ ID NO:62).

As shown in FIG. 5, the fingerprints were resolved on a denaturing acrylamide gel to determine the quality of the reactions. Differential display reactions were performed using the RNAIMAGE kit protocol (GenHunter Corporation) according to the manufacturer's suggestion except that four different starting concentrations of 800, 400, 200 and 100 ng of total RNA were used. One tenth of this material was then used for PCR. The anchored oligo(dT) primer H-T$_{11}$C (SEQ ID NO:84) was used with two different arbitrary primers, H-AP3 (SEQ ID NO:61) and H-AP4 (SEQ ID NO:62), as indicated. The arbitrary primer H-AP4

(SEQ ID NO:62) was used with two different anchored oligo(dT) primers, H-T$_{11}$C (SEQ ID NO:84) and H-T$_{11}$A (SEQ ID NO:85). The reactions that share either the arbitrary primer or the anchored oligo(dT) primer showed almost no visible overlap in the visible bands.

Figure 5A:
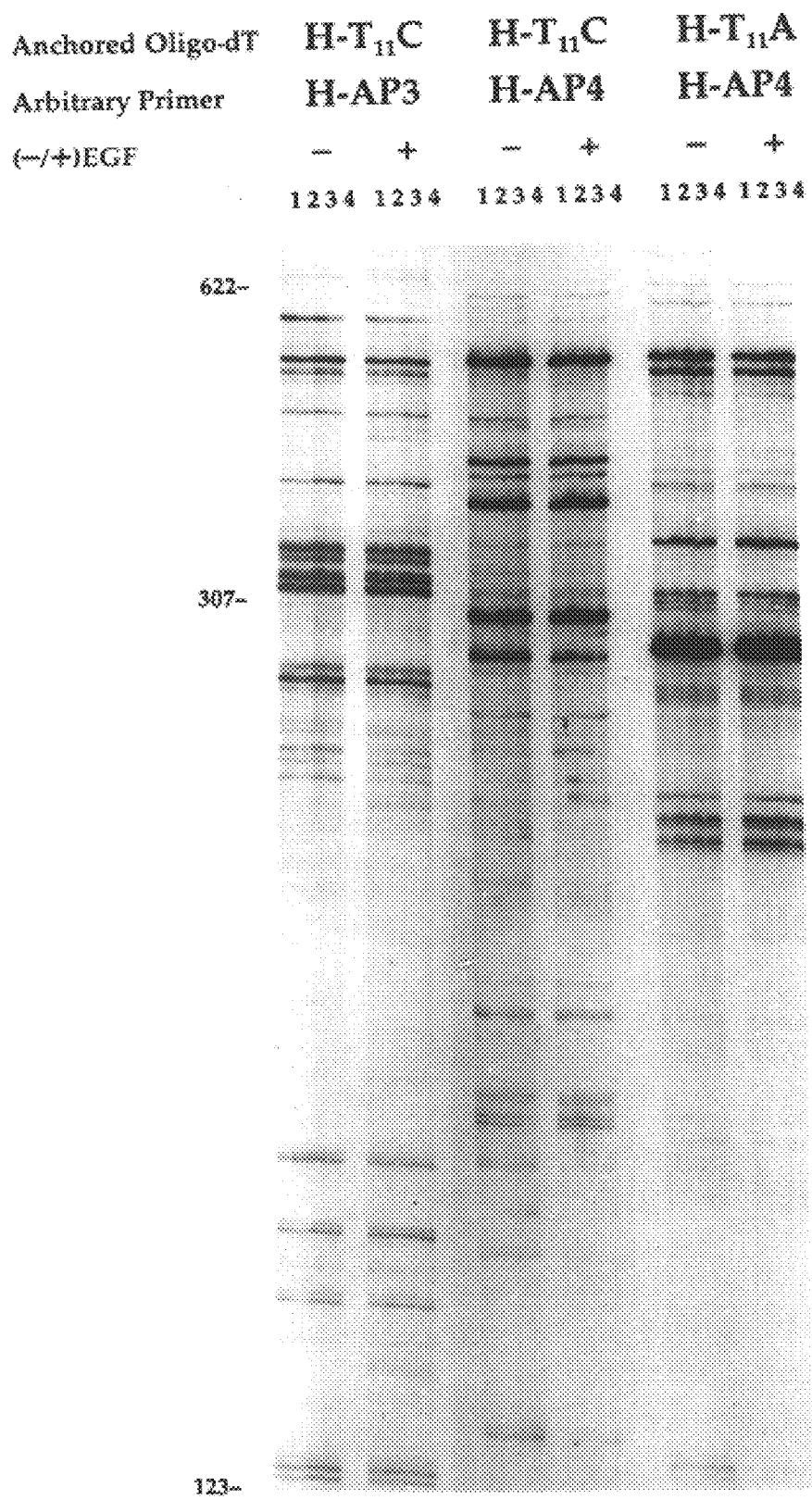
FIG. 5 shows differential display of untreated and EGF treated HaCaT cells. Panel A shows differential display reactions performed at four different starting concentrations of total RNA (designated 1, 2, 3 and 4 and corresponding to 800, 400, 200 and 100 ng, respectively), which was then used for PCR. An anchored oligo(dT) primer, H-T$_{11}$C or H-T$_{11}$A, was used in combination with one of two different arbitrary primers, H-AP3 or H-AP4, which are indicated above the lanes. Panel B shows differential display using the arbitrary primer KA2 with three different anchored oligo (dT) primers, T$_{13}$V, AT$_{15}$A and GT$_{15}$G, used at four different starting concentrations of RNA (designated 1, 2, 3 and 4 and corresponding to 1000, 500, 250 and 125 ng, respectively), which was then used for PCR.
Figure 5B:
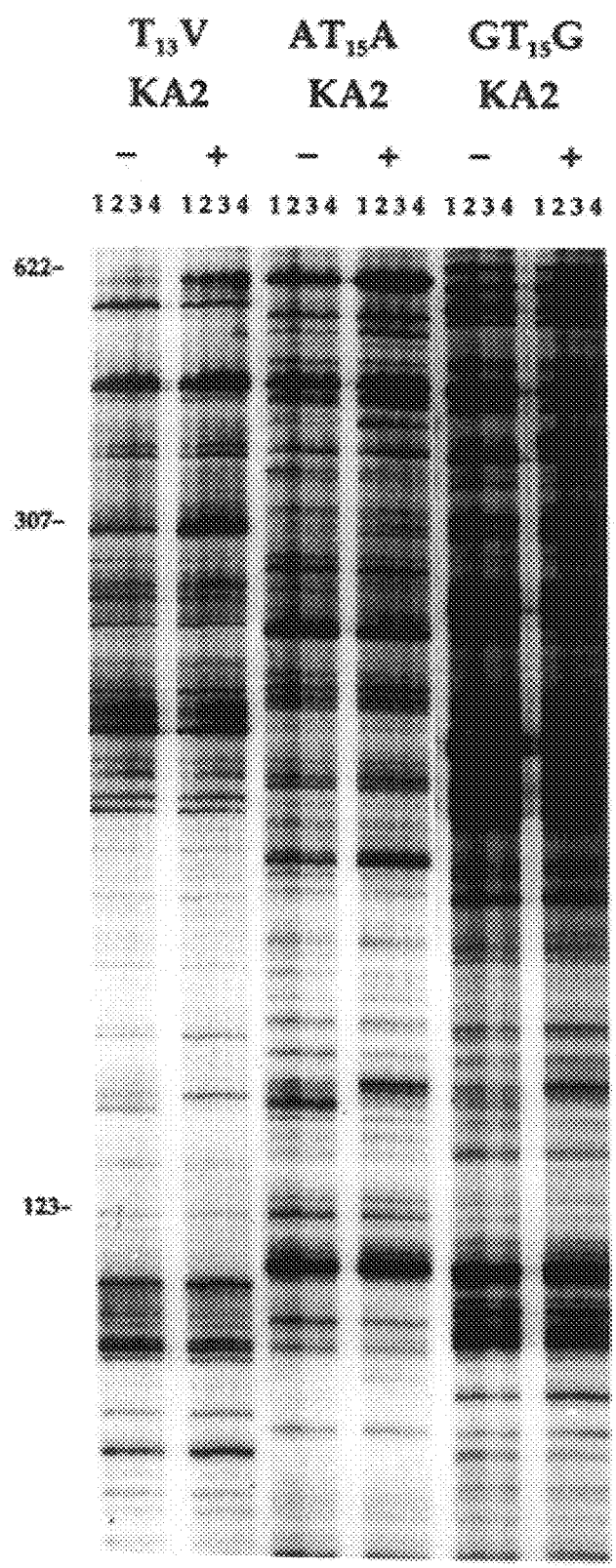

FIG. 5B shows differential display using a different set of primers. Differential display was performed using the arbitrary primer KA2 (SEQ ID NO:66) with three different anchored oligo(dT) primers, T$_{13}$V (SEQ ID NO:65), AT$_{15}$A (SEQ ID NO:63), and GT$_{15}$G (SEQ ID NO:64), as indicated. The differential display protocol was adjusted to yield more mass and a higher complexity of the generated products. The starting concentrations of RNA were 1000, 500, 250 and 125 ng. One fourth of this material was then used for PCR. As observed in FIG. 5A, using different oligo(dT) anchored primers changes the pattern of the displayed bands almost entirely.

The fingerprints generated about 30 to 50 clearly visible products (see FIG. 5A). Fingerprints were generally reproducible in the range from 100 to 800 ng of total mRNA used in these experiments, with very few RNA concentration dependent products. Three of the most reproducible fingerprints that shared either a oligo(dT) anchored primer or an arbitrary primer (FIG. 5A) were radiolabeled by random priming in the presence of three unlabeled dNTPs and $\alpha$-($^{32}$P) -dCTP, and each was used to probe identical arrays of 18,000 double spotted *E. coli* colonies carrying ESTs from the I.M.A.G.E. consortium. The arrays were hybridized and washed as described above.

The kit protocol used 0.2 $\mu$M of the arbitrary primer and 4 $\mu$M dNTPs compared to 1 $\mu$M primers and 200 $\mu$M dNTPs used in the RAP-PCR protocol described in Example II. The fingerprint reaction contained less than 40 ng of product in 20 $\mu$l, presumably because of limiting components. This was about five times less DNA than used in the method described in Example II. For this reason, it took about ten days with an intensifying screen in order to obtain an adequate exposure of X-ray film. Approximately 500 products were easily discernible with each target after a sufficient exposure. The number of reliably observable genes is usually increased by at least two-fold or more when using a phosphoimager screen, indicating the greater sensitivity of phosphoimaging compared to X-ray film. Furthermore, pooling of separate labeled fingerprints into the same target can increase throughput even further.

In order to reduce the exposure time for target hybridization to arrays, experiments were performed at the higher concentration of primer and dNTPs described in Example II using RAP-PCR protocols (FIG. 5B). These experiments yielded the expected increase in product mass and a corresponding reduction in exposure times for arrays.

Figure 6A:
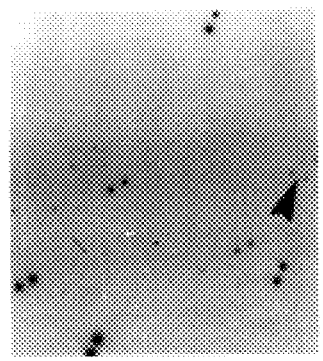
FIG. 6 shows hybridization of differential display reactions to cDNA arrays. Differential display products generated with the primers GT$_{15}$G and KA2 from untreated (Panel A) and EGF treated (Panel B) HaCaT cells were labeled by random priming and hybridized to cDNA arrays. A section representing less than 5% of a membrane is shown with a differentially regulated gene indicated by an arrow. Panel C shows hybridization of differential display products generated with the primers AT$_{15}$A and KA2 from untreated HaCaT cells.
Figure 6B:
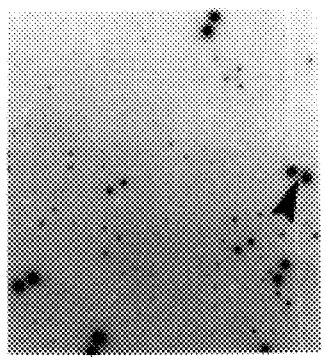
Figure 6C:
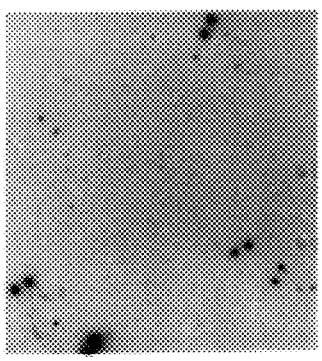

The selectivity of oligo(dT) primers was determined using different anchor bases. As shown in FIG. 6, differential display reactions were hybridized to cDNA arrays. The differential display products generated as described in FIG. 5A, with the primers GT$_{15}$G (SEQ ID NO:64) and KA2 (SEQ ID NO:66) from untreated (FIG. 6A) and EGF treated (FIG. 6B) HaCaT cells, were labeled by random priming and hybridized to cDNA arrays. A section representing less than 5% of a membrane is shown with a differentially regulated gene indicated by an arrow. FIG. 6C shows hybridization of differential display products generated with the primers AT$_{15}$A (SEQ ID NO:63) and KA2 (SEQ ID NO:66) from untreated HaCaT cells. Comparing FIG. 6A versus 6C, there is a significant overlap of hybridization signals that were not obvious from the polyacrylamide display (compare to FIG. 5B, lanes AT$_{15}$A/KA2 versus GT$_{15}$G/KA2).

When the arbitrary primer was changed while keeping the same anchor primer, the pattern of clones hybridized changed almost entirely, with typically less than 5% overlap between any two fingerprints. In contrast, targets containing the same arbitrary primer and different anchored primers shared about 30% of the clones to which they hybridized. FIGS. 6A and 6C show examples of such shared products from a small portion of an array.

Similar observations were made using fingerprints generated under a wide variety of conditions, including the protocols and primers from the GenHunter kit, modified protocols, and protocols using primers independent of those in the GenHunter kit. The possibility of this overlap being due to repeats was excluded by the use of genomic and total mRNA targets against the same membranes.

The overlap among targets that had different anchored primers but shared the same arbitrary primer was not reflected in any noticeable similarity in the fingerprint products when resolved on a denaturing polyacrylamide gel. For example, the targets used in FIGS. 6A and 6C are shown in FIG. 5B and show no easily discerned similarities, despite having 30% of the products in common. Many of the shared products were among the most intensely hybridizing clones on the array. Therefore, some of the products visible on the gel could share the arbitrary primer at one end but, during PCR, the products are preferentially primed at multiple different locations in the opposite direction by the different anchored primers. This would result in fingerprints that had little or no similarity in a polyacrylamide display while being compatible with the observation that targets with the same arbitrary primer but different anchored primers overlap by 30% in the clones to which they hybridize.

Shared products are a general phenomenon for anchored fingerprints that share an arbitrary primer under a fairly wide range of conditions. Overlap among fingerprints can be avoided by not using the same arbitrary primer with different anchored primers.

Comparison of the pattern of hybridizing clones with that generated by total genomic DNA indicated that the clones hybridizing to a target generated by the GenHunter fingerprint did not generally contain the Alu repetitive element that occurs in a few percent of mRNA 3' untranslated regions (UTRs). The clones hybridized by the target did not overlap significantly with clones hybridized by a total cDNA target derived from reverse transcription of poly(A)$^+$ mRNA, indicating that the genes sampled were not heavily biased towards the most abundant RNAs. These results are consistent with results obtained using only arbitrary primers for fingerprinting (see Example II) and indicate that arbitrary priming combined with anchored oligo(dT) priming can be used to monitor rare genes in cDNA arrays. These results also confirm that RAP-PCR and differential display are not heavily biased toward abundant transcripts.

Among over 2000 clones surveyed for differential gene expression between untreated and EGF treated HaCaT cells, there were 29 different clones that appeared to clearly reflect differential expression at one RNA concentration. The 12 clones having the highest signal to noise ratio and differential expression ratio were chosen and specific primers were designed for RT-PCR. An example of one of these differentially expressed genes is indicated by an arrow in FIG. 6A versus 6B.

Figure 7:
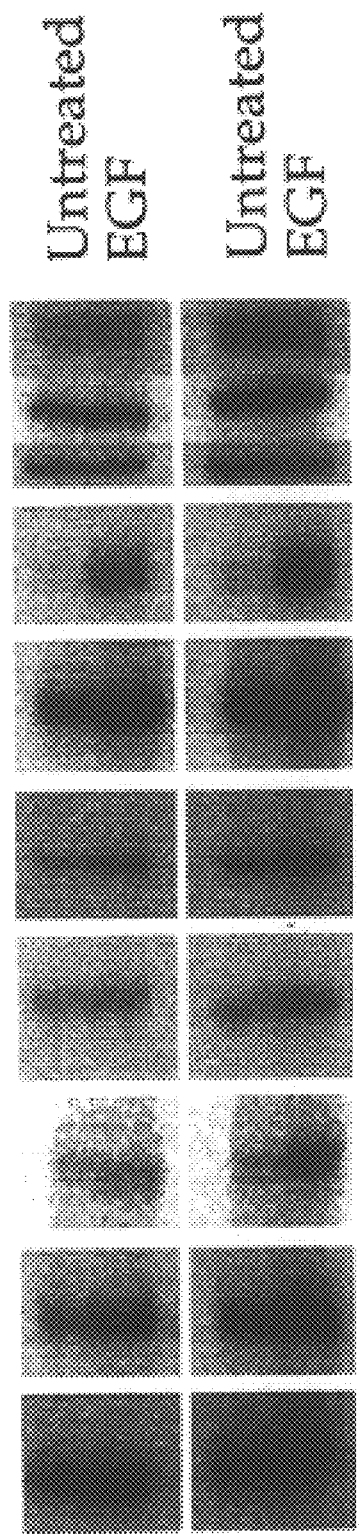
FIG. 7 shows confirmation of differential regulation of genes by EGF using low stringency RT-PCR. Reverse transcription was performed at twofold different RNA concentrations, and low stringency PCR was performed at different cycle numbers. The amount of input RNA used for initial first strand cDNA synthesis and used in each RAP-PCR reaction was 125 ng, left column and 250 ng, right column. The RT-PCR products from 19 cycle reactions were resolved on polyacrylamide-urea gels. Shown are the products for the control (unregulated) and genes exhibiting ≧1.6-fold regulation in response to EGF, corresponding to GenBank accession numbers R72714, H14529, H27389, H05545, H27969, R73247, and H21777.

Differential expression of at least 1.5-fold was confirmed for seven genes, which are shown in FIG. 7. Reverse transcription was performed at twofold different RNA concentrations. The reactions were diluted 4 fold in water and low stringency PCR was performed at different cycle numbers. The amount of input RNA/cDNA for each PCR reaction was 125 ng, left column and 250 ng, right column. The reactions shown in FIG. 7 were carried out for 10 cycles and resolved on polyacrylamide-urea gels. Shown are products for the control (unregulated) and genes differing by at least 1.6-fold. The regulated genes shown correspond to GenBank accession numbers R72714, H14529, H27389, H05545, H27969, R73247, and H21777.

The regulation of the genes shown in FIG. 7 are summarized in Table 2. Identified genes regulated by four hr treatment with EGF, corresponding GenBank accession numbers, and the fold-increase in expression relative to untreated cells are shown.

TABLE 2

EGF Regulated Genes.

| Gene | Accession # | Fold Up-regulation by EGF |
| --- | --- | --- |
| EGR1 | R72714, X52541 | 8.3 ± 3.4 |
| ACTB, beta-actin | H14529, M10277 | 2.0 ± 0.3 |
| A + U-rich element RNA binding factor | H27389, D89092, D89678 | 1.9 ± 0.3 |
| Protein phosphatase 2A catalytic subunit | H05545, J03804 | 1.6 ± 0.4 |
| Unknown | D31765, H27969 | 1.6 ± 0.4 |
| Inositol tris phosphate kinase | R73247, U51336 | 1.6 ± 0.3 |
| Alpha-tubulin isoform 1 | H21777, K00558 | 1.6 ± 0.3 |

Egr-1 was previously known to be differentially regulated by EGF in other cell types (Iwami et al., *Am. J. Physiol.* 270:H2100–H2107 (1996); Kujubu et al., *J. Neurosci. Res.* 36:58–65 (1993); Cao et al., *J. Biol. Chem.* 267:1345–1349 (1992); Ito et al., *Oncogene* 5:1755–1760 (1990)). The observations of changes in β-actin and α-tubulin expression are likely associated with the dramatic change in morphology these cells undergo after EGF treatment. Regulation of β-actin and α-tubulin genes by EGF has been observed in other cell types (Torok et al., *J. Cell Physiol.* 167:422–433 (1996); Hazan and Norton, *J. Biol. Chem.* 273:9078–9084 (1998); Shinji et al., *Hepatoaastroenterology* 44:239–244 (1997); Ball et al., *Cell Motil. Cytoskeleton* 23:265–278 (1992)). These observations independently validate the treatments and the method used to detect differential expression. The regulation of protein phosphatase 2A mRNA has not previously been observed but is consistent with the role of this protein in transduction of the EGF signal (Chajry et al., *Eur. J. Biochem.* 235:97–102 (1996)). Similarly, the gene associated with the metabolism of inositol phosphates had not previously been shown to be regulated by EGF but such regulation is consistent with the previous observation of increases in the compounds generated by this enzyme after EGF treatment in another ectodermal cell type (Contreras, *J. Neurochem.* 61:1035–1042 (1993)). Regulation of two other genes by EGF, an unknown gene, with GenBank accession number H27969, and an RNA binding protein, with GenBank accession number D89692, was not previously reported in any cell type. GenBank accesssion number D31765 corresponds to KIAA0061.

Five other genes were not confirmed to be regulated when RT-PCR was used. The number of false positives can vary from experiment to experiment and depends on the quality of the fingerprints and on the quality of the commercially available membranes. The number of false positives can be limited by using two RNA concentrations on arrays before confirmation by RT-PCR, as described in Example II. These experiments involved only a single concentration because the primary purpose was to determine the efficiency of coverage and overlap among targets made by the oligo (dT)-X anchored priming method. Nevertheless, over half of the differentially hybridizing clones observed at one concentration correspond to differentially expressed genes. When two array hybridizations were performed for each treatment at two different input template concentrations, the error rate was well below 10%.

SEQUENCE LISTING

```
<160> NUMBER OF SEQ ID NOS: 85

<210> SEQ ID NO 1
<211> LENGTH: 395
<212> TYPE: DNA
<213> ORGANISM: Homo sapiens
<220> FEATURE:
<221> NAME/KEY: unsure
<222> LOCATION: (82)
<221> NAME/KEY: unsure
<222> LOCATION: (115)..(116)
<221> NAME/KEY: unsure
<222> LOCATION: (314)
<221> NAME/KEY: unsure
<222> LOCATION: (350)
<221> NAME/KEY: unsure
<222> LOCATION: (359)
<221> NAME/KEY: unsure
<222> LOCATION: (383)

<400> SEQUENCE: 1 ttttttttt  acaacaatgc  agtcatttat  ttattgagta  tgtgcacatt  atggtattat     60
tactatactg  attatattta  anaagtgact  tctaattaga  aaatgtatcc  aaaannaaaa   120
cagcagatat  acaaaattaa  agagacagaa  gatagacatt  aacagataag  gcaacttata   180
```

```
cattgaggaa tccaaatcca atacatttaa acatttggga aatgagggggg acaaatggga      240 agccagatca aatttgtgta aaactattca gtatgtttcc cttggcttca tgtctgagga       300
agggctctcc cttncaatgg gggatggaca aactccaaat gccacacaan tgtttaacng       360
gtatactagg tttcacactg ggnacgggggg ttaaa                                 395
```

<210> SEQ ID NO 2
<211> LENGTH: 389
<212> TYPE: DNA
<213> ORGANISM: Homo sapiens
<220> FEATURE:
<221> NAME/KEY: unsure
<222> LOCATION: (230)
<221> NAME/KEY: unsure
<222> LOCATION: (384)

<400> SEQUENCE: 2

```
acacagcccc ccgcccagcc agcatcgcag ggcttcaggg accaaccgca tagctgccta        60 tgccccgca gaactggctg ctgcgtgtga actgaacaga cggagaagat gtgctaggga       120
gaatctgcct ccacagtcac ccatttcatt gctcgctgcg aaagagacgt gagactgaca       180
tatgccatta tctctttttcc agtattaaac actcatatgc ttatggcttn gagaaatttc      240
ttagttgggt gaattaaagg ttaatccgag aattagcatg gatataccgg gtcctcatgc       300
agcttggcag atatctgaga aatggtttaa ttcatgctca ggagctgtgt gccttttcca       360
tcccttccgg gtcccttacc cctnactttt                                       389
```

<210> SEQ ID NO 3
<211> LENGTH: 465
<212> TYPE: DNA
<213> ORGANISM: Homo sapiens
<220> FEATURE:
<221> NAME/KEY: unsure
<222> LOCATION: (384)
<221> NAME/KEY: unsure
<222> LOCATION: (411)
<221> NAME/KEY: unsure
<222> LOCATION: (445)

<400> SEQUENCE: 3

```
tttttttttt tatcaacatt tatatgcttt attgaaagtt gacaagtgca acagttaaat        60
acagtgacac cttacaattg tgtagagaac atgcacagaa acatatgcat ataactacta       120
tacaggtgat atgcagaaac ccctactggg aaatccattt cattagttag aactgagcat       180
ttttcaaagt attcaaccag actcaattga aagacttcag tgaacaagga tttacttcag       240
cgtattcagg caggctagga tttcaggatt acacaaagtg aggtaactgt gccaaattct       300
taaaatttct ttagggtgtg ggttttttgtc atgtagcagt ttttatgtgg atctattata     360
taaaagtcca cacctcctca gacngccaat ggaaacaact taaatttcca ntctgttaca       420
acctaattgg taggttacag tcccnttttg ttacaaatgg ttaca                      465
```

<210> SEQ ID NO 4
<211> LENGTH: 1718
<212> TYPE: DNA
<213> ORGANISM: Homo sapiens

<400> SEQUENCE: 4

```
ggcacgaggg gatccgcatc tgcctgggat catcaagccc tagaagctgg gtttctttaa        60
attagggctg ccgttttctg tttctccctg ggctgcggaa agccagaaga ttttatctag       120
```

-continued

| | |
|---|---|
| cttatacaag gctgctggtg ttccctcttt ttttccacga gggtgttttt ggctgcaatt | 180 |
| gcatgaaatc ccaatggtgt agaccagtgg cgatggatct aggagtttac caactgagac | 240 |
| attttttcaat ttctttcttg tcatccttgc tggggactga aaacgcttct gtgagacttg | 300 |
| ataatagctc ctctggtgca agtgtggtag ctattgacaa caaaatcgag caagctatgg | 360 |
| atctagtgaa aagccatttg atgtatgcgg tcagagaaga agtggaggtc ctcaaagagc | 420 |
| aaatcaaaga actaatagag aaaaattccc agctggagca ggagaacaat ctgctgaaga | 480 |
| cactggccag tcctgagcag cttgcccagt ttcaggccca gctgcagact ggctccccc | 540 |
| ctgccaccac ccagccacag ggcaccacac agccccccgc ccagccagca tcgcagggct | 600 |
| caggaccaac cgcatagctg cctatgcccc cgcagaactg gctgctgcgt gtgaactgaa | 660 |
| cagacggaga agatgtgcta gggagaatct gcctccacag tcacccattt cattgctcgc | 720 |
| tgcgaaagag acgtgagact gacatatgcc attatctctt ttccagtatt aaacactcat | 780 |
| atgcttatgg cttgagaaa tttcttagtt gggtgaatta aaggttaatc cgagaattag | 840 |
| catggatata ccgggacctc atgcagcttg gcagatatct gagaaatggt ttaattcatg | 900 |
| ctcaggagct gtgtgccttt ccatcccttc cggctcccta cccctcactt ccaagggttc | 960 |
| tctctcctgc ttgcgcttag tgtcctacat ggggttgtga agcgatggag ctcctcactg | 1020 |
| gactcgcctc tctcctctcc tccccccagg aggaacttga aaggagggta aaaagactaa | 1080 |
| aatgaggggg aacagagttc actgtacaaa tttgacaact gtcaccaaaa ttcataaaaa | 1140 |
| acaatagtac tgtgcctctt tcttctcaaa caatggatga cacaaaacta tgagagtgac | 1200 |
| aaaatggtga caggtagctg ggacctaggc tatcttacca tgaaggttgt tttgcttatt | 1260 |
| gtatatttgt gtatgtagtg taactatttt gtacaataga ggactgtaac tactatttag | 1320 |
| gttgtacaga ttgaaaattta gttgtttcat tggctgtctg aggaggtgtg gactttatata | 1380 |
| tatagatcta cataaaaact gctacatgac aaaaaccaca cctaaagaaa ttttaagaat | 1440 |
| ttggcacagt tactcacttt gtgtaatctg aaatctagct gctgaatacg ctgaagtaaa | 1500 |
| tccttgttca ctgaagtctt tcaattgagc tggttgaata ctttgaaaaa tgctcagttc | 1560 |
| taactaatga aatggatttc ccagtagggg tttctgcata tcacctgtat agtagttata | 1620 |
| tgcatatgtt tctgtgcatg ttctctacac aattgtaagg tgtcactgta tttaactgtt | 1680 |
| gcacttgtca actttcaata aagcatataa atgttgat | 1718 |

<210> SEQ ID NO 5
<211> LENGTH: 392
<212> TYPE: DNA
<213> ORGANISM: Homo sapiens
<220> FEATURE:
<221> NAME/KEY: unsure
<222> LOCATION: (342)
<221> NAME/KEY: unsure
<222> LOCATION: (362)

<400> SEQUENCE: 5

| | |
|---|---|
| gctcctacca cccagacacc caaacagccg tggccccaga ggtcctggcc aaatatgggg | 60 |
| gcctgcctag gttggtggaa cagtgctcct tatgtaaact gagccctttg tttagaaaac | 120 |
| aattccaaat gtgaaactag aatgagaggg aagagatagc atggcatgca gcacacacgg | 180 |
| ctgctccagt tcatggcctc ccaggggtgc tgggatgca tccaaagtgg ttgtctgaga | 240 |
| cagagttggg aaaccctcac caactgggcc tctttcacct tccacattat cccgctgcca | 300 |
| ccggttgccc tgttttcatt gcaggtttca gggaccagct tngggttgcg tgcgttttg | 360 |

-continued

```
cntttgccag ttcaggccga gggtgttagt tt                                392
```

<210> SEQ ID NO 6
<211> LENGTH: 429
<212> TYPE: DNA
<213> ORGANISM: Homo sapiens

<400> SEQUENCE: 6

```
ttttttttta aggacacgag agagccatat ttatttcaca tggacaagca tgattccatt     60
gcatgctgaa catgaaagct cgtatgagca aagtacccgt aacagcagaa ttatgtgctt    120
ttgtccacag ggagcaggga gaatcacaaa gttgttttca gagacagtgt ttttcaagca    180
cagttgagac cataggctct ggaagtcact ggtttatttc atcaccaaag ggtctgtctc    240
ccagggagtg gccggagtgc tttcagcttt gcaatctctc aatgaattga taaggtctga    300
ggagggctga ggatggtctc ccatcccacc acccagagca tctttgaagg aaatgaagct    360
cagaggggaa ggttacatgc cattgggaat ttaacaaggg ccattcctgg gttggacaat    420
gacagggga                                                            429
```

<210> SEQ ID NO 7
<211> LENGTH: 1305
<212> TYPE: DNA
<213> ORGANISM: Homo sapiens

<400> SEQUENCE: 7

```
cgcggctcag taattgaagg cctgaaacgc ccatgtgcca ctgactagga ggcttccctg     60
ctgcggcact tcatgaccca gcggcgcgcg gcccagtgaa gccaccgtgg tgtccagcat    120
ggccgcgctg ctcctgggcg cggtgctgct ggtgcccag cccagctag tgccttcccg    180
ccccgccgag ctaggccagc aggagcttct gcggaaagcg ggaccctcc aggatgacgt    240
ccgcgatggc gtgcccccaa acggctctgc ccagcagttg ccgcagacca tcatcatcgg    300
cgtgcgcaag ggcggcacgc gcgcactgct ggagatgctc agcctgcacc ccgacgtggc    360
ggccgcggag aacgaggtcc acttcttcga ctgggaggag cattacagcc acggcttggg    420
ctggtacctc agccagatgc ccttctcctg gccacaccag ctcacagtgg agaagacccc    480
cgcgtatttc acgtcgccca agtgcctga gcgagtctac agcatgaacc cgtccatccg    540
gctgctgctc atcctgcgag acccgtcgga gcgcgtgcta tctgactaca cccaagtgtt    600
ctacaaccac atgcagaagc acaagcccta cccgtccatc gaggagttcc tggtgcgcga    660
tggcaggctc aatgtggact acaaggccct caaccgcagc ctctaccacg tgcacatgca    720
gaactggctg cgcttttttcc cgctgcgcca catccacatt gtggacggcg accgcctcat    780
cagggacccc ttccctgaga tccaaaaggt cgagaggttc ctaaagctgt cgccgcagat    840
caatgcttcg aacttctact ttaacaaaac caagggcttt tactgcctgc gggacagcgg    900
ccgggaccgc tgcttacatg agtccaaagg ccgggcgcac ccccaagtcg atcccaaact    960
actcaataaa ctgcacgaat attttcatga gccaaataag aagttcttcg agcttgttgg   1020
cagaacattt gactggcact gatttgcaat aagctaagct cagaaacttt cctactgtaa   1080
gttctggtgt acatctgagg ggaaaaagaa ttttaaaaaa gcatttaagg tataaattat   1140
ttgtaaaatc cataaagtac ttctgtacag tattagattc acaattgcca tatatactag   1200
ttatattttt ctacttgtta aatggagggc attttgtatt gttttttcatg gttgttaaca   1260
ttgtgtaata tgtctctata tgaaggaact aaactatttc actga                   1305
```

```
<210> SEQ ID NO 8
<211> LENGTH: 331
<212> TYPE: DNA
<213> ORGANISM: Homo sapiens
<220> FEATURE:
<221> NAME/KEY: unsure
<222> LOCATION: (80)
<221> NAME/KEY: unsure
<222> LOCATION: (104)
<221> NAME/KEY: unsure
<222> LOCATION: (115)
<221> NAME/KEY: unsure
<222> LOCATION: (135)
<221> NAME/KEY: unsure
<222> LOCATION: (186)
<221> NAME/KEY: unsure
<222> LOCATION: (308)
<221> NAME/KEY: unsure
<222> LOCATION: (271)

<400> SEQUENCE: 8
gctcaggaca gatgccacac aaggatagat gctggcccag ggccaagagc ccagctccaa      60
ggggaatcag aactcaaatn gggccagatc cagcctgggg tctngagttg atctngaacc     120
cagactcaga cattngcacc taatccaggc agatccagga ctatatttgg gcctgctcca    180
gacctngatc ctggaggccc agttcaccct gatttaggag aagccaggaa tttcccagga    240
ccctgaaggg gccatgatgg caacagatct ngaacctcag cctggccaga cacaggccct   300
ccctgttncc cagagaaagg ggagcccact g                                   331

<210> SEQ ID NO 9
<211> LENGTH: 346
<212> TYPE: DNA
<213> ORGANISM: Homo sapiens
<220> FEATURE:
<221> NAME/KEY: unsure
<222> LOCATION: (40)
<221> NAME/KEY: unsure
<222> LOCATION: (286)
<221> NAME/KEY: unsure
<222> LOCATION: (320)

<400> SEQUENCE: 9
tttattgcac ttgcaacaga gtttaaataa gtcctgggtn tctggtgcca aggtgaggga      60
agggttgggc agagagatga ggggcagcat cagtgcagct ggcaggcaga acccaaattc    120
tgcaggccca ggacagtggg ctccccttc tctggggaac agggagggcc tgtgtctggc    180
caggctgagg ttccagatct gttgccatca tggccccttc agggtcctgg ggaaattcct    240
gggcttctcc taaatcaggg tgaactgggc ctccagggat caggtntggg agcaggccca    300
aatataagtc ctgggatctn cctgggatta gggtgccaat gtctga                   346

<210> SEQ ID NO 10
<211> LENGTH: 4132
<212> TYPE: DNA
<213> ORGANISM: Homo sapiens

<400> SEQUENCE: 10
cgctggggcc cccggcgccg accccgctg ctgccgctgc tgttgctgct gctgccgccg      60
ccacccaggg tcgggggctt caacttagac gcggaggccc cagcagtact ctcgggccc    120 ccgggctcct tcttcggatt ctcagtggag ttttaccggc cgggaacaga cggggtcagt    180
gtgctggtgg gagcacccaa ggctaatacc agccagccag gagtgctgca gggtggtgct    240
gtctacctct gtccttgggg tgccagcccc acacagtgca ccccattga atttgacagc    300
```

-continued

| | |
|---|---|
| aaaggctctc ggctcctgga gtcctcactg tccagctcag agggagagga gcctgtggag | 360 |
| tacaagtcct tgcagtggtt cggggcaaca gttcgagccc atggctcctc catcttggca | 420 |
| tgcgctccac tgtacagctg cgcacacaga aggagccac tgagcgaccc cgtgggcacc | 480 |
| tgctacctct ccacagataa cttcacccga attctggagt atgcaccctg ccgctcagat | 540 |
| ttcagctggg cagcaggaca gggttactgc caaggaggct tcagtgccga gttcaccaag | 600 |
| actggccgtg tggttttagg tggaccagga agctatttct ggcaaggcca gatcctgtct | 660 |
| gccactcagg agcagattgc agaatcttat taccccgagt acctgatcaa cctggttcag | 720 |
| gggcagctgc agactcgcca ggccagttcc atctatgatg acagctacct aggatactct | 780 |
| gtggctgttg gtgaattcag tggtgatgac acagaagact ttgttgctgg tgtgcccaaa | 840 |
| gggaacctca cttacggcta tgtcaccatc cttaatggct cagacattcg atccctctac | 900 |
| aacttctcag gggaacagat ggcctcctac tttggctatg cagtggccgc cacagacgtc | 960 |
| aatggggacg ggctggatga cttgctggtg ggggcacccc tgctcatgga tcggacccct | 1020 |
| gacgggcggc tcaggaggt gggcagggtc tacgtctacc tgcagcaccc agccggcata | 1080 |
| gagcccacgc ccaccttac cctcactggc catgatgagt ttggccgatt tggcagctcc | 1140 |
| ttgacccccc tgggggacct ggaccaggat ggctacaatg atgtggccat cggggctccc | 1200 |
| tttggtgggg agacccagca gggagtagtg tttgtatttc tgggggcccc aggagggctg | 1260 |
| ggctctaagc cttcccaggt tctgcagccc ctgtgggcag ccagccacac cccagacttc | 1320 |
| tttggctctg cccttcgagg aggccgagac ctggatggca atggatatcc tgatctgatt | 1380 |
| gtggggtcct ttggtgtgga caaggctgtg gtatacaggg gccgccccat cgtgtccgct | 1440 |
| agtgcctccc tcaccatctt ccccgccatg ttcaacccag aggagcggag ctgcagctta | 1500 |
| gaggggaacc ctgtggcctg catcaacctt agcttctgcc tcaatgcttc tggaaaacac | 1560 |
| gttgctgact ccattggttt cacagtggaa cttcagctgg actggcagaa gcagaaggga | 1620 |
| ggggtacggc gggcactgtt cctggcctcc acgcaggcaa ccctgaccca gaccctgctc | 1680 |
| atccagaatg gggctcgaga ggattgcaga gagatgaaga tctacctcag gaacgagtca | 1740 |
| gaatttcgag acaaactctc gccgattcac atcgctctca acttctcctt ggaccccaa | 1800 |
| gccccagtgg acagccacgg cctcaggcca gccctacatt atcagagcaa gagccggata | 1860 |
| gaggacaagg ctcagatctt gctggactgt ggagaagaca acatctgtgt gcctgacctg | 1920 |
| cagctggaag tgtttgggga gcagaaccat gtgtacctgg tgacaagaa tgccctgaac | 1980 |
| ctcactttcc atgcccagaa tgtgggtgag ggtggcgcct atgaggctga gcttcgggtc | 2040 |
| accgccctc cagaggctga gtactcagga ctcgtcagac acccagggaa cttctccagc | 2100 |
| ctgagctgtg actactttgc cgtgaaccag agccgcctgc tggtgtgtga cctgggcaac | 2160 |
| cccatgaagg caggagccag tctgtggggt ggccttcggt ttacagtccc tcatctccgg | 2220 |
| gacactaaga aaaccatcca gtttgacttc cagatcctca gcaagaatct caacaactcg | 2280 |
| caaagcgacg tggtttcctt tcggctctcc gtggaggctc aggcccaggt caccctgaac | 2340 |
| ggtgtctcca agcctgaggc agtgctattc ccagtaagcg actggcatcc ccgagaccag | 2400 |
| cctcagaagg aggaggacct gggacctgct gtccaccatg tctatgagct catcaaccaa | 2460 |
| ggccccagct ccattagcca gggtgtgctg gaactcagct gtcccccaggc tctggaaggt | 2520 |
| cagcagctcc tatatgtgac cagagttacg ggactcaact gcaccaccaa tcaccccatt | 2580 |
| aacccaaagg gcctggagtt ggatcccgag ggttccctgc accaccagca aaaacgggaa | 2640 |
| gctccaagcc gcagctctgc ttcctcggga cctcagatcc tgaaatgccc ggaggctgag | 2700 |

-continued

```
tgtttcaggc tgcgctgtga gctcgggccc ctgcaccaac aagagagcca aagtctgcag    2760
ttgcatttcc gagtctgggc caagactttc ttgcagcggg agcaccagcc atttagcctg    2820
cagtgtgagg ctgtgtacaa agccctgaag atgccctacc gaatcctgcc tcggcagctg    2880
ccccaaaaag agcgtcaggt ggccacagct gtgcaatgga ccaaggcaga aggcagctat    2940
ggcgtcccac tgtggatcat catcctagcc atcctgtttg gcctcctgct cctaggtcta    3000
ctcatctaca tcctctacaa gcttggattc ttcaaacgct ccctcccata tggcaccgcc    3060
atggaaaaag ctcagctcaa gcctccagcc acctctgatg cctgagtcct cccaatttca    3120
gactcccatt cctgaagaac cagtcccccc accctcattc tactgaaaag gaggggtctg    3180
ggtacttctt gaaggtgctg acggccaggg agaagctcct ctccccagcc cagagacata    3240
cttgaagggc cagagccagg ggggtgagga gctgggatc cctcccccc atgcactgtg      3300 aaggacccctt gtttacacat accctcttca tggatggggg aactcagatc caggacaga   3360 ggcccagcct ccctgaagcc tttgcatttt ggagagtttc ctgaaacaac ttggaaagat    3420
aactaggaaa tccattcaca gttctttggg ccagacatgc acaaggact tcctgtccag     3480 ctccaacctg caaagatctg tcctcagcct tgccagagat ccaaaagaag cccccagcta    3540
agaacctgga acttggggag ttaagacctg gcagctctgg acagccccac cctggtgggc    3600
caacaaagaa cactaactat gcatggtgcc ccaggaccag ctcaggacag atgccacaca    3660
aggatagatg ctggcccagg gccagagccc agctccaagg ggaatcagaa ctcaaatggg    3720
gccagatcca gcctggggtc tggagttgat ctggaaccca gactcagaca ttggcaccta    3780
atccaggcag atccaggact atatttgggc ctgctccaga cctgatcctg gaggcccagt    3840
tcaccctgat ttaggagaag ccaggaattt cccaggacct gaaggggcca tgatggcaac    3900
agatctggaa cctcagcctg ccagacaca ggccctccct gttccccaga gaaaggggag     3960
cccactgtcc tgggcctgca gaatttccct tctgcctgcc agctgcactg atgctgcccc    4020
tcatctctct gcccaacccct tccctcacct tggcaccaga cacccaggac ttatttaaac   4080
tctgttgcaa gtgcaataaa tctgacccag tgcccccact gaccagaact ag            4132
```

<210> SEQ ID NO 11
<211> LENGTH: 486
<212> TYPE: DNA
<213> ORGANISM: Homo sapiens
<220> FEATURE:
<221> NAME/KEY: unsure
<222> LOCATION: (376)
<221> NAME/KEY: unsure
<222> LOCATION: (395)
<221> NAME/KEY: unsure
<222> LOCATION: (467)

<400> SEQUENCE: 11

```
agcctgatct ctgtccaccg gtcctttata ccctcatgac ccgctgctgg gactacgacc     60
ccagtgaccg gccccgcttc accgagctgg tgtgcagcct cagtgacgtt tatcagatgg    120
agaaggacat tgccatggag caagagagga atgctcgcta ccgaaccccc aaaatcttgg    180
agcccacagc cttccaggaa ccccaccca agcccagccg acctaagtac agaccccctc     240
cgcaaaccaa cctcctgggc tccaaagctg cagttccagg ttcctgaggg tctgtgtgcc    300
agctctcctg acggcttcac cagccctatg ggagtattcc attcttcccg ttaaattcac    360
tggcacaccc cacctnttcc accgggcaca atgtntttca aaacgccac aggatggggg    420 ggagggaggg attttcattc caacccaggc aggccgagga agagggncca gcagttgttg   480
```

```
gggagg                                                                     486
```

<210> SEQ ID NO 12
<211> LENGTH: 393
<212> TYPE: DNA
<213> ORGANISM: Homo sapiens
<220> FEATURE:
<221> NAME/KEY: unsure
<222> LOCATION: (349)
<221> NAME/KEY: unsure
<222> LOCATION: (360)
<221> NAME/KEY: unsure
<222> LOCATION: (377)
<221> NAME/KEY: unsure
<222> LOCATION: (384)

<400> SEQUENCE: 12

```
ttttttttttt ttttgcaaat gggacaattt taattcaacc acaagtcaaa tagaaagaag    60
ttaaaagaat gtttatgcaa acacatgaga aaagaagggt gcagatgaga atgggggttg   120
gggagagaaa gaggaggagt aagaaaagag gaaaaagcaa gggaaagtaa aggaagaaag   180
agaaagaggg gcaggaagag agcggatttg gcccaaggtc ctatcttggc cgcatctctc   240
tgcttcttcc ccctgatgct tggtttgttg acaacacagc atcctgtgcc tgggactccc   300
aattagcttg ttcctgggac tgtgcccag ggtcctccct caggagggnc acatgctgtn   360
cagtccagac caaactncac attnaaataa ttt                                393
```

<210> SEQ ID NO 13
<211> LENGTH: 4089
<212> TYPE: DNA
<213> ORGANISM: Homo sapiens

<400> SEQUENCE: 13

```
gaattccgtc agcccttta ctcagccaca gcctccggag ccgttgcaca cctacctgcc    60
cggccgactt acctgtactt gccgccgtcc cggctcacct ggcggtgccc gaggagtagt   120
cgctggagtc cgcgcctccc tgggactgca atgtgccgat cttagctgct gcctgagagg   180
atgtctgggg tgtccgagcc cctgagtcga gtaaagttgg gcacgttacg ccggcctgaa   240
ggccctgcag agcccatggt ggtggtacca gtagatgtgg aaaaggagga cgtgcgtatc   300
ctcaaggtct gcttctatag caacagcttc aatcctggga aaaacttcaa actggtcaaa   360
tgcactgtcc agacggagat ccgggagatc atcacctcca tcctgctgag cgggcggatc   420
gggcccaaca tccggttggc tgagtgctat gggctgaggc tgaagcacat gaagtccgat   480
gagatccact ggctgcaccc acagatgacg gtgggtgagg tgcaggacaa gtatgagtgt   540
ctgcacgtgg aagccgagtg gaggtatgac cttcaaatcc gctacttgcc agaagacttc   600
atggagagcc tgaaggagga caggaccacg ctgctctatt tttaccaaca gctccggaac   660
gactacatgc agcgctacgc cagcaaggtc agcgagggca tggccctgca gctgggctgc   720
ctggagctca gcggttctt caaggatatg ccccacaatg cacttgacaa gaagtccaac   780
ttcgagctcc tagaaaagga agtgggggctg gacttgtttt tcccaaagca gatgcaggag   840
aacttaaagc ccaaacagtt ccggaagatg atccagcaga ccttccagca gtacgcctcg   900
ctcagggagg aggagtgcgt catgaagttc ttcaacactc tcgcccgtt cgccaacatc   960
gaccaggaga cctaccgctg tgaactcatt caaggatgga acattactgt ggacctggtc  1020
attgcccta aagggatccg ccagctgact agtcaggacg caaagcccac ctgcctggcc  1080
gagttcaagc agatcaggtc catcaggtgc ctcccgctgg aggagggcca ggcagtactt  1140
```

-continued

```
cagctgggca ttgaaggtgc cccccaggcc ttgtccatca aaacctcatc cctagcagag    1200
gctgagaaca tggctgacct catagacggc tactgccggc tgcagggtga gcaccaaggc    1260
tctctcatca tccatcctag gaaagatggt gagaagcgga acagcctgcc ccagatcccc    1320
atgctaaacc tggaggcccg gcggtcccac ctctcagaga gctgcagcat agagtcagac    1380
atctacgcag agattcccga cgaaaccctg cgaaggcccg gaggtccaca gtatggcatt    1440
gcccgtgaag atgtggtcct gaatcgtatt cttggggaag cttttttgg ggaggtctat     1500 gaaggtgtct acacaaatca taaaggggag aaaatcaatg tagctgtcaa gacctgcaag    1560
aaagactgca ctctggacaa caaggagaag ttcatgagcg aggcagtgat catgaagaac    1620
ctcgaccacc cgcacatcgt gaagctgatc ggcatcattg aagaggagcc cacctggatc    1680
atcatggaat tgtatcccta tggggagctg gccactacc tggagcggaa caagaactcc     1740
ctgaaggtgc tcaccctcgt gctgtactca ctgcagatat gcaaagccat ggcctacctg    1800
gagagcatca actgcgtgca cagggacatt gctgtccgga catcctggt ggcctcccct     1860 gagtgtgtga gctgggggga cttggtctt tcccggtaca ttgaggacga ggactattac     1920
aaagcctctg tgactcgtct ccccatcaaa tggatgtccc cagagtccat taacttccga    1980
cgcttcacga cagccagtga cgtctggatg ttcgccgtgt gcatgtggga gatcctgagc    2040
tttgggaagc agcccttctt ctggctggag aacaaggatg tcatcggggt gctggagaaa    2100
ggagaccggc tgcccaagcc tgatctctgt ccaccggtcc tttataccct catgacccgc    2160
tgctgggact acgaccccag tgaccggccc cgcttcaccg agctggtgtg cagcctcagt    2220
gacgtttatc agatggagaa ggacattgcc atggagcaag agaggaatgc tcgctaccga    2280 accccccaaaa tcttggagcc cacagccttc caggaacccc cacccaagcc cagccgacct    2340
aagtacagac cccctccgca aaccaacctc ctggctccaa agctgcagtt ccaggttcct    2400
gagggtctgt gtgccagctc tcctacgctc accagcccta tggagtatcc atctcccgtt    2460
aactcactgc acaccccacc tctccaccgg cacaatgtct tcaaacgcca cagcatgggg    2520
gaggaggact tcatccaacc cagcagccga gaagaggccc agcagctgtg ggaggctgaa    2580
aaggtcaaaa tgcggcaaat cctggacaaa cagcagaagc agatggtgga ggactaccag    2640
tggctcaggc aggaggagaa gtccctggac cccatggttt atatgaatga taagtcccca    2700
ttgacgccag agaaggaggt cggctacctg gagttcacag ggccccccaca gaagcccccg    2760 aggctgggcg cacagtccat ccagcccaca gctaacctgg accggaccga tgacctggtg    2820
tacctcaatg tcatggagct ggtgcggggcc gtgctggagc tcaagaatga gctctgtcag    2880
ctgccccccg agggctacgt ggtggtggtg aagaatgtgg gctgaccct gcggaagctc     2940 atcgggagcg tggatgatct cctgccttcc ttgccgtcat cttcacggac agagatcgag    3000
ggcacccaga aactgctcaa caaagacctg gcagagctca tcaacaagat gcggctggcg    3060
cagcagaacg ccgtgacctc cctgagtgag gagtgcaaga ggcagatgct gacggcttca    3120
cacaccctgc tgtggacgc caagaacctg ctcgacgctg tggaccaggc caaggttctg    3180
gccaatctgg cccacccacc tgcagagtga cggagggtgg gggccacctg cctgcgtctt    3240
ccgcccctgc ctgccatgta cctcccctgc cttgctgttg gtcatgtggg tcttccaggg    3300
agaaggccaa ggggagtcac cttcccttgc cactttgcac gacgccctct ccccacccct    3360 accctggct gtactgctca ggctgcagct ggacagaggg gactctgggc tatggacaca    3420
gggtgacggt gacaaagatg gctcagaggg ggactgctgc tgcctggcca ctgctcccta    3480
```

| | |
|---|---|
| agccagcctg gtccatgcag ggggctcctg ggggtgggga ggtgtcacat ggtgcccta | 3540 |
| gctttatata tggacatggc aggccgattt gggaaccaag ctattccttt cccttcctct | 3600 |
| tctcccctca gatgtccctt gatgcacaga gaagctgggg aggagctttg ttttcggggg | 3660 |
| tcaggcagcc agtgagatga gggatgggcc tggcattctt gtacagtgta tattgaaatt | 3720 |
| tatttaatgt gaggtttggt ctggactgac agcatgtgcc ctcctgaggg aggaccaggg | 3780 |
| cacagtccag gaacaagcta attgggagtc caggcacagg atgctgtgtt gtcaacaaac | 3840 |
| caagcatcag ggggaagaag cagagagatg cggccaagat aggaccttgg gccaaatccg | 3900 |
| ctctcttcct gccccctcttt ctctttcttc ctttactttc ccttgctttt ccctcttttc | 3960 |
| ttactcctcc tctttctctc ccccacccccc attctcatct gcaccttcct tttctcatgt | 4020 |
| gtttgcataa acattctttt aacttctttc tatttgactt gtggttgaat taaaattgtc | 4080 |
| ccatttgca | 4089 |

<210> SEQ ID NO 14
<211> LENGTH: 464
<212> TYPE: DNA
<213> ORGANISM: Homo sapiens
<220> FEATURE:
<221> NAME/KEY: unsure
<222> LOCATION: (146)
<221> NAME/KEY: unsure
<222> LOCATION: (448)

<400> SEQUENCE: 14

| | |
|---|---|
| gacctggaga tcaacgggga aaggtgaag ctgcagatct gggacacagc ggggcaggag | 60 |
| cgcttccgca ccatcacctc cacgtattat cgggggaccc acgggtcat ttgtggttta | 120 |
| cgacgtcacc agtgccgagt cctttntcaa cgtcaagcgg tggcttcacg aaatcaacca | 180 |
| gaactgtgat gatgtgtgcc gaatattagt gggtaataag aatgacgacc ctgagcggaa | 240 |
| ggtggtggag acggaagatg cctacaaatt cgccgggcag atgggcatcc agttgttcga | 300 |
| gaccagcgcc aaggagaatg tcaacgtggg aagagatgtt tcaactgcat tcacggagct | 360 |
| ggtcctccga gcaaagaaag acaaccttgg gcaaaacagc agcagcaaca acagaacgat | 420 |
| gttggttgaa gtttacgaag gaacattnaa cgaaagaaac gttt | 464 |

<210> SEQ ID NO 15
<211> LENGTH: 373
<212> TYPE: DNA
<213> ORGANISM: Homo sapiens

<400> SEQUENCE: 15

| | |
|---|---|
| tttttttttt tttttttttt taattgtgag gaatttaatt cacttgattt ggcttcattt | 60 |
| tcttgatctg ttaaaataat cctcccatag ccccctgcc agcccatct ctgcacgaac | 120 |
| ctaccccgac cttctgttg gaactgaaac ctgttggtgt aaatgagaag ccatggctgc | 180 |
| cctgggtttg gagctcagag gcatctagaa ggcaggacaa gaaatctgtt ggccaaaggg | 240 |
| caagacctgc cacctctgtg gaactgcagg gcctgccttg agaccaggtt ccccagctcc | 300 |
| cagaatggct gtggggacag gacaacgggg agggaaggga gctggcacag gccccggaga | 360 |
| aggggcaaga ccc | 373 |

<210> SEQ ID NO 16
<211> LENGTH: 730
<212> TYPE: DNA
<213> ORGANISM: Homo sapiens

```
<400> SEQUENCE: 16
gctgccggag cagcccgaag agctgcggat cgcgaggcca gtaccgaccc cgcccgcccg      60
cgcgctccgc ccccgcccgc catggcccgg gactacgacc acctcttcaa gctgctcatc     120
atcggcgaca gcggtgtggg caagagcagt ttactgttgc gttttgcaga caacactttc     180
tcaggcagct acatcaccac gatcggagtg gatttcaaga tccggaccgt ggagatcaac     240
ggggagaagg tgaagctgca gatctgggac acagcggggc aggagcgctt ccgcaccatc     300
acctccacgt attatcgggg gacccacggg gtcattgtgg tttacgacgt caccagtgcc     360
gagtcctttg tcaacgtcaa gcggtggctt cacgaaatca accagaactg tgatgatgtg     420
tgccgaatat tagtgggtaa taagaatgac gaccctgagc ggaaggtggt gggagacggaa    480
gatgcctaca aattcgccgg gcagatgggc atccagttgt tcgagaccag cgccaaggag     540
aatgtcaacg tggaagagat gttcaactgc atcacggagc tggtcctccg agcaaagaaa     600
gacaacctgg caaaacagca gcagcaacaa cagaacgatg tggtgaagct cacgaagaac     660
agtaaacgaa agaaacgctg ctgctaatgg cacccagtcc actgcagaga ctgcactgcg     720
gtccctcccc                                                            730

<210> SEQ ID NO 17
<211> LENGTH: 334
<212> TYPE: DNA
<213> ORGANISM: Homo sapiens
<220> FEATURE:
<221> NAME/KEY: unsure
<222> LOCATION: (61)
<221> NAME/KEY: unsure
<222> LOCATION: (223)
<221> NAME/KEY: unsure
<222> LOCATION: (230)
<221> NAME/KEY: unsure
<222> LOCATION: (304)

<400> SEQUENCE: 17
acagagtagc agctcagatg ccagagatcg aaagaaggct cgaatgagtg agctggaaca      60
naagtggtag atttagaaga agagaaccaa aaacttttgc tagaaaatca gcttttacga     120
gagaaaactc atggccttgt agttgagaac caggagttaa gacagcgctt ggggatggat     180
gccctggttg ctgaagagga ggcggagcaa ggggaatgaa gtnaggccan tgcgggtctg     240
ctgagtccgc agcactcaga ctacgtgcac ctctgcagca ggtgcaggcc cagttgtcac     300
cctncagaac atctcccccat ggattctggc ggta                                334

<210> SEQ ID NO 18
<211> LENGTH: 412
<212> TYPE: DNA
<213> ORGANISM: Homo sapiens
<220> FEATURE:
<221> NAME/KEY: unsure
<222> LOCATION: (120)
<221> NAME/KEY: unsure
<222> LOCATION: (153)
<221> NAME/KEY: unsure
<222> LOCATION: (210)
<221> NAME/KEY: unsure
<222> LOCATION: (372)
<221> NAME/KEY: unsure
<222> LOCATION: (381)
<221> NAME/KEY: unsure
<222> LOCATION: (411)

<400> SEQUENCE: 18
tttttttttg ctgcattgta ccttttaatt gcatgggtag ttttaaataa atggagaaag      60
```

```
cacctttcag aagctacact agcaggaaaa aattccatca agcatttaca tagtaaattn      120
ctataatttc acaaaagatt cttgatctta ctngaagtat acatgaggga aagagccccc      180
tcagcaggtg ttcccgttgc ttacagaagn aaactaaagg acctaaaact ggaggcaagc      240
cagggtgcca aaaggggga agagaaatga taaagaacca ttcataaatt ccatgtctac       300
ttcaaggaca tttgtctaat gacccttaca taataagtat tttaggggaa aactaccacc      360
ctttttaagg tnaaagtaca nttcttaaaa ggctggtagg tttctcaatt nt              412
```

<210> SEQ ID NO 19
<211> LENGTH: 1818
<212> TYPE: DNA
<213> ORGANISM: Homo sapiens

<400> SEQUENCE: 19

```
tagtctggag ctatggtggt ggtggcagcc gcgccgaacc cggccgacgg gacccctaaa       60
gttctgcttc tgtcggggca gcccgcctcc gccgccggag ccccggcggc caggctgccg      120
ctcatggtgc cagcccagag aggggccagc ccggaggcag cgagcggggg gctgccccag      180
gcgcgcaagc gacagcgcct cacgcacctg agccccgagg agaaggcgct gaggaggaaa      240
ctgaaaaaca gagtagcagc tcagactgcc agagatcgaa agaaggctcg aatgagtgag      300
ctggaacagc aagtggtaga tttagaagaa gagaaccaaa aacttttgct agaaaatcag      360
cttttacgag agaaaactca tggccttgta gttgagaacc aggagttaag acagcgcttg      420
gggatggatg ccctggttgc tgaagaggag gcggaagcca aggggaatga agtgaggcca      480
gtggccgggt ctgctgagtc cgcagcactc agactacgtg cacctctgca gcaggtgcag      540
gcccagttgt caccccctcca gaacatctcc ccatggattc tggcggtatt gactcttcag      600
attcagagtc tgtatatcctg ttgggcattc tggacaactt ggacccagtc atgttcttca      660
aatgcccttc cccagagcct gccagcctgg aggagctccc agaggtctac ccagaaggac      720
ccagttcctt accagcctcc ctttctctgt cagtggggac gtcatcagcc aagctggaag      780
ccattaatga actaattcgt tttgaccaca tatataccaa gcccctagtc ttagagatac      840
cctctgagac agagagccaa gctaatgtgg tagtgaaaat cgaggaagca cctctcagcc      900
cctcagagaa tgatcaccct gaattcattg tctcagtgaa ggaagaacct gtagaagatg      960
acctcgttcc ggagctgggt atctcaaatc tgctttcatc cagccactgc ccaaagccat     1020
cttcctgcct actggatgct acagtgactg tggatacggg ggttcccttt ccccattcag     1080
tgacatgtcc tctctgcttg gtgtaaacat tcttgggagg acacttttgc caatgaactc     1140
tttccccagc tgattagtgt ctaaggaatg atccaatact gttgcccttt tccttgacta     1200
ttacactgcc tggaggatag cagagaagcc tgtctgtact tcattcaaaa agccaaaata     1260
gagagtatac agtcctagag aatccctcta tttgttcaga tctcatagat gaccccagg      1320 tattgccttt tgacatccag cagtccaagg tattgagaca tattactgga agtaagaaat     1380
attactataa ttgagaacta cagcttttaa gattgtactt taagattgt acttttatct      1440 taaaagggtg gtagtttttcc ctaaaatact tattatgtaa gggtcattag acaaatgtct     1500
tgaagtagac atggaattta tgaatggtct ttatcatttc tcttccccct ttttggcatc     1560
ctggcttgcc tccagtttta ggtcctttag tttgcttctg caagcaacgg gaacacctgc     1620
tgagggggct ctttccctca tgtatacttc aagtaagatc aagaatcttt tgtgaaatta     1680
tagaaattta ctatgtaaat gcttgatgga attttttcct gctagtgtag cttctgaaag     1740
```

-continued

```
gtgctttctc catttattta aaaactaccc atgcaattaa aaggtacaat gcaaaaaaaa      1800
aaaaaaaaaa attttttt                                                    1818

<210> SEQ ID NO 20
<211> LENGTH: 350
<212> TYPE: DNA
<213> ORGANISM: Homo sapiens
<220> FEATURE:
<221> NAME/KEY: unsure
<222> LOCATION: (68)
<221> NAME/KEY: unsure
<222> LOCATION: (86)
<221> NAME/KEY: unsure
<222> LOCATION: (188)
<221> NAME/KEY: unsure
<222> LOCATION: (253)

<400> SEQUENCE: 20
aaacagtaat tctttagact ttattaaaaa atgacataaa gtgcatctta ttaaaaaatg        60
tataaaancc acataaattc cagggncccc tgtgcctggg cagtgttgat atcccttaga       120
gtggaggaag gtgagggatg gagggtgaac tggggactgg ggagaggacc aggtgcagt        180 tagttccncg tgtttgagtt caaagatgga gcgagggtgg atatggtggg aagggcaca       240 cggggttctca cgncaacaac ggaggaaggc aggcgacagt ctcttccctg aattctgagg     300
gaaaggcgta cattgtcacg aaatctctcc tgagctcgcg ctgtcctctc                 350

<210> SEQ ID NO 21
<211> LENGTH: 394
<212> TYPE: DNA
<213> ORGANISM: Homo sapiens
<220> FEATURE:
<221> NAME/KEY: unsure
<222> LOCATION: (208)
<221> NAME/KEY: unsure
<222> LOCATION: (345)
<221> NAME/KEY: unsure
<222> LOCATION: (361)
<221> NAME/KEY: unsure
<222> LOCATION: (373)
<221> NAME/KEY: unsure
<222> LOCATION: (378)

<400> SEQUENCE: 21
gaaggaactg gtctgctcac acttgctggc ttgcgcatca ggactggctt tatctcctga       60
ctcacggtgc aaaggtgcac tctgcgaacg ttaagtccgt ccccagcgct tggaatccta     120
cggcccccac agccggatcc cctcagcctt ccaggtcctc aactcccgtg gacgctgaac     180
aatggcctcc atgggctac aggtaatngg catcgcgctg gccgtcctgg gctggctggc      240
cgtcatgctg tgctgcgcgc tgcccatgtg gcgcgtgacg gcctttcatc ggcagcaaca     300
ttgtcaactt gcagaccatc tgggaagggc ctattggatg aactncgtgg ttcaaaagcc     360
ngtccaagat tgnatttnaa aggttttaac gatt                                   394

<210> SEQ ID NO 22
<211> LENGTH: 1665
<212> TYPE: DNA
<213> ORGANISM: Homo sapiens

<400> SEQUENCE: 22
gaaggaactg gttctgctca cacttgctgg cttgcgcatc aggactggct ttatctcctg       60
actcacggtg caaaggtgca ctctgcgaac gttaagtccg tccccagcgc ttggaatcct     120
acggccccca cagccggatc ccctcagcct tccaggtcct caactcccgt ggacgctgaa     180
```

```
caatggcctc catggggcta caggtaatgg gcatcgcgct ggccgtcctg ggctggctgg      240
ccgtcatgct gtgctgcgcg ctgcccatgt ggcgcgtgac ggccttcatc ggcagcaaca      300
ttgtcaccct gcagaccatc tgggagggcc tatggatgaa ctgcgtggtg cagagcaccg      360
gccagatgca gtgcaaggtg tacgactcgc tgctggcact gccgcaggac ctgcaggcgg      420
cccgcgccct cgtcatcatc agcatcatcg tggctgctct gggcgtgctg ctgtccgtgg      480 tgggggggcaa gtgtaccaac tgcctggagg atgaaagcgc caaggccaag accatgatcg      540
tggcgggcgt ggtgttcctg ttggccgcc ttatggtgat agtgccggtg tcctggacgg       600
cccacaacat catccaagac ttctacaatc cgctggtggc ctccgggcag aagcgggaga      660
tgggtgcctc gctctacgtc ggctgggccg cctccggcct gctgctcctt ggcgggggggc     720 tgctttgctg caactgtcca ccccgcacag acaagcctta ctccgccaag tattctgctg      780
cccgctctgc tgctgccagc aactacgtgt aaggtgccac ggctccactc tgttcctctc      840
tgctttgttc ttccctggac tgagctcagc gcaggctgtg accccaggag ggccctgcca      900
cgggccactg gctgctgggg actggggact ggcagagact gagccaggc aggaaggcag       960 cagccttcag cctctctggc ccactcggac aacttcccaa ggccgcctcc tgctagcaag     1020
aacagagtcc accctcctct ggatattggg gagggacgga agtgacaggg tgtggtggtg     1080
gagtggggag ctggcttctg ctggccagga tagcttaacc ctgactttgg gatctgcctg     1140
catcggcgtt ggccactgtc ccatttaca ttttccccac tctgtctgcc tgcatctcct     1200
ctgttccggg taggccttga tatcacctct gggactgtgc cttgctcacc gaaacccgcg    1260
cccaggagta tggctgaggc cttgcccacc cacctgcctg ggaagtgcag agtggatgga    1320
cgggtttaga ggggaggggc gaaggtgctg taaacaggtt tgggcagtgg tgggggaggg    1380
ggccagagag gcggctcagg ttgcccagct ctgtggcctc aggactctct gcctcacccg    1440
cttcagccca gggcccctgg agactgatcc cctctgagtc ctctgcccct tccaaggaca    1500
ctaatgagcc tggagggtg gcagggagga ggggacagct tcaccttgg aagtcctggg     1560 gttttttcctc ttccttcttt gtggtttctg ttttgtaatt taagaagagc tattcatcac    1620
tgtaattatt attattttct acaataaatg ggacctgtgc acagg                     1665

<210> SEQ ID NO 23
<211> LENGTH: 345
<212> TYPE: DNA
<213> ORGANISM: Homo sapiens
<220> FEATURE:
<221> NAME/KEY: unsure
<222> LOCATION: (291)

<400> SEQUENCE: 23
aggtcctact ggaaggagtt cctggtgatg tgcacgctct ttgtgctggc cgtgctgctc       60
ccagttttat tcttgctcta ccggcaccgg aacagcatga aagtcttcct gaagcagggg     120
gaatgtgcca gcgtgcaccc caagacctgc cctgtggtgc tgcccctga cccgcccca     180 ctcaacggcc tagggcccct agcaccccgc tcgatcaccg agggtaccag tccctgtcag    240
acagcccccc ggggttcccg agtcttcact gagtcagaga agaggccact nagcatccaa    300
gacagcttcg tgggaggtat ccccagtgtg ccccggccc cgggg                      345

<210> SEQ ID NO 24
<211> LENGTH: 2433
<212> TYPE: DNA
<213> ORGANISM: Homo sapiens
```

<400> SEQUENCE: 24

```
gaagaaaggc tgattagaaa atttgaagct gaaaacatct ccaactacac ggcccttctg        60
ctgagccagg atggaaagac gctgtatgtg ggggcccgag aggccctctt tgcacttaac       120
agcaacctca gcttcttgcc aggcggggag taccaagagc tactgtggag tgcagatgct       180
gacaggaagc agcagtgcag cttcaagggc aaggacccaa agcgtgactg tcaaaactac       240
atcaagatcc tcctgccact caacagcagc cacctgctca cctgtggcac ggccgccttc       300
agcccctgt gtgcttacat tcacatagcg agctttactt tagcccaaga tgaggccggt        360
aatgtcattc tggaggatgg caagggtcat tgtccctttg accccaactt caagtccacg       420
gctctggtgg ttgatggtga gctgtacact ggaacagtca gtagcttcca gggaaacgac       480
ccagccattt cccggagcca gagttcccgc ccaccaagac tgagagctc cctcaactgg        540
ctacaagacc ctgcctttgt ggcctcggct acgtccccg agagcctggg cagccccata        600
ggtgatgatg ataagatcta cttcttcttc agcgagacgg gccaggagtt tgagttcttt       660
gagaacacca tcgtgtcccg agttgcccga gtctgtaagg gcgatgaggg tggagagcgg       720
gtgttgcagc aacgctggac ctcctttctc aaggctcagc tcctgtgctc ccggcctgat       780
gatggctttc ccttttaacgt gctacaagat gtcttcaccc tgaaccccaa ccctcaggat     840
tggcgcaaga ccctttctat cggggtcttt acctcccagt ggcacagagg gaccacagaa       900
ggctctgcca tctgcgtctt caccatgaat gatgtgcaga aggcctttga cggcctgtac       960
aagaaagtaa acagagagac acagcagtgg tataccgaga cccaccaggt gcccacaccg      1020
cggccgggag cgtgcattac caacagtgcc cgggaacgga agatcaactc gtccctgcag      1080
ctcccagacc gagtgctgaa cttcctcaag gatcacttct tgatggatgg gcaggtccgc      1140
agtcgcctgc tgctgctgca gcccagagcc cgctaccagc gtgtggctgt gcaccgtgtg      1200
cctggcctgc acagcactta tgatgtccta tttctgggca ctggtgatgg ccgcctgcac      1260
aaagcagtga ccctgagctc cagagtccac atcattgagg agctgcagat cttccctcaa      1320
ggacagcctg tgcagaacct gctcttggac agccatgggg gactgttgta tgcctcctcc      1380
cattccgggg tggtgcaagt gcccgtagcc aactgcagcc tgtacccaac ctgtggagac      1440
tgcctcctgg ctcgagaccc ctactgcgcc tggactggct ctgcctgcag gctcgctagc      1500
ctctaccagc ctgatctggc ctccaggcca tgggaccagg acattgaggg tgccagtgtc      1560
aaggaactct gcaagaattc ctcatacaag gcccggtttc ttgtgccagg taagccatgt      1620
aaacaagtcc agatccaacc aaacacagtg aacaccctgg cctgcccact cctctcaaac      1680
ctggccactc ggctctgggt gcacaatgga gccccagtca atgcctctgc ctcctgccgc      1740
gtgttaccca ccggggacct gctgctggtg ggcagccagc agggtttggg ggtgttccag      1800
tgttggtcga tagaagaagg attccagcag cttgtggcca gctactgccc agaggtgatg      1860
gaggaggggg taatggacca aaagaaccag cgtgatggta ccccagtcat tatcaacaca      1920
tcacgagtga gtgcaccggc tggtggcagg acagctggg gtgcggacaa gtcctactgg      1980
aatgaattcc tggtgatgtg tactctgttt gtgtttgcta tggtgctttt gtttctgttc      2040
tttctctacc gacatcggga tggcatgaaa ctcttcctaa agcagggcga gtgtgccagt      2100
gtgcacccca agactcgccc tatagtgcta ccacctgaga cccgaccgct gaatggtgtc      2160
ggccctccta gcacccccact tgaccaccga ggctaccagg ctctgtcgga tagctcccca      2220
gggcccagag tcttcactga atcagagaag aggccactga gcatccagga cagctttgta      2280
```

-continued

```
gaggtgtctc ccgtgtgtcc ccggcccga gttcgactgg gctctgagat ccgagactct      2340
gtggtatgag agctgacttt agatgtggtc accctgacct cagggttgtg agtgtcagtg      2400
gaagtcagct acctctgctc tcacagaaca cag                                   2433

<210> SEQ ID NO 25
<211> LENGTH: 463
<212> TYPE: DNA
<213> ORGANISM: Homo sapiens
<220> FEATURE:
<221> NAME/KEY: unsure
<222> LOCATION: (368)
<221> NAME/KEY: unsure
<222> LOCATION: (402)
<221> NAME/KEY: unsure
<222> LOCATION: (458)

<400> SEQUENCE: 25
gtttggcaaa aactcaagcg gctgaaggaa ggaagaggtt ctccagagtc ggaactgagg       60
gttggaacta tacccgggac caaactcacg gaccactcga ggcctgcaaa ccttcctggg     120
aggacaggca ggccagatgg ccgctccact ggggaatgct cccagctgtg ctgtggagag     180
aagctgatgt tttggtgtat tgtcagccat cgtccttgga ctcggagact atggcctcgc     240
tccccaccct cctcttggaa ttacaagccc tggggtttga agctgacttt atagctgcaa     300
gtgtatctcc ttttatctgg tgcctcctca aacccagtct cagacactta aatgcagaca     360
acaccttnct cctgcagaca cctgggactg agccaaggag gncttgggga aggcccttag     420
ggggagcacc ctgatgggag aggacagagc agggggttnca gca                      463

<210> SEQ ID NO 26
<211> LENGTH: 331
<212> TYPE: DNA
<213> ORGANISM: Homo sapiens
<220> FEATURE:
<221> NAME/KEY: unsure
<222> LOCATION: (13)
<221> NAME/KEY: unsure
<222> LOCATION: (15)
<221> NAME/KEY: unsure
<222> LOCATION: (322)

<400> SEQUENCE: 26
agaaaaagcc cantnttcac tttattggag gtctctgcct ccattcacag gagaaaggag       60
ctgggagccc catcctaagg gtcccagcat cagcccactg gagggcctgg aacagtccag     120
cactctgtgg gagaggagtg gggaggggaa tgttttagaa aaaatagatc tctatgtaca     180
tctgacatat ttatatagca cataaattag ggagtgctct gaccctgcc cgtgagccc       240 aagcactgag cagggaggtg aacgccagtc cagaaagaag gtgctgggag cccctgctct     300
gtcctctcca tccacggtgc tncccctagg g                                    331

<210> SEQ ID NO 27
<211> LENGTH: 1907
<212> TYPE: DNA
<213> ORGANISM: Homo sapiens

<400> SEQUENCE: 27
cggccagata cctcagcgct acctggcgga actggatttc tctcccgcct gcggcctgc       60 ctgccacagc cggactccgc cactccggta gcctcatggc tgcaacctgt gagattagca     120
acatttttag caactactt c agtgcgatgt acagctcgga ggactccacc ctggcctctg    180 ttcccctgc tgccaccttt ggggccgatg acttggtact gaccctgagc aacccccaga     240
```

-continued

```
tgtcattgga gggtacagag aaggccagct ggttggggga acagcccag ttctggtcga    300 agacgcaggt tctggactgg atcagctacc aagtggagaa gaacaagtac gacgcaagcg    360
ccattgactt ctcacgatgt gacatggatg gcgccaccct ctgcaattgt gcccttgagg    420
agctgcgtct ggtctttggg cctctggggg accaactcca tgcccagctg cgagacctca    480
cttccagctc ttctgatgag ctcagttgga tcattgagct gctggagaag gatggcatgg    540
ccttccagga ggccctagac ccagggccct ttgaccaggg cagccccttt gcccaggagc    600
tgctggacga cggtcagcaa gccagcccct accaccccgg cagctgtggc gcaggagccc    660
cctcccctgg cagctctgac gtctccaccg cagggactgg tgcttctcgg agctcccact    720
cctcagactc cggtggaagt gacgtggacc tggatcccac tgatggcaag ctcttcccca    780
gcgatggttt tcgtgactgc aagaagggg atcccaagca cgggaagcgg aaacgaggcc    840
ggccccgaaa gctgagcaaa gagtactggg actgtctcga gggcaagaag agcaagcacg    900
cgcccagagg cacccacctg tgggagttca tccgggacat cctcatccac ccggagctca    960
acgagggcct catgaagtgg gagaatcggc atgaaggcgt cttcaagttc ctgcgctccg   1020
aggctgtggc ccaactatgg ggccaaaaga aaagaacag caacatgacc tacgagaagc   1080
tgagccgggc catgaggtac tactacaaac gggagatcct ggaacgggtg gatggccggc   1140
gactcgtcta caagtttggc aaaaactcaa gcggctggaa ggaggaagag gttctccaga   1200
gtcggaactg agggttggaa ctatacccgg gaccaaactc acggaccact cgaggcctgc   1260
aaaccttcct gggaggacag gcaggccaga tggcccctcc actgggaat gctcccagct   1320 gtgctgtgga gagaagctga tgttttggtg tattgtcagc catcgtcctt ggactcggag   1380
actatggcct cgcctcccca ccctcctctt ggaattacaa gccctgggt ttgaagctga   1440 ctttatagct gcaagtgtat ctccttttat ctggtgcctc ctcaaaccca gtctcagaca   1500
cttaaatgca gacaacacct tcttcctgca gacacttgga ctgagccaag gaggcttggg   1560
aggccctagg gagcaccgtg atggagagga cagagcaggg gctccagcac ttctttctgg   1620
actggcgttc acctccctgc tcagtgcttg gctccacgg gcagggtca gagcactccc   1680 taatttatgt gctatataaa tatgtcagat gtacatagag atctattttt tctaaaacat   1740 tccctcccc actcctctcc cacagagtgc tggactgttc caggccctcc agtgggctga   1800 tgctggacc cttaggatgg ggctcccagc tcctttctcc tgtgaatgga ggcagagacc   1860
tccaataaag tgccttctgg ctttttcta aaaaaaaaa aaaaaaa                  1907
```

<210> SEQ ID NO 28
<211> LENGTH: 467
<212> TYPE: DNA
<213> ORGANISM: Homo sapiens
<220> FEATURE:
<221> NAME/KEY: unsure
<222> LOCATION: (428)
<221> NAME/KEY: unsure
<222> LOCATION: (462)

<400> SEQUENCE: 28

```
agtactacaa gcatcattct ctcaaggaag ggttcagaac cttagataca actctgcagt     60
ttccatacaa ggagccagaa cattcagctg gacagagggg taatagagca ggcaacagct    120
tgttaagtcc aaaagtgctg ggcattgcat cgctcggtat gacttctgtg caagagatat    180
gagagagttg tccttgttga aaggagatgt ggtgaagatt tacacaaaga tgagtgcaaa    240
tggctggtgg agaggagaag taaatggcag ggtgggctgg tttccatcca catatgtggg    300
```

```
aaggaggatg aataaattca aatcccgtgt tgcaccctgc accaaaattt tcagaggaag      360
gggataatta ggaagcctgc acagcttcgt ggatttaact tgaagtgttt ttaaaaagct      420
ggcttttntg ggctgtttca acatcctccc tccttaggcc cntccta                   467
```

<210> SEQ ID NO 29
<211> LENGTH: 453
<212> TYPE: DNA
<213> ORGANISM: Homo sapiens
<220> FEATURE:
<221> NAME/KEY: unsure
<222> LOCATION: (240)
<221> NAME/KEY: unsure
<222> LOCATION: (387)
<221> NAME/KEY: unsure
<222> LOCATION: (438)

<400> SEQUENCE: 29

```
tttttttcc caacatgtaa ctctctcagt cttgtcagaa cacaacttct gctatggagg       60
aaatatttcc atcaggaaag ggccaagtta gtgtcttaac ttgactgcct tgaatgggga     120
ctctggaccc caggaagaat gtatttaggc tcctcacaaa aaagagtgat ggctgggcaa     180
aacaaatgta ctgcaagacc catcttccct ccagttaata cactcccagg gatgggnctg     240
cagaggggga gactctgaga gaagctggag gcccacaaaa gtccactgac cctctttctg     300
tcccagaaat gaataaagga cccagttgtg ctttccttcc aaaatcctca acaaagttgt     360
ttgtgctcca aggaaaatgt gggggantta aaaaaatcat gttcccgggt catctttgtg     420
tgtgttgcgg gggaggtngg tggggaggga aaa                                  453
```

<210> SEQ ID NO 30
<211> LENGTH: 4762
<212> TYPE: DNA
<213> ORGANISM: Homo sapiens

<400> SEQUENCE: 30

```
cccgccccgg cccagccgcg tcccggagcc gtcgggcatg gagccgtgga agcagtgcgc       60
gcagtggctc atccattgca aggtgctgcc caccaaccac cgggtgacct gggactcggc     120
tcaggtgttc gaccttgcgc agaccctccg cgatggagtc ctgctctgcc agctgcttaa     180
caacctccgg gcgcactcca tcaacctgaa ggagatcaac ctgaggccgc agatgtccca     240
gtttctctgt tgaagaaca taaggacatt tctcacggcc tgttgtgaga cgtttggaat     300
gaggaaaagt gaacttttcg aggcatttga cttgtttgat gttcgtgact tggagaggt      360 tatagaaaca ttatcacgac tttctcgaac acctatagca ttggccacag gaatcaggcc     420
cttcccaaca gaagaaagca ttaatgatga agacatctac aaaggccttc ctgatttaat     480
agatgaaacc cttgtggaag atgaagaaga tctctatgac tgtgtttatg gggaagatga     540
aggtggagaa gtctatgagg acttaatgaa ggcagaggaa gcacatcagc ccaaatgtcc     600
agaaaatgat atacgaagtt gttgtctagc agaaattaag cagacagaag aaaaatatac     660
agaaactttg gagtcaatag aaaaatattt catggcacca ctaaaaagat ttctgacagc     720
agcagaattt gattcagtat tcatcaacat tcctgaactt gtaaaacttc atcggaacct     780
aatgcaagag attcatgatt ccattgtaaa taaaaatgac cagaacttgt accaagtttt     840
tattaactac aaggaaagat tggttattta cgggcagtac tgcagtggag tggagtcagc     900
catctctagt ttagactaca tttctaagtc aaaagaagat gtcaaactga aattagagga     960
atgttccaaa agagcaaata tgggaaaatt tactcttcga gacttgcttg tggttcctat    1020
```

-continued

```
gcaacgtgtt ttaaagtacc accttctcct ccaggaactg gtcaaacata ccactgatcc   1080
gactgagaag gcaaatctga aactggctct tgatgccatg aaggacttgg cacaatatgt   1140
gaatgaagtg aaaagagata atgagaccct tcgtgaaatt aaacagtttc agctatctat   1200
agagaatttg aaccaaccag ttttgctttt tggacgacct cagggagatg gtgaaattcg   1260
aataaccact ctagacaagc ataccaaaca agaaaggcat atcttcttat ttgatttggc   1320
agtgatcgta tgtaagagaa aaggtgataa ctatgaaatg aaggaaataa tagatcttca   1380
gcagtacaag atagccaata atcctacaac cgataaagaa aacaaaaagt ggtcttatgg   1440
cttctacctc atccatacccc aaggacaaaa tgggttagaa ttttattgca aaacaaaaga   1500
tttaaagaag aaatggctag aacagtttga aatggctttg tctaacataa gaccagacta   1560
tgcagactcc aatttccacg acttcaagat gcataccttc actcgagtca catcctgcaa   1620
agtctgccag atgctcctga ggggaacatt ttatcaaggc tatttatgtt ttaagtgtgg   1680
agcgagagca cacaaagaat gtttgggaag agtagacaat tgtggcagag ttaattctgg   1740
tgaacaaggg acactcaaac taccagaaaa acggaccaat ggactgcgaa gaactcctaa   1800
acaggtggat ccaggtttac caaagatgca ggtcattagg aactattctg gaacaccacc   1860
cccagctctg catgaaggac ccccttttaca gctccaggcc ggggataccg ttgaacttct   1920
gaaaggagat gcacacagtc tgttttggca gggcagaaat ttagcatctg gagaggttgg   1980
attttttcca agtgatgcag tcaagccttg cccatgtgtg cccaaaccag tagattattc   2040
ttgccaaccc tggtatgctg agcaatggaa aagattgcaa gcagagaccg aacttattaa   2100
tagggtaaat agtacttacc ttgtgaggca caggaccaaa gagtcaggag aatatgcaat   2160
tagcattaag tacaataatg aagcaaagca catcaagatt ttaacaagag atggcttttt   2220
tcacattgca gaaaatagaa aatttaaaag tttaatggaa cttgtggagt actacaagca   2280
tcattctctc aaggaagggt tcagaacctt agatacaact ctgcagtttc catacaagga   2340
gccagaacat tcagctggac agagggggtaa tagagcaggc aacagcttgt taagtccaaa   2400
agtgctgggc attgccatcg ctcggtatga cttctgtgca agagatatga gagagttgtc   2460
cttgttgaaa ggagatgtgg tgaagattta cacaaagatg agtgcaaatg gctggtggag   2520
aggagaagta aatggcaggg tgggctggtt tccatccaca tatgtggaag aggatgaata   2580
aattcaaatc ccgtgttgca ccctgcacca aaaatttcag agaagggata aatagaagcc   2640
tgcacagcat cgtgaattaa ctgaagtgtt taaaaagctg catttctggc tgttcaacat   2700
cctccctcct tagcccctcc taagtcttaa tgctgagatt tctaaagatg ctggtactga   2760
cagattaatg gcttgcctag agctgtgcaa gaaacagcct gccagtctgt cattgtcagg   2820
gaccagggca aaaccaagag ctgttcttcc cagaagagcc ctgcaaacac attggttcgt   2880
gcttcccttt acttcttctg gtcagatacc atgaatgcca gtcatcagta aatcttaata   2940
cacttttgct ttattctcac atgccattca ccagattatt tgatggtaca agaagcaga    3000 agtgtaattt tccttttccc agcatgacga aaaattggag ttctgccatt tgagcagctt   3060
actggagaga tccagcctta cttgtcttaa attgtccaac aaggtgactc attgcccggc   3120
aaacactttt accctcagat gttactcatg atattataaa atatgaggcc agtgctcagg   3180
tttgcatcat aagtgagcta tccctgaagg gttttaatta cttatttggt gtcctgatta   3240
tatttgcaaa cttctttata aaaggtgaaa aaagcacaca aaagagaggg tgtcttcata   3300
ttaaaccttc acaaccttca tgatttcata ggattatttt ggaaatatag cacttgactt   3360
```

-continued

```
tatgaaagga tctgggctag gtatattagg ggtagttgcc aataacctga agaagctggc    3420
attgtttaca gaaacagatc aagggctata atttatgtca ttttatagca gcagtatcta    3480
ttaatacatg cctttcctc ccatccacct cccccgcaca cacacaaaga tgacctggga     3540
catgattttt ttattcccac attttcttgg agcacaaaca actttgttga ggattttgga    3600
aggaaagcac aactgggtcc tttattcatt tctgggacag aaagagggtc agtggacttt    3660
tgtgggcctc cagcttctct cagagtctcc ccctctgcag cccatcctgg gagtgtatta    3720
actggaggga agatgggtct tgcagtacat ttgttttgcc cagccatcac tctttttgt     3780 gaggagccta aatacattct tcctggggtc cagagtcccc attcaaggca gtcaagttaa    3840
gacactaact tggccctttc ctgatggaaa tatttcctcc atagcagaag ttgtgttctg    3900
acaagactga gagagttaca tgttgggaaa aaaagaagc attaacttag tagaactgaa     3960
ccaggagcat taagttctga aattttgaat catctctgaa atgaagcagg tgtagcctgc    4020
cctctcatca atccgtccgt ctgggtgcca gaactcaagg ttcagtggac acatccccct    4080
gttagagacc ctcatgggct aggactttc atctaggata gattcaagac ctttacctca     4140
gaattatgta aactgtgatt gtgttttaga aaaattatta tttgctaaaa ccatttaagt    4200
ctttgtatat gtgtaaatga tcacaaaaat gtattttata aaatgttctg tacaataaag    4260
ttacacctca aagtgtactc ttggaatgga ttctttcctg taaagtctta tctgcgactc    4320
tgtctcggga atgttttgtc tgttgccgtc agccgaactt tgttatggag ggagcagcct    4380
cacacaagca gaaacactcc tgtggatggt attgtagcat gtattgttta ttttagtcaa    4440
tagaccctct ccttataaat ggtgtttagt cttcctgttg catttcatgg gcctgggggt    4500
ttcctrgcag aggatattgg agccccttt tgtgacatta ccaattacat ctttgtccac     4560
gtttaatact ttgttttgga aaatttaaat gctgcagatt tgtgtagagt tctaatacca    4620
aagacagaag taaatgtttt ccatatactt tgtcttgcct gtatgcagcc cttgtgtaat    4680
atggtgaatt agagtggtat ttcactttgt attattttgt aaatatgtca atataataaa    4740
tagtgactaa aaaaaaaaaa aa                                              4762
```

<210> SEQ ID NO 31
<211> LENGTH: 422
<212> TYPE: DNA
<213> ORGANISM: Homo sapiens
<220> FEATURE:
<221> NAME/KEY: unsure
<222> LOCATION: (80)
<221> NAME/KEY: unsure
<222> LOCATION: (217)
<221> NAME/KEY: unsure
<222> LOCATION: (254)
<221> NAME/KEY: unsure
<222> LOCATION: (311)
<221> NAME/KEY: unsure
<222> LOCATION: (321)
<221> NAME/KEY: unsure
<222> LOCATION: (375)
<221> NAME/KEY: unsure
<222> LOCATION: (381)
<221> NAME/KEY: unsure
<222> LOCATION: (386)
<221> NAME/KEY: unsure
<222> LOCATION: (394)
<221> NAME/KEY: unsure
<222> LOCATION: (416)

<400> SEQUENCE: 31

```
ttttttactt tatttcgtt ttaattttt ggaaggatat acaccacata tcccatgggc      60
```

-continued

| | |
|---|---|
| aataaagcgc attcaatgtn tttataagcc aaacagtcac tttgtttaag caaacacaag | 120 |
| tacaaagtaa aatagaacca caaaataatg aactgcatgt tcataacata caaaaatcgc | 180 |
| cgcctactca gtaggtaact acaacattcc aactccngaa tatatttata aatttacatt | 240 |
| ttcagttaaa aaantagact tttgagagtt cagattttgt tttagatttt gttttcttac | 300 |
| attctggaga ncccgaagct ncagctcagc ccctcttccc ttattttgct ccccaaagcc | 360 |
| ttcccccaa atcancactg nctgncccc cctntaaggg cttagaggtg agcatntccc | 420 |
| ct | 422 |

<210> SEQ ID NO 32
<211> LENGTH: 3132
<212> TYPE: DNA
<213> ORGANISM: Homo sapiens

<400> SEQUENCE: 32

| | |
|---|---|
| ccgcagaact tggggagccg ccgccgccat ccgccgccgc agccagcttc cgccgccgca | 60 |
| ggaccggccc ctgccccagc ctccgcagcc gcggcgcgtc cacgcccgcc cgcgcccagg | 120 |
| gcgagtcggg gtcgccgcct gcacgcttct cagtgttccc cgcgccccgc atgtaacccg | 180 |
| gccaggcccc cgcaacggtg tcccctgcag ctccagcccc gggctgcacc ccccgcccc | 240 |
| gacaccagct ctccagcctg ctcgtccagg atggccgcgg ccaaggccga gatgcagctg | 300 |
| atgtccccgc tgcagatctc tgacccgttc ggatcctttc ctcactcgcc caccatggac | 360 |
| aactacccta agctggagga gatgatgctg ctgagcaacg gggctcccca gttcctcggc | 420 |
| gccgccgggg ccccagaggg cagcggcagc aacagcagca gcagcagcag cggggcggt | 480 |
| ggaggcggcg ggggcggcag caacagcagc agcagcagca gcaccttcaa ccctcaggcg | 540 |
| gacacgggcg agcagcccta cgagcacctg accgcagagt cttttcctga catctctctg | 600 |
| aacaacgaga aggtgctggt ggagaccagt taccccagcc aaaccactcg actgcccccc | 660 |
| atcacctata ctggccgctt tccctggag cctgcaccca acagtggcaa caccttgtgg | 720 |
| cccgagcccc tcttcagctt ggtcagtggc ctagtgagca tgaccaaccc accggcctcc | 780 |
| tcgtcctcag caccatctcc agcggcctcc tccgcctccg cctcccagag cccacccctg | 840 |
| agctgcgcag tgccatccaa cgacagcagt cccatttact cagcggcacc caccttcccc | 900 |
| acgccgaaca ctgacatttt ccctgagcca caaagccagg ccttcccggg ctcggcaggg | 960 |
| acagcgctcc agtacccgcc tcctgcctac cctgccgcca agggtggctt ccaggttccc | 1020 |
| atgatccccg actacctgtt tccacagcag caggggatc tgggcctggg caccccagac | 1080 |
| cagaagccct tccagggcct ggagagccgc acccagcagc cttcgctaac ccctctgtct | 1140 |
| actattaagg cctttgccac tcagtcgggc tcccaggacc tgaaggccct caataccagc | 1200 |
| taccagtccc agctcatcaa acccagccgc atgcgcaagt atcccaaccg gcccagcaag | 1260 |
| acgccccccc acgaacgccc ttacgcttgc ccagtggagt cctgtgatcg ccgcttctcc | 1320 |
| cgctccgacg agctcacccg ccacatccgc atccacacag ccagaagcc ttccagtgc | 1380 |
| cgcatctgca tgcgcaactt cagccgcagc gaccacctca ccacccacat ccgcacccac | 1440 |
| acaggcgaaa agcccttcgc ctgcgacatc tgtggaagaa agtttgccag gagcgatgaa | 1500 |
| cgcaagaggc ataccaagat ccacttgcgg cagaaggaca agaaagcaga caaagtgtt | 1560 |
| gtggcctctt cggccacctc ctctctctct tcctacccgt cccggttgc tacctcttac | 1620 |
| ccgtccccgg ttactacctc ttatccatcc ccggccacca cctcatcccc atcccctgtg | 1680 |
| cccacctcct tctcctctcc cggctcctcg acctacccat cccctgtgca cagtggcttc | 1740 |

-continued

```
ccctccccgt cggtggccac cacgtactcc tctgttcccc ctgctttccc ggcccaggtc    1800
agcagcttcc cttcctcagc tgtcaccaac tccttcagcg cctccacagg gctttcggac    1860
atgacagcaa cctttctcc caggacaatt gaaatttgct aaagggaaag gggaaagaaa     1920
gggaaaaggg agaaaaagaa acacaagaga cttaaaggac aggaggagga gatggccata    1980
ggagaggagg gttcctctta ggtcagatgg aggttctcag agccaagtcc tccctctcta    2040
ctggagtgga aggtctattg gccaacaatc cttcctgccc acttcccctt ccccaattac    2100
tattcccttt gacttcagct gcctgaaaca gccatgtcca agtcttcac ctctatccaa     2160
agaacttgat ttgcatggat tttggataaa tcatttcagt atcatctcca tcatatgcct    2220
gaccccttgc tcccttcaat gctagaaaat cgagttggca aaatgggtt tgggcccctc     2280
agagccctgc cctgcaccct tgtacagtgt ctgtgccatg gatttcgttt ttcttgggt     2340
actcttgatg tgaagataat ttgcatattc tattgtatta tttggagtta ggtcctcact    2400
tgggggaaaa aaaaaaaaaa aagccaagca aaccaatggt gatcctctat tttgtgatga    2460
tgctgtgaca ataagtttga accttttttt ttgaaacagc agtcccagta ttctcagagc    2520
atgtgtcaga gtgttgttcc gttaaccttt ttgtaaatac tgcttgaccg tactctcaca    2580
tgtggcaaaa tatggtttgg tttttctttt ttttttttga agtgttttt tcttcgtcct     2640
tttggtttaa aaagtttcac gtcttggtgc cttttgtgtg atgccccttg ctgatggctt    2700
gacatgtgca attgtgaggg acatgctcac ctctagcctt aaggggggca gggagtgatg    2760
atttgggga ggctttggga gcaaaataag gaagagggct gagctgagct tcggttctcc     2820
agaatgtaag aaaacaaaat ctaaacaaa atctgaactc tcaaaagtct attttttaa      2880
ctgaaaatgt aaatttataa atatattcag gagttggaat gttgtagtta cctactgagt    2940
aggcggcgat ttttgtatgt tatgaacatg cagttcatta ttttgtggtt ctatttact    3000
ttgtacttgt gtttgcttaa acaaagtgac tgtttggctt ataaacacat tgaatgcgct    3060
ttattgccca tgggatatgt ggtgtatatc cttccaaaaa attaaaacga aaataaagta    3120
gctgcgattg gg                                                        3132
```

<210> SEQ ID NO 33
<211> LENGTH: 464
<212> TYPE: DNA
<213> ORGANISM: Homo sapiens
<220> FEATURE:
<221> NAME/KEY: unsure
<222> LOCATION: (364)
<221> NAME/KEY: unsure
<222> LOCATION: (401)
<221> NAME/KEY: unsure
<222> LOCATION: (425)
<221> NAME/KEY: unsure
<222> LOCATION: (439)

<400> SEQUENCE: 33

```
ttaaggtata cactttatt caactggtct caagtcagtg tacaggtaag ccctggctgc    60
ctccacccac tcccagggag accaaaagcc ttcatacatc tcaagttggg ggacaaaaaa   120
gggggaaggg ggggcacgaa ggctcatcat tcaaaataaa acaaataaa aaagtattaa    180
ggcgaagatt aaaaaaattt tgcattacat aatttacacg aaagcaatgc tatcacctcc   240
cctgtgtgga cttgggagag gactgggcca ttctccttag gagagaagtg ggggtgggct   300
tttagggatg ggcaaggga ctttcctgtt aacaacgca tcttcatatt tgggaattg     360
actntttaaa aaaaccaac aatgtggcaa ttcaaagtcc ntcgggccac atttgtggaa    420
```

```
ctttnggggg gttgctcgnt cccacccgac tgttgttcac cttt            464
```

<210> SEQ ID NO 34
<211> LENGTH: 3646
<212> TYPE: DNA
<213> ORGANISM: Homo sapiens

<400> SEQUENCE: 34

```
gcccagcacc ccaaggcggc caacgccaaa actctccctc ctcctcttcc tcaatctcgc    60
tctcgctctt ttttttttc gcaaaaggag gggagagggg gtaaaaaaat gctgcactgt   120
gcggcgaagc cggtgagtga gcggcgcggg gccaatcagc gtgcgccgtt ccgaaagttg   180
cctttatgg ctcgagcggc cgcggcggcg ccctataaaa cccagcggcg cgacgcgcca   240
ccaccgccga daccgcgtcc gcccgcgagc acagagcctc gcctttgccg atccgccgcc   300
cgtccacacc cgccgccagg taagcccggc cagccgaccg gggcatgcgg ccgcggccct   360
tcgcccgtgc agagccgccg tctgggccgc agcggggggc gcatgggggcg gaaccggacc   420
gccgtggggg gcgcgggaga agcccctggg cctccggaga tggggacac cccacgccag   480
ttcgcaggcg cgaggccgcg ctcggggcggg cgcgctccgg gggtgccgct ctcggggcgg   540
gggcaaccgg cggggtcttt gtctgagccg ggctcttgcc aatggggatc gcacggtggg   600
cgcggcgtag cccccgtcag gcccggtggg ggctggggcg ccatgcgcgt gcgcgctggt   660
cctttgggcg ctaactgcgt gcgcgctggg aattggcgct aattgcgcgt gcgcgctggg   720
actcaatggc gctaatcgcg cgtgcgttct ggggcccggg cgcttgcgcc acttcctgcc   780
cgagccgctg gcgcccgagg gtgtggccgc tgcgtgcgcg cgcgcgaccc ggtcgctgtt   840
tgaaccgggc ggaggcgggg ctggcgcccg gttgggaggg ggttggggcc tggcttcctg   900
ccgcgcgccg cggggacgcc tccgaccagt gtttgccttt tatggtaata acgcggccgg   960
cccggcttcc tttgtcccca atctgggcgc gcgccggcgc ccctggcgg cctaaggact  1020
cggcgcgccg gaagtggcca gggcggggcc gacttcggct cacagcgcgc ccggctattc  1080
tcgcagctca ccatggatga tgatatcgcc gcgctcgtcg tcgacaacgg ctccggcatg  1140
tgcaaggccg gcttcgcggg cgacgatgcc ccccgggccg tcttcccctc catcgtgggg  1200
cgccccaggc accaggtagg ggagctggct gggtggggca gccccgggag cgggcgggag  1260
gcaagggcgc tttctctgca caggagcctc ccggtttccg gggtgggctg cgcccgtgct  1320
cagggcttct tgtcctttcc ttcccaggc gtgatggtgg gcatgggtca gaaggattcc  1380
tatgtgggcg acgaggccca gagcaagaga ggcatcctca ccctgaagta ccccatcgag  1440
cacggcatcg tcaccaactg ggacgacatg gagaaaatct ggcaccacac cttctacaat  1500
gagctgcgtg tggctcccga ggagcacccc gtgctgctga ccgaggcccc cctgaacccc  1560
aaggccaacc gcgagaagat gacccaggtg agtggcccgc tacctcttct ggtggccgcc  1620
tccctccttc ctggcctccc ggagctgcgc cctttctcac tggttctctc ttctgccgtt  1680
ttccgtagga ctctcttctc tgacctgagt ctccttgga actctgcagg ttctatttgc  1740
tttttcccag atgagctctt tttctggtgt ttgtctctct gactaggtgt ctgagacagt  1800
gttgtgggtg taggtactaa cactggctcg tgtgacaagg ccatgaggct ggtgtaaagc  1860
ggccttggag tgtgtattaa gtaggcgcac agtaggtctg aacagactcc ccatcccaag  1920
accccagcac acttagccgt gttctttgca ctttctgcat gtccccgtc tggcctggct  1980
gtccccagtg gcttccccag tgtgacatgg tgcatctctg ccttacagat catgtttgag  2040
```

-continued

```
accttcaaca ccccagccat gtacgttgct atccaggctg tgctatccct gtacgcctct      2100
ggccgtacca ctggcatcgt gatggactcc ggtgacgggg tcacccacac tgtgcccatc      2160 tacgagggt atgccctccc ccatgccatc ctgcgtctgg acctggctgg ccgggacctg       2220
actgactacc tcatgaagat cctcaccgag cgcggctaca gcttcaccac cacggccgag      2280
cgggaaatcg tgcgtgacat taaggagaag ctgtgctacg tcgccctgga cttcgagcaa      2340
gagatggcca cggctgcttc cagctcctcc ctggagaaga gctacgagct gcctgacggc      2400
caggtcatca ccattggcaa tgagcggttc cgctgccctg aggcactctt ccagccttcc      2460
ttcctgggtg agtggagact gtctcccggc tctgcctgac atgagggtta ccctcgggg      2520 ctgtgctgtg aagctaagt cctgccctca tttccctctc aggcatggag tcctgtggca      2580
tccacgaaac taccttcaac tccatcatga agtgtgacgt ggacatccgc aaagacctgt      2640
acgccaacac agtgctgtct gcggcacca ccatgtaccc tggcattgcc gacaggatgc       2700
agaaggagat cactgccctg gcacccagca caatgaagat caaggtgggt gtctttcctg      2760
cctgagctga cctgggcagg tcagctgtgg ggtcctgtgg tgtgtgggga gctgtcacat      2820
ccagggtcct cactgcctgt ccccttccct cctcagatca ttgctcctcc tgagcgcaag      2880
tactccgtgt ggatcggcgg ctccatcctg gcctcgctgt ccaccttcca gcagatgtgg      2940
atcagcaagc aggagtatga cgagtccggc ccctccatcg tccaccgcaa atgcttctag      3000
gcggactatg acttagttgc gttacaccct ttcttgacaa aacctaactt gcgcagaaaa      3060
caagatgaga ttggcatggc tttatttgtt tttttgttt tgtttggtt ttttttttt         3120 ttttggcttg actcaggatt taaaaactgg aacggtgaag gtgacagcag tcggttggag      3180
cgagcatccc ccaaagttca caatgtggcc gaggactttg attgcattgt tgtttttta      3240 atagtcattc caaatatgag atgcattgtt acaggaagtc ccttgccatc ctaaaagcca      3300
ccccacttct ctctaaggag aatggcccag tcctctccca agtccacaca ggggaggtga      3360
tagcattgct ttcgtgtaaa ttatgtaatg caaaatttt ttaatcttcg ccttaatact       3420 tttttattt gttttatttt gaatgatgag ccttcgtgcc ccccttccc ccttttgtc         3480 ccccaacttg agatgtatga aggcttttgg tctccctggg agtgggtgga ggcagccagg      3540
gcttacctgt acactgactt gagaccagtt gaataaaagt gcacaccta aaaatgaggc       3600 caagtgtgac tttgtggtgt ggctgggttg ggggcagcag agggtg                     3646
```

<210> SEQ ID NO 35
<211> LENGTH: 318
<212> TYPE: DNA
<213> ORGANISM: Homo sapiens
<220> FEATURE:
<221> NAME/KEY: unsure
<222> LOCATION: (9)
<221> NAME/KEY: unsure
<222> LOCATION: (51)
<221> NAME/KEY: unsure
<222> LOCATION: (119)
<221> NAME/KEY: unsure
<222> LOCATION: (247)
<221> NAME/KEY: unsure
<222> LOCATION: (301)
<221> NAME/KEY: unsure
<222> LOCATION: (313)

<400> SEQUENCE: 35

```
ctcgattng ggaagttgta gactgcacaa ttaaaacaga tccagtcact nggagatcaa        60
gaggatttgg atttgtgctt ttcaaagatg ctgctagtgt tgataaggtt ttggaactna      120
```

| | |
|---|---|
| aagaacacaa actggatggc aaattgatag atcccaaaag ggccaaagct ttaaaaggga | 180 |
| aagaacctcc caaaaaggtt tttgtgggtg gattgagccc ggatacttct gaagaacaaa | 240 |
| ttaaagnata ttttggagcc tttggagaga ttgaaaatat tgaacttccc atggatacaa | 300 |
| naacaaattg aanggaag | 318 |

<210> SEQ ID NO 36
<211> LENGTH: 1291
<212> TYPE: DNA
<213> ORGANISM: Homo sapiens

<400> SEQUENCE: 36

| | |
|---|---|
| gatctcttcc gccgccattt taaatccagc tccatacaac gctccgccgc cgctgctgcc | 60 |
| gcgacccgga ctgcgcgcca gcacccccct gccgacagct ccgtcactat ggaggatatg | 120 |
| aacgagtaca gcaatataga ggaattcgca gagggatcca agatcaacgc gagcaagaat | 180 |
| cagcaggatg acgtaaaat gtttattgga ggcttgagct gggatacaag caaaaaagat | 240 |
| ctgacagagt acttgtctcg atttggggaa gttgtagact gcacaattaa acagatcca | 300 |
| gtcactggga gatcaagagg atttggattt gtgcttttca aagatgctgc tagtgttgat | 360 |
| aaggtttttgg aactgaaaga cacaaactg atggcaaat tgatagatcc caaagggcc | 420 |
| aaagctttaa aagggaaaga acctcccaaa aaggtttttg tgggtggatt gagcccggat | 480 |
| acttctgaag aacaaattaa agaatatttt ggagcctttg gagagattga aaatattgaa | 540 |
| cttcccatgg atacaaaaac aaatgaaaga agaggatttt gttttatcac atatactgat | 600 |
| gaagagccag taaaaaatt gttagaaagc agataccatc aaattggttc tgggaagtgt | 660 |
| gaaatcaaag ttgcacaacc caagaggta tataggcagc aacagcaaca acaaaaaggt | 720 |
| ggaagaggtg ctgcagctgg tggacgaggt ggtacgaggg gtcgtggccg aggtcagggc | 780 |
| caaaactgga accaaggatt taataactat tatgatcaag gatatggaaa ttacaatagt | 840 |
| gcctatggtg gtgatcaaaa ctatagtggc tatggcggat atgattatac tgggtataac | 900 |
| tatgggaact atgatatgg acagggatat gcagactaca gtggccaaca gagcacttat | 960 |
| ggcaaggcat ctcgaggggg tggcaatcac caaacaatt accagccata ctaaaggaga | 1020 |
| acattggaga aaacaggagg agatgttaaa gtaacccatc ttgcaggacg acattgaaga | 1080 |
| ttggtcttct gttgatctaa gatgattatt ttgtaaaaga ctttctagtg tacaagacac | 1140 |
| cattgtgtcc aactgtatat agctgccaat tagttttctt tgttttttact ttgtcctttg | 1200 |
| ctatctgtgt tatgactcaa tgtggatttg tttatacaca ttttatttgt atcatttcat | 1260 |
| gttaaacctc aaataaatgc ttccttatgt g | 1291 |

<210> SEQ ID NO 37
<211> LENGTH: 2439
<212> TYPE: DNA
<213> ORGANISM: Homo sapiens

<400> SEQUENCE: 37

| | |
|---|---|
| gaattcgcag agggatccaa gatcaacgcg agcaagaatc agcaggatga cgtaaaatg | 60 |
| tttattggag gcttgagctg ggatacaagc aaaaaagatc tgacagagta cttgtctcga | 120 |
| tttggggaag ttgtagactg cacaattaaa acagatccag tcactgggag atcaaggagga | 180 |
| tttggatttg tgcttttcaa agatgctgct agtgttgata aggttttgga actgaaagaa | 240 |
| cacaaactgg atgcaaatt gatagatccc aaagggcca agctttaaa agggaaagaa | 300 |
| cctcccaaaa aggtttttgt gggtggattg agcccggata cttctgaaga acaaattaaa | 360 |

```
gaatattttg gagcctttgg agagattgaa aatattgaac ttcccatgga tacaaaaaca      420
aatgaaagaa gaggattttg ttttatcaca tatactgatg aagagccagt aaaaaaattg      480
ttagaaagca gataccatca aattggttct gggaagtgtg aaatcaaagt tgcacaaccc      540
aaagaggtat ataggcagca acagcaacaa caaaaaggtg aaagaggtgc tgcagctggt      600
ggacgaggtg gtacgagggg tcgtggccga ggtcagggcc aaaactggaa ccaaggattt      660
ataactatt atgatcaagg atatggaaat tacaatagtg cctatggtgg tgatcaaaac      720
tatagtggct atggcggata tgattatact gggtataact atgggaacta tggatatgga      780
cagggatatg cagactacag tggccaacag agcacttatg gcaaggcatc tcgaggcggt      840
ggcaatcacc aaaacaatta ccagccatac taaggagaa cattggagaa acaggagga      900
gatgttaaag taacccatct tgcaggacga cattgaagat tggtcttctg ttgatctaag      960
atgattattt tgtaaaagac tttctagtgt acaagacacc attgtgtcca actgtatata     1020
gctgccaatt agttttcttt gttttactt tgtcctttgc tatctgtgtt atgactcaat     1080
gtggatttgt ttatacacat tttatttgta tcatttcatg ttaaacctca aataaatgct     1140
tccttatgtg attgcttttc tgcgtcaggt actacatagc tctgtaaaaa atgtaattta     1200
aaataagcaa taattaaggc acagttgatt ttgtagagta ttggtccata cagagaaact     1260
gtggtccttt ataaatagcc agccagcgtc accctcttct ccaatttgta ggtgtattt      1320
atgctcttaa ggcttcatct tctccctgta actgagattt ctaccacacc tttgaacaat     1380
gttctttccc ttctggttat ctgaagactg tcctgaaagg aagacataag tgttgtgatt     1440
agtagaagct ttgtaatcat aacacaatga gtaattcttg tataaaagtt cagatacaaa     1500
aggagcactg taaaactggt aggagctatg gtttaagagc attggaagta gttacaactc     1560
aaggattttg gtagaaaggt atgagtttgg tcgaaaaatt aaaatagtgg caaataaga      1620
tttagttgtg ttttctcaga gccgccacaa gattgaacaa atgttttct gtttgggcat     1680
cctgaggaag ttgtattagc tgttaatgct ctgtgagttt agagaaaagt cttgatagta     1740
aatctagttt ttgacacagt gcatgaacta agtagttaaa tatttacata ttcagaaagg     1800
aatagtggaa aaggtatctt ggttatgaca aagtcattac aaatgtgact aagtcattac     1860
aaatgtgact gagtcattac agtggaccct ctgggtgcat tgaaaagaat ccgttttata     1920
tccaggtttc agaggacctg gaataataat aagctttgga ttttgcattc agtgtagttg     1980
gatttttggga ccttggcctc agtgttattt actgggattg gcatacgtgt tcacaggcag     2040
agtagttgat ctcacacaac gggtgatctc acaaaactgg taagtttctt atgctcatga     2100
gccctcccctt tttttttta atttggtgcc tgcaactttc ttaacaatga ttctacttcc     2160
tgggctatca cattataatg ctcttggcct ctttttttgct gctgttttgc tattcttaaa     2220
cttaggccaa gtaccaatgt tggctgttag aagggattct gttcattcaa catgcaactt     2280
tagggaatgg aagtaagttc attttttaagt tgtgtggtca gtaggtgcgg tgtctagggt     2340
agtgaatcct gtaagttcaa atttatgatt aggtgacgag ttgacattga gattgtcctt     2400
ttcccctgat caaaaaaatg aataaagcct ttttaaacg                            2439
```

<210> SEQ ID NO 38
<211> LENGTH: 459
<212> TYPE: DNA
<213> ORGANISM: Homo sapiens
<220> FEATURE:
<221> NAME/KEY: unsure
<222> LOCATION: (426)

<221> NAME/KEY: unsure
<222> LOCATION: (445)

<400> SEQUENCE: 38

| | | | | | |
|---|---|---|---|---|---|
| ttttacagat | ctttttgact | atcttcctct | cactgccttg | gtggatgggc | agatcttctg | 60 |
| tctacatggt | ggtctctcgc | catctataga | tacactggat | catatcagag | cacttgatcg | 120 |
| cctacaagaa | gttccccatg | agggtccaat | gtgtgacttg | ctgtggtcag | atccagatga | 180 |
| ccgtggtggt | tggggtatat | ctcctcgagg | agctggttac | accttgggc | aagatatttc | 240 |
| tgagacattt | aatcatgcca | atggcctcac | gttggtgtct | agagctcacc | agctagtgat | 300 |
| ggagggatat | aactggtgcc | atgaccggaa | tgtagtaacg | attttcagtg | ctccaaacta | 360 |
| ttgttatcgt | tgtggtaacc | aagctgcaat | catgggaact | tgacgatact | ctaaaatact | 420 |
| ctttcntgca | gttttgaccc | agcanctcgt | agggccgag | | | 459 |

<210> SEQ ID NO 39
<211> LENGTH: 1787
<212> TYPE: DNA
<213> ORGANISM: Homo sapiens

<400> SEQUENCE: 39

| | | | | | |
|---|---|---|---|---|---|
| gagagctcgg | ctctcggagg | aggaggcgca | cggccagcgg | cagtactgcg | gtgagagcca | 60 |
| gcggccagcg | ccacgctcaa | cagccgccag | aagtacacga | ggaaccggcg | gcggcgtgtg | 120 |
| cgtgtaagcc | ggcggcggcg | cgggaggagc | cggagcggca | gccggctggg | gcgggtggca | 180 |
| tcatggacga | gaaggtgttc | accaaggagc | tggaccagtg | gatcgagcag | ctgaacgagt | 240 |
| gcaagcagct | gtccgagtcc | caggtcaaga | gcctctgcga | aaggctaaa | gaaatcctga | 300 |
| caaaagaatc | caacgtgcaa | gaggttcgat | gtccagttac | tgtctgtgga | gatgtgcatg | 360 |
| ggcaatttca | tgatctcatg | gaactgttta | gaattggtgg | caaatcacca | gatacaaatt | 420 |
| acttgtttat | gggagattat | gttgacagag | gatattattc | agttgaaaca | gttacactgc | 480 |
| ttgtagctct | taaggttcgt | taccgtgaac | gcatcaccat | tcttcgaggg | aatcatgaga | 540 |
| gcagacagat | cacacaagtt | tatggtttct | atgatgaatg | tttaagaaaa | tatggaaatg | 600 |
| caaatgtttg | gaaatatttt | acagatcttt | ttgactatct | tcctctcact | gccttggtgg | 660 |
| atgggcagat | cttctgtcta | catggtggtc | tctcgccatc | tatagataca | ctggatcata | 720 |
| tcagagcact | tgatcgccta | caagaagttc | cccatgaggg | tccaatgtgt | gacttgctgt | 780 |
| ggtcagatcc | agatgaccgt | ggtggttggg | gtatatctcc | tcgaggagct | ggttacacct | 840 |
| tgggcaaga | tatttctgag | acatttaatc | atgccaatgg | cctcacgttg | gtgtctagag | 900 |
| ctcaccagct | agtgatggag | ggatataact | ggtgccatga | ccggaatgta | gtaacgattt | 960 |
| tcagtgctcc | aaactattgt | tatcgttgtg | gtaaccaagc | tgcaatcatg | gaacttgacg | 1020 |
| atactctaaa | atactctttc | ttgcagtttg | acccagcacc | tcgtagaggc | gagccacatg | 1080 |
| ttactcgtcg | taccccagac | tacttcctgt | aatgaaattt | taaacttgta | cagtattgcc | 1140 |
| atgaaccata | tatcgaccta | atggaaatgg | aagagcaac | agtaactcca | aagtgtcaga | 1200 |
| aaatagttaa | cattcaaaaa | acttgttttc | acatggacca | aaagatgtgc | catataaaaa | 1260 |
| tacaaagcct | cttgtcatca | acagccgtga | ccactttaga | atgaaccagt | tcattgcatg | 1320 |
| ctgaagcgac | attgttggtc | aagaaaccag | tttctggcat | agcgctattt | gtagttactt | 1380 |
| ttgtttctct | gagagactgc | agataataag | atgtaaacat | taacacctcg | tgaatacaat | 1440 |
| ttaacttcca | tttagctata | gctttactca | gcatgactgt | agataaggat | agcagcaaac | 1500 |

| | | | | | |
|---|---|---|---|---|---|
| aatcattgga | gcttaatgaa | cattttaaa | aataattacc | aaggcctccc | ttctacttgt | 1560 |
| gagttttgaa | attgttcttt | ttattttcag | ggataccgtt | taatttaatt | atatgatttg | 1620 |
| tctgcactca | gtttattccc | tactcaaatc | tcagccccat | gttgttcttt | gttattgtca | 1680 |
| gaacctggtg | agttgttttg | aacagaactg | tttttttcccc | ttcctgtaag | acgatgtgac | 1740 |
| tgcacaagag | cactgcagtg | tttttcataa | taaacttgtg | aactaac | | 1787 |

```
<210> SEQ ID NO 40
<211> LENGTH: 452
<212> TYPE: DNA
<213> ORGANISM: Homo sapiens
<220> FEATURE:
<221> NAME/KEY: unsure
<222> LOCATION: (33)..(34)
<221> NAME/KEY: unsure
<222> LOCATION: (59)
<221> NAME/KEY: unsure
<222> LOCATION: (82)
<221> NAME/KEY: unsure
<222> LOCATION: (112)
<221> NAME/KEY: unsure
<222> LOCATION: (126)
<221> NAME/KEY: unsure
<222> LOCATION: (164)
<221> NAME/KEY: unsure
<222> LOCATION: (184)
<221> NAME/KEY: unsure
<222> LOCATION: (225)
<221> NAME/KEY: unsure
<222> LOCATION: (244)
<221> NAME/KEY: unsure
<222> LOCATION: (253)
<221> NAME/KEY: unsure
<222> LOCATION: (272)
<221> NAME/KEY: unsure
<222> LOCATION: (307)
<221> NAME/KEY: unsure
<222> LOCATION: (316)
<221> NAME/KEY: unsure
<222> LOCATION: (329)
<221> NAME/KEY: unsure
<222> LOCATION: (335)
<221> NAME/KEY: unsure
<222> LOCATION: (381)
<221> NAME/KEY: unsure
<222> LOCATION: (396)
<221> NAME/KEY: unsure
<222> LOCATION: (417)
<221> NAME/KEY: unsure
<222> LOCATION: (422)
<221> NAME/KEY: unsure
<222> LOCATION: (429)
<221> NAME/KEY: unsure
<222> LOCATION: (448)

<400> SEQUENCE: 40
```

| | | | | | |
|---|---|---|---|---|---|
| gtttacagat | gccacttagt | tacactggtt | ttnnttttc | agtctcatct | gggttgganc | 60 |
| caaagacatt | cagaggcatg | gnaagaggca | aagcatcaga | catctcattg | gnggcaggta | 120 |
| cttccngact | actgtaccac | ctgctgtatc | cttccccacc | tcancacccc | caaagccatt | 180 |
| tagngccaaa | tgctacagta | aaaacccaat | gcatttacat | aaaanaatgc | ctaactgcat | 240 |
| attnacattt | ttnagaaaaa | aaatcccatt | angctcttct | agaaagttat | ggcaggaaag | 300 |
| gtaaggncca | aggctntgag | caagccatnt | gtggnaactt | aaagtagatg | agcactgagt | 360 |
| ttctccatag | ttggaaaaaa | ngccacactg | agcccnctttt | tcccgtggag | ggcaagntga | 420 |
| gnccctccnt | ttatacccccg | ttgagatntc | ag | | | 452 |

```
<210> SEQ ID NO 41
```

-continued

```
<211> LENGTH: 263
<212> TYPE: DNA
<213> ORGANISM: Homo sapiens
<220> FEATURE:
<221> NAME/KEY: unsure
<222> LOCATION: (214)
<221> NAME/KEY: unsure
<222> LOCATION: (231)
<221> NAME/KEY: unsure
<222> LOCATION: (238)

<400> SEQUENCE: 41
gagaaaaggg ttggggagaa gcctctgcag tcctggaaga tgtggggttc tgggtgagag      60
gcatcagccc cacaagtatg tttttgtgtc ttaagatagc agtttacttt gaaaaagtga     120
aaaaggcttc cgggctgtcc tctgcccagt gagatggagg acgctagaga aagtgctgag     180
tgtcccgaga gaggcccccg agccagtgca tggnaggtcc ttcggcctgg ntcagctngg     240
ctgcaggatg cccactttga gga                                              263

<210> SEQ ID NO 42
<211> LENGTH: 3049
<212> TYPE: DNA
<213> ORGANISM: Homo sapiens

<400> SEQUENCE: 42
cccgcgggca ggggcggcga gtgcgcgggc cgccgccctt ctcggcgggc agcgcgcgag      60
gaccaggccg aggaggaagt ggcggcggcg cggcgggct ccccgcccga ggaggaagat     120
gcagaccttt ctgaaaggga agagagttgg ctactggctg agcgagaaga aaatcaagaa     180
gctgaatttc caggctttcg ccgagctgtg caggaagcga gggatggagg ttgtgcagct     240
gaaccttagc cggccgatcg aggagcaggg cccctggac gtcatcatcc acaagctgac     300
tgacgtcatc cttgaagccg accagaatga tagccagtcc ctggagctgg tgcacaggtt     360
ccaggagtac atcgatgccc accctgagac catcgtcctg gacccgctcc ctgccatcag     420
aaccctgctt gaccgctcca gtcctatga gctcatccgg aagattgagg cctacatgga     480
agacgacagg atctgctcgc cacccttcat ggagctcacg agcctgtgcg gggatgacac     540
catgcggctg ctggagaaga acggcttgac tttcccattc atttgcaaaa ccagagtggc     600
tcatggcacc aactctcacg agatggctat cgtgttcaac caggagggcc tgaacgccat     660
ccagccaccc tgcgtggtcc agaatttcat caaccacaac gccgtcctgt acaaggtgtt     720
cgtggttggc gagtcctaca ccgtggtcca gaggccctca ctcaagaact tctccgcagg     780
cacatcagac cgtgagtcca tcttcttcaa cagccacaac gtgtcaaagc cggagtcgtc     840
atcggtcctg acgagctgg acaagatcga gggcgtgttc gagcggccga gcgacgaggt     900
catccgggag ctctcccggg ccctgcggca ggcactgggc gtgtcactct tcggcatcga     960
catcatcatc aacaaccaga cagggcagca cgccgtcatt gacatcaatg ccttcccagg    1020 ctacagggc gtgagcgagt tcttcacaga cctcctgaac cacatcgcca ctgtcctgca    1080
gggccagagc acagccatgg cagccacagg ggacgtggcc ctgctgaggc acagcaagct    1140
tctggccgag ccggcgggcg gcctggtggg cgagcggaca tgcaacgcca gccccggctg    1200
ctgcggcagc atgatgggcc aggacgcgcc ctggaaagct gaggccgacg cgggcggcac    1260
cgccaagctg ccgcaccaga gactcggctg caacgccggc gtgtctccca gcttccagca    1320
gcattgtgtg gcctccctgg ccaccaaggc ctcctcccaa tagccacgga gccgggaccc    1380
agagggcagc gcaggcgcag gagcacaccc gctgggccag cagctcccaa cggcgatgct    1440
```

-continued

```
actactaaga atccccagtg atctgattct tctgtttttt aattttttaac ctgattttct     1500 gatgtcatga tctaaatgag gggtagaaga gagtaccagg tggtccaccg ttggggagcg     1560
gggccgtccg cctgctctct actgtgcaga cctcctaact gagtttacac acgcttgtgt     1620
tgcaacacta ggtctggatg ggaggtgagg ggggtgcgta tactgccatg ccagtgtctg     1680
tgcacatccc tgtctgttgt ctccatggcc actgtggact gggacccttg aagcctgccc     1740
atgtgggtgt gggaggctga tcagtgcgtg tgagagtggc ttcccttctg cctgactccc     1800
cactccctga cctgccccct ccttgttttt cctcctactg gtctccacca aggctttgtt     1860
agcccccacc ctgcctggtg tgcagctaac ccctccctcc ccacagccag aggaggccac     1920
agacccctca gggagttccg cgctgggtc tgggctgtgc tccctcacta aagggaagga     1980
aaggaagctg ggcgtcctcc gggcccccca acacacgtcc catttagccc tgcacagcgg     2040
tctccttccc ctaagccagc actgctgctc cctggagccg ggaaggaggc tgcctggctg     2100
gaggccgagc cgatgggcct gtgctgagga tttgtgctgt gatttgggca aatcattcca     2160
ggtctttggg cctccacccc ctcgtctcta gtggacattt gagatcagag agcaccacag     2220
ggctggcttt gtgccctaac ccctgggatg cagcctgcct ttccataaag tcacctaggt     2280
gaggataggc gcgggagcct cggcatgaca ccatggagat cggggccctc ttcccagtgg     2340
gttcactcct tttcacacct gctgggtccc tcctcgccca gcaggcctgg tccacctctc     2400
attgcaagcc cgcaagcact gagccgagta aggtgcttag tgtgagccac ccgcccccca     2460
tagcttctgc acacctcaga ctcaccccat caccttggca gcaaagcact gctctgccgt     2520 ctgaccctg atccaggcag cagcccctc cgcagagaaa agggttgggg agaagcctct     2580
gcagtcctgg aagatgtggg gtgctgggtg agaggcatca gcccccacaa gtatgttttt     2640
gtgtcttaag atagcagttt actttgaaaa agtgaaaaag gcttccgggc tgtcctctgc     2700
ccagtgagat ggaggacgct agagaaagtg ctgagtgtcc cgagagaggc ccccgagcca     2760
gtgcatggag gtcttcggcc tggctcagct gggctgcagg atgcccactt tgaggaggga     2820
ggcacagggc ttgggcgagg ggcagaggcc atcagaactg cccggctttt ttggaaactg     2880
aggacccaac aactaaccac gtttacacga cttgagtttt gaaccccgat taatgtctgt     2940
acgtcacctt tcctagttct gaccctgagc cctggggaac aggaaagcgt ggctggcctc     3000
ttgcactgct ttgtctccaa aataaaactac tgaaatcaaa ccgcatttc               3049
```

```
<210> SEQ ID NO 43
<211> LENGTH: 417
<212> TYPE: DNA
<213> ORGANISM: Homo sapiens
<220> FEATURE:
<221> NAME/KEY: unsure
<222> LOCATION: (198)
<221> NAME/KEY: unsure
<222> LOCATION: (260)
<221> NAME/KEY: unsure
<222> LOCATION: (299)
<221> NAME/KEY: unsure
<222> LOCATION: (344)
<221> NAME/KEY: unsure
<222> LOCATION: (373)
<221> NAME/KEY: unsure
<222> LOCATION: (378)
<221> NAME/KEY: unsure
<222> LOCATION: (384)
<221> NAME/KEY: unsure
<222> LOCATION: (410)

<400> SEQUENCE: 43
```

-continued

```
ggttgagccc tacaactgca tcctcaccac ccacaccacc ctggagcact ctgattgtgc      60
cttcatggta gacaatgagg ccatctatga catctgtcgt agaaacctcg atatcgagcg     120
cccaacctac accaacctta accgccttat tagccagatt gtgtcctcca tcactgcttc     180
cctgagattt gatggagncc tgaatgttga cctgacagaa ttccagacca acctgggtgc     240 cctaccccg catccacttn cctctggcca catatgcccc tgtcatctct gctgagaang     300
cctaccacga acagcttact gtagtagaga tcaccaatgc ttgntttgag ccagccaacc    360
agatggtgaa atntggancc ttgncattgg taaattacat ggggtttgcn gtctgtt      417
```

<210> SEQ ID NO 44
<211> LENGTH: 1596
<212> TYPE: DNA
<213> ORGANISM: Homo sapiens

<400> SEQUENCE: 44

```
tgtcggggac ggtaaccggg acccgtgctc tgctcctgtc gccttcgcct cctgaatccc      60
tagccatatg cgtgagtgca tctccatcca cgttggccag gctggtgtcc agattggcaa     120
tgcctgctgg gagctctact gcctggaaca cggcatccac cccgatggcc agatgccaag    180
tgacaagacc attgggggag gagatgactc cttcaacacc ttcttcagtg agacgggcgc    240
tggcaagcac gtgccccggg ctgtgtttgt agacttggaa cccacagtca ttgatgaagt    300
tcgcactggc acctaccgcc agctcttcca ccctgagcag ctcatcacag gcaaggaaga    360
tgctgccaat aactatgccc gagggcacta caccattggc aaggagatca ttgaccttgt    420
gttggaccga attcgcaagc tggctgacca gtgcacccgt cttcagggct tcttggtttt    480
ccacagcttt ggtgggggaa ctggttctgg gttcacctcc ctgctcatgg aacgcctgtc    540
agttgattat ggcaagaaat ccaagctgga gttctccatt tacccggcac cccaggtttc    600
cacagctgta gttgagccct acaactccat cctcaccacc acaccaccc tggagcactc    660 tgattgtgcc ttcatggtag acaatgaggc catctatgac atctgtcgta gaaacctcga    720
tatcgagcgc caacctaca ctaaccttaa ccgccttatt agccagattg tgtcctccat    780
cactgcttcc ctgagatttg atggagccct gaatgttgac ctgacagaat tccagaccaa    840
cctggtcccc taccccgca tccacttccc tctggccaca tatgccctg tcatctctgc    900 tgagaaagcc taccatgaac agctttctgt agcagacatc accaatgctt gctttgagcc    960
agccaaccag atggtgaaat gtgaccctgg ccatggtaaa tacatggctt gctgcctgtt    1020
gtaccgtggt gacgtggttc ccaaagatgt caatgctgcc attgccacca tcaaaaccaa    1080
gcgcacgatc cagtttgtgg attggtgccc cactggcttc aaggttggca tcaactacca    1140 gcctccact gtggtgcctg gtggagacct ggccaaggta cagagagctg tgtgcatgct    1200
gagcaacacc acagccattg ctgaggcctg ggctcgcctg gaccacaagt ttgacctgat    1260
gtatgccaag cgtgcctttg ttcactggta cgtgggtgag gggatggagg aaggcgagtt    1320
ttcagaggcc cgtgaagata tggctgccct tgagaaggat tatgaggagg ttggtgtgga    1380
ttctgttgaa ggagagggtg aggaagaagg agaggaatac taattatcca ttccttttgg    1440
ccctgcagca tgtcatgctc ccagaatttc agcttcagct taactgacag atgttaaagc    1500
tttctggtta gattgttttc acttggtgat catgtctttt ccatgtgtac ctgtaatatt    1560
tttccatcat atctcaaagt aaagtcatta acatca                              1596
```

<210> SEQ ID NO 45
<211> LENGTH: 4276

<212> TYPE: DNA
<213> ORGANISM: Homo sapiens

<400> SEQUENCE: 45

| | |
|---|---:|
| ctgtgaccca gaagtcttcg aattcactgg tttttcagac tctgccacgg cacatgcgac | 60 |
| gaagagccat gagccacaac gtcaaacgcc ttcccagacg gttacaggag attgcccaga | 120 |
| aagaggcgga gaaagccgta catcagaaaa aagaacattc aaaaaataaa tgccataaag | 180 |
| ctcgaagatg tcacatgaac cggacgctag aatttaaccg tagacaaaag aagaacattt | 240 |
| ggttagaaac tcacatctgg cacgccaagc ggtttcatat ggtcaagaag tggggctact | 300 |
| gccttgggga gaggccaaca gtcaagagcc acagagcctg ctatcgagcc atgacgaacc | 360 |
| ggtgcctcct gcaggattta tcctattact gttgtttgga gttgaaaggc aaagaggaag | 420 |
| aaatactaaa ggcgctttct ggaatgtgta acatagacac agggctgacg tttgcagcag | 480 |
| ttcactgctt gtctggaaag cgccaaggga gccttgtgct ttatcgggtg aataaatatc | 540 |
| ccagagaaat gcttgggcct gttacgttta tctggaagtc ccagaggacc ccgggtgacc | 600 |
| cttctgagag caggcagctg tggatctggc tgcatccaac ccttaaacag gatatcttag | 660 |
| aggaaataaa agcagcgtgc cagtgtgtgg aacccatcaa atcagctgtc tgcatcgctg | 720 |
| acccacttcc aacaccatcc caagaaaaaa gccaaactga attgcctgac gagaaaattg | 780 |
| gcaagaaaag aaaaggaaa gatgatggag aaaatgctaa accaattaaa aaaattatcg | 840 |
| gtgatggaac tagagatcca tgtctaccat actcttggat ctctccaacc acaggcatta | 900 |
| taatcagcga tttgacgatg gagatgaaca gattccggct gattgggcca ctttcccact | 960 |
| ccatcctaac tgaagcaata aaagctgctt ctgtccacac tgtgggagag gacacagagg | 1020 |
| agacacctca ccgctggtgg atagaaacct gtaagaaacc tgacagcgtt tcccttcatt | 1080 |
| gcagacaaga agccattttc gagttgttgg gaggaataac atcaccagca gaaattccgg | 1140 |
| caggtactat tctgggactg acagttgggg atcctcgaat aaatttgccc caaaagaagt | 1200 |
| ccaaagcttt gcccaatcca gaaaaatgcc aagataatga gaaagttaga cagctgcttc | 1260 |
| tggagggtgt gcctgtggaa tgtacgcata gctttatctg gaaccaagat atctgtaaga | 1320 |
| gtgtcacaga gaataaaatc tcggatcagg atttaaaccg gatgaggagt gaattgctgg | 1380 |
| tgcctgggtc acagcttatt ttaggtcccc atgaatccaa gataccta ctttttgattc | 1440 |
| agcagccagg aaaagtgact ggtgaagatc gactaggctg gggaagtggc tgggatgtcc | 1500 |
| tactcccaaa gggctggggc atggctttct ggattccatt tatttatcga ggtgtgagag | 1560 |
| tcggagggtt gaaagagtct gcagtgcatt ctcagtataa gaggtcgcct aatgtcccag | 1620 |
| gcgattttcc agactgccct gccgggatgc tgtttgcgga agagcaagct aagaatcttc | 1680 |
| ttgaaaagta caaagacgc cctcctgcaa aacggcccaa ctacgttaag cttggcactc | 1740 |
| tggcaccttt ctgctgtccc tgggagcagt taactcaaga ctgggagtca agagtccagg | 1800 |
| cttacgaaga accttctgta gcttcatctc caaatggtaa ggagagtgac ctaagaagat | 1860 |
| ctgaggtgcc ttgtgctccc atgcctaaaa aaactcatca gccatctgat gaagtgggca | 1920 |
| catccataga gcacccccagg gaggcagagg aggtaatgga tgcagggtgt caagaatcgg | 1980 |
| cagggcctga gaggatcaca gaccaggagg ccagtgaaaa ccatgttgct gccacaggga | 2040 |
| gtcacctctg cgttctcagg agtagaaaat tactgaagca actgtcagcc tggtgtgggc | 2100 |
| ccagttctga ggatagtcgg ggaggccggc gagctcccgg cagaggccag caaggattga | 2160 |
| ccagagaggc ttgcctgtcc atcttgggcc acttccccag ggccctggtt tgggtcagcc | 2220 |

```
tgtccctgct cagcaagggc agccccgagc ctcacaccat gatctgtgtc ccagccaagg    2280
aggacttcct ccagctccat gaggactggc attactgtgg gccccaggaa tccaaacaca    2340
gtgacccatt caggagcaag atcctgaaac agaaagagaa gaagaaaagg gagaagaggc    2400
agaagccagg acgtgcctct tctgatggcc cggcggggga agagcccgtg gctgggcagg    2460
aagctctgac tctagggctg tggtcaggcc tctgccgcg tgtgacgttg cactgctcca     2520
gaactctcct aggctttgtg actcaggag attttttccat ggctgttggc tgtggagaag    2580
ccctggggtt tgttagcttg acaggcttgc tggatatgct gtccagccag cctgcagcgc    2640
agagggcttt agtgctactg aggcctcccg cctctctgca gtatcgattt gcgaggattg    2700
ctattgaggt gtgaatgcgt gcttgtatcc cagcagggca tagataatac gttattattg    2760
tctgccaagt tctacatgtg gagaatctgc ttctgcttta aaatatcatg tgaaactccc    2820
tggaaacaag aataaaaat tatgtattat gcagatgatg aaatgtttac atcattccag     2880
taatgtcatt gattttcatc tttccctgtc cttgctgtaa tacttttaaa ttatttggcc    2940
aaaagctttg tattatgatc tcttggtctg tgtagttgtg gctgaaaata atgagaagct    3000
ctacgagtta tcatcccctt ttttgttag aaacaaaggg cttgtcaggt ctatttgaaa     3060
aacctcatag tcatgtgata agcaacaata gatgtttaat gatttcactg ttatagcaga    3120
agacaagaga agacgcttgg cctctgtaca tgaaatatgg gctcctgatg gacctcattc    3180
aattctgtac tgtgatttcc atgccgaaca actcaagcct taagagagaa aatcatggac    3240
aactgatttc tgcctgtttt caggcaggca cagtttatgg cgtcagtgct aggctggaat    3300
tagaaagtgg gggtctatga cgtggacttc ctgactcttt gatctctttg ttgttgacca    3360
acacttgatc ctactagtta cttaattttt ttaagtaaaa aattattatt attttgtttc    3420
tgcaaagatt ttctcaaagc catagaggag catttctcag aatatgttct atgatatgtg    3480
tcacctaaaa aagtaagaga ttccaaggtc aggttgatat ggaaactcta ggttaaataa    3540
agttaagcat ttctttatga aagaacttct ggaaacttcc atgtgataat gtgcattgcg    3600
gatctctagg aagaaatga tagtgtatag tattttctaa atacttgtga ttcctaaagt     3660
tctcttacaa ggagcccttt gtaggaccag tgttcttagt agcgcgcttt gggcagtgtg    3720
gctgtgtagt gcatagctac ctctgcaagg tgataactaa gccggcaagc tgcctttcaa    3780
cactcatgca gtcacgttgt ccacctgaga ttctcaacag ggtataaaag gaaggtctca    3840
tcttgcctca caggaagagt gggctcagtg tggcttttttt ccaactatgg agaaactcag    3900
tgctcatcta ctttaagttt ccacatatgg cttgctcata gccttggtcc ttaccttttcc   3960 tgccataact ttctagaaga gcttaatggg attttttttct aaaaaatgta aatatgcagt    4020
taggcattat tttatgtaaa tgcattgggt ttttactgta gcatttggca ctaaatggct    4080
ttgggggtga tgaggtgggg aaggatacag caggtggtac agtagtcagg aagtacctgc    4140
caccaatgag atgtctgatg ctttgcctct taccatgcct ctgaatgtct ttggatccaa    4200
cccagatgag actgaaaaaa aaaaaacagt gtaactaagt ggcatctgta aacagaataa    4260
atgaaaatgt cacctg                                                    4276
```

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 46
gtagcccagc                                              10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 47
gccacccaga                                              10

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 48
acgaagaaga agag                                         14

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 49
aggggcacca                                              10

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 50
aatgaggggg acaaatggga agc                               23

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 51
ggagagccct tcctcagaca tgaag                             25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 52
tgacaaaatg gtgacaggta gctgg                             25

<210> SEQ ID NO 53
<211> LENGTH: 24
<212> TYPE: DNA

```
<213> ORGANISM: Artificial Sequence
<220> FEATURE:
<223> OTHER INFORMATION: Description of Artificial Sequence: Primer

<400> SEQUENCE: 53
aagtccacac ctcctcagac agcc                                              24

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 54
cccagacacc caaacagccg tg                                                22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
tggagcagcc gtgtgtgctg                                                   20

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 56 aagcttttt tttttg                                                        16

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 57 aagcttttt tttta                                                         16

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 58 aagcttttt tttttc                                                        16

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 59
aagcttgatt gcc                                                          13
```

```
<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 60
aagcttcgac tgt                                                          13

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 61
aagctttggt cag                                                          13

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 62
aagcttctca acg                                                          13

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 63 atttttttttt tttttta                                                     17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 64 gtttttttttt tttttg                                                      17

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 65
tttttttttt tttv                                                         14

<210> SEQ ID NO 66
<211> LENGTH: 11
<212> TYPE: DNA
<213> ORGANISM: Artificial Sequence
<220> FEATURE:
```

<223> OTHER INFORMATION: Description of Artificial Sequence: Primer

<400> SEQUENCE: 66
ggtgcctttg g                                                                11

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 67
gcaccagggg                                                                  10

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 68
tttttttttt ttttt                                                            15

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 69
cacgtcttgg tgcctttgt gtg                                                    23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 70
gaagctcagc tcagccctct tcc                                                   23

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 71
ccagggagac caaaagcctt catac                                                 25

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 72 cacagggag gtgatagcat tgc                                                    23

```
<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 73
gtgcttttca aagatgctgc tagtg                                    25

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 74
gctcaatcca cccacaaaaa cc                                       22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 75
tcctctcact gccttggtgg atg                                      23

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 76
cacagcaagt cacacattgg accc                                     24

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 77
ccaaagacat tcagaggcat gg                                       22

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 78
gaggtgggga aggatacagc ag                                       22

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Primer
```

<400> SEQUENCE: 79
gaaaagggtt ggggagaagc ctc                                    23

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 80
tctctagcgt cctccatctc actgg                                  25

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 81
acaactgcat cctcaccacc cac                                    23

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 82
ggacacaatc tggctaataa ggcgg                                  25

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 83
aagctttttt tttttg                                            16

<210> SEQ ID NO 84
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 84
aagctttttt tttttc                                            16

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 85
aagctttttt tttttta                                           16

These results demonstrate that an arbitrarily sampled target generated using differential display and arbitrary primers can detect genes differentially expressed in response to EGF.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

We claim:

1. A method for detecting one or more species of nucleic acids in a population of nucleic acid molecules, said method comprising:
   (a) contacting said nucleic acids with one or two arbitrary oligonucleotides under conditions such that nucleic acids that bind said one or two arbitrary oligonucleotides are selected and/or amplified to generate an arbitrarily sampled target;
   (b) hybridizing said arbitrarily sampled target to an array of nucleic acid molecules;
   (c) detecting hybridization of nucleic acids in the arbitrarily sampled target to nucleic acids on said array;
   thereby detecting said one or more species of nucleic acid molecules in said population.

2. A method for detecting one or more species of nucleic acids in a population of nucleic acid molecules, said method comprising:
   (a) contacting said nucleic acids with one or more arbitrary oligonucleotides under conditions such that nucleic acids that bind said one or more arbitrary oligonucleotides are selected and/or amplified to generate an arbitrarily sampled target;
   (b) hybridizing said arbitrarily sampled target to an array of nucleic acid molecules;
   (c) detecting hybridization of nucleic acids in the arbitrarily sampled target to nucleic acids on said array;
   (d) repeating steps (a) to (c) at least two times, wherein said one or more arbitrary oligonucleotides differ each said time; thereby detecting said one or more species of nucleic acid molecules in said population.

3. The method of claim 1, wherein said arbitrarily sampled target is generated by amplification primed by said one or two arbitrary oligonucleotides.

4. The method of claim 1, wherein said arbitrarily sampled target is selected by isolating said nucleic acids that bind said one or two arbitrary oligonucleotides.

5. The method of claim 2, wherein said arbitrarily sampled target is generated by amplification primed by said one or more arbitrary oligonucleotides.

6. The method of claim 2, wherein said arbitrarily sampled target is selected by isolating said nucleic acids that bind said one or more arbitrary oligonucleotides.

7. The method of claim 1 or 2, wherein said nucleic acids are not contacted with an oligonucleotide containing an oligodT sequence.

8. The method of claim 1 or 2, wherein the nucleic acids of the arbitrarily sampled target have a detectable moiety.

9. The method of claim 8, wherein the detectable moiety is a fluorescent or radioactive label.

10. The method of claim 1 or 2, wherein the method of detecting hybridization of nucleic acids in the arbitrarily sampled target to nucleic acids on said array does not require a detectable moiety.

11. The method of claim 1 or 2, wherein the nucleic acids in the array are oligonucleotides.

12. The method of claim 1 or 2, wherein the nucleic acids in the array are peptide-nucleic acids.

13. The method of claim 1 or 2, wherein the nucleic acids in the array are cDNA clones.

14. The method of claim 1 or 2, wherein the nucleic acids in the array are EST clones.

15. The method of claim 1 or 2, wherein said arbitrary sampled target is generated by RNA arbitrarily primed polymerase chain reaction (RAP-PCR).

16. The method of claim 1 or 2, wherein one of said arbitrary oligonucleotides comprises an RNA polymerase promoter and said generation of the arbitrarily sampled target includes use of an RNA polymerase.

17. The method of claim 1 or 2, wherein said arbitrarily sampled target is further amplified.

18. The method of claim 17, wherein said amplified target is generated using polymerase chain reaction.

19. The method of claim 1 or 2, wherein said arbitrarily sampled target is not further amplified.

20. The method of claim 1, 2, 3 or 5, wherein said array is a non-dot blot array.

21. The method of claim 20, wherein the solid support is nylon membrane, derivatized glass, or silicon.

22. The method of claim 21, wherein the nucleic acids of the array are in a configuration of at least 2 spots per $cm^2$.

23. The method of claim 21, wherein the nucleic acids of the array are in a configuration of at least 5 spots per $cm^2$.

24. The method of claim 21, wherein the nucleic acids of the array are in a configuration of at least 10 spots per $cm^2$.

25. The method of claim 21, wherein the molecules of the array are attached to a solid support in a configuration up to 1000 spots per $cm^2$.

26. The method of claim 1 or 2, wherein said nucleic acids on said array are positionally addressed.

27. The method of claim 1, 2, 3 or 5, wherein said population of nucleic acid molecules is genomic DNA.

28. The method of claim 1, 2, 3 or 5, wherein said population of nucleic acid molecules is RNA.

29. The method of claim 1, 2, 3 or 5, wherein said population of nucleic acid molecules is cDNA.

30. The method of claim 1, 2, 3 or 5, wherein said population of nucleic acid molecules is from a mammalian cell.

31. The method of claim 30, wherein said population of nucleic acid molecules is RNA from a mammalian cell.

32. The method of claim 30, wherein said population of nucleic acid molecules is mRNA from a mammalian cell.

33. The method of claim 1 or 2, wherein said population of nucleic acid molecules is from a eukaryotic cell.

34. The method of claim 1 or 2, wherein said population of nucleic acid molecules is RNA from a eukaryotic cell.

35. The method of claim 1 or 2, wherein said population of nucleic acid molecules is from a prokaryotic cell.

36. The method of claim 1 or 2, wherein said population of nucleic acid molecules is RNA from a prokaryotic cell.

37. The method of claim 1 or 2, wherein said population of nucleic acid molecules is mRNA from a prokaryotic cell.

38. The method of claim 1, 2, 3 or 5, wherein said population of nucleic acid molecules is cDNA derived from mRNA from a mammalian cell.

39. The method of claim 1 or 2, wherein at least one of said nucleic acids is a less abundant nucleic acid molecule of said population.

40. The method of claim 1 or 2, wherein said population of nucleic acid molecules comprises 1000 or more nucleic acid molecules.

41. The method of claim 1, 2, 3 or 5, wherein said population of nucleic acid molecules comprises at least 20,000 mRNAs.

42. The method of claim 21, wherein said population of nucleic acid molecules comprises at least 20,000 mRNAs.

43. The method of claim 1 further comprising repeating steps (a)–(c), at least one time, wherein said one or two arbitrary oligonucleotides differ each said time.

44. The method of claim 1, 2, 3 or 5, wherein substantially all of the nucleic acid molecules in said population are detected.

45. The method of claim 21, wherein substantially all of the nucleic acid molecules in said population are detected.

46. The method of claim 39, wherein said less abundant nucleic acid molecule is less than 10% as abundant as the most abundant nucleic acid molecule in said population of nucleic acid molecules.

47. The method of claim 39, wherein said less abundant nucleic acid molecule is less than 1% as abundant as the most abundant nucleic acid molecule in said population of nucleic acid molecules.

48. The method of claim 39, wherein said less abundant nucleic acid molecule is less than 0.1% as abundant as the most abundant nucleic acid molecule in said population of nucleic acid molecules.

49. The method of claim 1, 2, 3 or 5, wherein at least one of said species of nucleic acids is less than 0.01% as abundant as the most abundant nucleic acid molecule in said population of nucleic acid molecules.

50. The method of claim 49, wherein said at least one of said species of nucleic acids is present at 1 copy per cell.

51. The method of claim 1, wherein steps(a)–(c) are repeated at least twice.

52. The method of claim 1, wherein steps(a)–(c) are repeated at least three times.

53. The method of claim 1, wherein steps(a)–(c) are repeated multiple times.

* * * * *